United States Patent
Nakaie et al.

(10) Patent No.: US 10,700,283 B2
(45) Date of Patent: Jun. 30, 2020

(54) ANILINE DERIVATIVES AND USES THEREOF

(71) Applicant: NISSAN CHEMICAL INDUSTRIES, LTD., Tokyo (JP)

(72) Inventors: Naoki Nakaie, Funabashi (JP); Taichi Nakazawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 359 days.

(21) Appl. No.: 15/026,821

(22) PCT Filed: Oct. 3, 2014

(86) PCT No.: PCT/JP2014/076598
§ 371 (c)(1),
(2) Date: Apr. 1, 2016

(87) PCT Pub. No.: WO2015/050253
PCT Pub. Date: Apr. 9, 2015

(65) Prior Publication Data
US 2016/0301011 A1    Oct. 13, 2016

(30) Foreign Application Priority Data

Oct. 4, 2013 (JP) ................. 2013-209201
May 23, 2014 (JP) ................. 2014-106771
Aug. 19, 2014 (JP) ................. 2014-166692

(51) Int. Cl.
*H01L 51/00* (2006.01)
*C07D 333/76* (2006.01)
(Continued)

(52) U.S. Cl.
CPC ........ *H01L 51/0059* (2013.01); *C07C 209/60* (2013.01); *C07C 211/54* (2013.01); *C07C 211/55* (2013.01); *C07C 211/58* (2013.01); *C07C 211/60* (2013.01); *C07C 211/61* (2013.01); *C07D 209/88* (2013.01); *C07D 333/76* (2013.01); *C08G 73/0266* (2013.01); *C09D 5/22* (2013.01); *C09D 5/24* (2013.01); *C09D 7/40* (2018.01); *C09D 7/63* (2018.01); *C09D 179/02* (2013.01); *H01L 51/006* (2013.01); *H01L 51/0052* (2013.01); *H01L 51/0061* (2013.01); *H01L 51/0072* (2013.01); *H01L 51/0074* (2013.01); *H01L 51/0094* (2013.01); *C07C 2603/26* (2017.05); *C07C 2603/97* (2017.05); *H01L 51/0056* (2013.01); *H01L 51/0058* (2013.01); *H01L 51/506* (2013.01); *H01L 51/5056* (2013.01); *H01L 51/5088* (2013.01)

(58) Field of Classification Search
CPC ............... H01L 59/0059; H01L 59/006; H01L 59/0061; H01L 59/0072; H01L 51/0059; C07C 211/54; C07C 211/55; C07C 211/57; C07C 211/58; C07C 211/60; C07C 211/61; C07D 209/82; C07D 209/88; C08G 73/0266
See application file for complete search history.

(56) References Cited

U.S. PATENT DOCUMENTS 8,906,519 B2    12/2014  Kato et al.
2002/0102434 A1  8/2002  Inoue et al.
(Continued)

FOREIGN PATENT DOCUMENTS

JP    2003-75955 A    3/2003
JP    2003-238501 A   8/2003
(Continued)

OTHER PUBLICATIONS

EPO machine translation of TW 200906909. (Year: 2018).*
STIC search report. (Year: 2018).*
Iranmanesh, A. and N. A. Gholami, "Computing the Szeged Index of Styrylbenzene Dendrimer and Triarylamine Dendrimer of Generation 1-3," MATCH Commun. Math. Comput. Chem. (2009), vol. 62, pp. 371-379.
International Search Report dated Jan. 6, 2015, in PCT International Application No. PCT/JP2014/076598.
Office Action dated Oct. 6, 2017, in Taiwan Patent Application No. 10621027180.

*Primary Examiner* — Daniel P Malley, Jr.
(74) *Attorney, Agent, or Firm* — Birch, Stewart, Kolasch & Birch, LLP

(57) ABSTRACT

Aniline derivatives such as those represented by the formula shown, for example, have good solubility with respect to organic solvents, and are able to provide an organic electroluminescent element having excellent luminance characteristics when a thin film containing said aniline derivatives is used as a charge transporting substance in a hole injection layer.

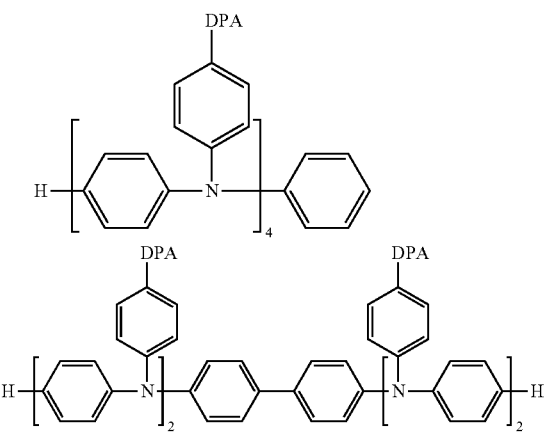

(In the formula, DPA represents a diphenylamino group.)

17 Claims, No Drawings

(51) Int. Cl.
*C07C 211/54* (2006.01)
*C07C 211/58* (2006.01)
*C07C 211/61* (2006.01)
*C07D 209/88* (2006.01)
*C09D 5/24* (2006.01)
*C09D 179/02* (2006.01)
*C07C 211/60* (2006.01)
*C08G 73/02* (2006.01)
*C09D 7/40* (2018.01)
*C09D 5/22* (2006.01)
*C09D 7/63* (2018.01)
*C07C 209/60* (2006.01)
*C07C 211/55* (2006.01)
*H01L 51/50* (2006.01)

(56) References Cited

U.S. PATENT DOCUMENTS

2005/0208334 A1    9/2005    Lee et al.
2010/0230639 A1    9/2010    Yamada et al.
2010/0258788 A1*  10/2010    Radu .................... C07C 211/54
                                                                257/40
2014/0183414 A1*   7/2014    Umemoto ........... H01L 51/0035
                                                               252/500
2017/0040539 A1*   2/2017    Park ................... H01L 51/0035

FOREIGN PATENT DOCUMENTS

| JP | 2005-166680 A | 6/2005 | |
| JP | 2005-276832 A | 10/2005 | |
| TW | 200906909 * | 1/2006 | ............ C08G 73/02 |
| WO | WO 2006/025342 A1 | 3/2006 | |
| WO | WO 2007/079103 A2 | 7/2007 | |
| WO | WO 2008/032616 A1 | 3/2008 | |
| WO | WO 2008/129947 A1 | 10/2008 | |
| WO | WO 2010/058777 A1 | 5/2010 | |
| WO | WO 2013/084664 A1 | 6/2013 | |

* cited by examiner

ANILINE DERIVATIVES AND USES THEREOF

TECHNICAL FIELD

The present invention relates to aniline derivatives and use thereof.

BACKGROUND ART

In organic electroluminescence (hereinafter referred to as organic EL) elements, a charge transporting thin film including an organic compound is used as a light emitting layer or a charge injection layer. Particularly, a hole injection layer serves for transfer of electric charges between an anode and a hole transport layer or a light emitting layer, thereby fulfilling an important function for achieving low-voltage driving and high luminance in the organic EL element.

Methods for forming a hole injection layer are generally classified into dry process represented by the vapor deposition method and wet process represented by the spin coating method. When these processes are compared, the wet process permits more efficient production of thin films with high flatness over a wider area. Under the present trend toward organic EL displays of larger areas, therefore, there is a demand for a hole injection layer that can be formed by a wet process.

In consideration of the above-mentioned circumstances, the present inventors have developed charge transporting materials which are applicable to various wet processes and which give thin films capable of realizing excellent EL element characteristics when applied to the hole injection layer in organic EL elements, and compounds which are to be used for the charge transporting materials and show good solubility in organic solvents (see, for example, Patent Documents 1 to 4).

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

Like the technologies of the above-mentioned Patent Documents that the present inventors have developed, the present invention has an object to provide aniline derivatives which show good solubility in organic solvents and can realize organic EL elements with excellent luminance characteristics when applied to a hole injection layer in the form of a thin film, a method of preparing the aniline derivatives, charge transporting substances including the aniline derivatives, charge transporting materials containing the charge transporting substances, charge transporting varnishes containing the charge transporting substances, charge transporting thin films obtained from the varnishes, charge transporting thin films prepared by a vapor deposition method using the aniline derivatives, and organic EL elements including the thin films.

Besides, it is another object of the present invention to provide amine compounds or aryl compounds preferable for use as precursor of the aniline derivatives, and a method of preparing the compounds.

Means for Solving the Problems

The present inventors made extensive and intensive investigations for achieving the above object, and have found out that specific aniline derivatives which cannot assume the quinonediimine structure show excellent solubility in organic solvents, that thin films exhibiting high charge transporting properties can be obtained from varnishes prepared by dissolving the aniline derivatives in organic solvents, and that high-luminance elements can be obtained when the thin films are applied to a hole injection layer in organic EL elements. On the basis of the findings, the inventors have completed the present invention.

Specifically, the present invention provides the following.

1. An aniline derivative represented by the formula (1) or (2)

[Chemical Formula 1]

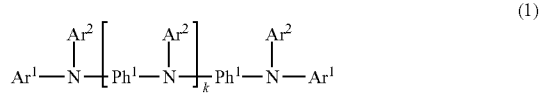

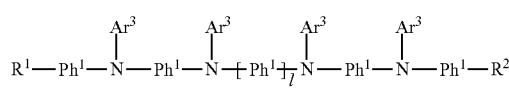

[wherein $R^1$ and $R^2$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $Ph^1$ represents a group represented by the formula (P1):

[Chemical Formula 2]

(wherein $R^3$ to $R^6$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom), $Ar^1$ independently represents a group represented by any of the formulas (B1) to (B11):

[Chemical Formula 3]
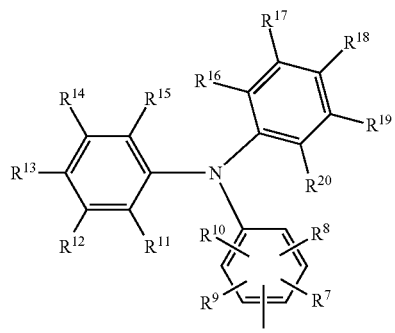
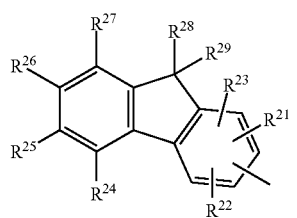
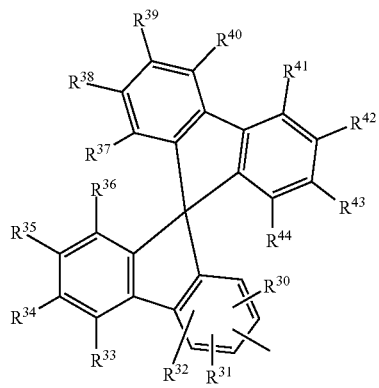
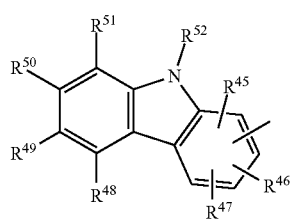
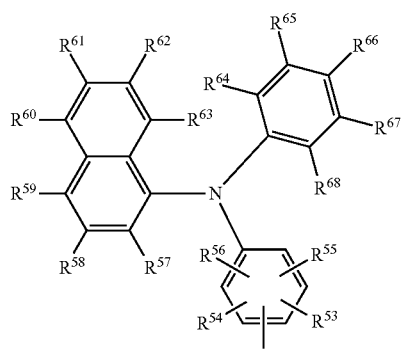
(B1)
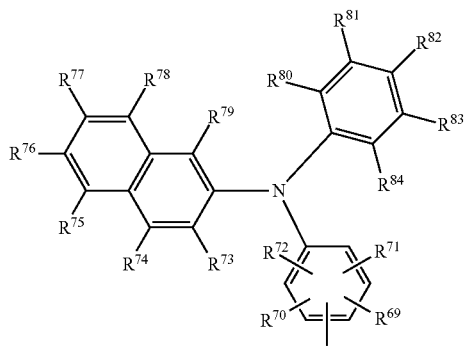
(B2)
(B3)
(B4)
(B5)
(B6)
(B7)
(B8)
(B9)
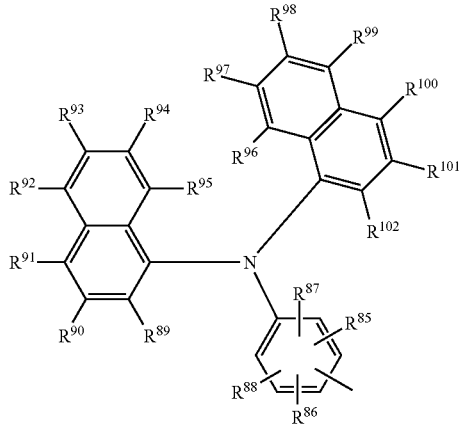
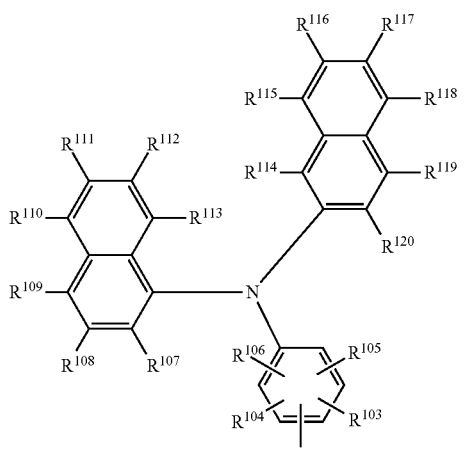
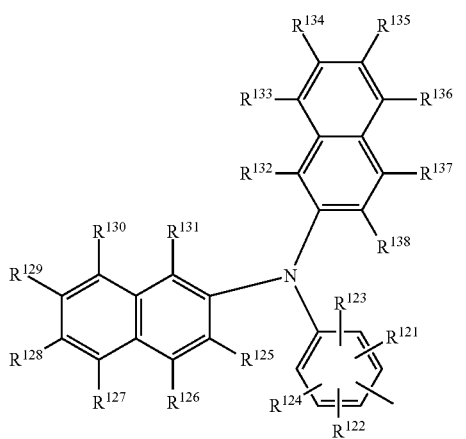

-continued (B10)

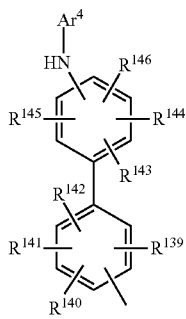

(B11)

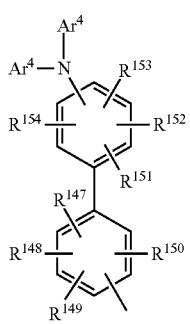

(wherein $R^7$ to $R^{27}$, $R^{30}$ to $R^{51}$ and $R^{53}$ to $R^{154}$ independently represent a hydrogen atom, a halogen atom, a nitro group, a cyano group, or a diphenylamino group, alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $R^{28}$ and $R^{29}$ independently represent an aryl group having 6 to 20 carbon atoms or heteroaryl group having 2 to 20 carbon atoms which may be substituted with $Z^1$, $R^{52}$ represents a hydrogen atom, an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $Ar^4$ independently represents an aryl group having 6 to 20 carbon atoms which may be substituted with a di(aryl groups having 6 to 20 carbon atoms)amino group, $Z^1$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^2$, $Z^2$ represents a halogen atom, a nitro group, a cyano group, or an aryl group having 6 to 20 carbon atoms or heteroaryl group having 2 to 20 carbon atoms which may be substituted with $Z^3$, $Z^3$ represents a halogen atom, a nitro group or a cyano group, $Z^4$ represents a halogen atom, a nitro group, a cyano group, or an aryl group having 6 to 20 carbon atoms or heteroaryl group having 2 to 20 carbon atoms which may be substituted with $Z^5$, and $Z^5$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^3$), $Ar^2$ independently represents a group represented by any of the formulas (A1) to (A18):

[Chemical Formula 4]

(A1)

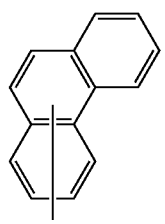
(A2)

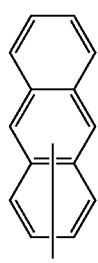
(A3)

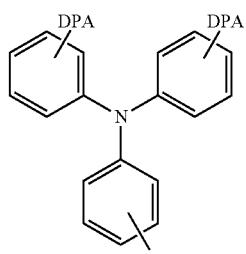
(A4)

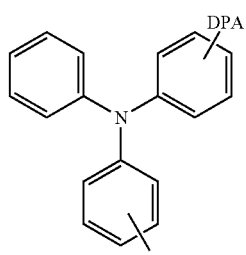
(A5)

(A6)

(A7)
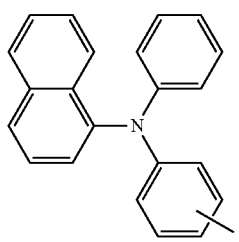
(A8)
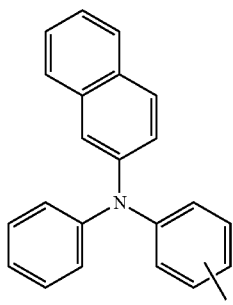
(A9)
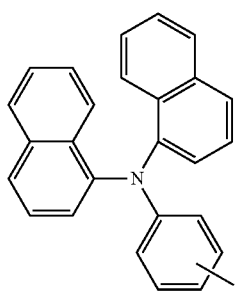
(A10)
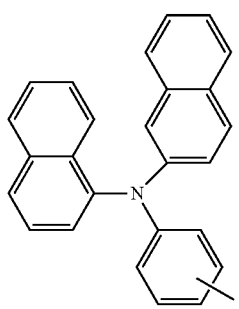
(A11)
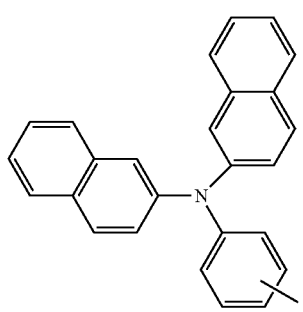
(A12)
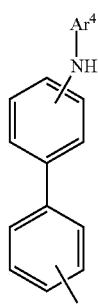
(A13)
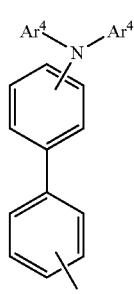
(A14)
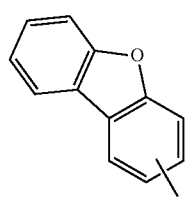
(A15)
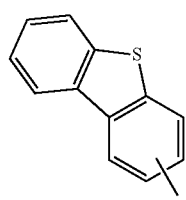
(A16)
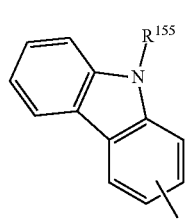
(A17)
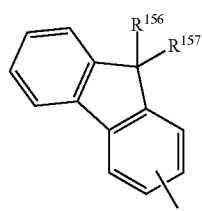

-continued (A18)

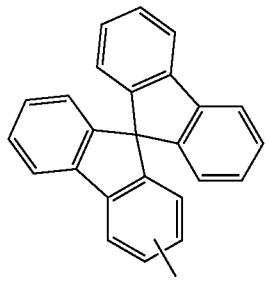

(wherein $R^{155}$ represents an hydrogen atom or an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $R^{156}$ and $R^{157}$ independently represent an aryl group having 6 to 20 carbon atoms or heteroaryl group having 2 to 20 carbon atoms which may be substituted with $Z^1$, DPA represents a diphenylamino group, and $Ar^4$, $Z^1$ and $Z^3$ to $Z^5$ have the same meanings as above), $Ar^3$ represents a group represented by any of the formulas (C1) to (C8):

[Chemical Formula 5]

(C1)

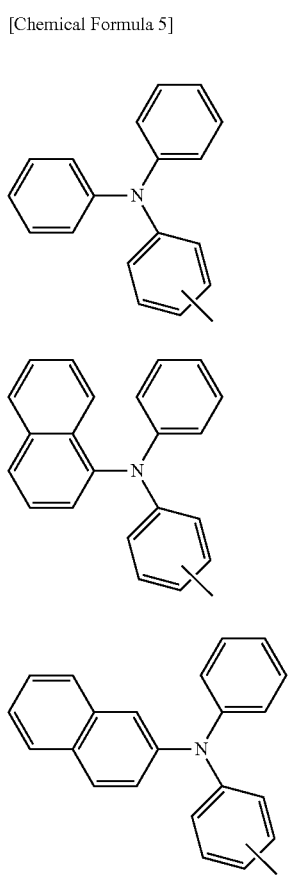

(C2)

(C3)

-continued (C4)

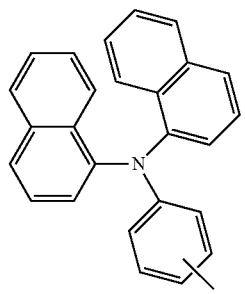

(C5)

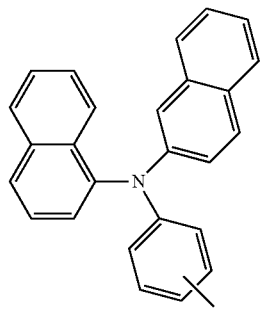

(C6)

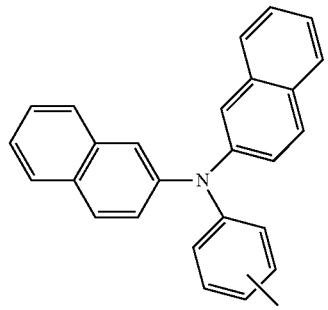

(C7)

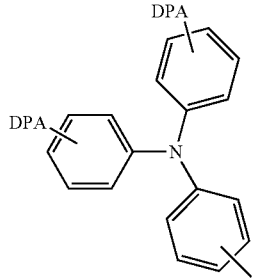

(C8)

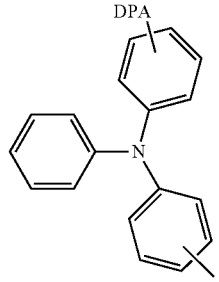

letter k represents an integer of 1 to 10, and
letter l represents 1 or 2].

2. The aniline derivative of 1,
wherein $Ar^1$ is a group represented by any of the formulas (B1') to (B11'):

[Chemical Formula 6]
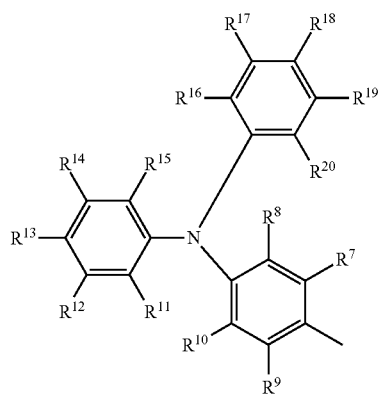
(B1′)
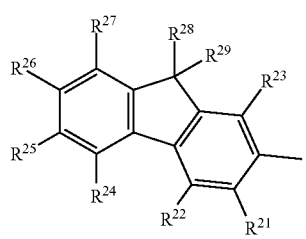
(B2′)
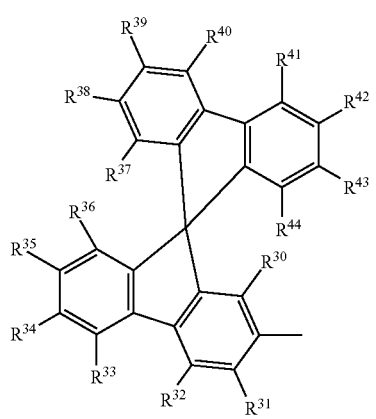
(B3′)
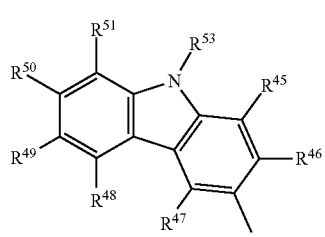
(B4′)
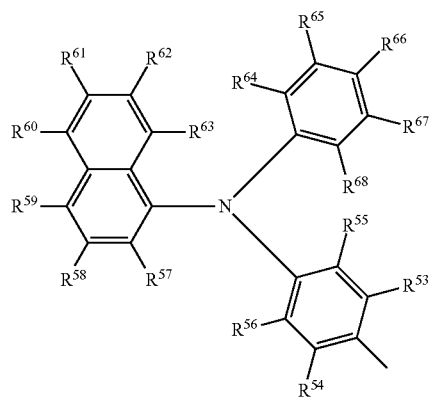
(B5′)
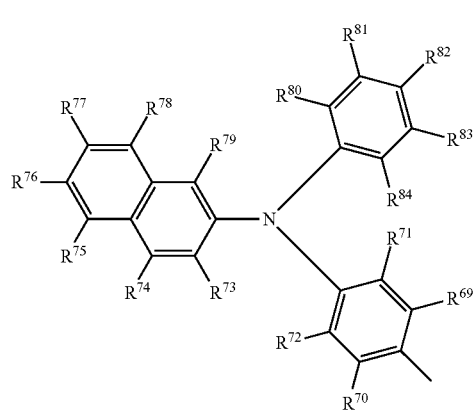
(B6′)
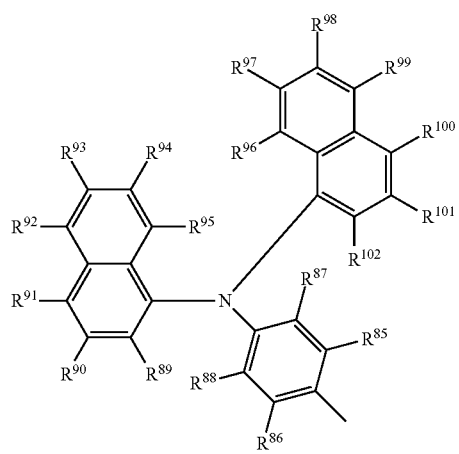
(B7′)

-continued
(B8′)
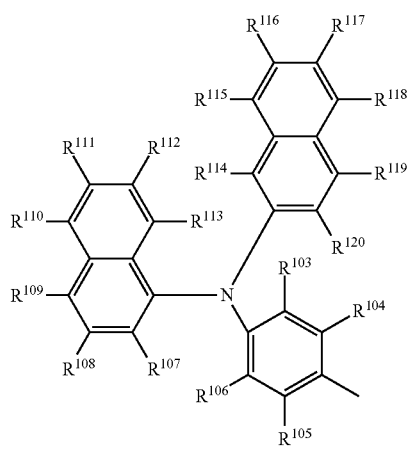
(B9′)
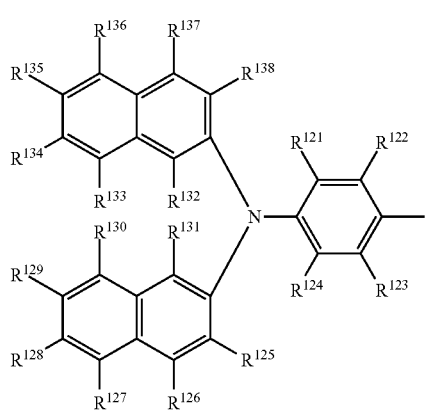
(B10′)
(B11′)
(wherein R⁷ to R¹⁵⁴ and Ar⁴ have the same meanings as above), and
Ar³ is a group represented by any of the formulas (C1′) to (C8′):
[Chemical Formula 7]
(C1′)
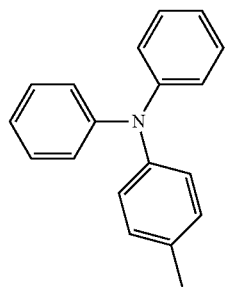
(C2′)
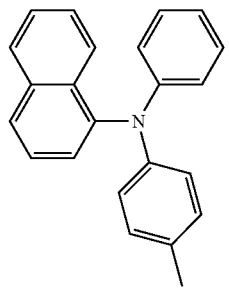
(C3′)
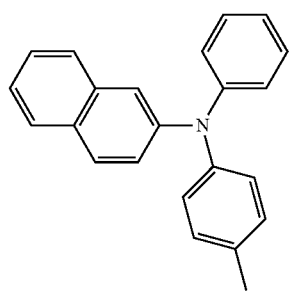
(C4′)
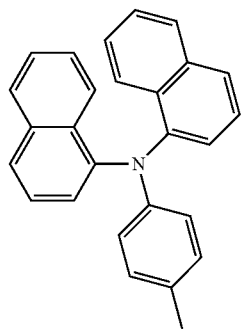

-continued (C5')
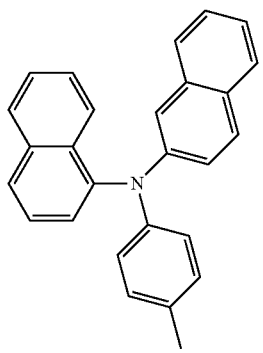

(C6')
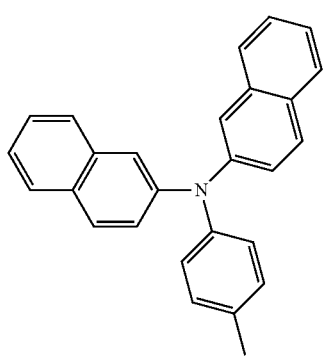

(C7')

(C8')

(wherein DPA has the same meaning as above).

3. The aniline derivative of 1 or 2, wherein the $R^3$ to $R^6$, $R^7$ to $R^{27}$, $R^{30}$ to $R^{51}$ and $R^{53}$ to $R^{154}$ are each a hydrogen atom.

4. The aniline derivative of 1, represented by the formula (1-1):

[Chemical Formula 8]

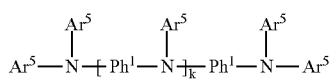 (1-1)

[wherein $Ar^5$ simultaneously represent a group represented by any of the formulas (D1) to (D13), and $Ph^1$ and letter k have the same meanings as above:

[Chemical Formula 9]

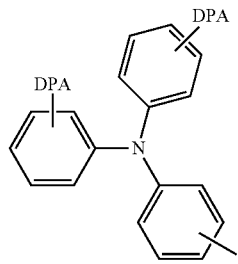 (D1)

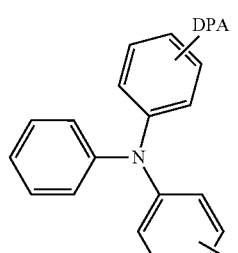 (D2)

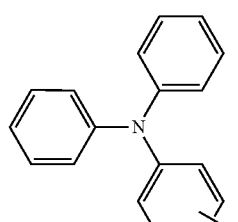 (D3)

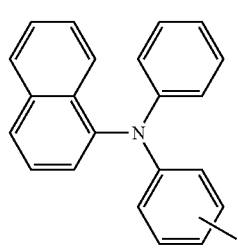 (D4)

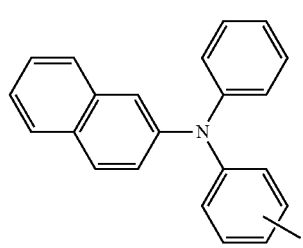 (D5)

-continued (D6) 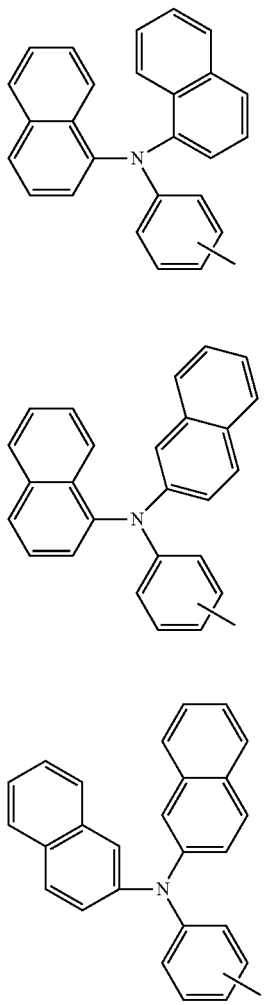

(D7)

(D8)

(D9) 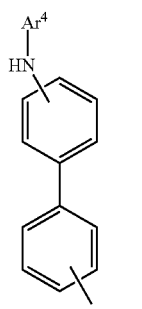

(D10) 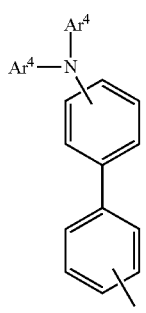

(D11) 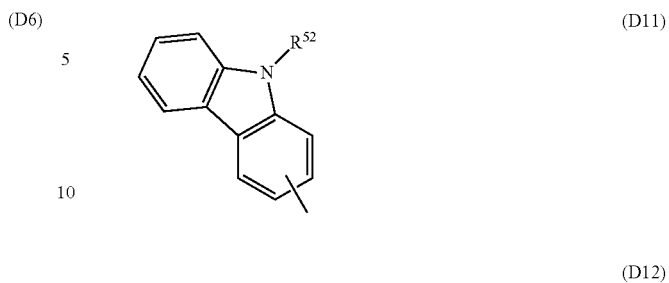

(D12) 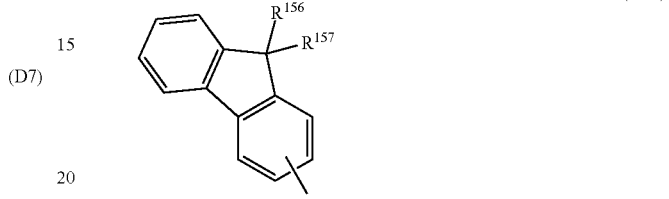

(D13) 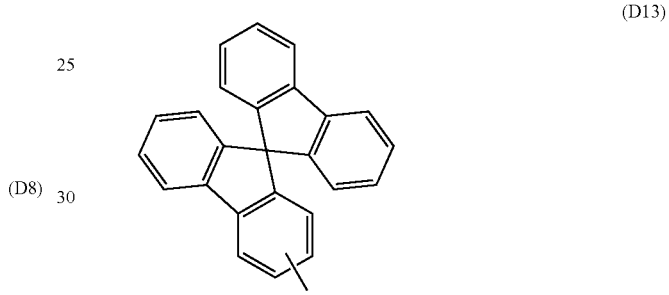

(wherein $R^{52}$, $R^{156}$, $R^{157}$, $A^4$ and DPA have the same meanings as above)].

5. The aniline derivative of 1, represented by the formula (1-3), (1-4), (1-9) or (1-10):

[Chemical Formula 10]

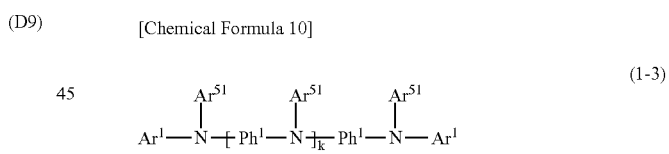 (1-3)

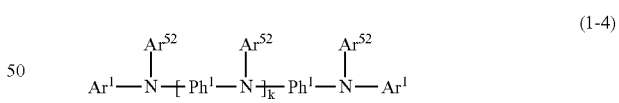 (1-4)

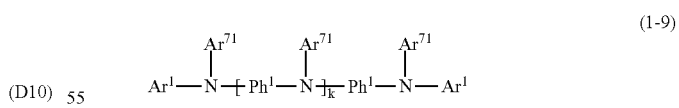 (1-9)

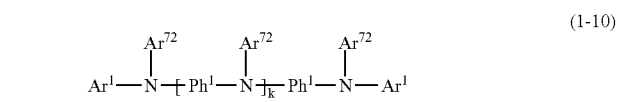 (1-10)

[wherein $Ar^{51}$ represents a group represented by the formula (F1-1), $Ar^{52}$ represents a group represented by the formula (F2-1), $Ar^{71}$ represents a group represented by the formula (F2-2), $Ar^{72}$ represents a group represented by the formula (F1-2), and $Ph^1$, $Ar^1$ and letter k have the same meanings as above:

[Chemical Formula 11]

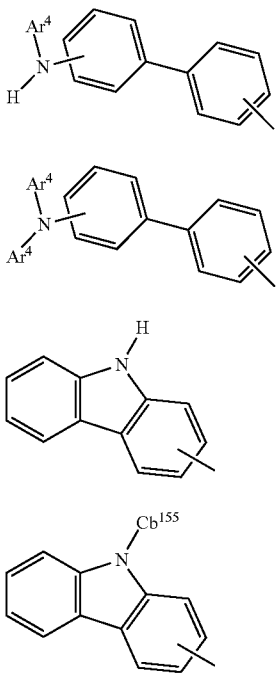

(F1-1)

(F1-2)

(F2-1)

(F2-2)

(wherein $Cb^{155}$ represents an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, and $Z^1$, $Z^4$ and $Ar^4$ have the same meanings as above)].

6. The aniline derivative of 1, represented by the formula (1-5), (1-6), (1-11) or (1-12):

[Chemical Formula 12]

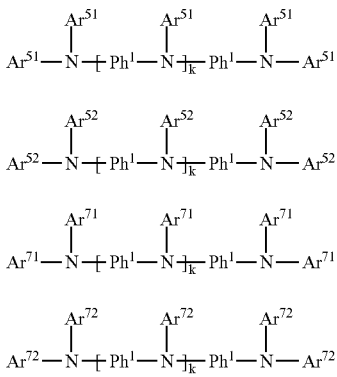

(1-5)

(1-6)

(1-11)

(1-12)

[wherein $Ar^{51}$ represents a group represented by the formula (F1-1), $Ar^{52}$ represents a group represented by the formula (F2-1), $Ar^{71}$ represents a group represented by the formula (F2-2), $Ar^{72}$ represents a group represented by the formula (F1-2), and $Ph^1$ and letter k have the same meanings as above:

[Chemical Formula 13]

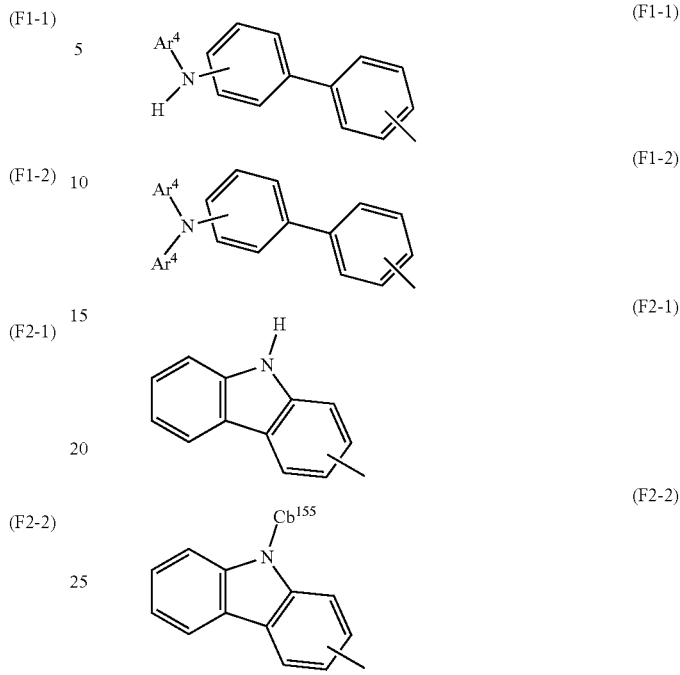

(F1-1)

(F1-2)

(F2-1)

(F2-2)

(wherein $Cb^{155}$ represents an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, and $Z^1$, $Z^4$ and $Ar^4$ have the same meanings as above)].

7. A charge transporting substance including the aniline derivative of any one of 1 to 6.

8. A charge transporting material including the charge transporting substance of 7.

9. A charge transporting varnish including the charge transporting substance of 7 and an organic solvent.

10. The charge transporting varnish of 9, further including a dopant substance.

11. The charge transporting varnish of 10, wherein the dopant substance includes at least one selected from halotetracyanoquinodimethanes and benzoquinone derivatives.

12. The charge transporting varnish of 11, wherein the dopant substance further includes a heteropoly-acid compound.

13. The charge transporting varnish of any one of 9 to 12, further including an organic silane compound.

14. A charge transporting thin film produced by use of the charge transporting varnish of any one of 9 to 13.

15. A charge transporting thin film produced by a vapor deposition method using the aniline derivative of any one of 1 to 6.

16. An organic electroluminescence element including the charge transporting thin film of 14 or 15.

17. An organic electroluminescence element of 16, wherein the charge transporting thin film is a hole injection layer, a hole transport layer or a hole injection transport layer.

18. A method of preparing the aniline derivative of any one of 1 to 3, the method characterized by reacting an amine compound represented by the formula (3):

[Chemical Formula 14]

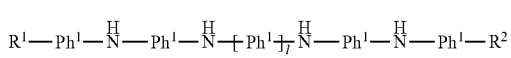
(3)

(wherein $Ar^1$, $Ph^1$ and letter k have the same meanings as above) with an aryl compound represented by the formula (4):

[Chemical Formula 15]

$Ar^2$—X (4)

(wherein X represents a halogen atom or a pseudo-halogen group, and $Ar^2$ has the same meaning as above) in the presence of a catalyst, or
reacting an amine compound represented by the formula (5):

[Chemical Formula 16]

(5)

$R^1$—$Ph^1$—$\overset{H}{N}$—$Ph^1$—$\overset{H}{N}$$\left[\text{Ph}^1\overset{H}{N}\right]_l$$Ph^1$—$\overset{H}{N}$—$Ph^1$—$R^2$ (wherein $R^1$, $R^2$, $Ph^1$ and letter l have the same meanings as above) with an aryl compound represented by the formula (6):

[Chemical Formula 17]

$Ar^3$—X (6)

(wherein X and $Ar^3$ have the same meanings as above) in the presence of a catalyst.
19. The method of preparing the aniline derivative of 4, the method characterized by
reacting an amine compound represented by the formula (7):

[Chemical Formula 18]

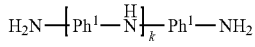
(7)

(wherein $Ph^1$ and letter k have the same meanings as above) with an aryl compound represented by the formula (8):

[Chemical Formula 19]

$Ar^5$—X (8)

(wherein X represents a halogen atom or a pseudo-halogen group, and $Ar^5$ has the same meaning as above) in the presence of a catalyst.
20. A method of preparing the aniline derivative of 5, the method characterized by
(A) deprotecting an aryl compound represented by the formula (1-3P):

[Chemical Formula 20]

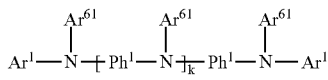
(1-3P)

[wherein $Ar^{61}$ represents a group represented by the formula (P-1), and $Ph^1$, $Ar^1$ and letter k have the same meaning as above:

[Chemical Formula 21]

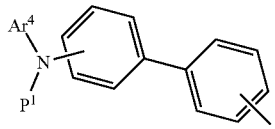
(P-1)

(wherein $P^1$ represents a protective group for an amino group, and $Ar^4$ represents an aryl group having 6 to 20 carbon atoms which may be substituted with a di(aryl groups having 6 to 20 carbon atoms)amino group)] or an aryl compound represented by the formula (1-4P):

[Chemical Formula 22]

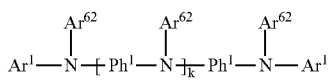
(1-4P)

[wherein $Ar^{62}$ represents a group represented by the formula (P-2), and $Ph^1$, $Ar^1$ and letter k have the same meanings as above:

[Chemical Formula 23]

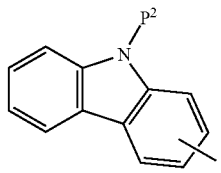
(P-2)

(wherein $P^2$ represents a protective group for an amino group)],
(B) reacting an aniline derivative represented by the formula (1-3):

[Chemical Formula 24]

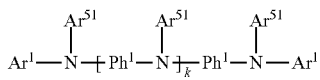
(1-3)

[wherein $Ar^{51}$ represents a group represented by the formula (F1-1), and $Ph^1$, $Ar^1$ and letter k have the same meanings as above:

[Chemical Formula 25]

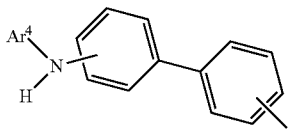
(F1-1)

(wherein $Ar^4$ has the same meaning as above)] with an aryl compound represented by the formula (10):

[Chemical Formula 26]

$Ar^4$—X   (10)

(wherein X represents a halogen atom or a pseudo-halogen group, and $Ar^4$ has the same meaning as above) in the presence of a catalyst, or reacting an aniline derivative represented by the formula (1-4):

[Chemical Formula 27]

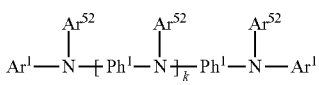
(1-4)

(wherein $Ar^{52}$ represents a group represented by the formula (F2-1), and $Ph^1$, $Ar^1$ and letter k have the same meanings as above):

[Chemical Formula 28]

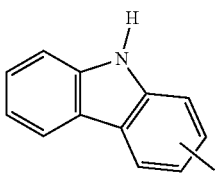
(F2-1)

with a hydrocarbon compound represented by the formula (11):

[Chemical Formula 29]

$Cb^{155}$-X   (11)

(wherein $Cb^{155}$ represents an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, and $Z^1$, $Z^4$ and X have the same meanings as above) in the presence of a catalyst, or (C) reacting an aniline derivative represented by the above formula (1-3) with a base and reacting the resulting reaction product with an aryl compound represented by the above formula (10), or reacting an aniline derivative represented by the above formula (1-4) with a base and reacting the resulting reaction product with a hydrocarbon compound represented by the above formula (11).

21. A method of preparing the aniline derivative of 6, the method characterized by (A) deprotecting an aryl compound represented by the formula (1-5P):

[Chemical Formula 30]

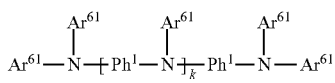
(1-5P)

[wherein $Ar^{61}$ represents a group represented by the formula (P-1), and $Ph^1$ and letter k have the same meanings as above:

[Chemical Formula 31]

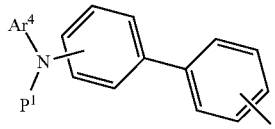
(P-1)

(wherein $P^1$ represents a protective group for an amino group, $Ar^4$ represents an aryl group having 6 to 20 carbon atoms which may be substituted with a di(aryl groups having 6 to 20 carbon atoms)amino group)] or an aryl compound represented by the formula (1-6P):

[Chemical Formula 32]

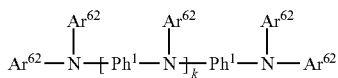
(1-6P)

[wherein $Ar^{62}$ represents a group represented by the formula (P-2), and $Ph^1$ and letter k have the same meanings as above:

[Chemical Formula 33]

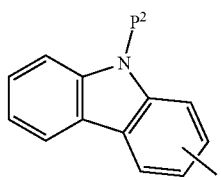
(P-2)

(wherein $P^2$ represents a protective group for an amino group)], (B) reacting an aniline derivative represented by the formula (1-5):

[Chemical Formula 34]

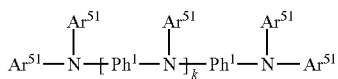
(1-5)

[wherein $Ar^{51}$ represents a group represented by the formula (F1-1), and $Ph^1$ and letter k have the same meanings as above:

[Chemical Formula 35]

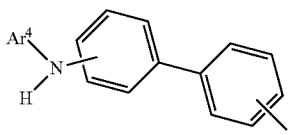

(F1-1)

(wherein Ar⁴ have the same meaning as above)] with an aryl compound represented by the formula (10):

[Chemical Formula 36]

$Ar^4-X$ (10)

(wherein X represents a halogen atom or a pseudo-halogen group, and Ar⁴ has the same meaning as above) in the presence of a catalyst, or reacting an aniline derivative represented by the formula (1-6):

[Chemical Formula 37]

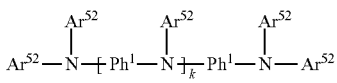

(1-6)

(wherein Ar⁵² represents a group represented by the formula (F2-1), and Ph¹ and letter k have the same meanings as above):

[Chemical Formula 38]

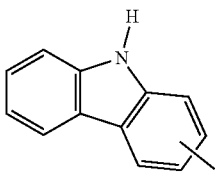

(F2-1)

with a hydrocarbon compound represented by the formula (11):

[Chemical Formula 39]

$Cb^{155}-X$ (11)

(wherein $Cb^{155}$ represents an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, and $Z^1$, $Z^4$ and X have the same meanings as above)] in the presence of a catalyst, or (C) reacting an aniline derivative represented by the above formula (1-5) with a base and reacting the resulting reaction product with an aryl compound represented by the above formula (10), or reacting an aniline derivative represented by the above formula (1-6) with a base and reacting the resulting reaction product with an aryl compound represented by the above formula (11).

22. An amine compound represented by the formula (3'):

[Chemical Formula 40]

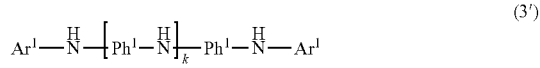

(3')

[wherein Ph¹ represents a group represented by the formula (P1):

[Chemical Formula 41]

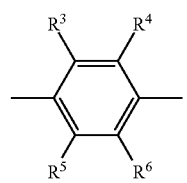

(P1)

(wherein R³ to R⁶ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom), Ar¹ independently represents a group represented by any of the formulas (B1) to (B11) (provided that two Ar¹ do not simultaneously represent a group represented by the formula (B1)):

[Chemical Formula 42]

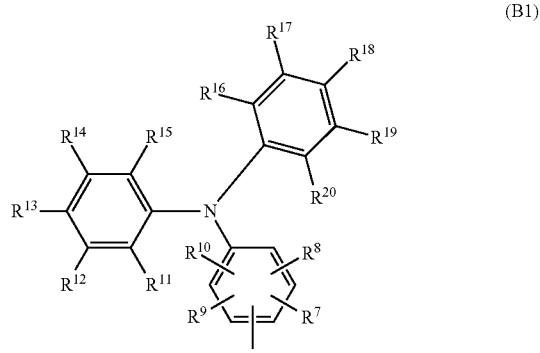

(B1)

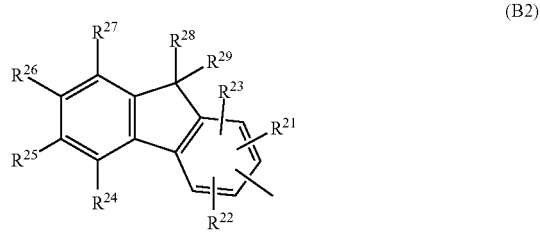

(B2)

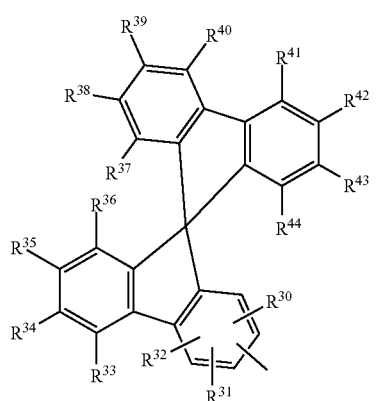 (B3)
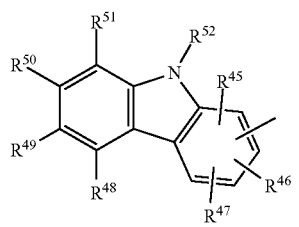 (B4)
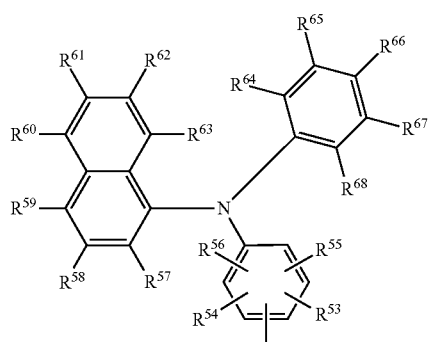 (B5)
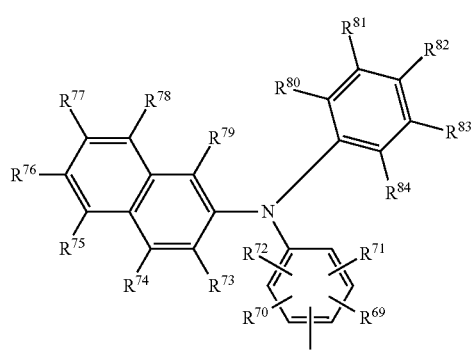 (B6)
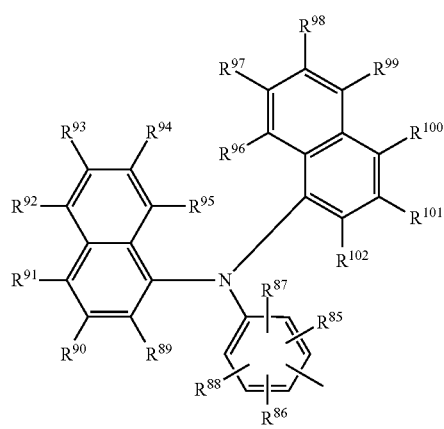 (B7)
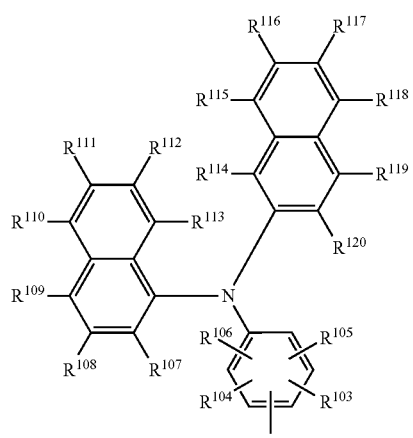 (B8)
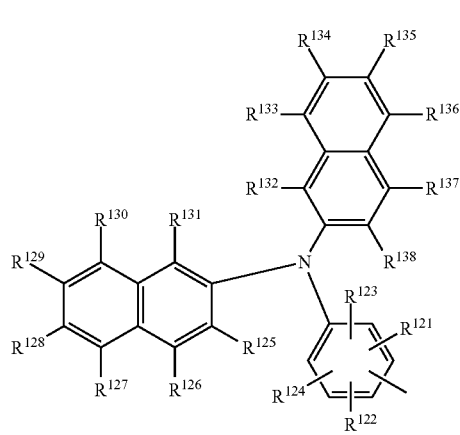 (B9)
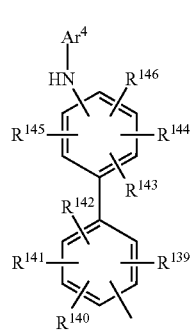 (B10)

-continued (B11)

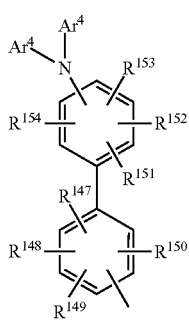

(wherein $R^7$ to $R^{27}$, $R^{30}$ to $R^{51}$ and $R^{53}$ to $R^{154}$ independently represent a hydrogen atom, a halogen atom, a nitro group, a cyano group, or a diphenylamino group, alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $R^{28}$ and $R^{29}$ independently represent an aryl group having 6 to 20 carbon atoms or heteroaryl group having 2 to 20 carbon atoms which may be substituted with $Z^1$, $R^{52}$ represents a hydrogen atom, an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $Ar^4$ independently represents an aryl group having 6 to 20 carbon atoms which may be substituted with a di(aryl groups having 6 to 20 carbon atoms)amino group, $Z^1$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^2$, $Z^2$ represents a halogen atom, a nitro group, a cyano group, or an aryl group having 6 to 20 carbon atoms or heteroaryl group having 2 to 20 carbon atoms which may be substituted with $Z^3$, $Z^3$ represents a halogen atom, a nitro group or a cyano group, $Z^4$ represents a halogen atom, a nitro group, a cyano group, or an aryl group having 6 to 20 carbon atoms or heteroaryl group having 2 to 20 carbon atoms which may be substituted with $Z^5$, and $Z^5$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^3$), and letter k represents an integer of 1 to 10].

23. An aryl compound represented by the formula (1-3P) or (1-4P):

[Chemical Formula 43]

(1-3P)

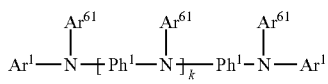

(1-4P)

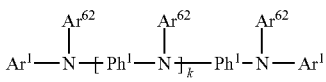

[wherein $Ph^1$ represents a group represented by the formula (P1)

[Chemical Formula 44]

(P1)

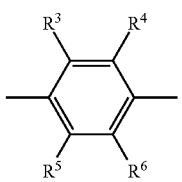

(wherein $R^3$ to $R^6$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom), $Ar^1$ independently represents a group represented by any of the formulas (B1) to (B11) (provided that two $Ar^1$ do not simultaneously represent a group represented by the formula (B1)):

[Chemical Formula 45]

(B1)

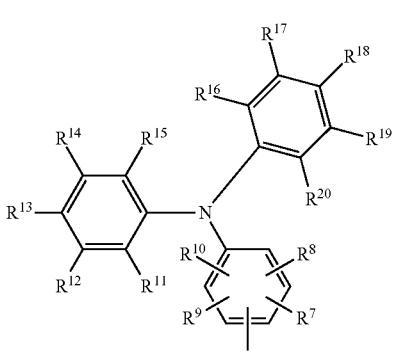

(B2)

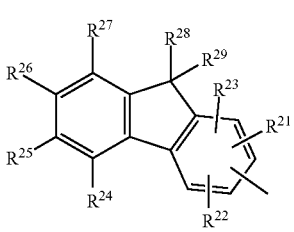

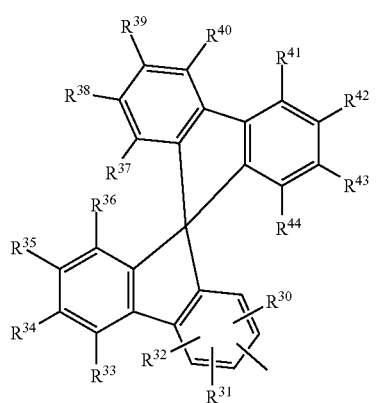 (B3)
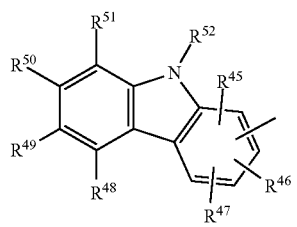 (B4)
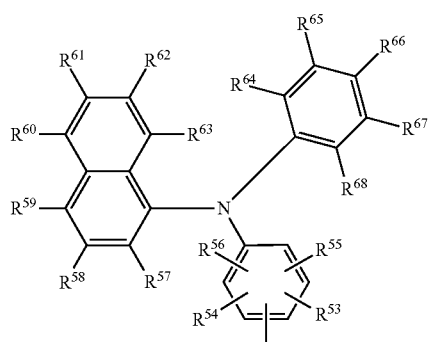 (B5)
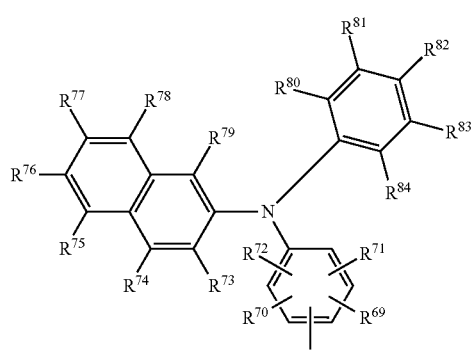 (B6)
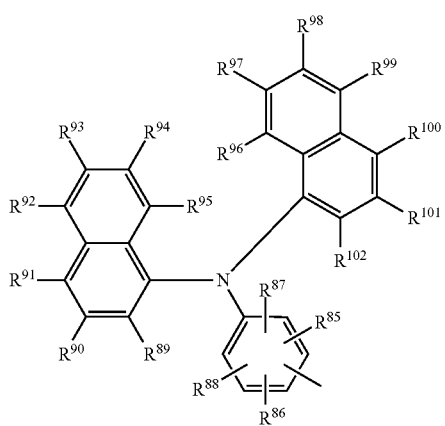 (B7)
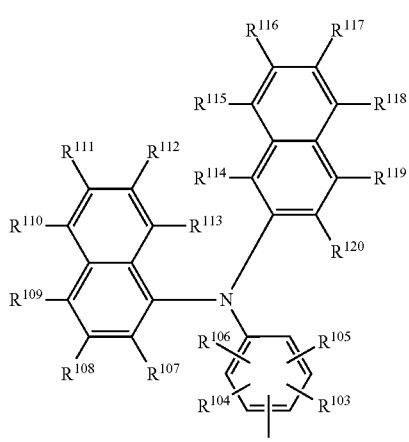 (B8)
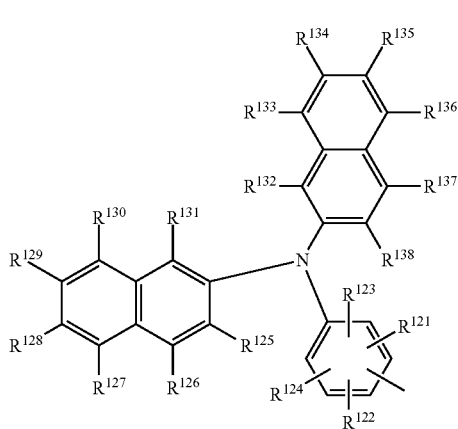 (B9)
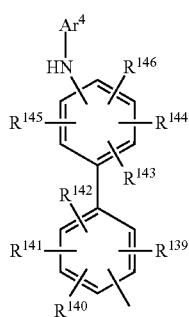 (B10)

-continued (B11)

[structure with Ar⁴, N, R¹⁵³, R¹⁵², R¹⁵¹, R¹⁴⁷, R¹⁵⁰, R¹⁴⁸, R¹⁴⁹, R¹⁵⁴]

(wherein $R^7$ to $R^{27}$, $R^{30}$ to $R^{51}$ and $R^{53}$ to $R^{154}$ independently represent a hydrogen atom, a halogen atom, a nitro group, a cyano group, or a diphenylamino group, alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $R^{28}$ and $R^{29}$ independently represent an aryl group having 6 to 20 carbon atoms or heteroaryl group having 2 to 20 carbon atoms which may be substituted with $Z^1$, $R^{52}$ represents a hydrogen atom, an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $Ar^4$ independently represents an aryl group having 6 to 20 carbon atoms which may be substituted with a di(aryl groups having 6 to 20 carbon atoms)amino group, $Z^1$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^2$, $Z^2$ represents a halogen atom, a nitro group, a cyano group, or aryl group having 6 to 20 carbon atoms or heteroaryl group having 2 to 20 carbon atoms which may be substituted with $Z^3$, $Z^3$ represents a halogen atom, a nitro group or a cyano group, $Z^4$ represents a halogen atom, a nitro group, a cyano group, or an aryl group having 6 to 20 carbon atoms or heteroaryl group having 2 to 20 carbon atoms which may be substituted with $Z^5$, and $Z^5$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^3$), letter k represents an integer of 1 to 10, $Ar^{61}$ represents a group represented by the formula (P-1):

[Chemical Formula 46]

(P-1)

[structure with Ar⁴, N, P¹, biphenyl]

(wherein $P^1$ represents a protective group for an amino group, and $Ar^4$ represents an aryl group having 6 to 20 carbon atoms which may be substituted with a di(aryl groups having 6 to 20 carbon atoms)amino group), and $Ar^{62}$ represents a group represented by the formula (P-2), and $Ph^1$, $Ar^1$ and letter k have the same meanings as above:

[Chemical Formula 47]

(P-2)

[carbazole structure with P²]

(wherein $P^2$ represents a protective group for an amino group)].

24. An aryl compound represented by the formula (1-5P) or (1-6P):

[Chemical Formula 48]

$$Ar^{61}-N(Ar^{61})-[Ph^1-N(Ar^{61})]_k-Ph^1-N(Ar^{61})-Ar^{61}$$ (1-5P)

$$Ar^{62}-N(Ar^{62})-[Ph^1-N(Ar^{62})]_k-Ph^1-N(Ar^{62})-Ar^{62}$$ (1-6P)

[wherein $Ar^{61}$ represents a group represented by the formula (P-1):

[Chemical Formula 49]

(P-1)

[structure with Ar⁴, N, P¹, biphenyl]

(wherein $P^1$ represents a protective group for an amino group, $Ar^4$ represents an aryl group having 6 to 20 carbon atoms which may be substituted with a di(aryl groups having 6 to 20 carbon atoms)amino group], $Ar^{62}$ represents a group represented by the formula (P-2), and $Ph^1$ and letter k have the same meanings as above:

[Chemical Formula 50]

(P-2)

[carbazole structure with P²]

(wherein $P^2$ represents a protective group for an amino group)].

25. A method of preparing the amine compound of 22, the method characterized by reacting an amine compound represented by the formula (10):

[Chemical Formula 51]

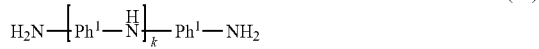
(10)

(wherein Ph$^1$ and letter k have the same meanings as above) with an aryl compound represented by the formula (11):

[Chemical Formula 52]

Ar$^1$—X  (11)

(wherein X represents a halogen atom or a pseudo-halogen group, and Ar$^1$ has the same meaning as above) in the presence of a catalyst.

26. A method of preparing the aryl compound of 23, the method characterized by reacting an amine compound represented by the formula (3):

[Chemical Formula 53]

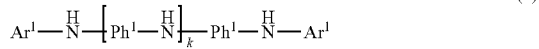
(3)

(wherein Ph$^1$, Ar$^1$ and letter k have the same meanings as above) with an aryl compound represented by the formula (G1P):

[Chemical Formula 54]

Ar$^{61}$—X  (G1P)

(wherein X represents a halogen atom or a pseudo-halogen group, and Ar$^{61}$ has the same meaning as above) or an aryl compound represented by the formula (G2P):

[Chemical Formula 55]

Ar$^{62}$—X  (G2P)

(wherein X and Ar$^{62}$ have the same meanings as above) in the presence of a catalyst.

27. A method of preparing the aryl compound of 24, the method characterized by reacting an amine compound represented by the formula (7):

[Chemical Formula 56]

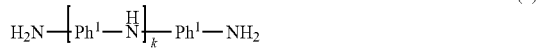
(7)

(wherein Ph$^1$ and letter k have the same meanings as above) with an aryl compound represented by the formula (G1P):

[Chemical Formula 57]

Ar$^{61}$—X  (G1P)

(wherein X represents a halogen atom or a pseudo-halogen group, and Ar$^{61}$ has the same meaning as above) or an aryl compound represented by the formula (G2P):

[Chemical Formula 58]

Ar$^{62}$—X  (G2P)

(wherein X and Ar$^{62}$ have the same meanings as above) in the presence of a catalyst.

Advantageous Effects of the Invention

The aniline derivatives of the present invention are highly soluble in organic solvents, and charge transporting varnishes can be easily prepared by dissolving the aniline derivatives solely or together with a dopant in an organic solvent.

Thin films prepared from the charge transporting varnishes of the present invention show high charge transporting properties and, therefore, can be suitably used as thin films for electronic devices such as organic EL elements. Especially, by application of the thin film to a hole injection layer of an organic EL element, an organic EL element having excellent luminance characteristics can be obtained. In addition, the thin film can be used also as a hole transport layer or a hole injection transport layer of an organic EL element.

Besides, the charge transporting varnishes of the present invention, even when used in various wet processes by which films with large areas can be formed such as a spin coating process or a slit coating process, enable thin films with excellent charge transporting properties to be produced with good reproducibility, and can therefore be sufficiently compatible with the progress in the field of organic EL elements in recent years.

In addition, the aniline derivatives of the present invention are not only excellent in charge transporting properties but capable of sublimation. Therefore, by a vapor deposition method using the aniline derivatives, charge transporting thin films can be easily produced, and by applying the thin films to hole injection layers of organic EL elements, it is possible to obtain organic EL elements having excellent luminescence characteristics.

Furthermore, when the amine compounds and aryl compounds of the present invention are used, the aniline derivatives can be easily prepared.

EMBODIMENT FOR CARRYING OUT THE INVENTION

The present invention will be described more in detail below.

The aniline derivatives according to the present invention are represented by the formula (1) or (2).

[Chemical Formula 59]

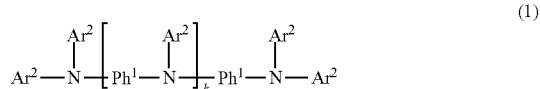
(1)

(2)

In the formula (2), R$^1$ and R$^2$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom.

Examples of the halogen atom include fluorine atom, chlorine atom, bromine atom, and iodine atom, among which preferred is the fluorine atom.

The alkyl group having 1 to 20 carbon atoms may be any of straight chain, branched chain and cyclic ones, and examples thereof include straight chain or branched chain alkyl groups having 1 to 20 carbon atoms such as methyl group, ethyl group, n-propyl group, isopropyl group, n-butyl group, isobutyl group, s-butyl group, t-butyl group, n-pentyl group, n-hexyl group, n-heptyl group, n-octyl group, n-nonyl group, and n-decyl group; and cyclic alkyl groups having 3 to 20 carbon atoms such as cyclopropyl group, cyclobutyl group, cyclopentyl group, cyclohexyl group, cycloheptyl group, cyclooctyl group, cyclononyl group, cyclodecyl group, bicyclobutyl group, bicyclopentyl group, bicyclohexyl group, bicycloheptyl group, bicyclooctyl group, bicyclononyl group, and bicyclodecyl group.

Specific examples of the alkenyl group having 2 to 20 carbon atoms include ethenyl group, n-1-propenyl group, n-2-propenyl group, 1-methylethenyl group, n-1-butenyl group, n-2-butenyl group, n-3-butenyl group, 2-methyl-1-propenyl group, 2-methyl-2-propenyl group, 1-ethylethenyl group, 1-methyl-1-propenyl group, 1-methyl-2-propenyl group, n-1-pentenyl group, n-1-decenyl group, and n-1-eicosenyl group.

Specific examples of the alkynyl group having 2 to 20 carbon atoms include ethynyl group, n-1-propynyl group, n-2-propynyl group, n-1-butynyl group, n-2-butynyl group, n-3-butynyl group, 1-methyl-2-propynyl group, n-1-pentynyl group, n-2-pentynyl group, n-3-pentynyl group, n-4-pentynyl group, 1-methyl-n-butynyl group, 2-methyl-n-butynyl group, 3-methyl-n-butynyl group, 1,1-dimethyl-n-propynyl group, n-1-hexynyl group, n-1-decynyl group, n-1-pentadecynyl group, and n-1-eicosynyl group.

Specific examples of the aryl group having 6 to 20 carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, and 9-phenanthryl group.

Specific examples of the heteroaryl group having 2 to 20 carbon atoms include oxygen-containing heteroaryl groups such as 2-thienyl group, 3-thienyl group, 2-furanyl group, 3-furanyl group, 2-oxazolyl group, 4-oxazolyl group, 5-oxazolyl group, 3-isooxazolyl group, 4-isooxazolyl group, and 5-isooxazolyl group, sulfur-containing heteroaryl groups such as 2-thiazolyl group, 4-thiazolyl group, 5-thiazolyl group, 3-isothiazolyl group, 4-isothiazolyl group, and 5-isothiazolyl group, and nitrogen-containing heteroaryl group such as 2-imidazolyl group, 4-imidazolyl group, 2-pyridyl group, 3-pyridyl group, 4-pyridyl group, 2-pyrazyl group, 3-pyrazyl group, 5-pyrazyl group, 6-pyrazyl group, 2-pyrimidyl group, 4-pyrimidyl group, 5-pyrimidyl group, 6-pyrimidyl group, 3-pyridazyl group, 4-pyridazyl group, 5-pyridazyl group, 6-pyridazyl group, 1,2,3-triazin-4-yl group, 1,2,3-triazin-5-yl group, 1,2,4-triazin-3-yl group, 1,2,4-triazin-5-yl group, 1,2,4-triazin-6-yl group, 1,3,5-triazin-2-yl group, 1,2,4,5-tetrazin-3-yl group, 1,2,3,4-tetrazin-5-yl group, 2-quinolinyl group, 3-quinolinyl group, 4-quinolinyl group, 5-quinolinyl group, 6-quinolinyl group, 7-quinolinyl group, 8-quinolinyl group, 1-isoquinolinyl group, 3-isoquinolinyl group, 4-isoquinolinyl group, 5-isoquinolinyl group, 6-isoquinolinyl group, 7-isoquinolinyl group, 8-isoquinolinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, and 8-cinnolinyl group.

Among these, $R^1$ and $R^2$ preferably represent a hydrogen atom, a fluorine atom, a cyano group, an alkyl group having 1 to 20 carbon atoms which may be substituted with a halogen atom, an aryl group having 6 to 20 carbon atoms which may be substituted with a halogen group, or a heteroaryl group having 2 to 20 carbon atoms which may be substituted with a halogen atom, more preferably a hydrogen atom, a fluorine atom, a cyano group, an alkyl group having 1 to 10 carbon atoms which may be substituted with a halogen atom or a phenyl group which may be substituted with a halogen atom, further preferably a hydrogen atom, a fluorine atom, a methyl group or a trifluoromethyl group, and most preferably a hydrogen atom.

$Ph^1$ in the above formulas (1) and (2) represents a group represented by the formula (P1):

[Chemical Formula 60]

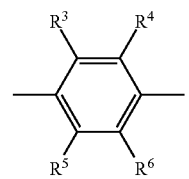

(P1)

Here, $R^3$ to $R^6$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, and specific examples thereof include the same atoms and groups as described in the above $R^1$ and $R^2$.

Particularly, $R^3$ to $R^6$ preferably represent a hydrogen atom, a fluorine atom, a cyano group, an alkyl group having 1 to 20 carbon atoms which may be substituted with a halogen atom, an aryl group having 6 to 20 carbon atoms which may be substituted with a halogen atom or a heteroaryl group having 2 to 20 carbon atoms which may be substituted with a halogen atom, more preferably a hydrogen atom, a fluorine atom, a cyano group, an alkyl group having 1 to 10 carbon atoms which may be substituted with a halogen atom or a phenyl group which may be substituted with a halogen atom, further preferably a hydrogen atom, a fluorine atom, a methyl group or a trifluoromethyl group, and most preferably a hydrogen atom.

A specific example of the group preferable as $Ph^1$ will be given below, but this is not restrictive.

[Chemical Formula 61]

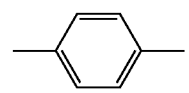

(P1-1)

$Ar^1$ in the above formula (1) independently represents a group represented by any of the formulas (B1) to (B11), particularly preferably a group represented by any of the formulas (B1') to (B11').

[Chemical Formula 62]
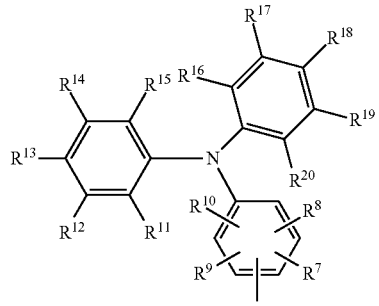 (B1)
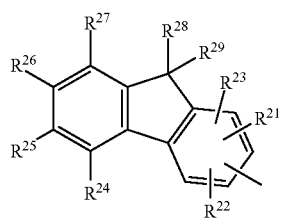 (B2)
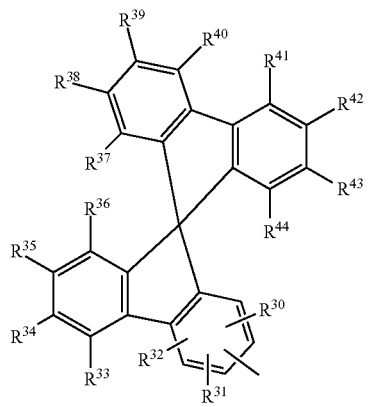 (B3)
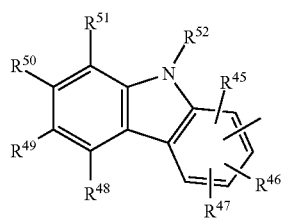 (B4)
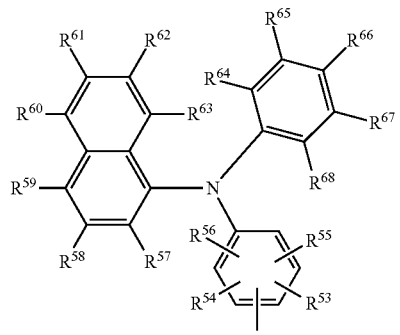 (B5)
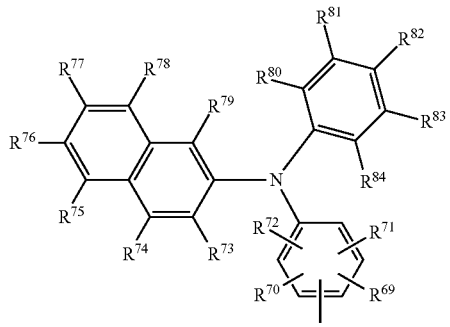 (B6)
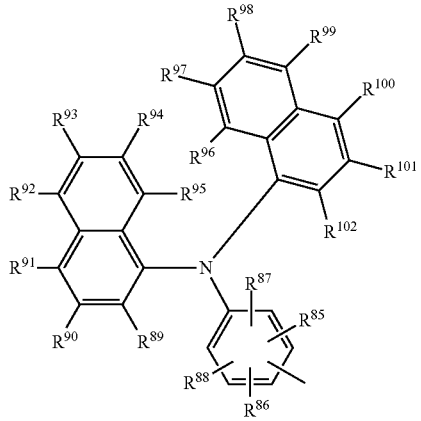 (B7)
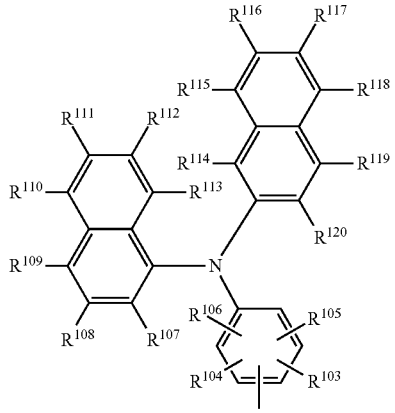 (B8)
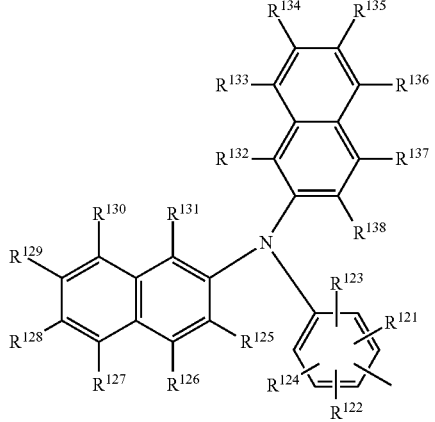 (B9)

-continued
(B10) 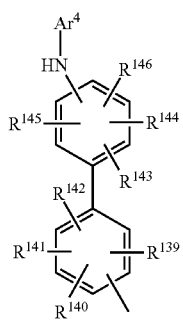
(B11) 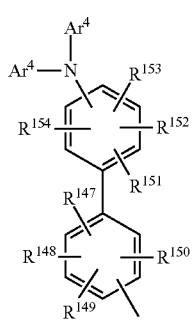
[Chemical Formula 63]
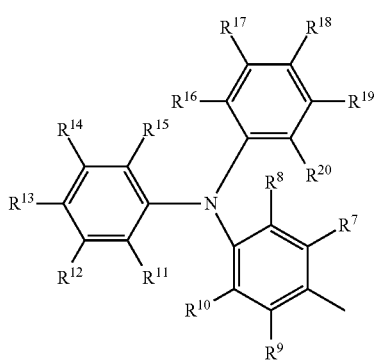
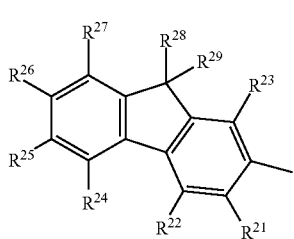
-continued
(B3′) 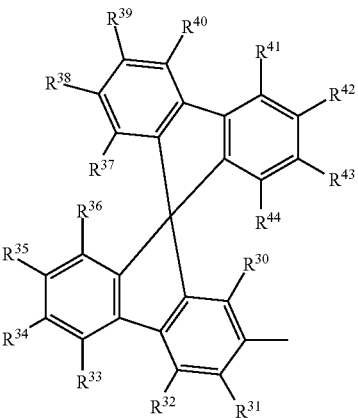
(B4′) 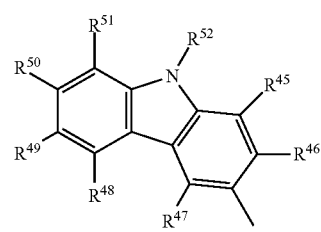
(B5′) 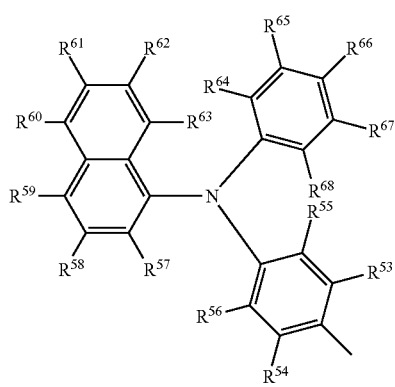
(B6′) 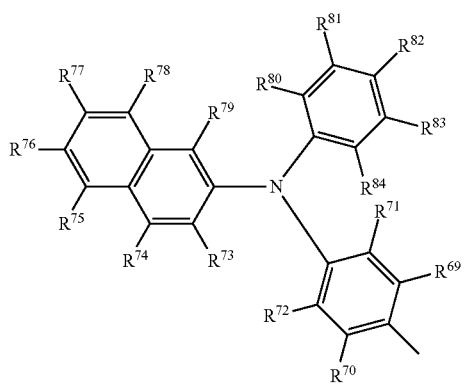

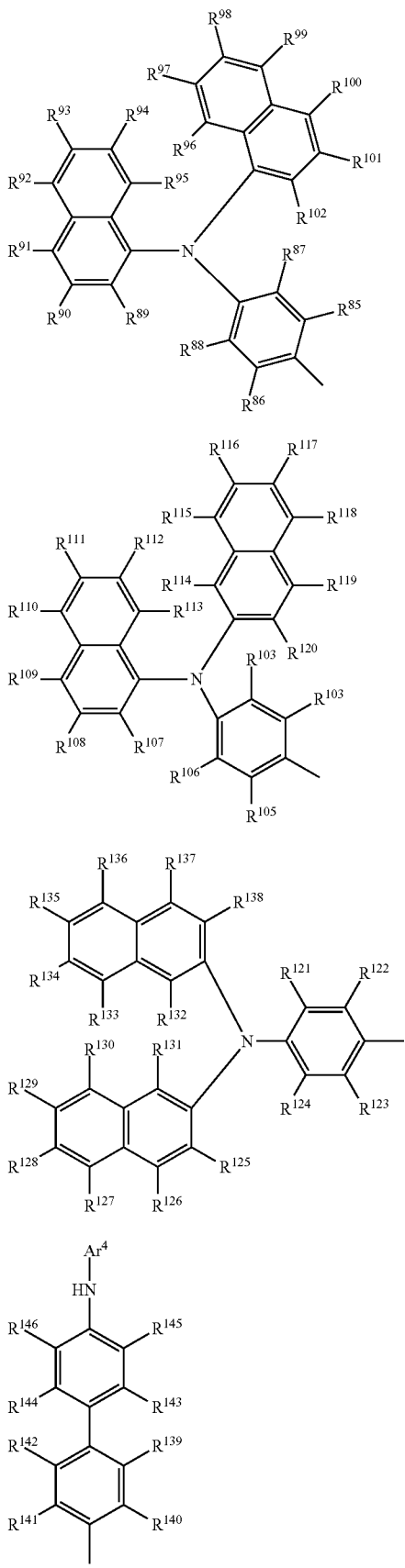

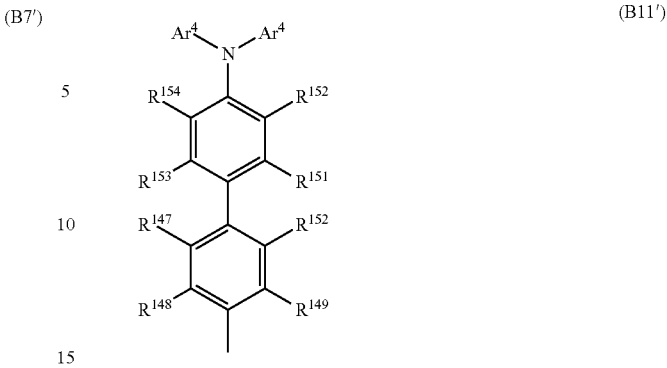

Here, $R^7$ to $R^{27}$, $R^{30}$ to $R^{51}$ and $R^{53}$ to $R^{154}$ independently represent a hydrogen atom, a halogen atom, a nitro group, a cyano group, or a diphenylamino group, alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom; $R^{28}$ and $R^{29}$ independently represent an aryl group having 6 to 20 carbon atoms or heteroaryl group having 2 to 20 carbon atoms which may be substituted with $Z^1$; $R^{52}$ represents a hydrogen atom, an alkyl group having 1 to 20 carbon atoms, alkenyl group having 2 to 20 carbon atoms or alkynyl group having 2 to 20 carbon atoms which may be substituted with $Z^4$ or an aryl group having 6 to 20 carbon atoms or heteroaryl group having 2 to 20 carbon atoms which may be substituted with $Z^1$; $Z^1$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^2$; $Z^2$ represents a halogen atom, a nitro group, a cyano group, or an aryl group having 6 to 20 carbon atoms or heteroaryl group having 2 to 20 carbon atoms which may be substituted with $Z^3$; $Z^3$ represents a halogen atom, a nitro group or a cyano group; $Z^4$ represents a halogen atom, a nitro group, a cyano group, or an aryl group having 6 to 20 carbon atoms or heteroaryl group having 2 to 20 carbon atoms which may be substituted with $Z^5$; $Z^5$ represents a halogen atom, a nitro group, a cyano group or an alkyl group having 1 to 20 carbon atoms, alkenyl group having 2 to 20 carbon atoms or alkynyl group having 2 to 20 carbon atoms which may be substituted with $Z^3$; and specific examples of the halogen atom, alkyl group having 1 to 20 carbon atoms, alkenyl group having 2 to 20 carbon atoms, alkynyl group having 2 to 20 carbon atoms, aryl group having 6 to 20 carbon atoms and heteroaryl group having 2 to 20 carbon atoms include the same atoms and groups as described in the above $R^1$ and $R^2$.

Particularly, $R^7$ to $R^{27}$, $R^{30}$ to $R^{51}$ and $R^{53}$ to $R^{154}$ preferably represent a hydrogen atom, a fluorine atom, a cyano group, a diphenylamino group which may be substituted with a halogen atom, an alkyl group having 1 to 20 carbon atoms which may be substituted with a halogen atom, an aryl group having 6 to 20 carbon atoms which may be substituted with a halogen atom, or a heteroaryl group having 2 to 20 carbon atoms which may be substituted with a halogen atom, more preferably a hydrogen atom, a fluorine atom, a cyano group, an alkyl group having 1 to 10 carbon atoms which may be substituted with a halogen atom, or a phenyl group which may be substituted with a halogen atom, further preferably a hydrogen atom, a fluorine atom, a methyl group or a trifluoromethyl group, and most preferably a hydrogen atom.

In addition, $R^{28}$ and $R^{29}$ preferably represent an aryl group having 6 to 14 carbon atoms which may be substituted with $Z^1$, or a heteroaryl group having 2 to 14 carbon atoms which may be substituted with $Z^1$, more preferably an aryl group having 6 to 14 carbon atoms which may be substituted with $Z^1$, and further preferably a phenyl group which may be substituted with $Z^1$, a 1-naphthyl group which may be substituted with $Z^1$, or a 2-naphthyl group which may be substituted with $Z^1$.

Besides, $R^{52}$ preferably represents a hydrogen atom, an aryl group having 6 to 20 carbon atoms which may be substituted with $Z^1$, a heteroaryl group having 2 to 20 carbon atoms which may be substituted with $Z^1$, or an alkyl group having 1 to 20 carbon atoms which may be substituted with $Z^4$, more preferably a hydrogen atom, an aryl group having 6 to 14 carbon atoms which may be substituted with $Z^1$, a heteroaryl group having 2 to 14 carbon atoms which may be substituted with $Z^1$, or an alkyl group having 1 to 10 carbon atoms which may be substituted with $Z^4$, further preferably a hydrogen atom, an aryl group having 6 to 14 carbon atoms which may be substituted with $Z^1$, a nitrogen-containing heteroaryl group having 2 to 14 carbon atoms which may be substituted with $Z^1$, or an alkyl group having 1 to 10 carbon atoms which may be substituted with $Z^4$, and still further preferably a hydrogen atom, a phenyl group which may be substituted with $Z^1$, a 1-naphthyl group which may be substituted with $Z^1$, a 2-naphthyl group which may be substituted with $Z^1$, a 2-pyridyl group which may be substituted with $Z^1$, a 3-pyridyl group which may be substituted with $Z^1$, a 4-pyridyl group which may be substituted with $Z^1$, or a methyl group which may be substituted with $Z^4$.

In addition, $Ar^4$ independently represents an aryl group having 6 to 20 carbon atoms which may be substituted with a di(aryl groups having 6 to 20 carbon atoms)amino group. Specific examples of the aryl group having 6 to 20 carbon atoms include the same groups as described in $R^1$ and $R^2$, and specific examples of the di(aryl groups having 6 to 20 carbon atoms)amino group include diphenylamino group, 1-naphthylphenylamino group, di(1-naphthyl)amino group, 1-naphthyl-2-naphthylamino group, and di(2-naphthyl)amino group.

$Ar^4$ preferably represents a phenyl group, a 1-naphthyl group, a 2-nephthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a p-(diphenylamino) phenyl group, a p-(1-naphthylphenylamino)phenyl group, a p-(di(1-naphthyl)amino)phenyl group, a p-(1-naphthyl-2-naphthylamino)phenyl group, or a p-(di(2-naphthyl)amino) phenyl group, more preferably a p-(diphenylamino)phenyl group.

Specific examples of the group preferable as $Ar^1$ will be given below, but these are not restrictive.

{Chemical Formula 64]

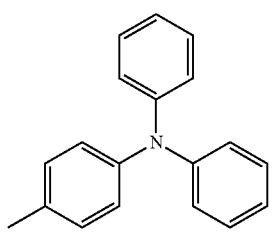
(B1-1)

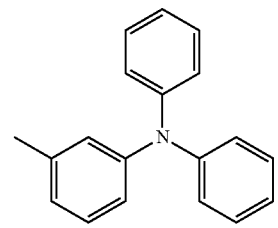
(B1-2)

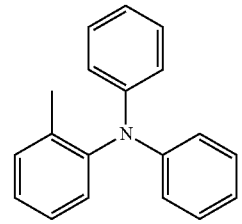
(B1-3)

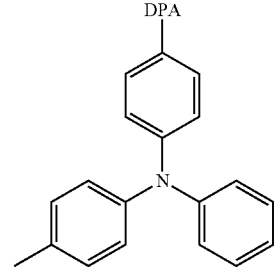
(B1-4)

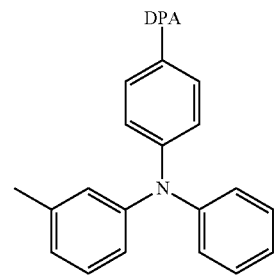
(B1-5)

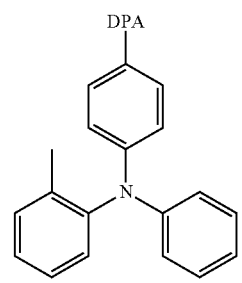
(B1-6)

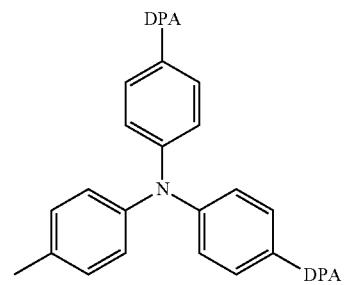
(B1-7)

(B1-8)
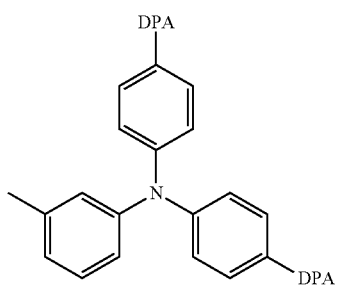
[Chemical Formula 65]
(B1-10)
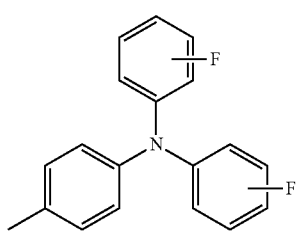
(B1-11)
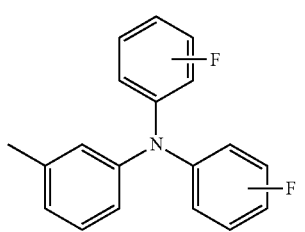
(B1-12)
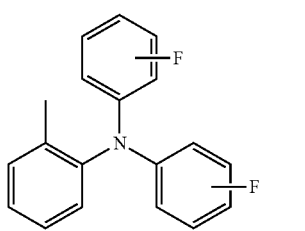
(B1-13)
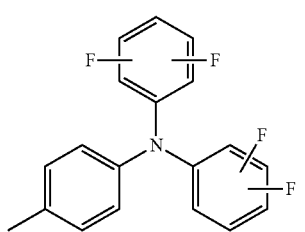
(B1-14)
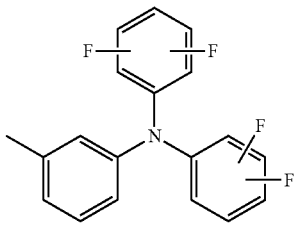
(B1-15)
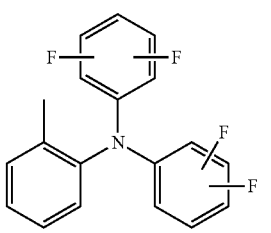
(B1-16)
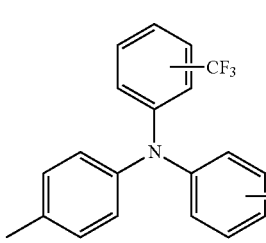
(B1-17)
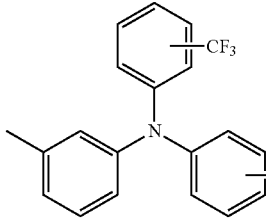
(B1-18)
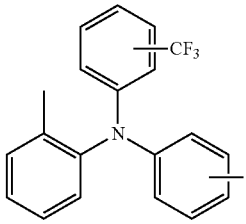
(B1-19)
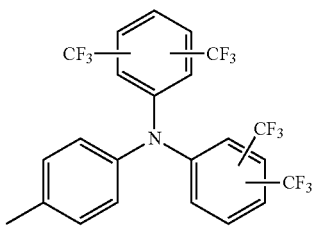
(B1-20)
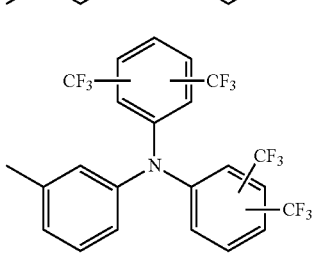

(B1-21)
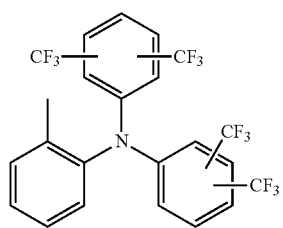
[Chemical Formula 66]
(B2-1)
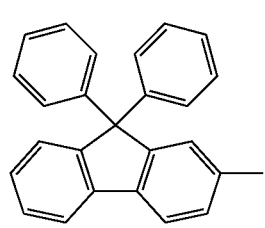
(B2-2)
(B2-3)
(B2-4)
(B2-5)
(B2-6)
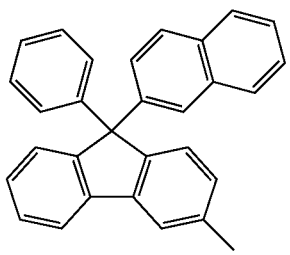
(B2-7)
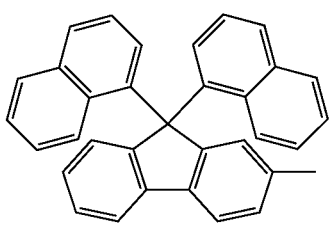
(B2-8)
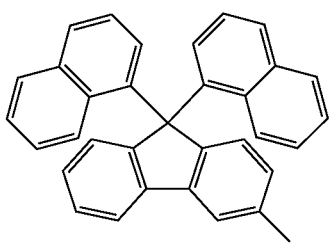
(B2-9)
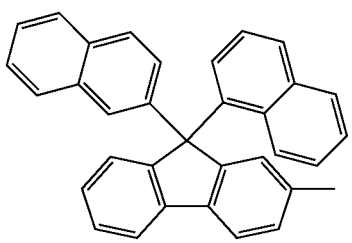
(B2-10)
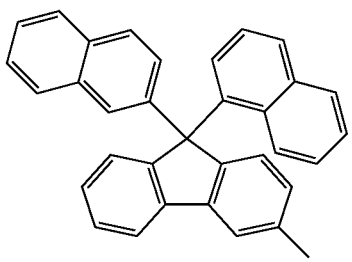
(B2-11)
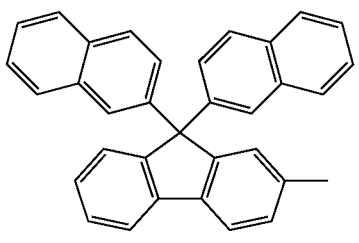

-continued
(B2-12)
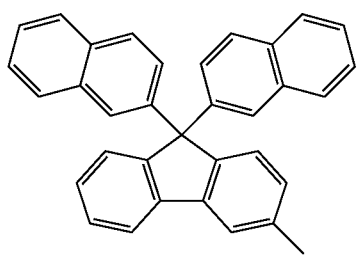
(B3-1)
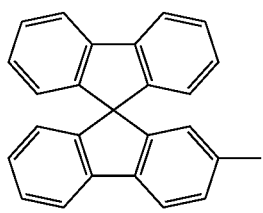
(B3-2)
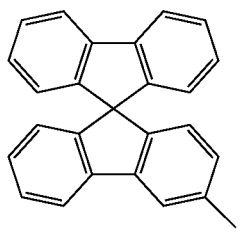
[Chemical Formula 67]
(B4-1)
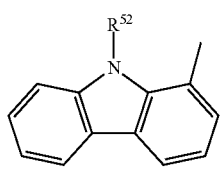
(B4-2)
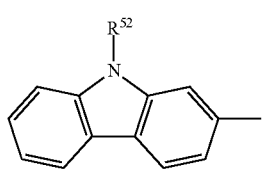
(B4-3)
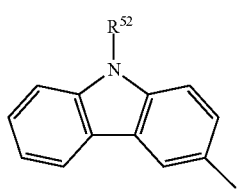
(B4-4)
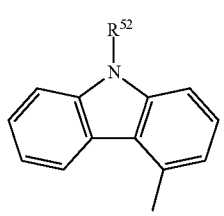
(In the formulas, $R^{52}$ has the same meaning as above.)
[Chemical Formula 68]
(B5-1)
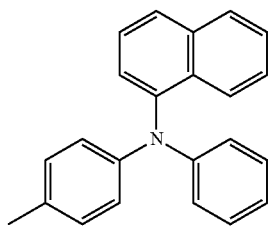
(B5-2)
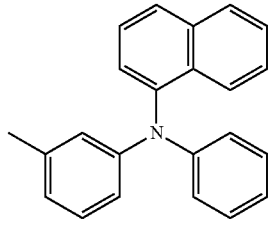
(B5-3)
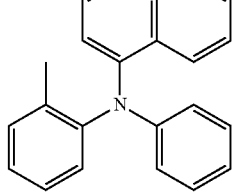
(B6-1)
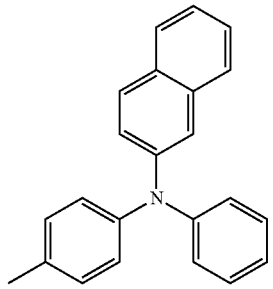
(B6-2)
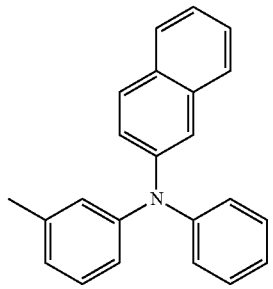
(B6-3)
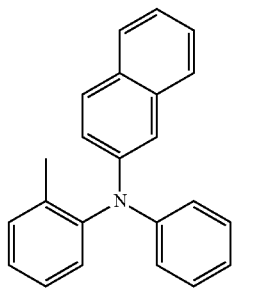

(B7-1)
(B7-2)
(B7-3)
(B8-1)
(B8-2)
(B8-3)
(B9-1)
(B9-2)
(B9-3)

[Chemical Formula 69]

(B10-1)
(B10-2)

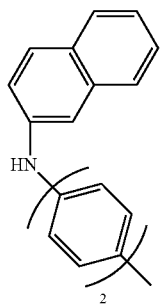
(B10-3)
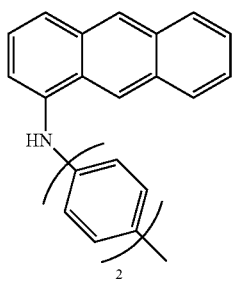
(B10-4)
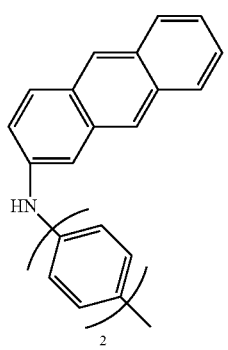
(B10-5)
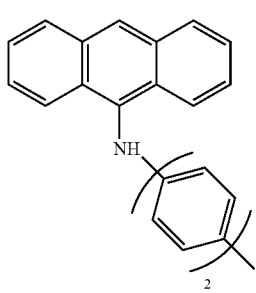
(B10-6)
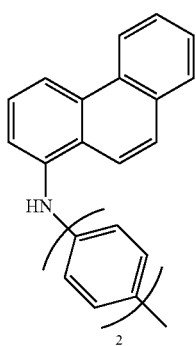
(B10-7)
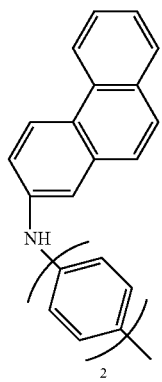
(B10-8)
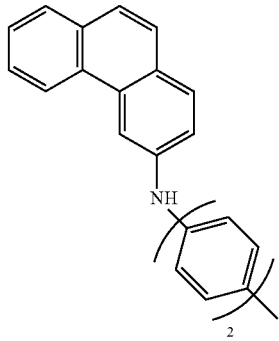
(B10-9)
(B10-10)
(B10-11)

[Chemical Formula 70]
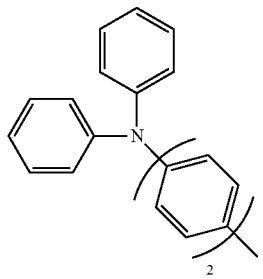 (B11-1)
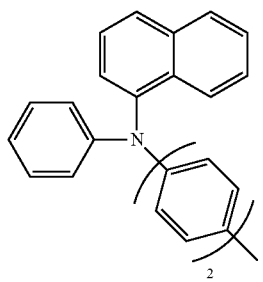 (B11-2)
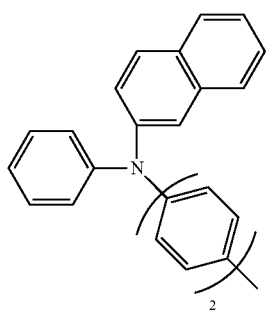 (B11-3)
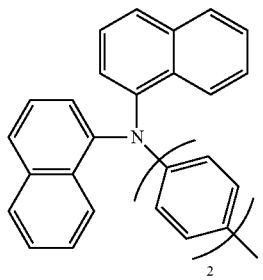 (B11-4)
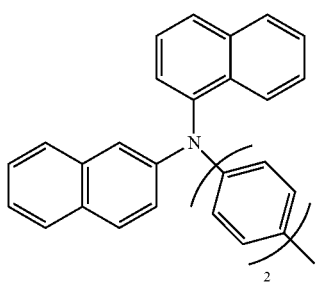 (B11-5)
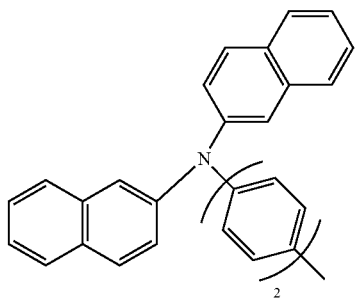 (B11-6)
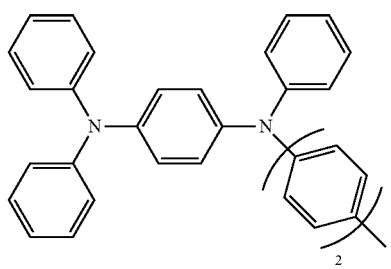 (B11-7)
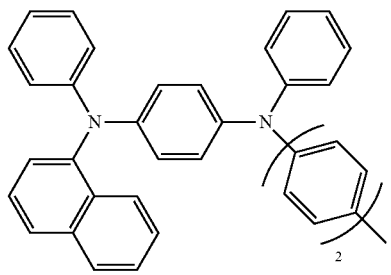 (B11-8)
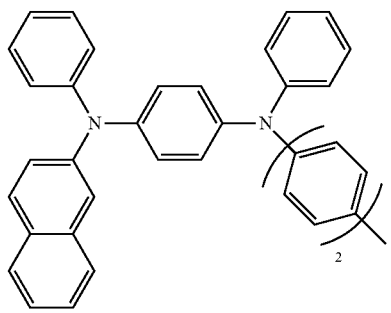 (B11-9)
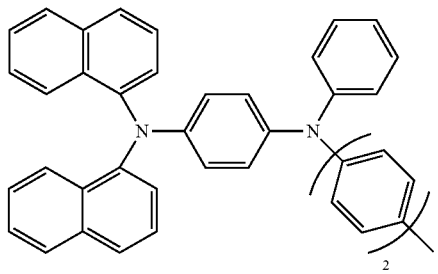 (B11-10)

(B11-11)
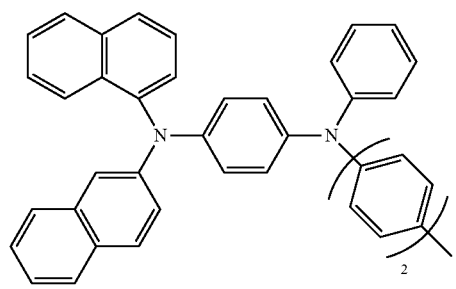
(B11-12)
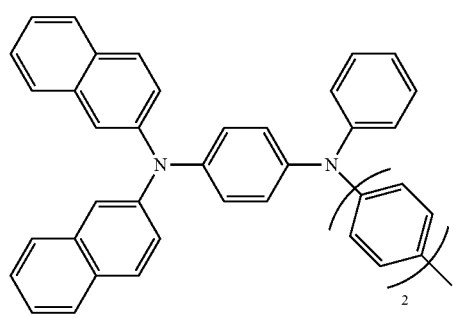
[Chemical Formula 71]
(B11-13)
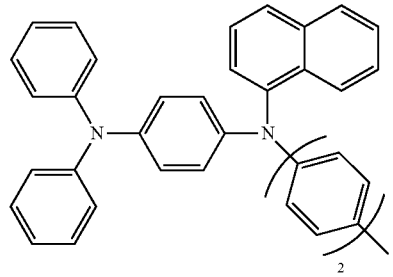
(B11-14)
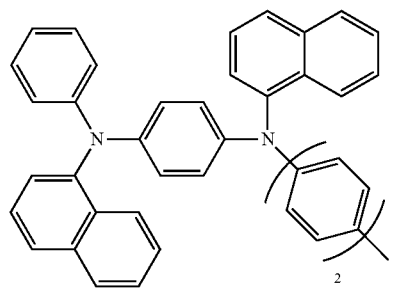
(B11-15)
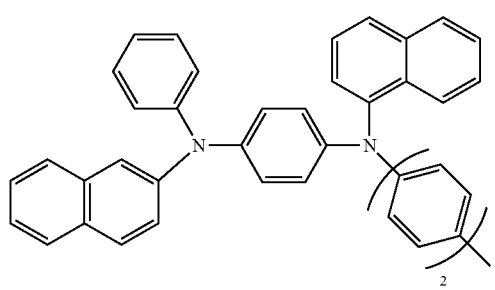
(B11-16)
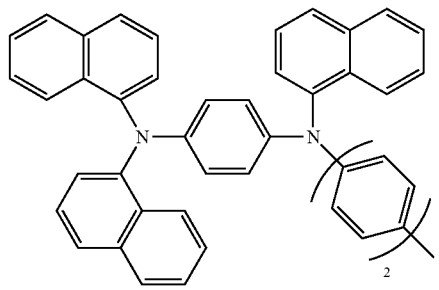
(B11-17)
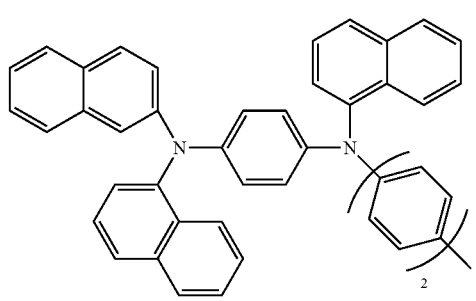
(B11-18)
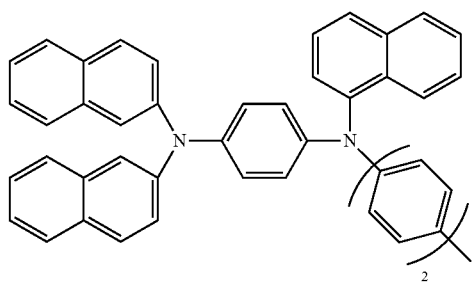
(B11-19)
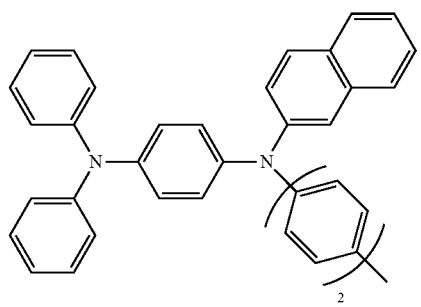
(B11-20)
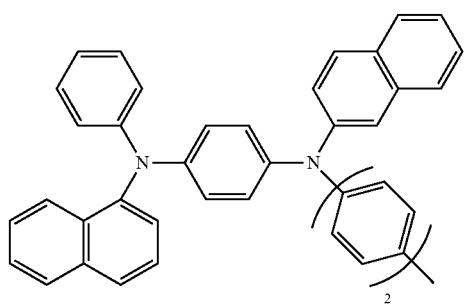

(B11-21) 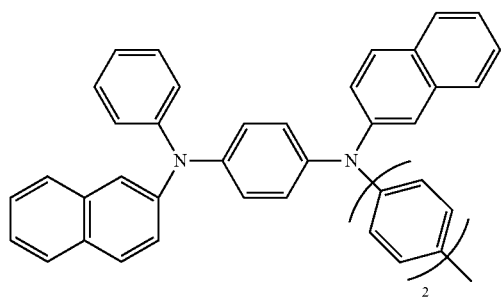
[Chemical Formula 72]
(A1) 
(B11-22) 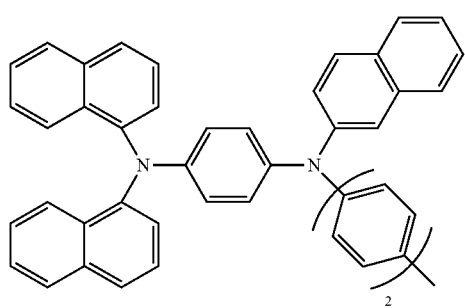
(A2) 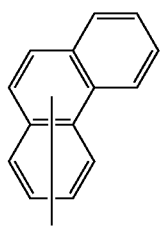
(A3) 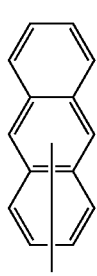
(B11-23) 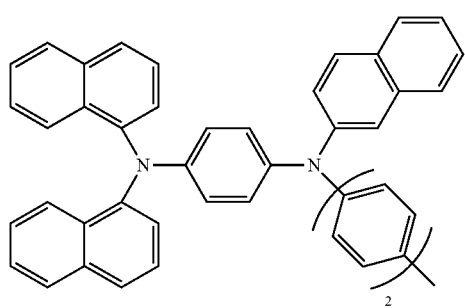
(A4) 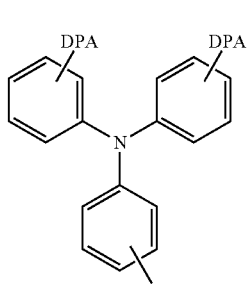
(A5) 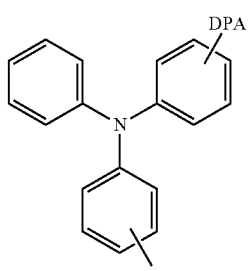
(B11-24) 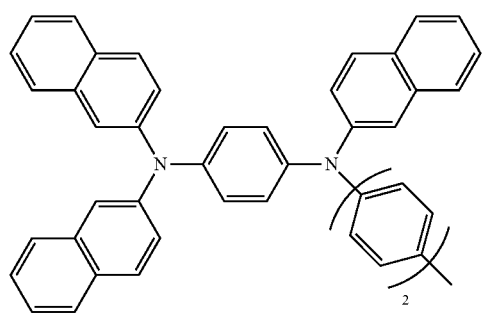
(A6) 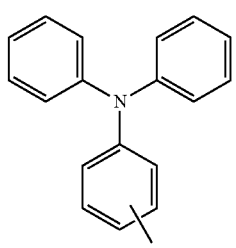
Ar² in the above formula (1) independently represents a group represented by any of the formulas (A1) to (A18).

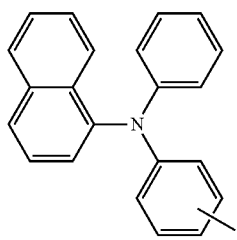 (A7)
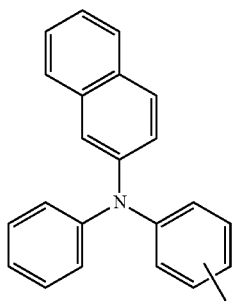 (A8)
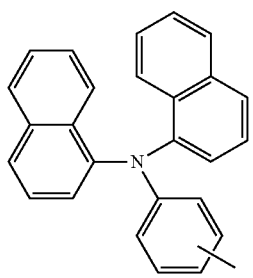 (A9)
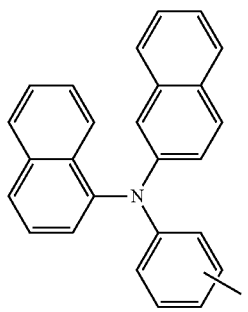 (A10)
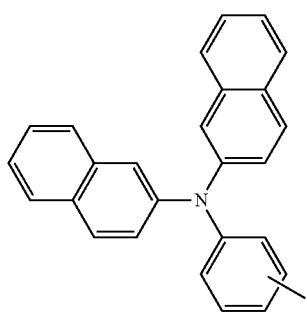 (A11)
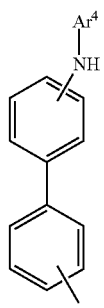 (A12)
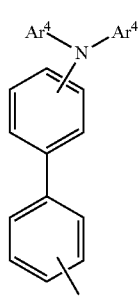 (A13)
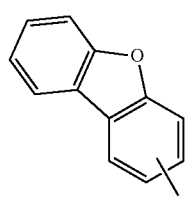 (A14)
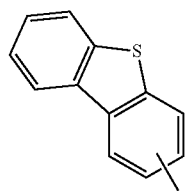 (A15)
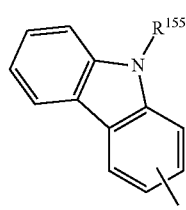 (A16)
(A17)

(A18)

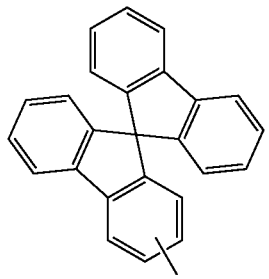

Here, $R^{155}$ in the formula represents a hydrogen atom, an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$; $R^{156}$ and $R^{157}$ independently represent an aryl group having 6 to 20 carbon atoms or heteroaryl group having 2 to 20 carbon atoms which may be substituted with $Z^1$; DPA represents a diphenylamino group; and $Ar^4$, $Z^1$, and $Z^3$ to $Z^5$ have the same meanings as above. Specific examples of the halogen atom, alkyl group having 1 to 20 carbon atoms, alkenyl group having 2 to 20 carbon atoms, alkynyl group having 2 to 20 carbon atoms, aryl group having 6 to 20 carbon atoms and heteroaryl group having 2 to 20 carbon atoms include the same atoms and groups as described in the above $R^1$ and $R^2$.

Particularly, $R^{155}$ preferably represents a hydrogen atom, an aryl group having 6 to 20 carbon atoms which may be substituted with $Z^1$, a heteroaryl group having 2 to 20 carbon atoms which may be substituted with $Z^1$, or an alkyl group having 1 to 20 carbon atoms which may be substituted with $Z^4$, more preferably a hydrogen atom, an aryl group having 6 to 14 carbon atoms which may be substituted with $Z^1$, a heteroaryl group having 2 to 14 carbon atoms which may be substituted with $Z^1$, or an alkyl group having 1 to 10 carbon atoms which may be substituted with $Z^4$, further preferably a hydrogen atom, an aryl group having 6 to 14 carbon atoms which may be substituted with $Z^1$, a nitrogen-containing heteroaryl group having 2 to 14 carbon atoms which may be substituted with $Z^1$, or an alkyl group having 1 to 10 carbon atoms which may be substituted with $Z^4$, and still further preferably a hydrogen atom, a phenyl group which may be substituted with $Z^1$, a 1-naphthyl group which may be substituted with $Z^1$, a 2-naphthyl group which may be substituted with $Z^1$, a 2-pyridyl group which may be substituted with $Z^1$, a 3-pyridyl group which may be substituted with $Z^1$, a 4-pyridyl group which may be substituted with $Z^1$, or a methyl group which may be substituted with $Z^4$.

Besides, $R^{156}$ and $R^{157}$ preferably represent an aryl group having 6 to 14 carbon atoms which may be substituted with $Z^1$ or a heteroaryl group having 2 to 14 carbon atoms which may be substituted with $Z^1$, more preferably an aryl group having 6 to 14 carbon atoms which may be substituted with $Z^1$, and further preferably a phenyl group which may be substituted with $Z^1$, a 1-naphthyl group which may be substituted with $Z^1$, or a 2-naphthyl group which may be substituted with $Z^1$.

Specific examples of the group preferable as $Ar^2$ will be given below, but these are not restrictive.

[Chemical Formula 73]

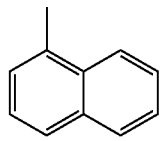

(A1-1)

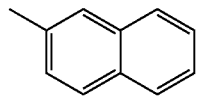

(A1-2)

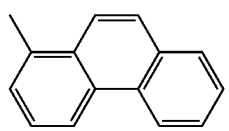

(A2-1)

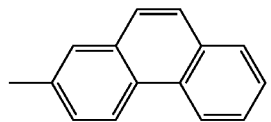

(A2-2)

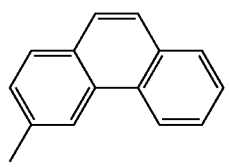

(A2-3)

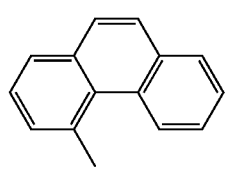

(A2-4)

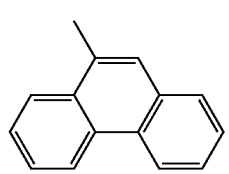

(A2-5)

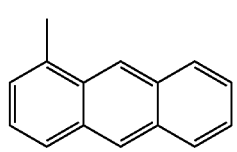

(A3-1)

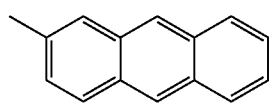

(A3-2)

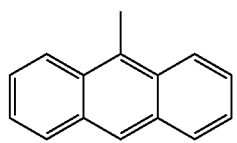

(A3-3)

-continued
(A4-1)
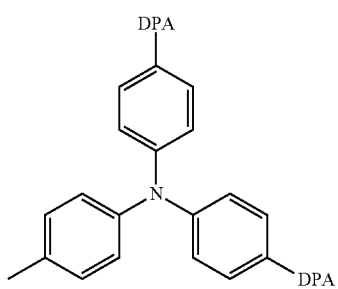
(A4-2)
(A4-3)
(A5-1)
(A5-2)
-continued
(A5-3)
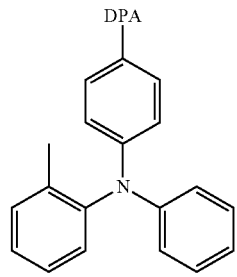
[Chemical Formula 74]
(A6-1)
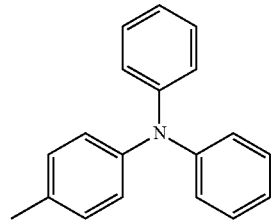
(A6-2)
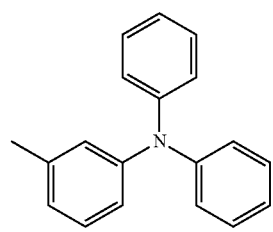
(A6-3)
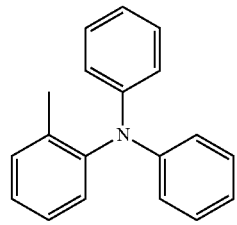
(A6-4)
(A6-5)
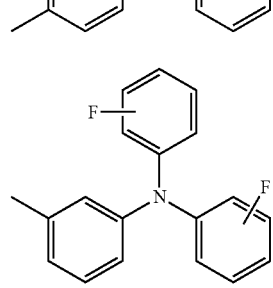

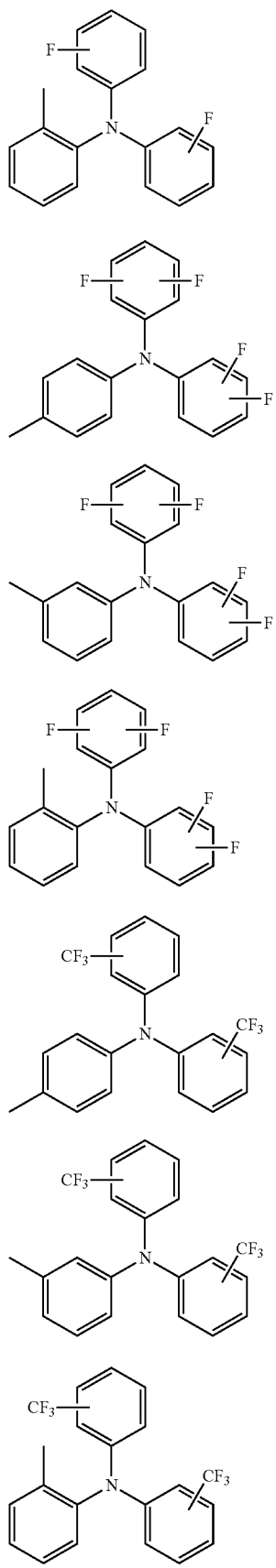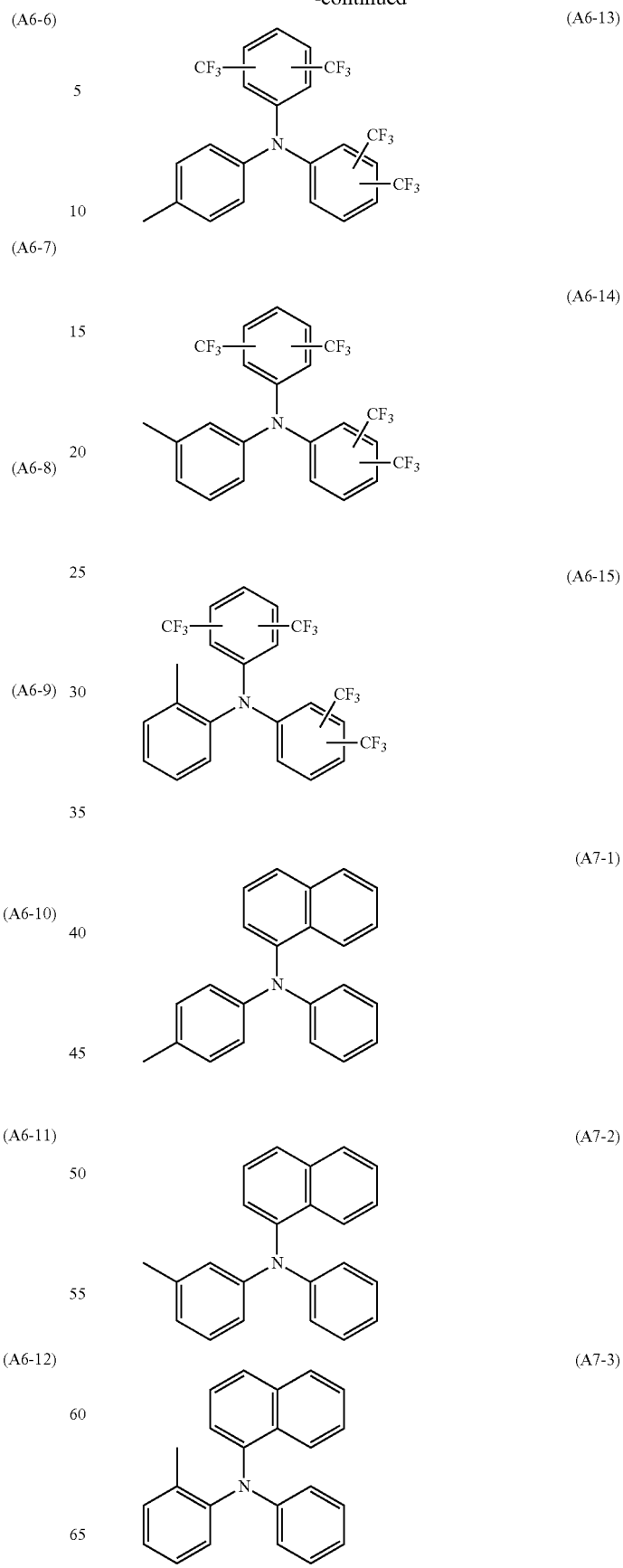

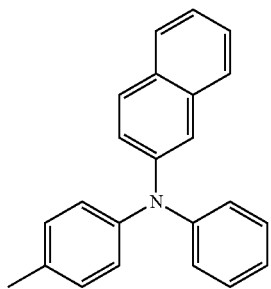 (A8-1)
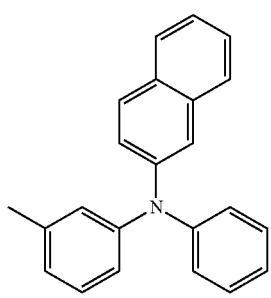 (A8-2)
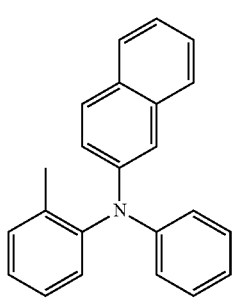 (A8-3)
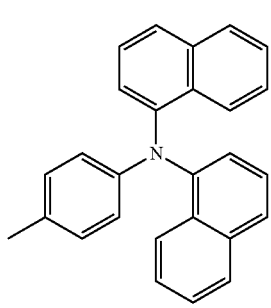 (A9-1)
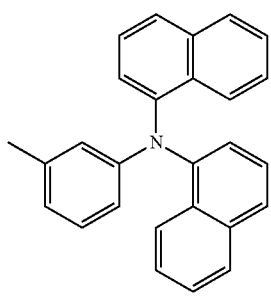 (A9-2)
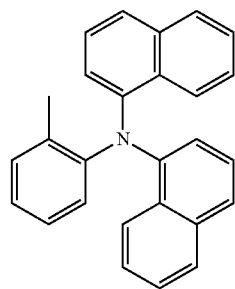 (A9-3)
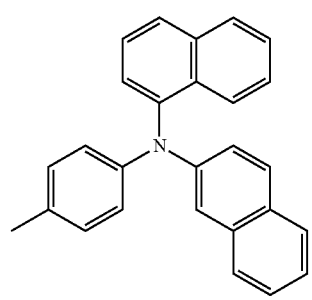 (A10-1)
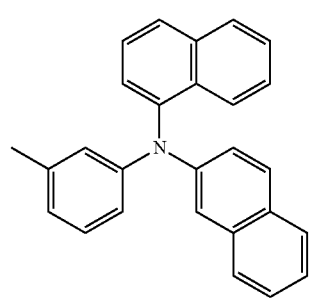 (A10-2)
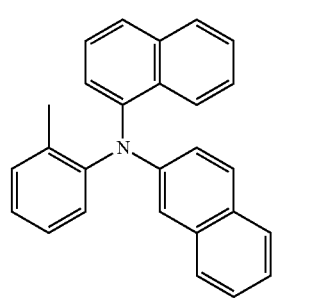 (A10-3)
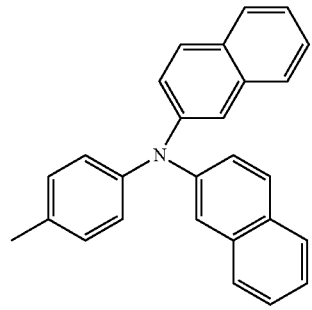 (A11-1)

(A11-2)
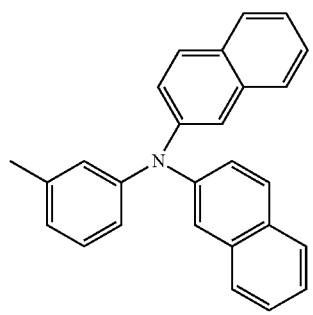
(A11-3)
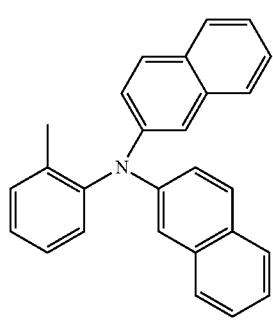
[Chemical Formula 75]
(A12-1)
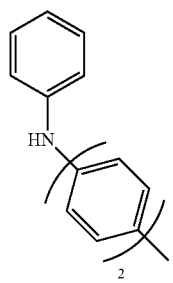
(A12-2)
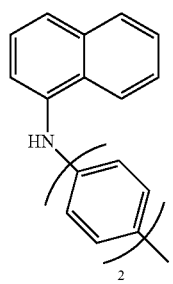
(A12-3)
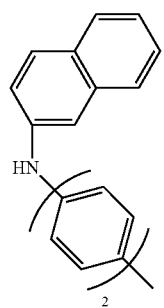
(A12-4)
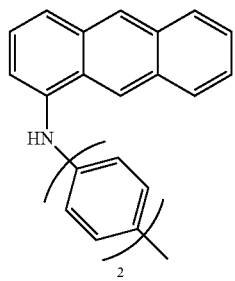
(A12-5)
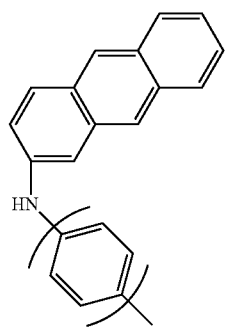
(A12-6)
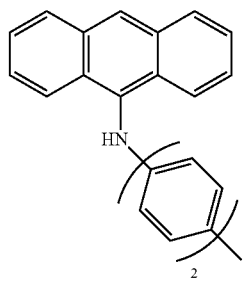
(A12-7)
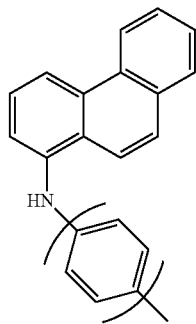

-continued
(A12-8)
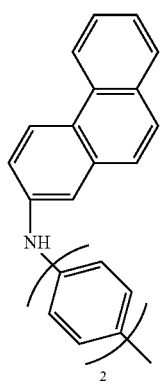
(A12-9)
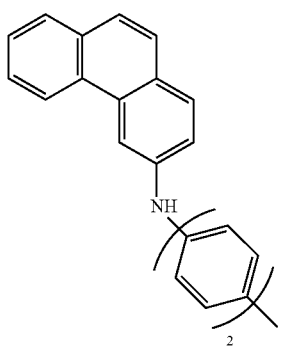
(A12-10)
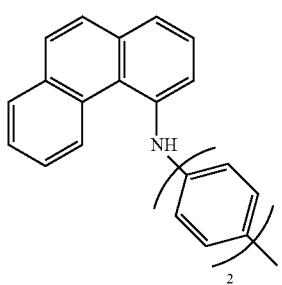
(A12-11)
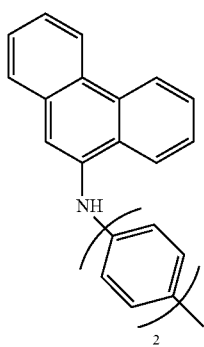
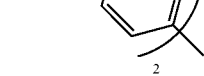
[Chemical Formula 76]
(A13-1)
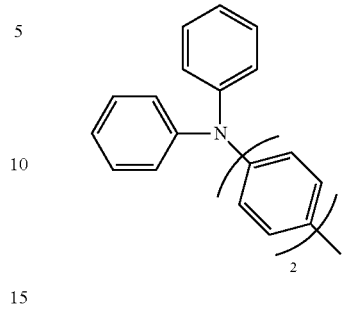
(A13-2)
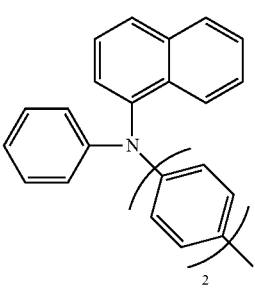
(A13-3)
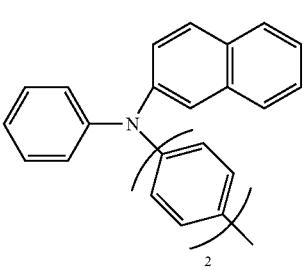
(A13-4)
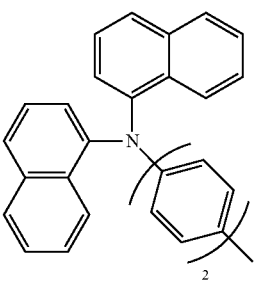
(A13-5)
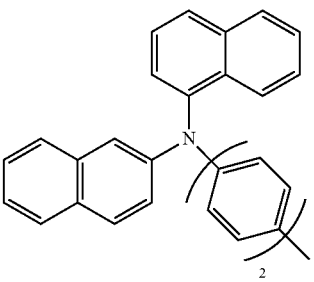

(A13-6)
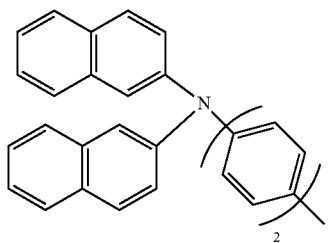
(A13-7)
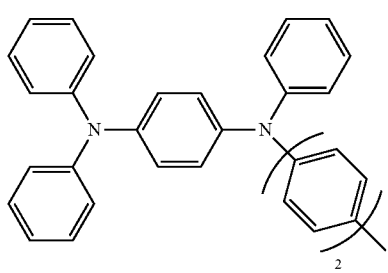
(A13-8)
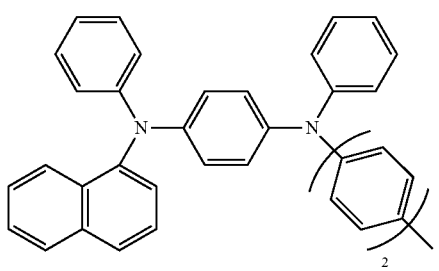
(A13-9)
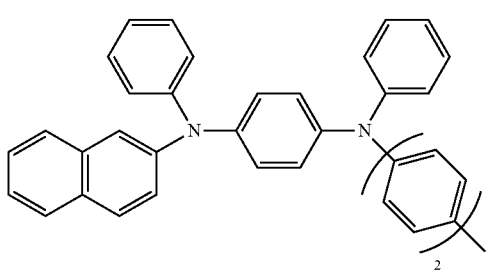
(A13-10)
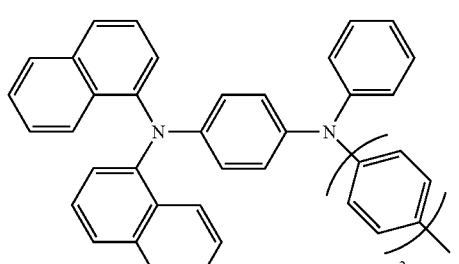
(A13-11)
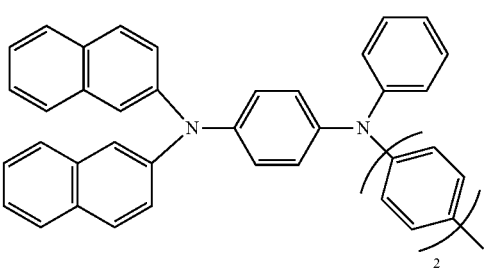
(A13-12)
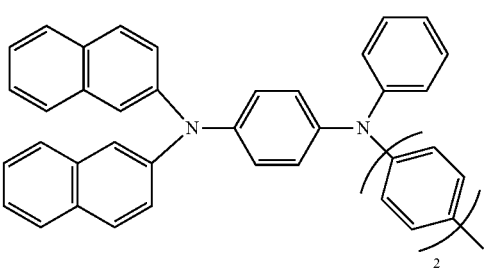
[Chemical Formula 77]
(A13-13)
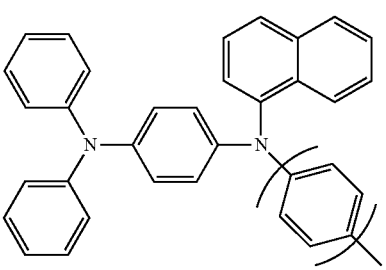
(A13-14)
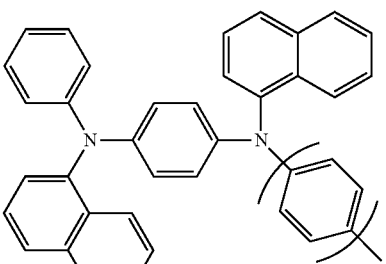
(A13-15)
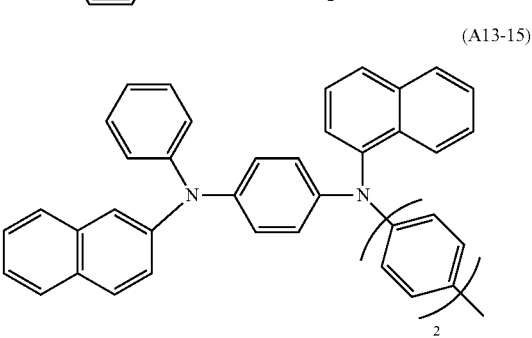

-continued
(A13-16)
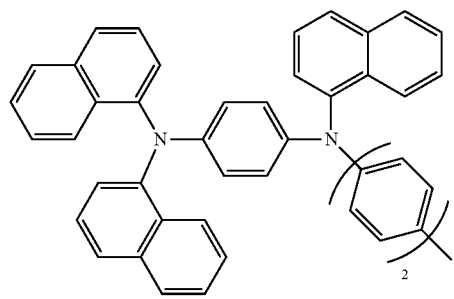
(A13-17)
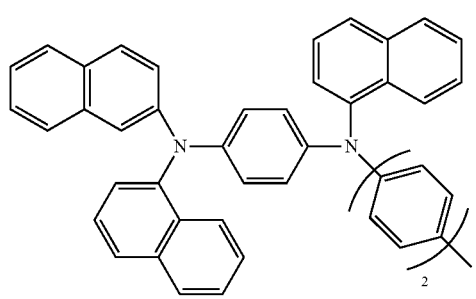
(A13-18)
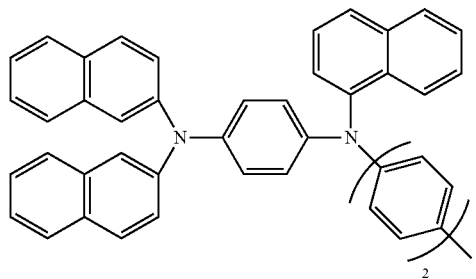
(A13-19)
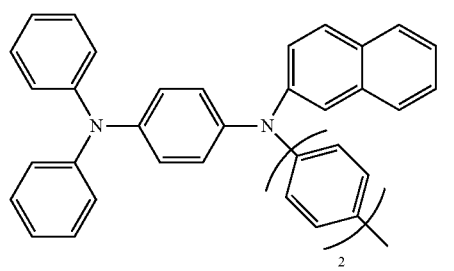
(A13-20)
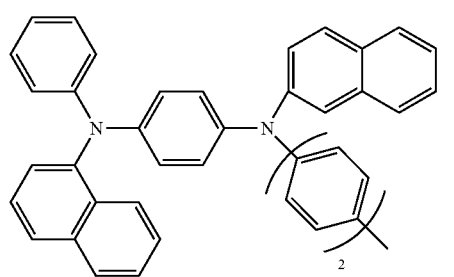
-continued
(A13-21)
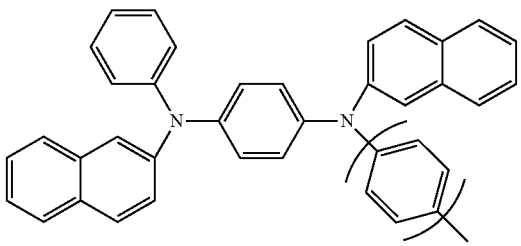
(A13-22)
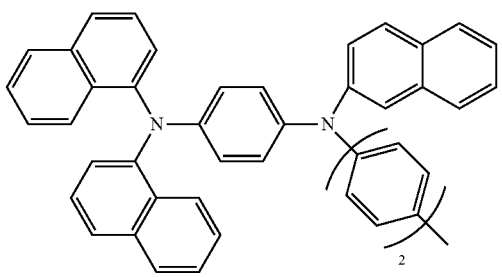
(A13-23)
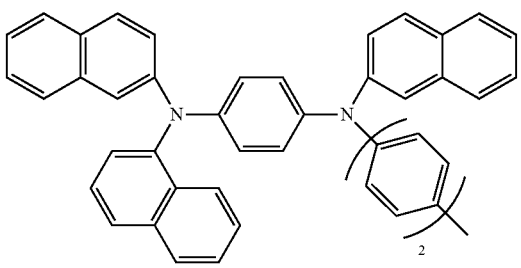
(A13-24)
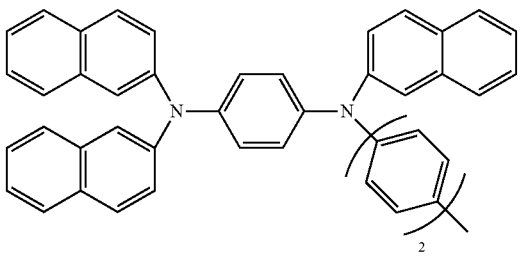
[Chemical Formula 78]
(A14-1)
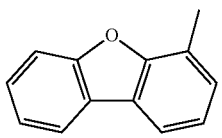
(A14-2)
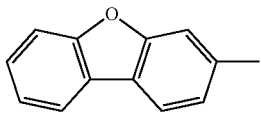
(A14-3)
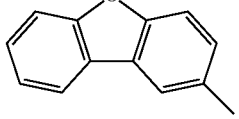

-continued
(A14-4)
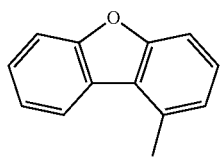
(A15-1)
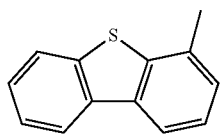
(A15-2)
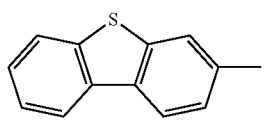
(A15-3)
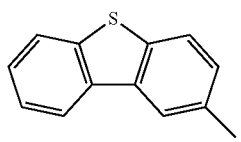
(A15-4)
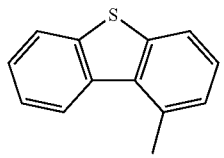
(A16-1)
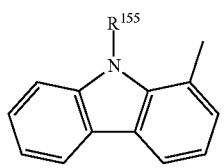
(A16-2)
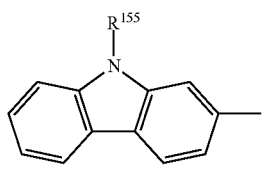
(A16-3)
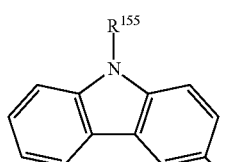
(A16-4)
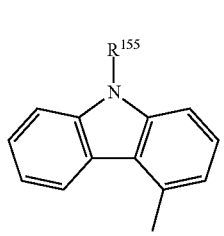
(In the formulas, $R^{155}$ has the same meaning as above.)
[Chemical Formula 79]
(A17-1)
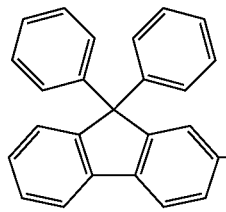
(A17-2)
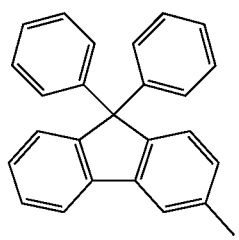
(A17-3)
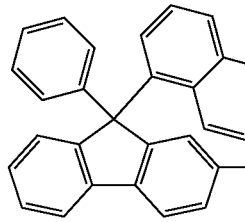
(A17-4)
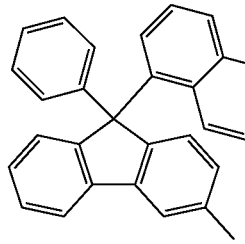
(A17-5)
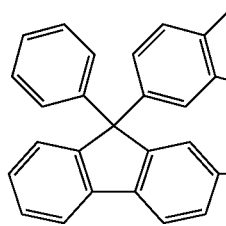
(A17-6)
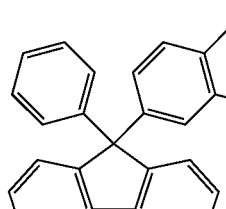

(A17-7)
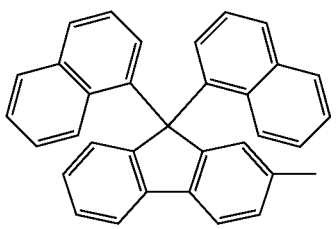

(A17-8)
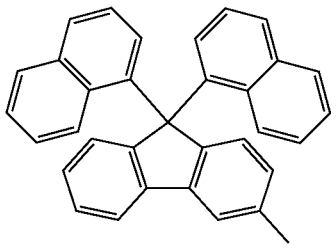

(A17-9)
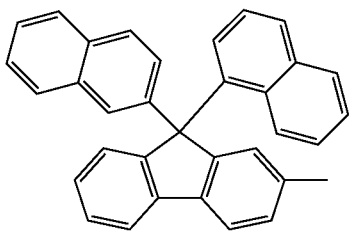

(A17-10)
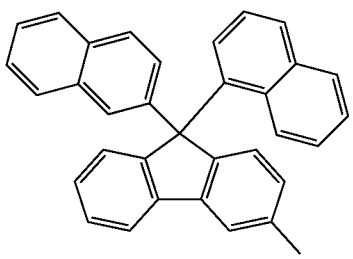

(A17-11)
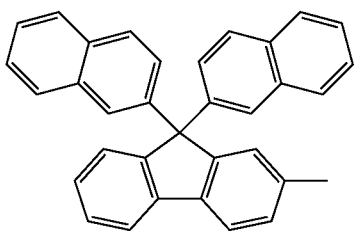

(A17-12)
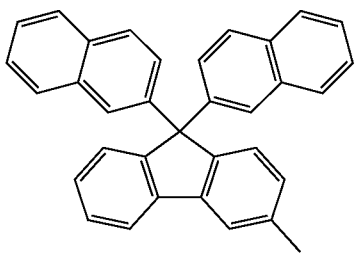

(A18-1)
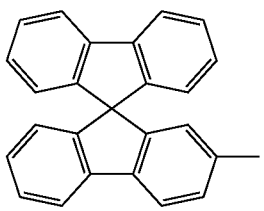

(A18-2)
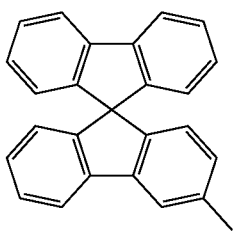

Note that in the formula (1), it is preferable that $Ar^1$ are all the same group and $Ar^2$ are all the same group, and it is more preferable that $Ar^1$ and $Ar^2$ are all the same group, taking into account the easiness of synthesis of the aniline derivative to be obtained. In other words, the aniline derivative represented by the formula (1) is more preferably an aniline derivative represented by the formula (1-1).

In addition, the aniline derivative represented by the formula (1) is preferably an aniline derivative represented by the formula (1-1), since the aniline derivative of the formula (1-1) can be synthesized comparatively easily using a comparatively inexpensive bis(4-aminophenyl)amine as a raw material compound as will be described later and has excellent solubility in organic solvents.

[Chemical Formula 80]

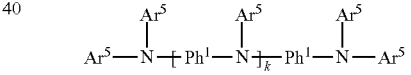

(1-1)

In the formula (1-1), $Ph^1$ and letter k have the same meanings as above, and $Ar^5$ simultaneously represents a group represented by any of the formulas (D1) to (D13), particularly with a group represented by any of the formulas (D1') to (D13') being preferable.

Note that specific examples of $Ar^5$ include the same groups as those described above as specific examples of the group preferable as $Ar^1$.

[Chemical Formula 81]

(D1)
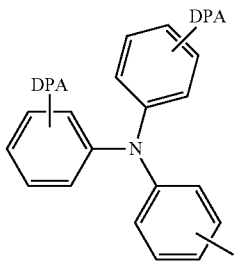

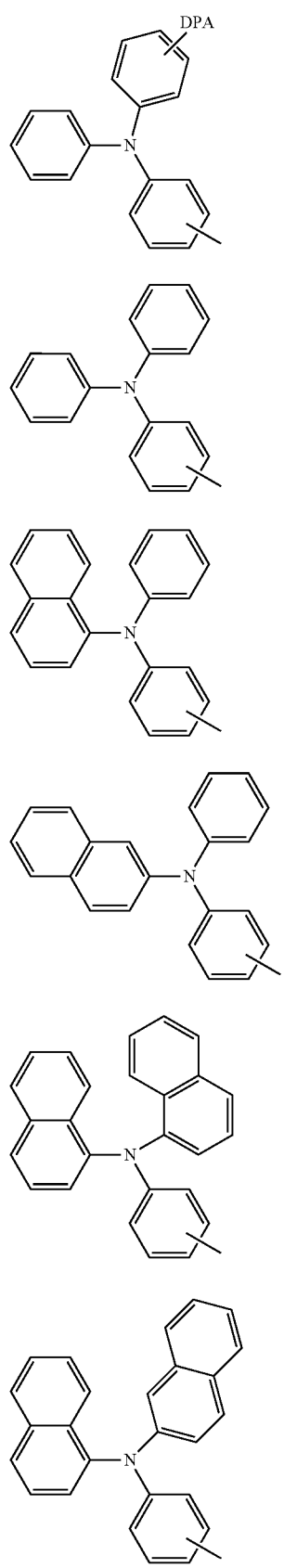
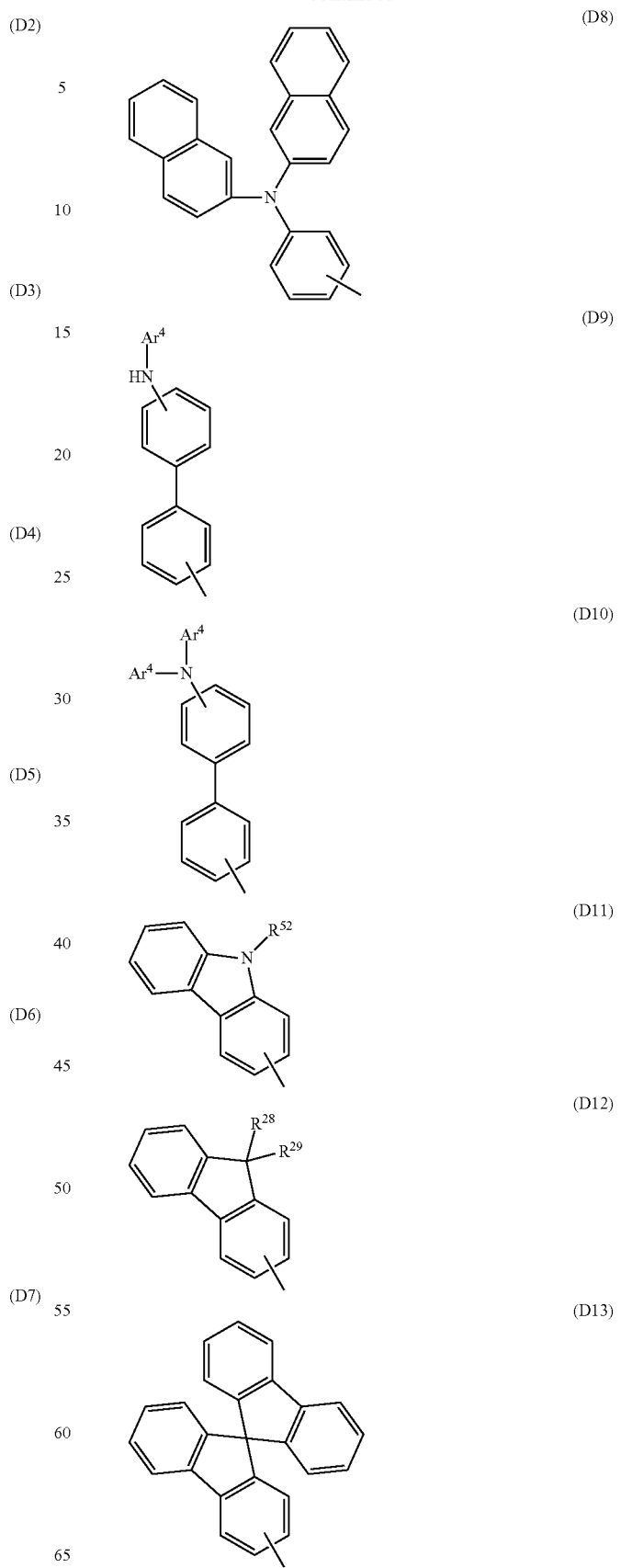

(In the formulas, R$^{25}$, R$^{29}$, R$^{52}$, Ar$^4$ and DPA have the same meanings as above.)
[Chemical Formula 82]
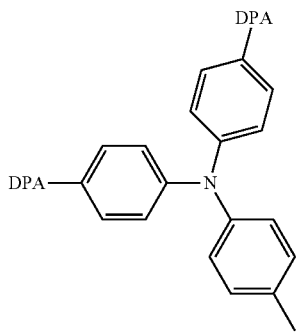
(D1′)
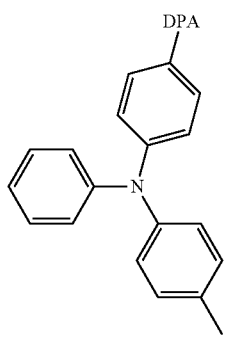
(D2′)
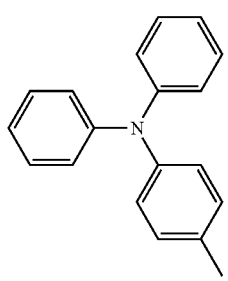
(D3′)
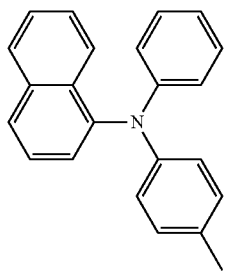
(D4′)
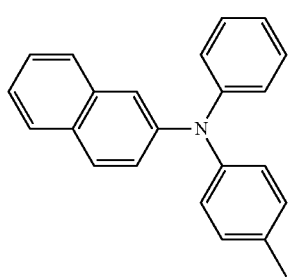
(D5′)
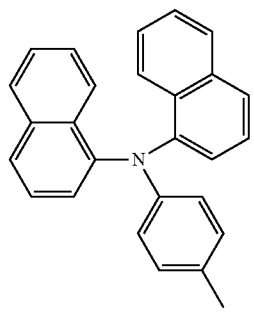
(D6′)
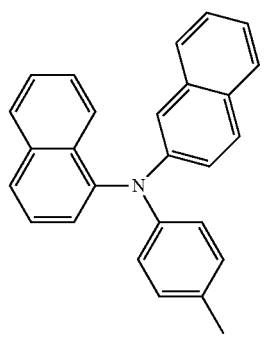
(D7′)
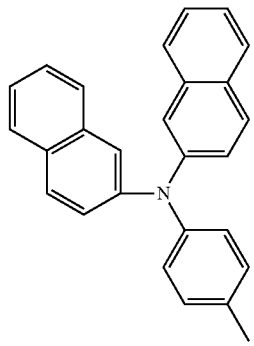
(D8′)
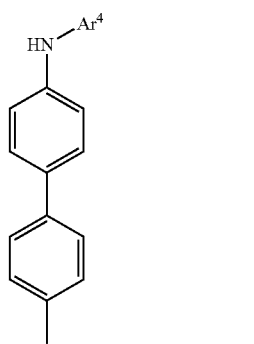
(D9′)

-continued

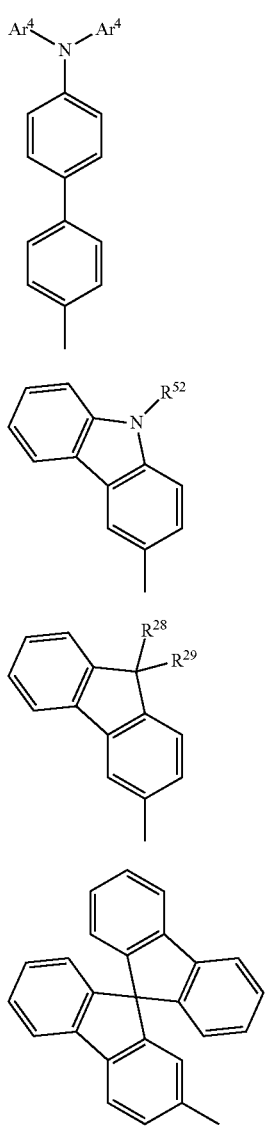

(D10′)

(D11′)

(D12′)

(D13′)

(In the formulas, $R^{28}$, $R^{29}$, $R^{52}$, $Ar^4$ and DPA have the same meanings as above.)

In addition, the aniline derivative represented by the formula (1) is preferably an aniline derivative represented by the formula (1-2), since the aniline derivative of the formula (1-2) can be synthesized comparatively easily using comparatively inexpensive bis(4-aminophenyl)amine as a raw material compound as will be described later and is excellent in solubility of the obtained aniline derivative in organic solvents.

[Chemical Formula 83]

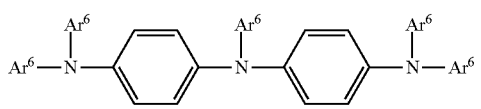

(1-2)

The above $Ar^6$ simultaneously represents a group represented by any of the formulas (E1) to (E14).

[Chemical Formula 84]

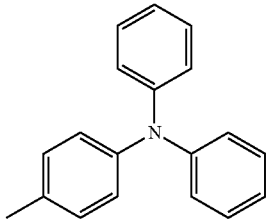 (E1)

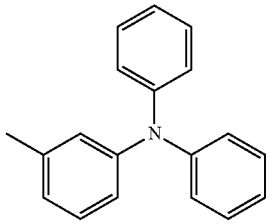 (E2)

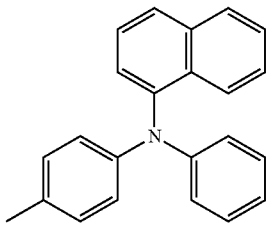 (E3)

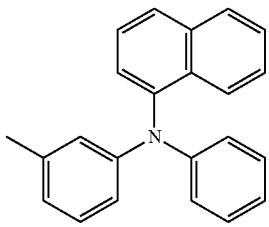 (E4)

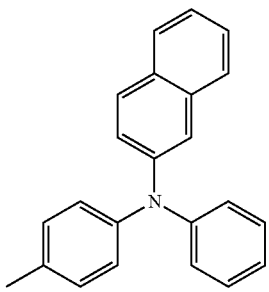 (E5)

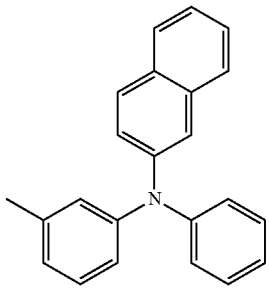 (E6)

(E7) 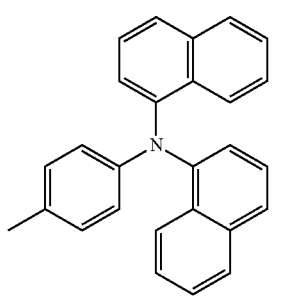
(E8) 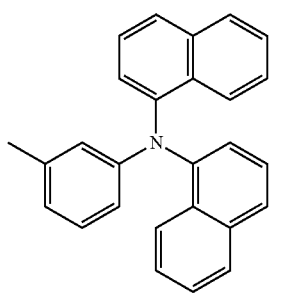
(E9) 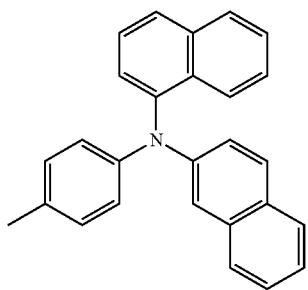
(E10) 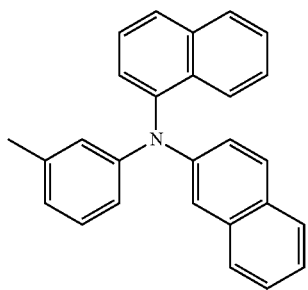
(E11) 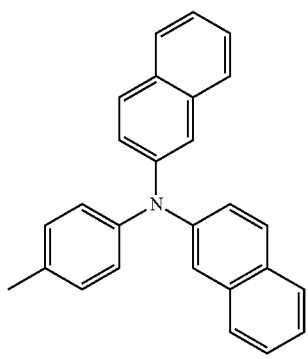
(E12) 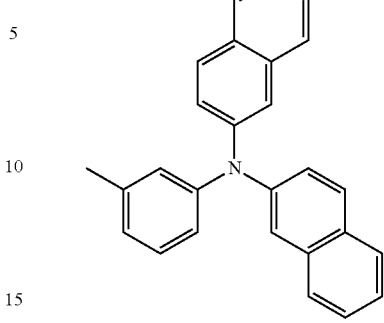
(E13) 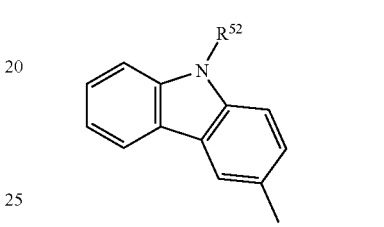
(E14) 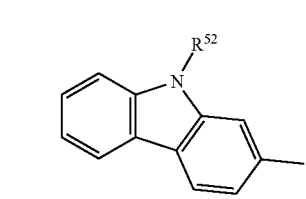
(In the formulas, $R^{52}$ has the same meaning as above.)
$Ar^3$ in the above formula (2) represents a group represented by any of the formulas (C1) to (C8), particularly with a group represented by any of the formulas (C1') to (C8') being preferable.
[Chemical Formula 85]
(C1) 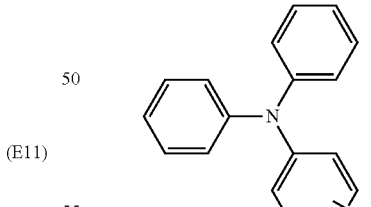
(C2) 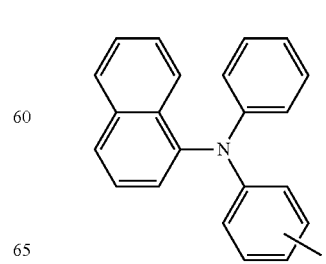

-continued
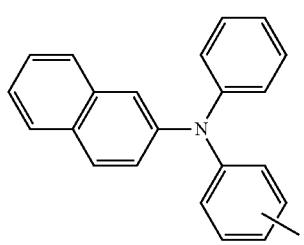 (C3)
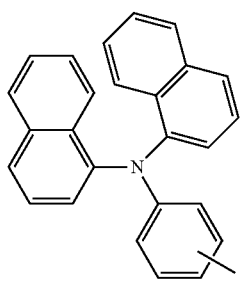 (C4)
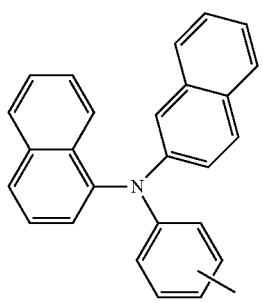 (C5)
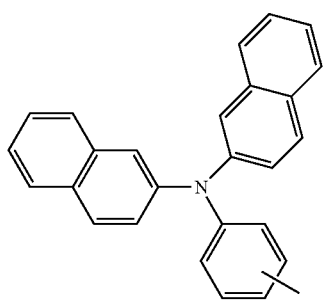 (C6)
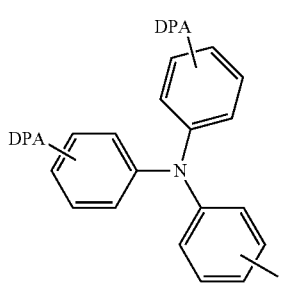 (C7)
-continued
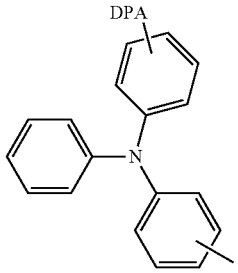 (C8)
[Chemical Formula 86]
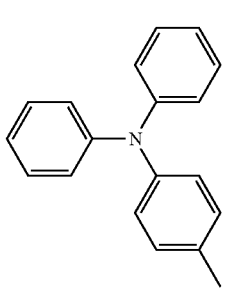 (C1′)
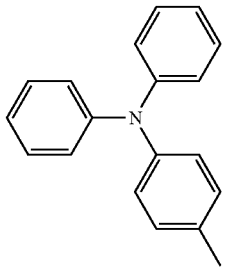 (C2′)
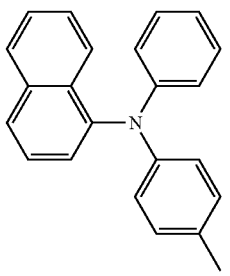 (C3′)
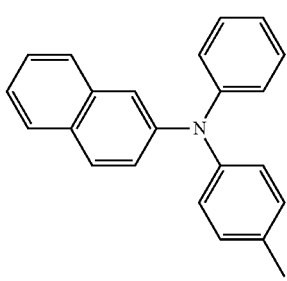 (C4′)
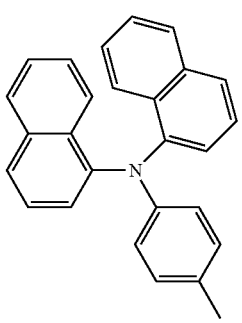

-continued

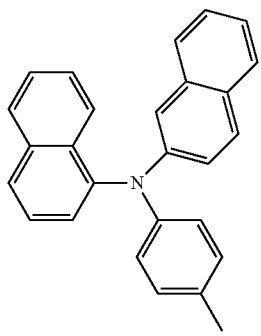
(C5′)

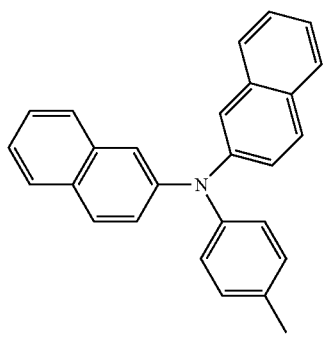
(C6′)

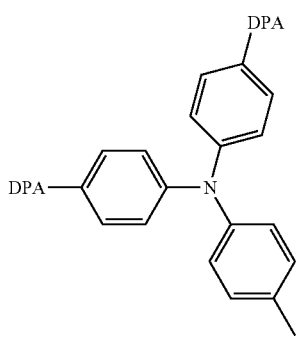
(C7′)

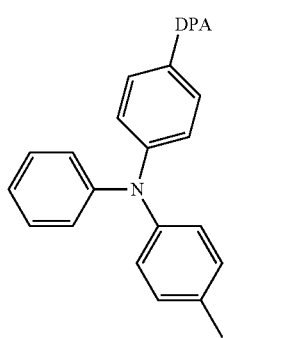
(C8′)

In the above formula (1), letter k represents an integer of 1 to 10, and from the viewpoint of enhancing solubility of the compound in organic solvents, letter k is preferably 1 to 5, more preferably 1 to 3, further preferably 1 or 2, and most preferably 1.

In the above formula (2), letter l represents 1 or 2.

Note that in $R^{28}$, $R^{29}$, $R^{52}$ and $R^{155}$ to $R^{157}$, $Z^1$ is preferably a halogen atom, a nitro group, a cyano group, an alkyl group having 1 to 10 carbon atoms which may be substituted with $Z^2$, an alkenyl group having 2 to 10 carbon atoms which may be substituted with $Z^2$, or an alkynyl group having 2 to 10 carbon atoms which may be substituted with $Z^2$, more preferably a halogen atom, a nitro group, a cyano group, an alkyl group having 1 to 3 carbon atoms which may be substituted with $Z^2$, an alkenyl group having 2 or 3 carbon atoms which may be substituted with $Z^2$, or an alkynyl group having 2 or 3 carbon atoms which may be substituted with $Z^2$, and further preferably a fluorine atom, an alkyl group having 1 to 3 carbon atoms which may be substituted with $Z^2$, an alkenyl group having 2 or 3 carbon atoms which may be substituted with $Z^2$, or an alkynyl group having 2 or 3 carbon atoms which may be substituted with $Z^2$.

In $R^{28}$, $R^{29}$, $R^{52}$ and $R^{155}$ to $R^{157}$, $Z^4$ is preferably a halogen atom, a nitro group, a cyano group, or an aryl group having 6 to 14 carbon atoms which may be substituted with $Z^5$, more preferably a halogen atom, a nitro group, a cyano group, an aryl group having 6 to 10 carbon atoms which may be substituted with $Z^5$, further preferably a fluorine atom, or an aryl group having 6 to 10 carbon atoms which may be substituted with $Z^5$, and still further preferably a fluorine atom or a phenyl group which may be substituted with $Z^5$.

In $R^{28}$, $R^{29}$, $R^{52}$ and $R^{155}$ to $R^{157}$, $Z^2$ is preferably a halogen atom, a nitro group, a cyano group, or an aryl group having 6 to 14 carbon atoms which may be substituted with $Z^3$, more preferably a halogen atom, a nitro group, a cyano group, or an aryl group having 6 to 10 carbon atoms which may be substituted with $Z^3$, further preferably a fluorine atom, or an aryl group having 6 to 10 carbon atoms which may be substituted with $Z^3$, and still further preferably a fluorine atom, or a phenyl group which may be substituted with $Z^3$.

In $R^{28}$, $R^{29}$, $R^{52}$ and $R^{155}$ to $R^{157}$, $Z^5$ is preferably a halogen atom, a nitro group, a cyano group, an alkyl group having 1 to 10 carbon atoms which may be substituted with $Z^3$, an alkenyl group having 2 to 10 carbon atoms which may be substituted with $Z^3$, or an alkynyl group having 2 to 10 carbon atoms which may be substituted with $Z^3$, more preferably a halogen atom, a nitro group, a cyano group, an alkyl group having 1 to 3 carbon atoms which may be substituted with $Z^3$, an alkenyl group having 2 or 3 carbon atoms which may be substituted with $Z^3$, or an alkynyl group having 2 or 3 carbon atoms which may be substituted with $Z^3$, and further preferably a fluorine atom, an alkyl group having 1 to 3 carbon atoms which may be substituted with $Z^3$, an alkenyl group having 2 or 3 carbon atoms which may be substituted with $Z^3$, or an alkynyl group having 2 or 3 carbon atoms which may be substituted with $Z^3$.

In $R^{28}$, $R^{29}$, $R^{52}$ and $R^{155}$ to $R^{157}$, $Z^3$ is preferably a halogen atom, more preferably a fluorine atom.

While in $R^7$ to $R^{27}$, $R^{30}$ to $R^{51}$ and $R^{53}$ to $R^{154}$, $Z^1$ is preferably a halogen atom, a nitro group, a cyano group, an alkyl group having 1 to 3 carbon atoms which may be substituted with $Z^2$, an alkenyl group having 2 or 3 carbon atoms which may be substituted with $Z^2$, or an alkynyl group having 2 or 3 carbon atoms which may be substituted with $Z^2$, more preferably a halogen atom, or an alkyl group having 1 to 3 carbon atoms which may be substituted with $Z^2$, and further preferably a fluorine atom or a methyl group which may be substituted with $Z^2$.

In $R^7$ to $R^{27}$, $R^{30}$ to $R^{51}$ and $R^{53}$ to $R^{154}$, $Z^4$ is preferably a halogen atom, a nitro group, a cyano group, or an aryl group having 6 to 10 carbon atoms which may be substituted with $Z^5$, more preferably a halogen atom, or an aryl group having 6 to 10 carbon atoms which may be substituted with $Z^5$, and further preferably a fluorine atom, or a phenyl group which may be substituted with $Z^5$.

In $R^7$ to $R^{27}$, $R^{30}$ to $R^{51}$ and $R^{53}$ to $R^{154}$, $Z^2$ is preferably a halogen atom, a nitro group, a cyano group, or an aryl group having 6 to 10 carbon atoms which may be substituted with $Z^3$, more preferably a halogen atom, or an aryl group having 6 to 10 carbon atoms which may be substituted with $Z^3$, and further preferably a fluorine atom, or a phenyl group which may be substituted with $Z^3$.

In $R^7$ to $R^{27}$, $R^{30}$ to $R^{51}$ and $R^{53}$ to $R^{154}$, $Z^5$ is preferably a halogen atom, a nitro group, a cyano group, an alkyl group having 1 to 3 carbon atoms which may be substituted with $Z^3$, an alkenyl group having 2 or 3 carbon atoms which may be substituted with $Z^3$, and an alkynyl group having 2 or 3 carbon atoms which may be substituted with $Z^3$, more preferably a halogen atom, or an alkyl group having 1 to 3 carbon atoms which may be substituted with $Z^3$, and further preferably a fluorine atom, or a methyl group which may be substituted with $Z^3$.

In $R^7$ to $R^{27}$, $R^{30}$ to $R^{51}$ and $R^{53}$ to $R^{154}$, $Z^3$ is preferably a halogen atom, more preferably a fluorine atom.

In the present invention, specific examples of the group preferable as $R^{52}$ and $R^{155}$ include, but are not limited to, the following groups.

[Chemical Formula 87]

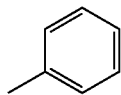
(N1)

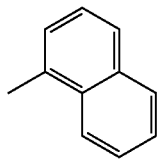
(N2)

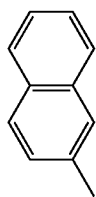
(N3)

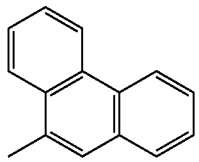
(N4)

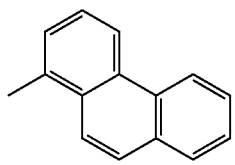
(N5)

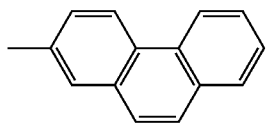
(N6)

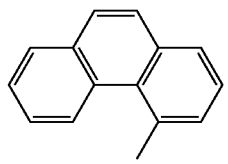
(N7)

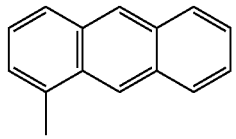
(N8)

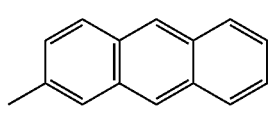
(N9)

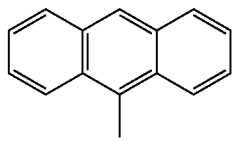
(N10)

[Chemical Formula 88]

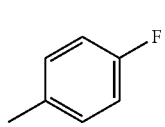
(N11)

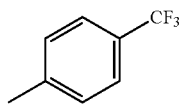
(N12)

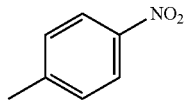
(N13)

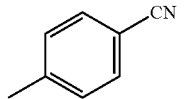
(N14)

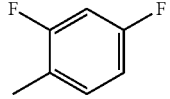
(N15)

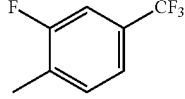
(N16)

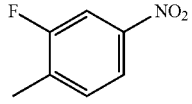
(N17)

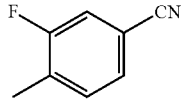
(N18)

(N19) 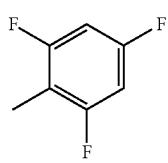
(N20) 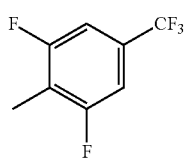
(N21) 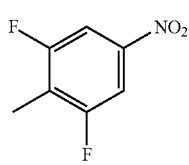
(N22) 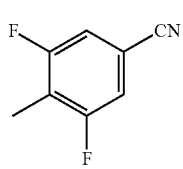
(N23) 
(N24) 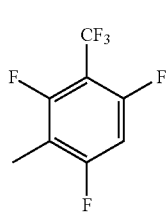
(N25) 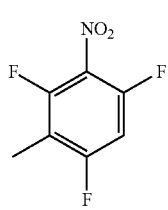
(N26) 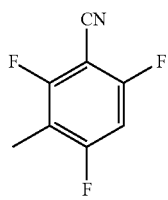
(N27) 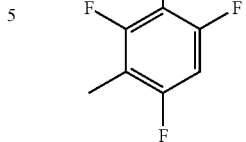
(N28) 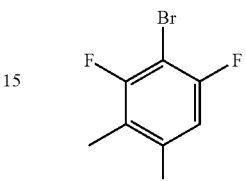
(N29) 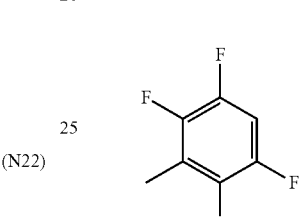
(N30) 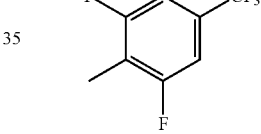
(N31) 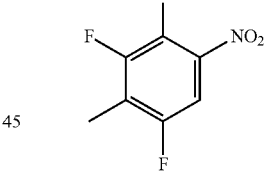
(N32) 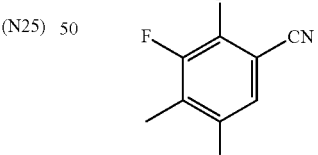
[Chemical Formula 89]
(N33) 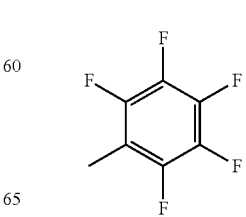

101
-continued
(N34) 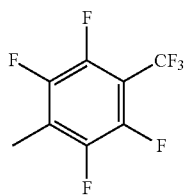
(N35) 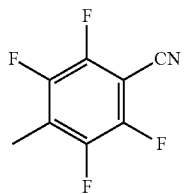
(N36) 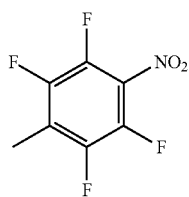
(N37) 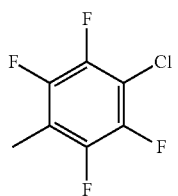
(N38) 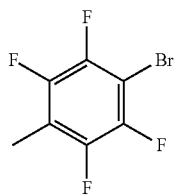
(N39) 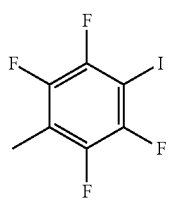
(N40) 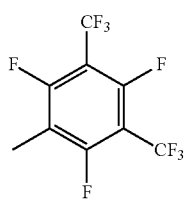
(N41) 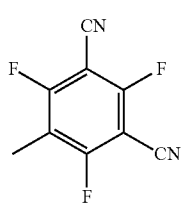
102
-continued
(N42) 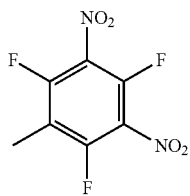
(N43) 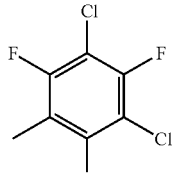
(N44) 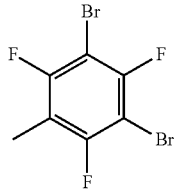
(N45) 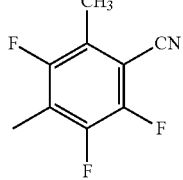
(N46) 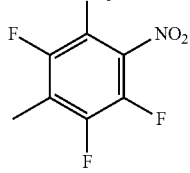
(N47) 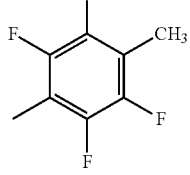
(N48) 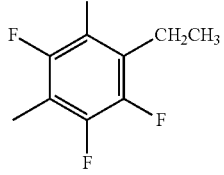
(N49) 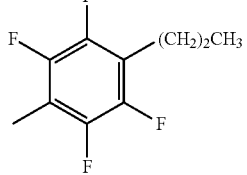

(N50) 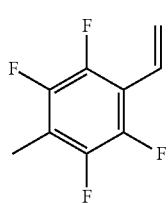
(N51) 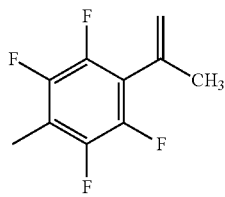
(N52) 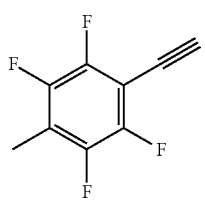
(N53) 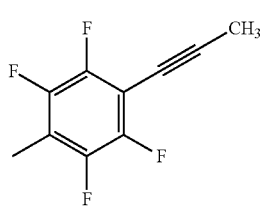
[Chemical Formula 90]
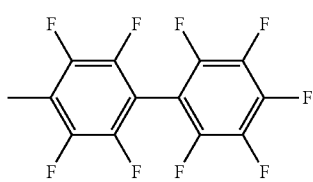
[Chemical Formula 91]
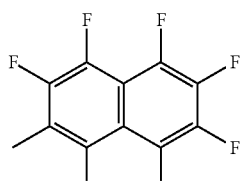
(N56)
(N57)
(N58)
(N59) 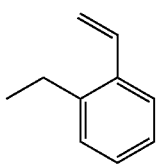
(N60) 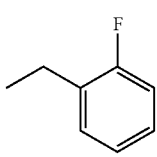
(N61) 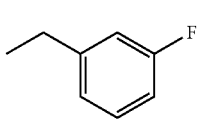
(N62) 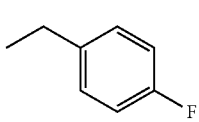
(N63) 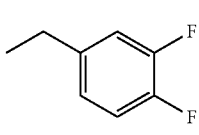
(N64) 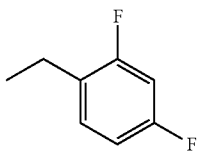
(N65) 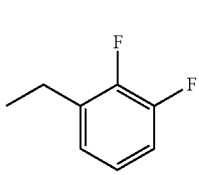
(N66) 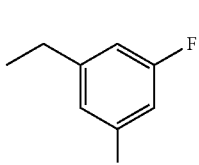
(N67) 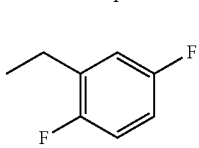
(N68) 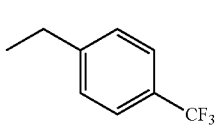
(N69) 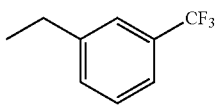

-continued

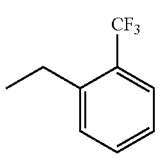

[Chemical Formula 92]

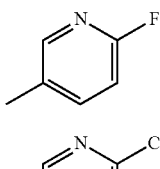 (N70)

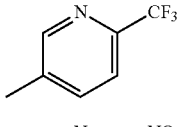 (N71)

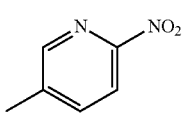 (N72)

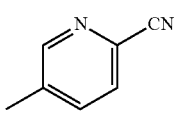 (N73)

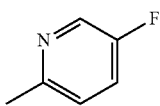 (N74)

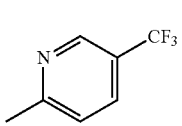 (N75)

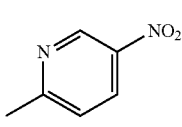 (N76)

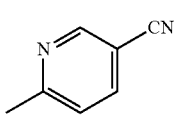 (N77)

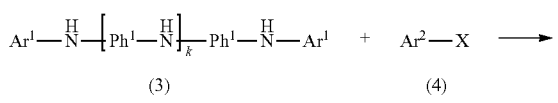 (N78)

In the present invention, the number of carbon atoms in the above alkyl group, alkenyl group and alkynyl group is preferably up to 10, more preferably up to 6, and further preferably up to 4.

Besides, the number of carbon atoms in the above aryl group and heteroaryl group is preferably up to 14, more preferably up to 10, and further preferably up to 6.

The aniline derivative represented by the formula (1) of the present invention can be prepared by reacting an amine compound represented by the formula (3) with an aryl compound represented by the formula (4) in the presence of a catalyst.

[Chemical Formula 93]

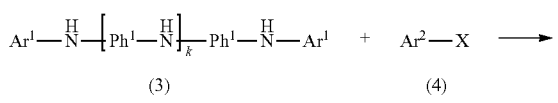

-continued

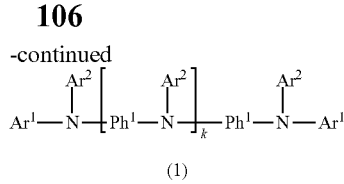
(1)

(In the formula, X represents a halogen atom or a pseudo-halogen group, and $Ar^1$, $Ar^2$, $Ph^1$ and letter k have the same meanings as above.)

Particularly, the aniline derivative represented by the formula (1-1) can be prepared by reacting an amine compound represented by the formula (7) with an aryl compound represented by the formula (8) in the presence of a catalyst.

[Chemical Formula 94]

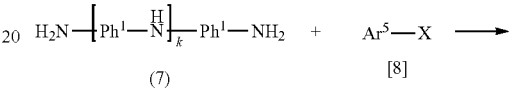

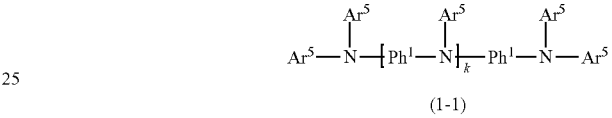
(1-1)

(In the formula, X, $Ar^5$, $Ph^1$ and letter k have the same meanings as above.)

In addition, the aniline derivative represented by the formula (1-2) can be prepared by reacting bis(4-aminophenyl)amine with an aryl compound represented by the formula (9) in the presence of a catalyst.

[Chemical Formula 95]

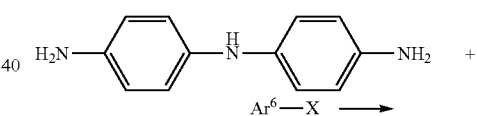

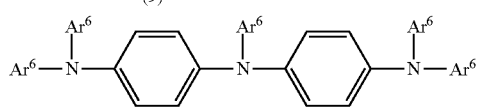
(1-2)

(In the formula, X and $Ar^6$ have the same meanings as above.)

Besides, the aniline derivative represented by the formula (2) of the present invention can be prepared by reacting an amine compound represented by the formula (5) with an aryl compound represented by the formula (6) in the presence of a catalyst.

[Chemical Formula 96]

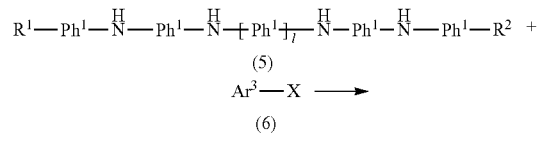

-continued

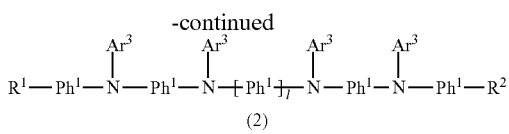

(In the formula, X, $R^1$, $R^2$, $Ar^3$, $Ph^1$ and letter 1 have the same meanings as above.)

Examples of the halogen atom include the same halogen atoms as above.

Examples of the pseudo-halogen group include (fluoro)alkylsulfonyloxy groups such as methanesulfonyloxy group, trifluoromethanesulfonyloxy group, and nonafluorobutanesulfonyloxy group; and aromatic sulfonyloxy groups such as benzenesulfonyloxy group and toluenesulfonyloxy group.

The ratio between the amount of the amine compound represented by the formula (3), (5) or (7) or bis(4-aminophenyl)amine used and the amount of the aryl compound represented by the formula (4), (6), (8) or (9) used can be such that the amount of the aryl compound is at least one equivalent, a preferable amount being approximately 1 to 1.2 equivalents, relative to the amount of substance of the whole NH groups in the amine compound or bis(4-aminophenyl)amine.

Examples of the catalyst to be used for the above reactions include copper catalysts such as copper chloride, copper bromide, and copper iodide; and palladium catalysts such as $Pd(PPh_3)_4$ (tetrakis(triphenylphosphine)palladium), $Pd(PPh_3)_2Cl_2$ (bis(triphenylphosphine)dichloropalladium), $Pd(dba)_2$ (bis(dibenzylideneacetone)palladium), $Pd_2(dba)_3$ (tris(dibenzylideneacetone)dipalladium), $Pd(P-t-Bu_3)_2$ (bis(tri(t-butylphosphine))palladium), and $Pd(OAc)_2$ (palladium acetate). These catalysts may be used either singly or in combination of at least two of them. Besides, these catalysts may be used together with a known suitable ligand.

Examples of such a ligand include tertiary phosphines such as triphenylphosphine, tri-o-tolylphosphine, diphenylmethylphosphine, phenyldimethylphosphine, trimethylphosphine, triethylphosphine, tributylphosphine, tri-tert-butylphosphine, di-t-butyl(phenyl)phosphine, di-tert-butyl(4-dimethylaminophenyl)phosphine, 1,2-bis(diphenylphosphino)ethane, 1,3-bis(diphenylphosphino)propane, 1,4-bis(diphenylphosphino)butane, and 1,1'-bis(diphenylphosphino)ferrocene, and tertiary phosphites such as trimethyl phosphite, triethyl phosphite, and triphenyl phosphite.

The amount of the catalyst to be used can be approximately 0.2 mol, a preferable amount being approximately 0.15 mol, relative to 1 mol of the aryl compound represented by the formula (4), (6), (8) or (9).

Besides, in the case where the ligand is used, the amount of the ligand to be used can be 0.1 to 5 equivalents, a preferable amount being 1 to 2 equivalents, relative to the metal complex used.

In the case where all the raw material compounds are solid or from the viewpoint of efficiently obtaining the desired aniline derivative, each of the above reactions is carried out in a solvent. In the case where a solvent is used, the kind of the solvent is not particularly limited so long as the solvent does not adversely influence the reaction. Specific examples of the solvent include fatty hydrocarbons (pentane, n-hexane, n-octane, n-decane, and decalin), halogenated fatty hydrocarbons (chloroform, dichloromethane, and dichloroethane, carbon tetrachloride), aromatic hydrocarbons (benzene, nitrobenzene, toluene, o-xylene, m-xylene, p-xylene, and mesitylene), halogenated aromatic hydrocarbons (chlorobenzene, bromobenzene, o-dichlorobenzene, m-dichlorobenzene, and p-dichlorobenzene), ethers (diethyl ether, diisopropyl ether, t-butyl methyl ether, tetrahydrofuran, dioxane, 1,2-dimethoxyethane, and 1,2-diethoxyethane), ketones (acetone, methyl ethyl ketone, methyl isobutyl ketone, di-n-butyl ketone, and cyclohexanone), amides (N,N-dimethylformamide and N,N-dimethylacetamide), lactams and lactones (N-methylpyrrolidone and γ-butyrolactone), ureas (N,N-dimethylimidazolidinone and tetramethylurea), sulfoxides (dimethyl sulfoxide and sulfolane), and nitriles (acetonitrile, propionitrile, and butyronitrile). These solvents may be used either singly or as a mixture of at least two of them.

The reaction temperature may be appropriately set within the range from the melting point to the boiling point of the solvent used. Particularly, a temperature of approximately 0 to 200° C. is preferable, and a temperature of 20 to 150° C. is more preferable.

After the reaction is over, a post-treatment is conducted according to an ordinary method, whereby the desired aniline derivative can be obtained.

In the aforementioned method of preparing the aniline derivative represented by the above formula (1), the amine compound represented by the formula (3') which can be used as a raw material can be efficiently prepared by reacting an amine compound represented by the formula (10) with an aryl compound represented by the formula (11) in the presence of a catalyst.

[Chemical Formula 97]

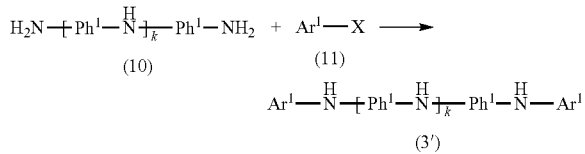

(In the formula, X, $Ar^1$, $Ph^1$ and letter k have the same meanings as above, provided that two $Ar^1$ do not simultaneously represent a group represented by the formula (B1).)

The aforementioned method of preparing the amine compound represented by the formula (3') is a method wherein the amine compound represented by the formula (10) and the aryl compound represented by the formula (11) are put into a coupling reaction. The amounts of the amine compound represented by the formula (10) and the aryl compound represented by the formula (11) to be used, in terms of ratio by amount of substance, are preferably approximately 2 to 2.4 of the aryl compound relative to 1 of the amine compound.

Other various conditions concerning catalyst, ligand, solvent, and reaction temperature in the coupling reaction are the same as the conditions described above with respect to the method of preparing the aniline derivative represented by the formula (1).

In the case of preparing the aniline derivative of the present invention wherein in the formula (1), $Ar^1$ is a group represented by the formula (B4) with $R^{52}$ being a hydrogen atom or a group represented by the formula (B10) or $Ar^2$ is a group represented by the formula (A12) or a group represented by the formula (A16) with $R^{155}$ (inclusive of $R^{52}$ in the formula (1-1)) being a hydrogen atom, an aryl compound having a protective group on an amino group can be used in the aforementioned reaction.

Specifically, in the aforementioned reaction, in place of an aryl compound (formula (G1)) represented by the formula (4) with $Ar^2$ being a group represented by the formula (A12), an aryl compound (formula (G2)) represented by the formula (4) with $Ar^2$ being a group represented by the formula (A16) and with $R^{155}$ being a hydrogen atom, an aryl compound (formula (G1)) represented by the formula (8) with $Ar^5$ being a group represented by the formula (D9), an aryl compound (formula (G2)) represented by the formula (8) with $Ar^5$ being a group represented by the formula (D11) and with $R^{52}$ being a hydrogen atom, an aryl compound (formula (G3)) represented by the formula (9) with $Ar^6$ being a group represented by the formula (E13) and with $R^{52}$ being a hydrogen atom, an aryl compound (formula (G4)) represented by the formula (9) with $Ar^6$ being a group represented by the formula (E14) and with $R^{52}$ being a hydrogen atom, an aryl compound (formula (G5)) represented by the formula (11) with $Ar^1$ being a group represented by the formula (B4) and with $R^{52}$ being a hydrogen atom, and an aryl compound (formula (G6)) represented by the formula (11) with $Ar^1$ being a group represented by the formula (B10), there are used aryl compounds (formulas (G1P) to (G6P)) wherein the amino group of each aryl compound is protected, and while using them, each of the protected aryl compounds and the aforementioned amine compound are reacted with each other in the presence of a catalyst, and deprotection is carried out at an appropriate timing.

[Chemical Formula 98]

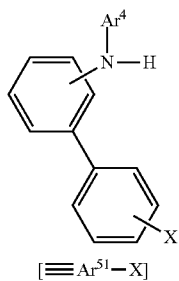

(G1)

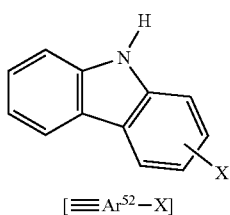

(G2)

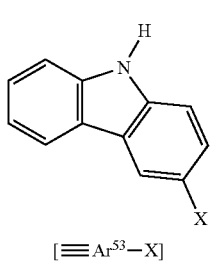

(G3)

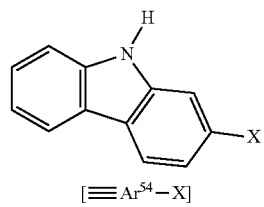

(G4)

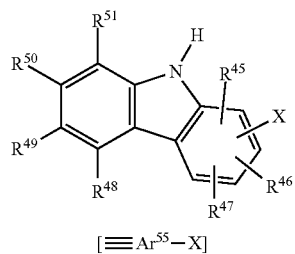

(G5)

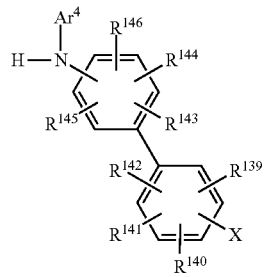

(G6)

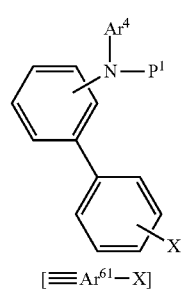

(G1P)

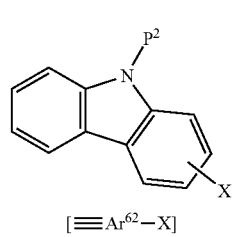

(G2P)

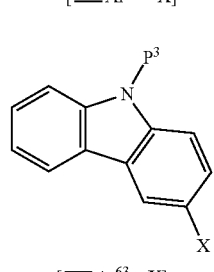

(G3P)

-continued

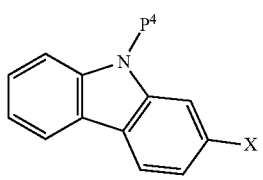
(G4P)

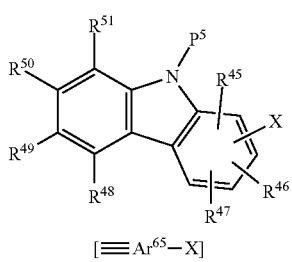
(G5P)

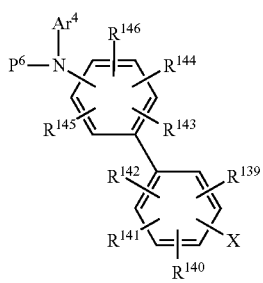
(G6P)

(In the formulas, X, $R^{45}$ to $R^{51}$, $R^{139}$ to $R^{146}$ and $Ar^4$ have the same meanings as above.)

$P^1$ to $P^6$ independently represent a protective group for an amino group. As such a protective group, conventional protective groups can be used. Examples of the usable protective groups include, but are not limited to: oxycarbonyl type protective groups such as substituted or unsubstituted alkoxycarbonyl groups (e.g., methoxycarbonyl group, ethoxycarbonyl group, t-butoxycarbonyl group, 2,2,2-trichloroethoxycarbonyl group, allyloxycarbonyl group, and 9-fluorenylmethyloxycarbonyl group), substituted or unsubstituted aralkyloxycarbonyl groups (e.g., benzyloxycarbonyl group), and substituted or unsubstituted aryloxycarbonyl groups (e.g., phenoxycarbonyl group); formyl group; carbonyl type protective groups such as substituted or unsubstituted alkanoyl groups (e.g., acetyl group, trifluoroacetyl group, and t-butanoyl group) and substituted or unsubstituted arylcarbonyl groups (e.g., benzoyl group); alkyl type protective groups such as substituted or unsubstituted alkyl groups (e.g., t-butyl group) and substituted or unsubstituted aralkyl groups (e.g., benzyl group, benzhydryl group, and trityl group); substituted or unsubstituted sulfonyl type protective groups (e.g., benzenesulfonyl group, p-toluenesulfonyl group, and 2-nitrobenzenefulfonyl group).

Among these, the oxycarbonyl type protective groups, carbonyl type protective groups, and alkyl type protective groups are preferable.

Note that $Ar^{51}$ to $Ar^{56}$ and $Ar^{61}$ to $Ar^{66}$ each represent a monovalent group represented by removing X (halogen atom or pseudo-halogen group) of each aryl compound. For example, $Ar^{61}$ to $Ar^{66}$ each represent the following groups.

[Chemical Formula 99]

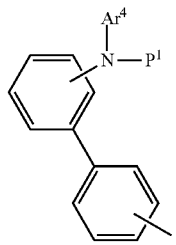
(P-1)

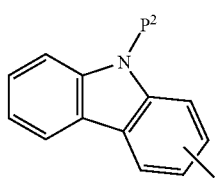
(P-2)

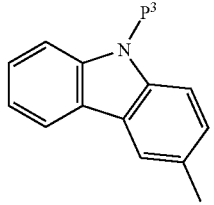
(P-3)

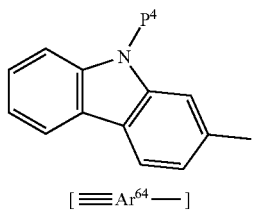
(P-4)

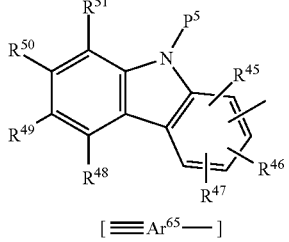
(P-5)

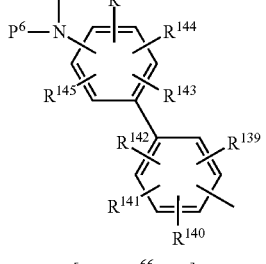
(P-6)

(In the formulas, $P^1$ to $P^6$, $R^{45}$ to $R^{51}$, $R^{139}$ to $R^{146}$ and $Ar^4$ have the same meanings as above.)

More specific examples of the aforementioned method of preparing the aryl compound having a protective group for an amino group include, but are not limited to, the followings.

[Chemical Formula 100]

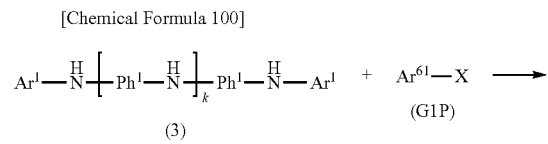

(3) (G1P)

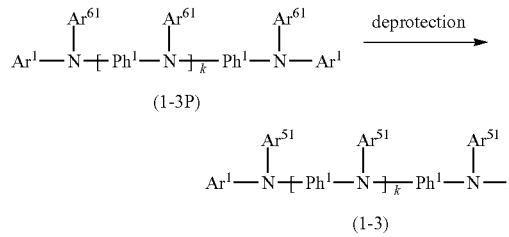

(1-3P)

(1-3)

[Chemical Formula 101]

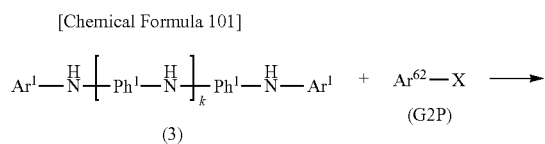

(3) (G2P)

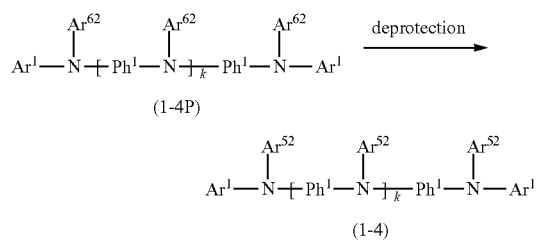

(1-4P)

(1-4)

[Chemical Formula 102]

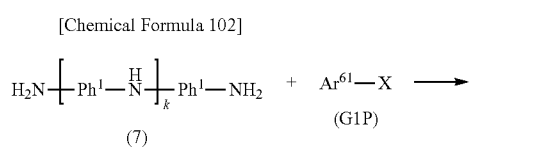

(7) (G1P)

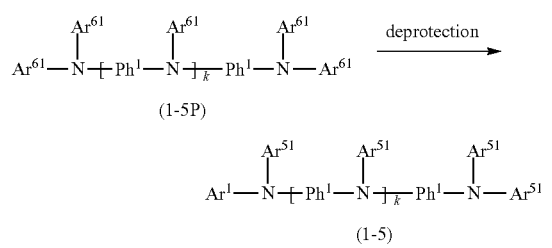

(1-5P)

(1-5)

[Chemical Formula 103]

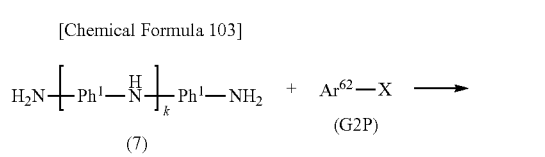

(7) (G2P)

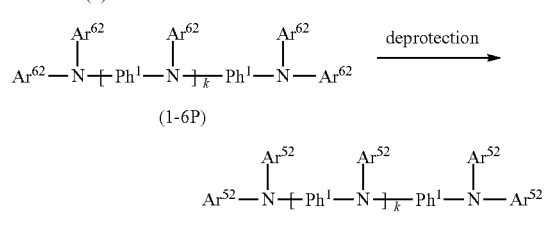

(1-6P)

(1-6)

[Chemical Formula 104]

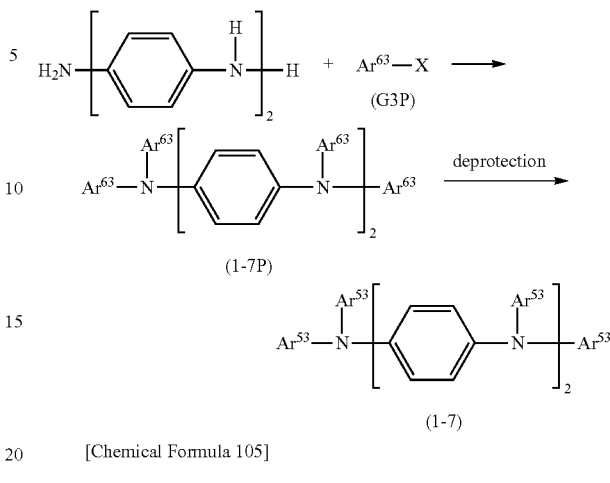

(1-7P)

(1-7)

[Chemical Formula 105]

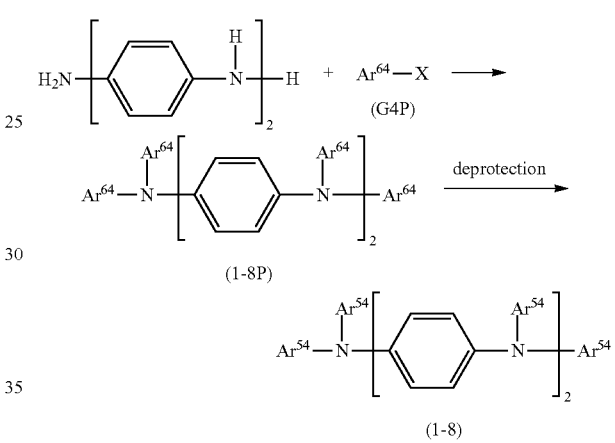

(1-8P)

(1-8)

[Chemical Formula 106]

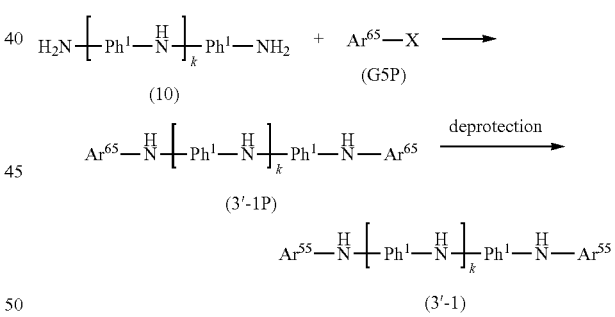

(10) (G5P)

(3'-1P)

(3'-1)

[Chemical Formula 107]

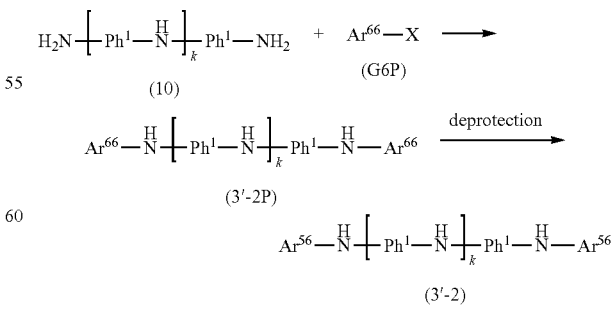

(10) (G6P)

(3'-2P)

(3'-2)

In such a method of preparing the aryl compound having a protective group as above, various conditions concerning the ratio of amounts of the raw materials used, catalyst, ligand, solvent, and reaction temperature are the same as the conditions described above concerning the aniline derivative represented by the formula (1) or the amine compound represented by the formula (3').

Besides, the deprotection may be carried out by an appropriate known method, in which a treatment under an acidic or basic conditions or a treatment under an oxidizing or a reducing conditions may be conducted, by an appropriate known method in consideration of the properties of the protective group, with reference to, for example, GREEN'S PROTECTIVE GROUPS in Organic Synthesis, 4th Edition.

In the case of preparing the aniline derivative of the present invention having a tertiary amine moiety and represented by the formula (1) wherein $Ar^1$ is a group represented by the formula (B4) with $R^{52}$ being not a hydrogen atom or a group represented by the formula (B11) or wherein $Ar^2$ is a group represented by the formula (A13) or a group represented by the formula (A16) with $R^{155}$ (inclusive of $R^{52}$ in the formula (1-1)) being not a hydrogen atom, the aniline derivative of the present invention having a secondary amine moiety and represented by the formula (1) wherein $Ar^1$ is a group represented by the formula (B4) and $R^{52}$ is a hydrogen atom or a group represented by the formula (B10) or wherein $Ar^2$ is a group represented by the formula (A12) or a group represented by the formula (A16) and $R^{155}$ (inclusive of $R^{52}$ in the formula (1-1)) is a hydrogen atom may be used. Also, an amine compound having a secondary amine moiety and represented by the formula (3) wherein $Ar^1$ is a group represented by the formula (B4) with $R^{52}$ being a hydrogen atom or a group represented by the formula (B10) may also be used.

Specifically, as shown in the following, the amine moiety of the aniline derivative or amine compound having the secondary amine moiety is reacted with an aryl compound represented by the formula (10) or a hydrocarbon compound represented by the formula (11) or (12).

[Chemical Formula 108]

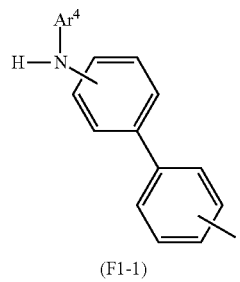

(F1-1)

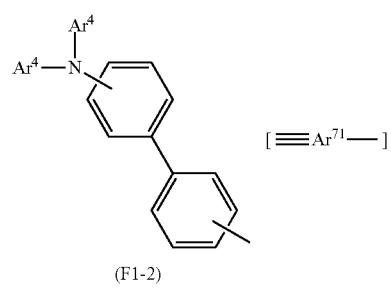

(F1-2)

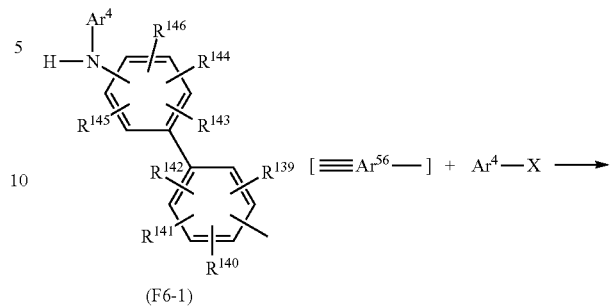

(F6-1)

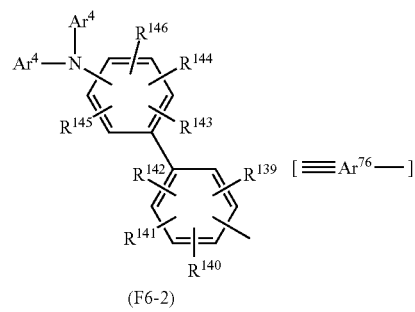

(F6-2)

(In the formulas, X, $R^{139}$ to $R^{146}$ and $Ar^4$ have the same meanings as above.)

[Chemical Formula 109]

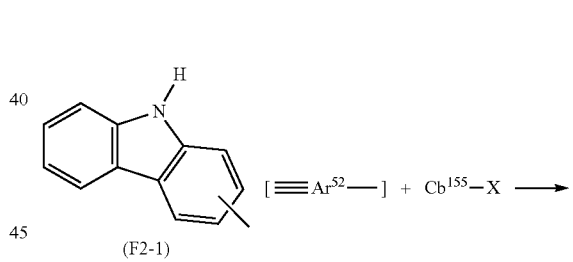

(F2-1)

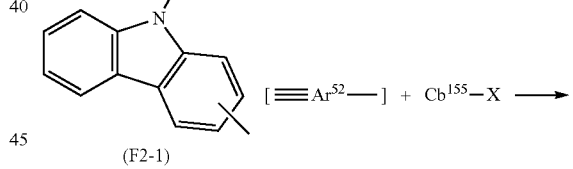

(F2-2)

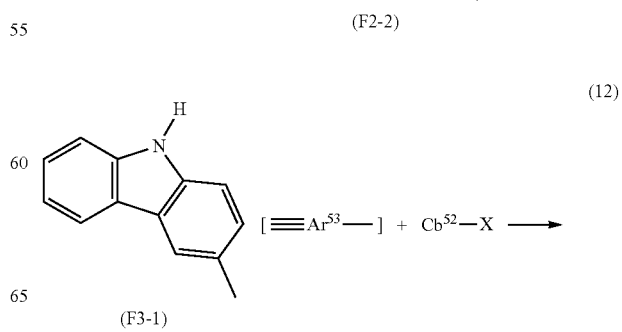

(F3-1)

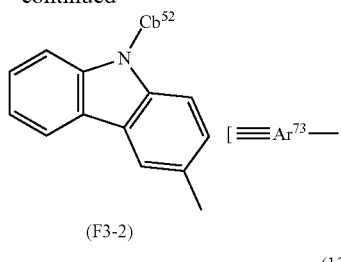

(F3-2)

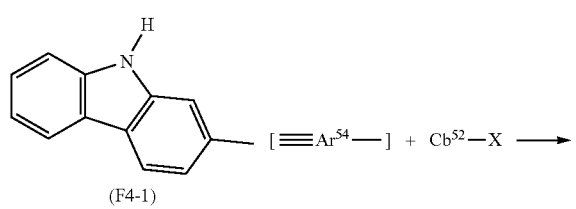

(F4-1)

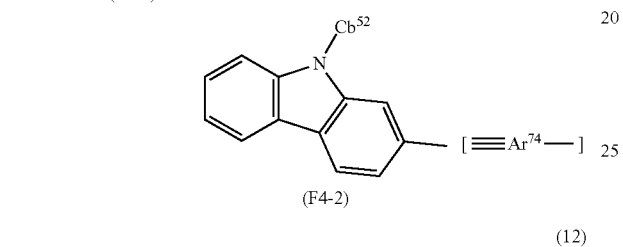

(F4-2)

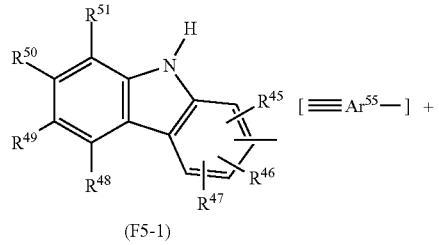

(F5-1)

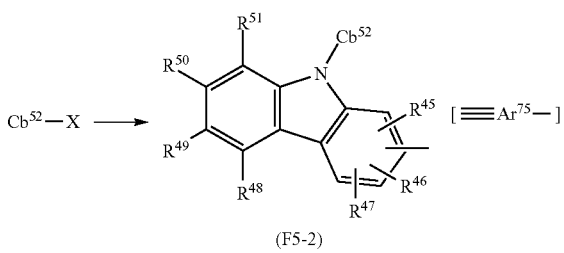

(F5-2)

(In the formulas, X and $R^{45}$ to $R^{51}$ have the same meanings as above.)

$Cb^{52}$ and $Cb^{155}$ independently represent an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, and examples of the alkyl group, alkenyl group, alkynyl group, aryl group and heteroaryl group include the same groups as above-mentioned. $Z^1$ and $Z^4$ have the same meanings as above.

More specific examples of the aforementioned method of preparing the aniline derivative or amine compound having the secondary amine moiety include, but are not limited to, the followings.

[Chemical Formula 110]

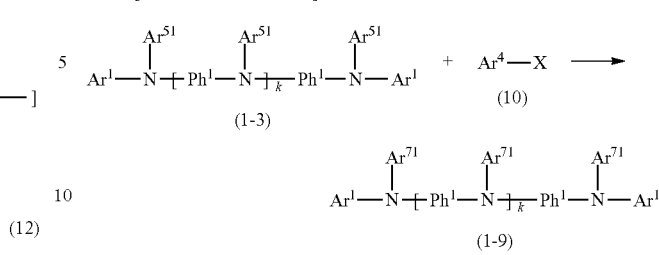

(1-3)    (10)

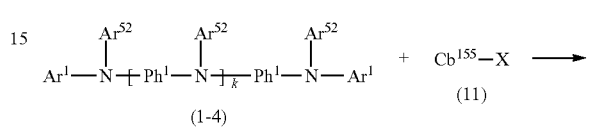

(1-9)

[Chemical Formula 111]

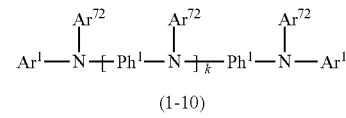

(1-4)    (11)

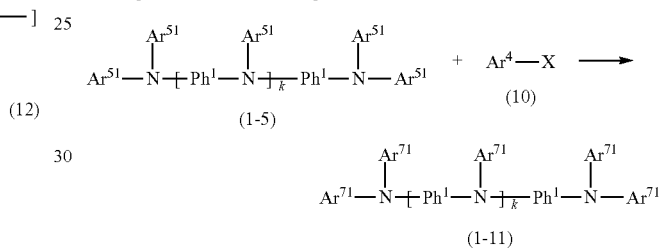

(1-10)

[Chemical Formula 112]

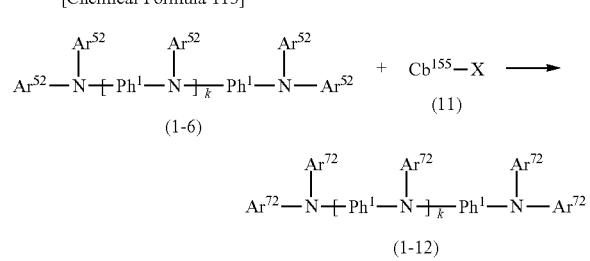

(1-5)    (10)

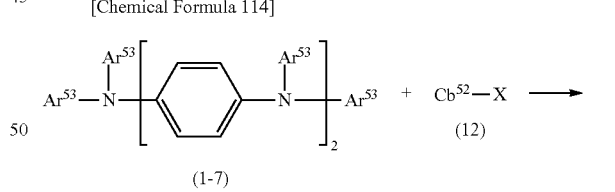

(1-11)

[Chemical Formula 113]

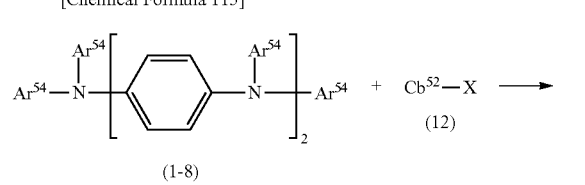

(1-6)    (11)

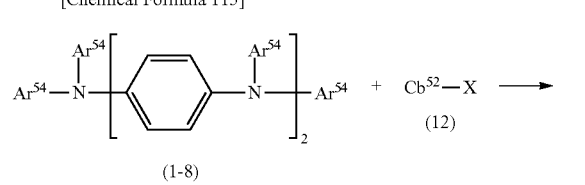

(1-12)

[Chemical Formula 114]

(1-7)

(1-13)

[Chemical Formula 115]

(1-8)    (12)

-continued

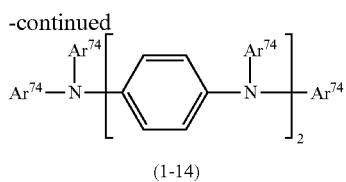

(1-14)

[Chemical Formula 116]

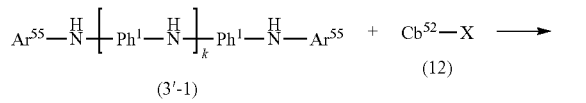

(3'-1)

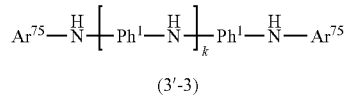

(3'-3)

[Chemical Formula 117]

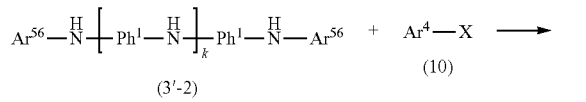

(3'-2)

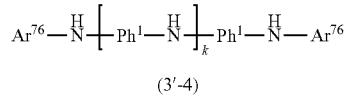

(3'-4)

The ratio between the amount of the aniline derivative represented by the formulas (1-3) to (1-8) used and the amount of the aryl compound represented by the formula (10) or the hydrocarbon compound represented by the formulas (11) and (12) used can be such that the amount of the aryl compound or the hydrocarbon compound is at least one equivalent relative to the amount of substance of whole NH groups of the aniline derivative, a preferable amount being approximately 1 to 1.2 equivalents.

Besides, the ratio between the amount of the amine compound represented by the formulas (3'-1) to (3'-2) used and the amount of the aryl compound represented by the formula (10) or the hydrocarbon compound represented by the formula (12) used, in ratio of amount of substance, is preferably such that the amount of the aryl compound represented by the formula (10) or the hydrocarbon compound represented by the formula (12) is approximately 2 to 2.4 relative to 1 of the amine compound represented by the formulas (3'-1) and (3'-2).

Other conditions than the amounts used are as follows.

In the case of preparing the aniline derivatives represented by the formulas (1-9) to (1-14) or the amine compounds represented by the formulas (3'-3) and (3'-4) by use of the aforementioned catalyst such as copper or palladium, the conditions concerning catalyst, ligand, solvent, and reaction temperature can be the conditions described above concerning the method of preparing the aniline derivative represented by the formula (1).

Besides, in the case of preparing the aniline derivatives represented by the formulas (1-9) to (1-14) or the amine compounds represented by the formulas (3'-3) and (3'-4) by a substitution reaction using the aryl compound represented by the formula (1), the hydrocarbon compound represented by the formula (11) with $Cb^{155}$ being an alkyl group having 1 to 20 carbon atoms which may be substituted with $Z^4$ or an aryl group having 6 to 20 carbon atoms or heteroaryl group having 2 to 20 carbon atoms which may be substituted with $Z^1$, or a hydrocarbon represented by the formula (12) with $Cb^{52}$ being an alkyl group having 1 to 20 carbon atoms which may be substituted with $Z^4$ or an aryl group having 6 to 20 carbon atoms or heteroaryl group having 2 to 20 carbon atoms which may be substituted with $Z^1$, the aniline derivatives represented by the formulas (1-3) to (1-8) or the amine compounds represented by the formulas (3'-1) and (3'-2) are reacted with a base in a solvent, and the resulting reaction products are reacted with the hydrocarbon compound represented by the formulas (11) and (12) or the aryl compound represented by the formula (10).

Examples of the base include alkali metals themselves, alkali metal hydroxides, alkoxy alkali metals, alkali metal carbonates, and alkali metal hydrogen carbonates such as lithium, sodium, potassium, lithium hydride, sodium hydride, potassium hydroxide, t-butoxylithium, t-butoxysodium, t-butoxypotassium, lithium hydroxide, sodium hydroxide, potassium hydroxide, sodium carbonate, potassium carbonate, sodium hydrogen carbonate, and potassium hydrogen carbonate; alkaline earth metal carbonate such as calcium carbonate; organic lithium such as n-butyllithium, s-butyllithium, and t-butyllithium; and amines such as triethylamine, diisopropylethylamine, tetramethylethylenediamine, triethylenediamine, and pyridine, but the base is not particularly restricted so long as the base is one ordinarily used for this kind of reaction. Especially, sodium hydride, sodium carbonate and potassium carbonate are preferable, since they are easy to handle.

The amount of the base to be used is approximately 1 to 1.2 equivalents relative to the whole NH groups of the aniline derivative represented by the formulas (1-3) to (1-8), or approximately 2 to 2.4 relative to 1 mole of the amine compound represented by the formulas (3'-1) and (3'-2).

Specific examples of the solvent include the solvents set forth as examples in the method of preparing the aniline derivative represented by the formula (1).

The reaction temperature may be appropriately set within the range from the melting point to the boiling point of the solvent to be used. Particularly, a temperature of approximately 20 to 150° C. is preferable.

After the reaction is over, a post-treatment is carried out according to an ordinary method, such as liquid separating treatment, column chromatography, reprecipitation, and recrystallization.

Note that though not possible to generally saying because of being influenced by the structures of the raw materials and the kind of the solvent used, it is preferable to adopt a substitution reaction in the case where X is a fluorine atom, and to adopt a reaction using a catalyst in the case where X is other than a fluorine atom.

Note that the amine compound represented by the formula (3) with two $Ar^1$ being both a group represented by the formula (B1), which can be used as a raw material in the aforementioned method of preparing the aniline derivative represented by the formula (1) can also be synthesized by the methods described in PCT Patent Publication Nos. WO 2008/129947 and WO 2013/08466.

The charge transporting material of the present invention contains the charge transporting substance including the aniline derivative represented by the formula (1) or (2), and is preferably in the form of a varnish from the viewpoint of obtaining a large-area thin film with good reproducibility.

Specific examples of the aniline derivative represented by the formula (1) or (2) will be given below, but these are not restrictive. Note that in the formulas and tables, "Me" represents a methyl group, "Et" an ethyl group, "Pr$^n$" an n-propyl group, "Pr$^i$" an i-propyl group, "Bu$^n$" an n-butyl group, "Bu$^i$" an i-butyl group, "Bu$^s$" an s-butyl group, "Bu$^t$" a t-butyl group, "DPA" a diphenylamino group, and "SBF" represents a 9,9'-spirobi[9H-fluoren]-2-yl group.

TABLE

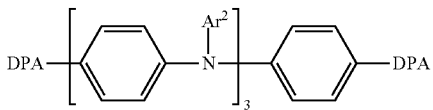

| Compound | Ar² |
|---|---|
| (J1-1) | (A1-1) |
| (J1-2) | (A1-2) |
| (J1-3) | (A2-1) |
| (J1-4) | (A2-2) |
| (J1-5) | (A2-3) |
| (J1-6) | (A2-4) |
| (J1-7) | (A2-5) |
| (J1-8) | (A3-1) |
| (J1-9) | (A3-2) |
| (J1-10) | (A3-3) |
| (J1-11) | (A4-1) |
| (J1-12) | (A4-2) |
| (J1-13) | (A4-3) |
| (J1-14) | (A5-1) |
| (J1-15) | (A5-2) |
| (J1-16) | (A5-3) |
| (J1-17) | (A6-1) |
| (J1-18) | (A6-2) |
| (J1-19) | (A6-3) |
| (J1-20) | (A6-4) |
| (J1-21) | (A6-5) |
| (J1-22) | (A6-6) |
| (J1-23) | (A6-7) |
| (J1-24) | (A6-8) |
| (J1-25) | (A6-9) |
| (J1-26) | (A6-10) |
| (J1-27) | (A6-11) |
| (J1-28) | (A6-12) |
| (J1-29) | (A6-13) |
| (J1-30) | (A6-14) |
| (J1-31) | (A6-15) |
| (J1-32) | (A7-1) |
| (J1-33) | (A7-2) |
| (J1-34) | (A7-3) |
| (J1-35) | (A8-1) |
| (J1-36) | (A8-2) |
| (J1-37) | (A8-3) |
| (J1-38) | (A9-1) |
| (J1-39) | (A9-2) |
| (J1-40) | (A9-3) |
| (J1-41) | (A10-1) |
| (J1-42) | (A10-2) |
| (J1-43) | (A10-3) |
| (J1-44) | (A11-1) |
| (J1-45) | (A11-2) |
| (J1-46) | (A11-3) |
| (J1-47) | (A12-1) |
| (J1-48) | (A12-2) |
| (J1-49) | (A12-3) |
| (J1-50) | (A12-4) |
| (J1-51) | (A12-5) |
| (J1-52) | (A12-6) |
| (J1-53) | (A12-7) |
| (J1-54) | (A12-8) |
| (J1-55) | (A12-9) |
| (J1-56) | (A12-10) |
| (J1-57) | (A12-11) |
| (J1-58) | (A13-1) |
| (J1-59) | (A13-2) |
| (J1-60) | (A13-3) |
| (J1-61) | (A13-4) |
| (J1-62) | (A13-5) |
| (J1-63) | (A13-6) |
| (J1-64) | (A13-7) |
| (J1-65) | (A13-8) |
| (J1-66) | (A13-9) |
| (J1-67) | (A13-10) |
| (J1-68) | (A13-11) |
| (J1-69) | (A13-12) |
| (J1-70) | (A13-13) |

TABLE-continued

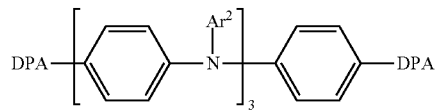

| Compound | Ar² |
|---|---|
| (J1-71) | (A13-14) |
| (J1-72) | (A13-15) |
| (J1-73) | (A13-16) |
| (J1-74) | (A13-17) |
| (J1-75) | (A13-18) |
| (J1-76) | (A13-19) |
| (J1-77) | (A13-20) |
| (J1-78) | (A13-21) |
| (J1-79) | (A13-22) |
| (J1-80) | (A13-23) |
| (J1-81) | (A13-24) |
| (J1-82) | (A14-1) |
| (J1-83) | (A14-2) |
| (J1-84) | (A14-3) |
| (J1-85) | (A14-4) |
| (J1-86) | (A15-1) |
| (J1-87) | (A15-2) |
| (J1-88) | (A15-3) |
| (J1-89) | (A15-4) |
| (J1-90) | (A17-1) |
| (J1-91) | (A17-2) |
| (J1-92) | (A17-3) |
| (J1-93) | (A17-4) |
| (J1-94) | (A17-5) |
| (J1-95) | (A17-6) |
| (J1-96) | (A17-7) |
| (J1-97) | (A17-8) |
| (J1-98) | (A17-9) |
| (J1-99) | (A17-10) |
| (J1-100) | (A17-11) |
| (J1-101) | (A17-12) |
| (J1-102) | (A18-1) |
| (J1-103) | (A18-2) |

TABLE 2

| Compound | Ar² |
|---|---|
| (J2-1) | (A1-1) |
| (J2-2) | (A1-2) |
| (J2-3) | (A2-1) |
| (J2-4) | (A2-2) |
| (J2-5) | (A2-3) |
| (J2-6) | (A2-4) |
| (J2-7) | (A2-5) |
| (J2-8) | (A3-1) |
| (J2-9) | (A3-2) |
| (J2-10) | (A3-3) |
| (J2-11) | (A4-1) |
| (J2-12) | (A4-2) |
| (J2-13) | (A4-3) |
| (J2-14) | (A5-1) |
| (J2-15) | (A5-2) |
| (J2-16) | (A5-3) |
| (J2-17) | (A6-1) |
| (J2-18) | (A6-2) |
| (J2-19) | (A6-3) |
| (J2-20) | (A6-4) |
| (J2-21) | (A6-5) |
| (J2-22) | (A6-6) |
| (J2-23) | (A6-7) |

TABLE 2-continued

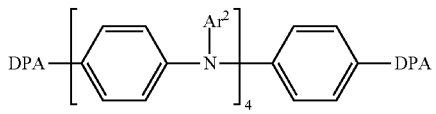

(J2)

| Compound | Ar² |
|---|---|
| (J2-24) | (A6-8) |
| (J2-25) | (A6-9) |
| (J2-26) | (A6-10) |
| (J2-27) | (A6-11) |
| (J2-28) | (A6-12) |
| (J2-29) | (A6-13) |
| (J2-30) | (A6-14) |
| (J2-31) | (A6-15) |
| (J2-32) | (A7-1) |
| (J2-33) | (A7-2) |
| (J2-34) | (A7-3) |
| (J2-35) | (A8-1) |
| (J2-36) | (A8-2) |
| (J2-37) | (A8-3) |
| (J2-38) | (A9-1) |
| (J2-39) | (A9-2) |
| (J2-40) | (A9-3) |
| (J2-41) | (A10-1) |
| (J2-42) | (A10-2) |
| (J2-43) | (A10-3) |
| (J2-44) | (A11-1) |
| (J2-45) | (A11-2) |
| (J2-46) | (A11-3) |
| (J2-47) | (A12-1) |
| (J2-48) | (A12-2) |
| (J2-49) | (A12-3) |
| (J2-50) | (A12-4) |
| (J2-51) | (A12-5) |
| (J2-52) | (A12-6) |
| (J2-53) | (A12-7) |
| (J2-54) | (A12-8) |
| (J2-55) | (A12-9) |
| (J2-56) | (A12-10) |
| (J2-57) | (A12-11) |
| (J2-58) | (A13-1) |
| (J2-59) | (A13-2) |
| (J2-60) | (A13-3) |
| (J2-61) | (A13-4) |
| (J2-62) | (A13-5) |
| (J2-63) | (A13-6) |
| (J2-64) | (A13-7) |
| (J2-65) | (A13-8) |
| (J2-66) | (A13-9) |
| (J2-67) | (A13-10) |
| (J2-68) | (A13-11) |
| (J2-69) | (A13-12) |
| (J2-70) | (A13-13) |
| (J2-71) | (A13-14) |
| (J2-72) | (A13-15) |
| (J2-73) | (A13-16) |
| (J2-74) | (A13-17) |
| (J2-75) | (A13-18) |
| (J2-76) | (A13-19) |
| (J2-77) | (A13-20) |
| (J2-78) | (A13-21) |
| (J2-79) | (A13-22) |
| (J2-80) | (A13-23) |
| (J2-81) | (A13-24) |
| (J2-82) | (A14-1) |
| (J2-83) | (A14-2) |
| (J2-84) | (A14-3) |
| (J2-85) | (A14-4) |
| (J2-86) | (A15-1) |
| (J2-87) | (A15-2) |
| (J2-88) | (A15-3) |
| (J2-89) | (A15-4) |
| (J2-90) | (A17-1) |
| (J2-91) | (A17-2) |
| (J2-92) | (A17-3) |
| (J2-93) | (A17-4) |

TABLE 2-continued

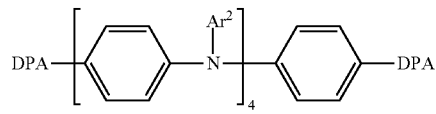

(J2)

| Compound | Ar² |
|---|---|
| (J2-94) | (A17-5) |
| (J2-95) | (A17-6) |
| (J2-96) | (A17-7) |
| (J2-97) | (A17-8) |
| (J2-98) | (A17-9) |
| (J2-99) | (A17-10) |
| (J2-100) | (A17-11) |
| (J2-101) | (A17-12) |
| (J2-102) | (A18-1) |
| (J2-103) | (A18-2) |

TABLE 3

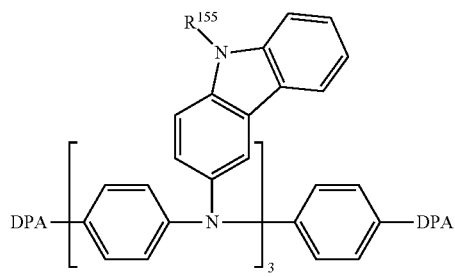

(J3)

| Compound | R¹⁵⁵ |
|---|---|
| (J3-1) | (N1) |
| (J3-2) | (N2) |
| (J3-3) | (N3) |
| (J3-4) | (N4) |
| (J3-5) | (N5) |
| (J3-6) | (N6) |
| (J3-7) | (N7) |
| (J3-8) | (N8) |
| (J3-9) | (N9) |
| (J3-10) | (N10) |
| (J3-11) | (N11) |
| (J3-12) | (N12) |
| (J3-13) | (N13) |
| (J3-14) | (N14) |
| (J3-15) | (N15) |
| (J3-16) | (N16) |
| (J3-17) | (N17) |
| (J3-18) | (N18) |
| (J3-19) | (N19) |
| (J3-20) | (N20) |
| (J3-21) | (N21) |
| (J3-22) | (N22) |
| (J3-23) | (N23) |
| (J3-24) | (N24) |
| (J3-25) | (N25) |
| (J3-26) | (N26) |
| (J3-27) | (N27) |
| (J3-28) | (N28) |
| (J3-29) | (N29) |
| (J3-30) | (N30) |
| (J3-31) | (N31) |
| (J3-32) | (N32) |
| (J3-33) | (N33) |
| (J3-34) | (N34) |
| (J3-35) | (N35) |
| (J3-36) | (N36) |
| (J3-37) | (N37) |
| (J3-38) | (N38) |
| (J3-39) | (N39) |

TABLE 3-continued

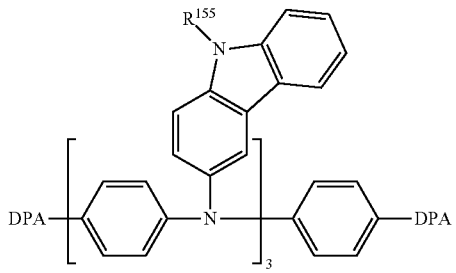

(J3)

| Compound | R¹⁵⁵ |
|---|---|
| (J3-40) | (N40) |
| (J3-41) | (N41) |
| (J3-42) | (N42) |
| (J3-43) | (N43) |
| (J3-44) | (N44) |
| (J3-45) | (N45) |
| (J3-46) | (N46) |
| (J3-47) | (N47) |
| (J3-48) | (N48) |
| (J3-49) | (N49) |
| (J3-50) | (N50) |
| (J3-51) | (N51) |
| (J3-52) | (N52) |
| (J3-53) | (N53) |
| (J3-54) | (N54) |
| (J3-55) | (N55) |
| (J3-56) | (N56) |
| (J3-57) | (N57) |
| (J3-58) | (N58) |
| (J3-59) | (N59) |
| (J3-60) | (N60) |
| (J3-61) | (N61) |
| (J3-62) | (N62) |
| (J3-63) | (N63) |
| (J3-64) | (N64) |
| (J3-65) | (N65) |
| (J3-66) | (N66) |
| (J3-67) | (N67) |
| (J3-68) | (N68) |
| (J3-69) | (N69) |
| (J3-70) | (N70) |
| (J3-71) | (N71) |
| (J3-72) | (N72) |
| (J3-73) | (N73) |
| (J3-74) | (N74) |
| (J3-75) | (N75) |
| (J3-76) | (N76) |
| (J3-77) | (N77) |
| (J3-78) | (N78) |
| (J3-95) | —H |
| (J3-96) | —Me |
| (J3-97) | —Et |
| (J3-98) | —Pr$^n$ |
| (J3-99) | —Pr$^i$ |
| (J3-100) | —Bu$^n$ |
| (J3-101) | —Bu$^i$ |
| (J3-102) | —Bu$^s$ |
| (J3-103) | —Bu$^t$ |

TABLE 4

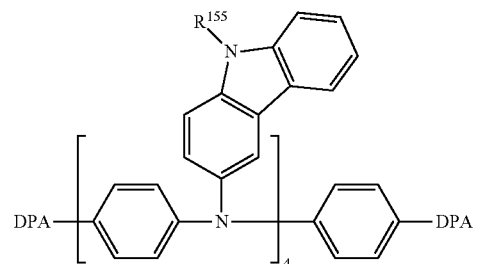

(J4)

| Compound | R¹⁵⁵ | Compound | R¹⁵⁵ | Compound | R¹⁵⁵ | Compound | R¹⁵⁵ |
|---|---|---|---|---|---|---|---|
| (J4-1) | (N1) | (J4-27) | (N27) | (J4-53) | (N53) | (J4-95) | —H |
| (J4-2) | (N2) | (J4-28) | (N28) | (J4-54) | (N54) | (J4-96) | —Me |
| (J4-3) | (N3) | (J4-29) | (N29) | (J4-55) | (N55) | (J4-97) | —Et |
| (J4-4) | (N4) | (J4-30) | (N30) | (J4-56) | (N56) | (J4-98) | —Pr$^n$ |
| (J4-5) | (N5) | (J4-31) | (N31) | (J4-57) | (N57) | (J4-99) | —Pr$^i$ |
| (J4-6) | (N6) | (J4-32) | (N32) | (J4-58) | (N58) | (J4-100) | —Bu$^n$ |
| (J4-7) | (N7) | (J4-33) | (N33) | (J4-59) | (N59) | (J4-101) | —Bu$^i$ |
| (J4-8) | (N8) | (J4-34) | (N34) | (J4-60) | (N60) | (J4-102) | —Bu$^s$ |
| (J4-9) | (N9) | (J4-35) | (N35) | (J4-61) | (N61) | (J4-103) | —Bu$^t$ |
| (J4-10) | (N10) | (J4-36) | (N36) | (J4-62) | (N62) | | |
| (J4-11) | (N11) | (J4-37) | (N37) | (J4-63) | (N63) | | |
| (J4-12) | (N12) | (J4-38) | (N38) | (J4-64) | (N64) | | |
| (J4-13) | (N13) | (J4-39) | (N39) | (J4-65) | (N65) | | |
| (J4-14) | (N14) | (J4-40) | (N40) | (J4-66) | (N66) | | |
| (J4-15) | (N15) | (J4-41) | (N41) | (J4-67) | (N67) | | |
| (J4-16) | (N16) | (J4-42) | (N42) | (J4-68) | (N68) | | |
| (J4-17) | (N17) | (J4-43) | (N43) | (J4-69) | (N69) | | |
| (J4-18) | (N18) | (J4-44) | (N44) | (J4-70) | (N70) | | |
| (J4-19) | (N19) | (J4-45) | (N45) | (J4-71) | (N71) | | |
| (J4-20) | (N20) | (J4-46) | (N46) | (J4-72) | (N72) | | |
| (J4-21) | (N21) | (J4-47) | (N47) | (J4-73) | (N73) | | |
| (J4-22) | (N22) | (J4-48) | (N48) | (J4-74) | (N74) | | |
| (J4-23) | (N23) | (J4-49) | (N49) | (J4-75) | (N75) | | |
| (J4-24) | (N24) | (J4-50) | (N50) | (J4-76) | (N76) | | |
| (J4-25) | (N25) | (J4-51) | (N51) | (J4-77) | (N77) | | |
| (J4-26) | (N26) | (J4-52) | (N52) | (J4-78) | (N78) | | |

TABLE 5

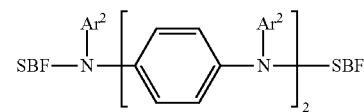

(J5)

| Compound | Ar² | Compound | Ar² |
|---|---|---|---|
| (J5-1) | (A1-1) | (J5-53) | (A12-7) |
| (J5-2) | (A1-2) | (J5-54) | (A12-8) |
| (J5-3) | (A2-1) | (J5-55) | (A12-9) |
| (J5-4) | (A2-2) | (J5-56) | (A12-10) |
| (J5-5) | (A2-3) | (J5-57) | (A12-11) |
| (J5-6) | (A2-4) | (J5-58) | (A13-1) |
| (J5-7) | (A2-5) | (J5-59) | (A13-2) |
| (J5-8) | (A3-1) | (J5-60) | (A13-3) |
| (J5-9) | (A3-2) | (J5-61) | (A13-4) |
| (J5-10) | (A3-3) | (J5-62) | (A13-5) |
| (J5-11) | (A4-1) | (J5-63) | (A13-6) |
| (J5-12) | (A4-2) | (J5-64) | (A13-7) |
| (J5-13) | (A4-3) | (J5-65) | (A13-8) |
| (J5-14) | (A5-1) | (J5-66) | (A13-9) |
| (J5-15) | (A5-2) | (J5-67) | (A13-10) |
| (J5-16) | (A5-3) | (J5-68) | (A13-11) |
| (J5-17) | (A6-1) | (J5-69) | (A13-12) |
| (J5-18) | (A6-2) | (J5-70) | (A13-13) |
| (J5-19) | (A6-3) | (J5-71) | (A13-14) |
| (J5-20) | (A6-4) | (J5-72) | (A13-15) |
| (J5-21) | (A6-5) | (J5-73) | (A13-16) |
| (J5-22) | (A6-6) | (J5-74) | (A13-17) |

TABLE 5-continued (J5)

SBF—N(Ar²)—[C₆H₄—N(Ar²)—SBF]₂

| Compound | Ar² | Compound | Ar² |
|---|---|---|---|
| (J5-23) | (A6-7) | (J5-75) | (A13-18) |
| (J5-24) | (A6-8) | (J5-76) | (A13-19) |
| (J5-25) | (A6-9) | (J5-77) | (A13-20) |
| (J5-26) | (A6-10) | (J5-78) | (A13-21) |
| (J5-27) | (A6-11) | (J5-79) | (A13-22) |
| (J5-28) | (A6-12) | (J5-80) | (A13-23) |
| (J5-29) | (A6-13) | (J5-81) | (A13-24) |
| (J5-30) | (A6-14) | (J5-82) | (A14-1) |
| (J5-31) | (A6-15) | (J5-83) | (A14-2) |
| (J5-32) | (A7-1) | (J5-84) | (A14-3) |
| (J5-33) | (A7-2) | (J5-85) | (A14-4) |
| (J5-34) | (A7-3) | (J5-86) | (A15-1) |
| (J5-35) | (A8-1) | (J5-87) | (A15-2) |
| (J5-36) | (A8-2) | (J5-88) | (A15-3) |
| (J5-37) | (A8-3) | (J5-89) | (A15-4) |
| (J5-38) | (A9-1) | (J5-90) | (A17-1) |
| (J5-39) | (A9-2) | (J5-91) | (A17-2) |
| (J5-40) | (A9-3) | (J5-92) | (A17-3) |
| (J5-41) | (A10-1) | (J5-93) | (A17-4) |
| (J5-42) | (A10-2) | (J5-94) | (A17-5) |
| (J5-43) | (A10-3) | (J5-95) | (A17-6) |
| (J5-44) | (A11-1) | (J5-96) | (A17-7) |
| (J5-45) | (A11-2) | (J5-97) | (A17-8) |
| (J5-46) | (A11-3) | (J5-98) | (A17-9) |
| (J5-47) | (A12-1) | (J5-99) | (A17-10) |
| (J5-48) | (A12-2) | (J5-100) | (A17-11) |
| (J5-49) | (A12-3) | (J5-101) | (A17-12) |
| (J5-50) | (A12-4) | (J5-102) | (A18-1) |
| (J5-51) | (A12-5) | (J5-103) | (A18-2) |
| (J5-52) | (A12-6) | | |

TABLE 6

(J6)

SBF—N(Ar²)—[C₆H₄—N(Ar²)—SBF]₃

| Compound | Ar² | Compound | Ar² |
|---|---|---|---|
| (J6-1) | (A1-1) | (J6-53) | (A12-7) |
| (J6-2) | (A1-2) | (J6-54) | (A12-8) |
| (J6-3) | (A2-1) | (J6-55) | (A12-9) |
| (J6-4) | (A2-2) | (J6-56) | (A12-10) |
| (J6-5) | (A2-3) | (J6-57) | (A12-11) |
| (J6-6) | (A2-4) | (J6-58) | (A13-1) |
| (J6-7) | (A2-5) | (J6-59) | (A13-2) |
| (J6-8) | (A3-1) | (J6-60) | (A13-3) |
| (J6-9) | (A3-2) | (J6-61) | (A13-4) |
| (J6-10) | (A3-3) | (J6-62) | (A13-5) |
| (J6-11) | (A4-1) | (J6-63) | (A13-6) |
| (J6-12) | (A4-2) | (J6-64) | (A13-7) |
| (J6-13) | (A4-3) | (J6-65) | (A13-8) |
| (J6-14) | (A5-1) | (J6-66) | (A13-9) |
| (J6-15) | (A5-2) | (J6-67) | (A13-10) |
| (J6-16) | (A5-3) | (J6-68) | (A13-11) |
| (J6-17) | (A6-1) | (J6-69) | (A13-12) |
| (J6-18) | (A6-2) | (J6-70) | (A13-13) |
| (J6-19) | (A6-3) | (J6-71) | (A13-14) |
| (J6-20) | (A6-4) | (J6-72) | (A13-15) |
| (J6-21) | (A6-5) | (J6-73) | (A13-16) |
| (J6-22) | (A6-6) | (J6-74) | (A13-17) |
| (J6-23) | (A6-7) | (J6-75) | (A13-18) |
| (J6-24) | (A6-8) | (J6-76) | (A13-19) |
| (J6-25) | (A6-9) | (J6-77) | (A13-20) |
| (J6-26) | (A6-10) | (J6-78) | (A13-21) |

TABLE 6-continued (J6)

SBF—N(Ar²)—[C₆H₄—N(Ar²)—SBF]₃

| Compound | Ar² | Compound | Ar² |
|---|---|---|---|
| (J6-27) | (A6-11) | (J6-79) | (A13-22) |
| (J6-28) | (A6-12) | (J6-80) | (A13-23) |
| (J6-29) | (A6-13) | (J6-81) | (A13-24) |
| (J6-30) | (A6-14) | (J6-82) | (A14-1) |
| (J6-31) | (A6-15) | (J6-83) | (A14-2) |
| (J6-32) | (A7-1) | (J6-84) | (A14-3) |
| (J6-33) | (A7-2) | (J6-85) | (A14-4) |
| (J6-34) | (A7-3) | (J6-86) | (A15-1) |
| (J6-35) | (A8-1) | (J6-87) | (A15-2) |
| (J6-36) | (A8-2) | (J6-88) | (A15-3) |
| (J6-37) | (A8-3) | (J6-89) | (A15-4) |
| (J6-38) | (A9-1) | (J6-90) | (A17-1) |
| (J6-39) | (A9-2) | (J6-91) | (A17-2) |
| (J6-40) | (A9-3) | (J6-92) | (A17-3) |
| (J6-41) | (A10-1) | (J6-93) | (A17-4) |
| (J6-42) | (A10-2) | (J6-94) | (A17-5) |
| (J6-43) | (A10-3) | (J6-95) | (A17-6) |
| (J6-44) | (A11-1) | (J6-96) | (A17-7) |
| (J6-45) | (A11-2) | (J6-97) | (A17-8) |
| (J6-46) | (A11-3) | (J6-98) | (A17-9) |
| (J6-47) | (A12-1) | (J6-99) | (A17-10) |
| (J6-48) | (A12-2) | (J6-100) | (A17-11) |
| (J6-49) | (A12-3) | (J6-101) | (A17-12) |
| (J6-50) | (A12-4) | (J6-102) | (A18-1) |
| (J6-51) | (A12-5) | (J6-103) | (A18-2) |
| (J6-52) | (A12-6) | | |

TABLE 7

(J7)

| Compound | R¹⁵⁵ | Compound | R¹⁵⁵ |
|---|---|---|---|
| (J7-1) | (N1) | (J7-45) | (N45) |
| (J7-2) | (N2) | (J7-46) | (N46) |
| (J7-3) | (N3) | (J7-47) | (N47) |
| (J7-4) | (N4) | (J7-48) | (N48) |
| (J7-5) | (N5) | (J7-49) | (N49) |
| (J7-6) | (N6) | (J7-50) | (N50) |
| (J7-7) | (N7) | (J7-51) | (N51) |
| (J7-8) | (N8) | (J7-52) | (N52) |
| (J7-9) | (N9) | (J7-53) | (N53) |
| (J7-10) | (N10) | (J7-54) | (N54) |
| (J7-11) | (N11) | (J7-55) | (N55) |
| (J7-12) | (N12) | (J7-56) | (N56) |
| (J7-13) | (N13) | (J7-57) | (N57) |
| (J7-14) | (N14) | (J7-58) | (N58) |
| (J7-15) | (N15) | (J7-59) | (N59) |
| (J7-16) | (N16) | (J7-60) | (N60) |
| (J7-17) | (N17) | (J7-61) | (N61) |
| (J7-18) | (N18) | (J7-62) | (N62) |
| (J7-19) | (N19) | (J7-63) | (N63) |
| (J7-20) | (N20) | (J7-64) | (N64) |
| (J7-21) | (N21) | (J7-65) | (N65) |
| (J7-22) | (N22) | (J7-66) | (N66) |
| (J7-23) | (N23) | (J7-67) | (N67) |

TABLE 7-continued

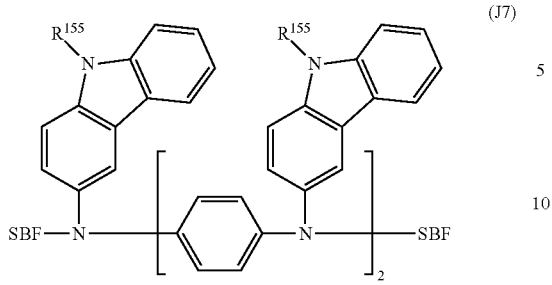
(J7)

| Compound | $R^{155}$ | Compound | $R^{155}$ |
|---|---|---|---|
| (J7-24) | (N24) | (J7-68) | (N68) |
| (J7-25) | (N25) | (J7-69) | (N69) |
| (J7-26) | (N26) | (J7-70) | (N70) |
| (J7-27) | (N27) | (J7-71) | (N71) |
| (J7-28) | (N28) | (J7-72) | (N72) |
| (J7-29) | (N29) | (J7-73) | (N73) |
| (J7-30) | (N30) | (J7-74) | (N74) |
| (J7-31) | (N31) | (J7-75) | (N75) |
| (J7-32) | (N32) | (J7-76) | (N76) |
| (J7-33) | (N33) | (J7-77) | (N77) |
| (J7-34) | (N34) | (J7-78) | (N78) |
| (J7-35) | (N35) | (J7-95) | —H |
| (J7-36) | (N36) | (J7-96) | —Me |
| (J7-37) | (N37) | (J7-97) | —Et |
| (J7-38) | (N38) | (J7-98) | —Pr$^n$ |
| (J7-39) | (N39) | (J7-99) | —Pr$^i$ |
| (J7-40) | (N40) | (J7-100) | —Bu$^n$ |
| (J7-41) | (N41) | (J7-101) | —Bu$^i$ |
| (J7-42) | (N42) | (J7-102) | —Bu$^s$ |
| (J7-43) | (N43) | (J7-103) | —Bu$^t$ |
| (J7-44) | (N44) | | |

TABLE 8

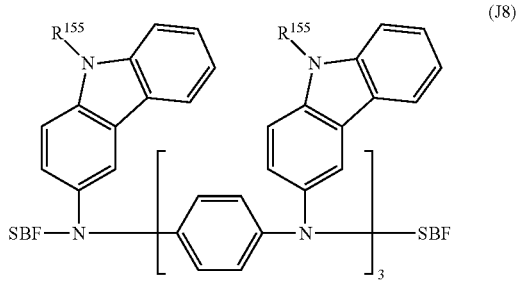
(J8)

| Compound | $R^{155}$ | Compound | $R^{155}$ |
|---|---|---|---|
| (J8-1) | (N1) | (J8-45) | (N45) |
| (J8-2) | (N2) | (J8-46) | (N46) |
| (J8-3) | (N3) | (J8-47) | (N47) |
| (J8-4) | (N4) | (J8-48) | (N48) |
| (J8-5) | (N5) | (J8-49) | (N49) |
| (J8-6) | (N6) | (J8-50) | (N50) |
| (J8-7) | (N7) | (J8-51) | (N51) |
| (J8-8) | (N8) | (J8-52) | (N52) |
| (J8-9) | (N9) | (J8-53) | (N53) |
| (J8-10) | (N10) | (J8-54) | (N54) |
| (J8-11) | (N11) | (J8-55) | (N55) |
| (J8-12) | (N12) | (J8-56) | (N56) |
| (J8-13) | (N13) | (J8-57) | (N57) |
| (J8-14) | (N14) | (J8-58) | (N58) |
| (J8-15) | (N15) | (J8-59) | (N59) |
| (J8-16) | (N16) | (J8-60) | (N60) |
| (J8-17) | (N17) | (J8-61) | (N61) |
| (J8-18) | (N18) | (J8-62) | (N62) |
| (J8-19) | (N19) | (J8-63) | (N63) |
| (J8-20) | (N20) | (J8-64) | (N64) |

TABLE 8-continued

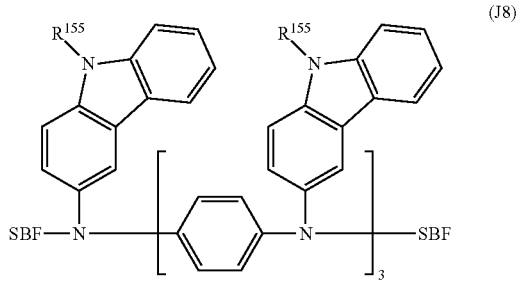
(J8)

| Compound | $R^{155}$ | Compound | $R^{155}$ |
|---|---|---|---|
| (J8-21) | (N21) | (J8-65) | (N65) |
| (J8-22) | (N22) | (J8-66) | (N66) |
| (J8-23) | (N23) | (J8-67) | (N67) |
| (J8-24) | (N24) | (J8-68) | (N68) |
| (J8-25) | (N25) | (J8-69) | (N69) |
| (J8-26) | (N26) | (J8-70) | (N70) |
| (J8-27) | (N27) | (J8-71) | (N71) |
| (J8-28) | (N28) | (J8-72) | (N72) |
| (J8-29) | (N29) | (J8-73) | (N73) |
| (J8-30) | (N30) | (J8-74) | (N74) |
| (J8-31) | (N31) | (J8-75) | (N75) |
| (J8-32) | (N32) | (J8-76) | (N76) |
| (J8-33) | (N33) | (J8-77) | (N77) |
| (J8-34) | (N34) | (J8-78) | (N78) |
| (J8-35) | (N35) | (J8-95) | —H |
| (J8-36) | (N36) | (J8-96) | —Me |
| (J8-37) | (N37) | (J8-97) | —Et |
| (J8-38) | (N38) | (J8-98) | —Pr$^n$ |
| (J8-39) | (N39) | (J8-99) | —Pr$^i$ |
| (J8-40) | (N40) | (J8-100) | —Bu$^n$ |
| (J8-41) | (N41) | (J8-101) | —Bu$^i$ |
| (J8-42) | (N42) | (J8-102) | —Bu$^s$ |
| (J8-43) | (N43) | (J8-103) | —Bu$^t$ |
| (J8-44) | (N44) | | |

TABLE 9

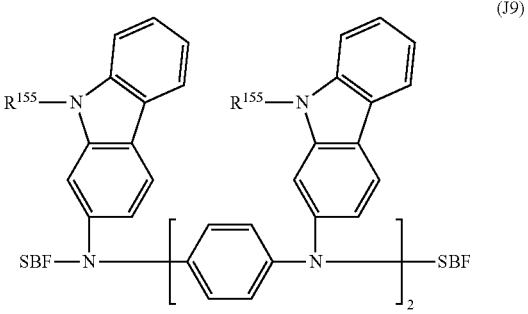
(J9)

| Compound | $R^{155}$ | Compound | $R^{155}$ |
|---|---|---|---|
| (J9-1) | (N1) | (J9-45) | (N45) |
| (J9-2) | (N2) | (J9-46) | (N46) |
| (J9-3) | (N3) | (J9-47) | (N47) |
| (J9-4) | (N4) | (J9-48) | (N48) |
| (J9-5) | (N5) | (J9-49) | (N49) |
| (J9-6) | (N6) | (J9-50) | (N50) |
| (J9-7) | (N7) | (J9-51) | (N51) |
| (J9-8) | (N8) | (J9-52) | (N52) |
| (J9-9) | (N9) | (J9-53) | (N53) |
| (J9-10) | (N10) | (J9-54) | (N54) |
| (J9-11) | (N11) | (J9-55) | (N55) |
| (J9-12) | (N12) | (J9-56) | (N56) |
| (J9-13) | (N13) | (J9-57) | (N57) |
| (J9-14) | (N14) | (J9-58) | (N58) |
| (J9-15) | (N15) | (J9-59) | (N59) |
| (J9-16) | (N16) | (J9-60) | (N60) |

TABLE 9-continued

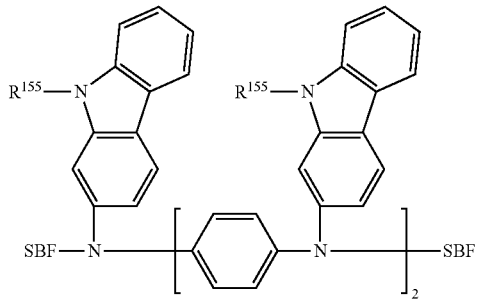

(J9)

| Compound | R¹⁵⁵ | Compound | R¹⁵⁵ |
|---|---|---|---|
| (J9-17) | (N17) | (J9-61) | (N61) |
| (J9-18) | (N18) | (J9-62) | (N62) |
| (J9-19) | (N19) | (J9-63) | (N63) |
| (J9-20) | (N20) | (J9-64) | (N64) |
| (J9-21) | (N21) | (J9-65) | (N65) |
| (J9-22) | (N22) | (J9-66) | (N66) |
| (J9-23) | (N23) | (J9-67) | (N67) |
| (J9-24) | (N24) | (J9-68) | (N68) |
| (J9-25) | (N25) | (J9-69) | (N69) |
| (J9-26) | (N26) | (J9-70) | (N70) |
| (J9-27) | (N27) | (J9-71) | (N71) |
| (J9-28) | (N28) | (J9-72) | (N72) |
| (J9-29) | (N29) | (J9-73) | (N73) |
| (J9-30) | (N30) | (J9-74) | (N74) |
| (J9-31) | (N31) | (J9-75) | (N75) |
| (J9-32) | (N32) | (J9-76) | (N76) |
| (J9-33) | (N33) | (J9-77) | (N77) |
| (J9-34) | (N34) | (J9-78) | (N78) |
| (J9-35) | (N35) | (J9-95) | —H |
| (J9-36) | (N36) | (J9-96) | —Me |
| (J9-37) | (N37) | (J9-97) | —Et |
| (J9-38) | (N38) | (J9-98) | —Prⁿ |
| (J9-39) | (N39) | (J9-99) | —Prⁱ |
| (J9-40) | (N40) | (J9-100) | —Buⁿ |
| (J9-41) | (N41) | (J9-101) | —Buⁱ |
| (J9-42) | (N42) | (J9-102) | —Buˢ |
| (J9-43) | (N43) | (J9-103) | —Buᵗ |
| (J9-44) | (N44) | | |

TABLE 10

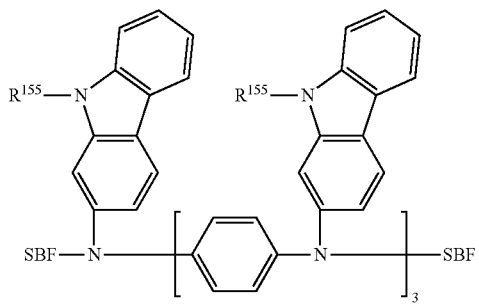

(J10)

| Compound | R¹⁵⁵ | Compound | R¹⁵⁵ |
|---|---|---|---|
| (J10-1) | (N1) | (J10-45) | (N45) |
| (J10-2) | (N2) | (J10-46) | (N46) |
| (J10-3) | (N3) | (J10-47) | (N47) |
| (J10-4) | (N4) | (J10-48) | (N48) |
| (J10-5) | (N5) | (J10-49) | (N49) |
| (J10-6) | (N6) | (J10-50) | (N50) |
| (J10-7) | (N7) | (J10-51) | (N51) |
| (J10-8) | (N8) | (J10-52) | (N52) |
| (J10-9) | (N9) | (J10-53) | (N53) |
| (J10-10) | (N10) | (J10-54) | (N54) |

TABLE 10-continued

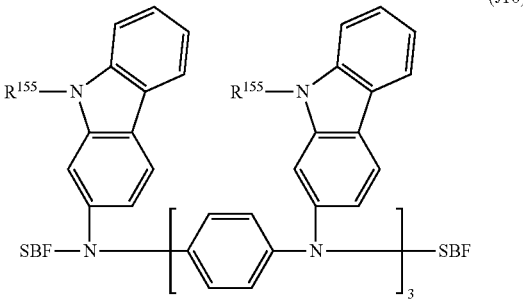

(J10)

| Compound | R¹⁵⁵ | Compound | R¹⁵⁵ |
|---|---|---|---|
| (J10-11) | (N11) | (J10-55) | (N55) |
| (J10-12) | (N12) | (J10-56) | (N56) |
| (J10-13) | (N13) | (J10-57) | (N57) |
| (J10-14) | (N14) | (J10-58) | (N58) |
| (J10-15) | (N15) | (J10-59) | (N59) |
| (J10-16) | (N16) | (J10-60) | (N60) |
| (J10-17) | (N17) | (J10-61) | (N61) |
| (J10-18) | (N18) | (J10-62) | (N62) |
| (J10-19) | (N19) | (J10-63) | (N63) |
| (J10-20) | (N20) | (J10-64) | (N64) |
| (J10-21) | (N21) | (J10-65) | (N65) |
| (J10-22) | (N22) | (J10-66) | (N66) |
| (J10-23) | (N23) | (J10-67) | (N67) |
| (J10-24) | (N24) | (J10-68) | (N68) |
| (J10-25) | (N25) | (J10-69) | (N69) |
| (J10-26) | (N26) | (J10-70) | (N70) |
| (J10-27) | (N27) | (J10-71) | (N71) |
| (J10-28) | (N28) | (J10-72) | (N72) |
| (J10-29) | (N29) | (J10-73) | (N73) |
| (J10-30) | (N30) | (J10-74) | (N74) |
| (J10-31) | (N31) | (J10-75) | (N75) |
| (J10-32) | (N32) | (J10-76) | (N76) |
| (J10-33) | (N33) | (J10-77) | (N77) |
| (J10-34) | (N34) | (J10-78) | (N78) |
| (J10-35) | (N35) | (J10-95) | —H |
| (J10-36) | (N36) | (J10-96) | —Me |
| (J10-37) | (N37) | (J10-97) | —Et |
| (J10-38) | (N38) | (J10-98) | —Prⁿ |
| (J10-39) | (N39) | (J10-99) | —Prⁱ |
| (J10-40) | (N40) | (J10-100) | —Buⁿ |
| (J10-41) | (N41) | (J10-101) | —Buⁱ |
| (J10-42) | (N42) | (J10-102) | —Buˢ |
| (J10-43) | (N43) | (J10-103) | —Buᵗ |
| (J10-44) | (N44) | | |

TABLE 11

(J11)

| Compound | R¹⁵⁵ | Compound | R¹⁵⁵ |
|---|---|---|---|
| (J11-1) | (N1) | (J11-45) | (N45) |
| (J11-2) | (N2) | (J11-46) | (N46) |
| (J11-3) | (N3) | (J11-47) | (N47) |
| (J11-4) | (N4) | (J11-48) | (N48) |
| (J11-5) | (N5) | (J11-49) | (N49) |
| (J11-6) | (N6) | (J11-50) | (N50) |
| (J11-7) | (N7) | (J11-51) | (N51) |
| (J11-8) | (N8) | (J11-52) | (N52) |
| (J11-9) | (N9) | (J11-53) | (N53) |

TABLE 11-continued (J11)

| Compound | R¹⁵⁵ | Compound | R¹⁵⁵ |
|---|---|---|---|
| (J11-10) | (N10) | (J11-54) | (N54) |
| (J11-11) | (N11) | (J11-55) | (N55) |
| (J11-12) | (N12) | (J11-56) | (N56) |
| (J11-13) | (N13) | (J11-57) | (N57) |
| (J11-14) | (N14) | (J11-58) | (N58) |
| (J11-15) | (N15) | (J11-59) | (N59) |
| (J11-16) | (N16) | (J11-60) | (N60) |
| (J11-17) | (N17) | (J11-61) | (N61) |
| (J11-18) | (N18) | (J11-62) | (N62) |
| (J11-19) | (N19) | (J11-63) | (N63) |
| (J11-20) | (N20) | (J11-64) | (N64) |
| (J11-21) | (N21) | (J11-65) | (N65) |
| (J11-22) | (N22) | (J11-66) | (N66) |
| (J11-23) | (N23) | (J11-67) | (N67) |
| (J11-24) | (N24) | (J11-68) | (N68) |
| (J11-25) | (N25) | (J11-69) | (N69) |
| (J11-26) | (N26) | (J11-70) | (N70) |
| (J11-27) | (N27) | (J11-71) | (N71) |
| (J11-28) | (N28) | (J11-72) | (N72) |
| (J11-29) | (N29) | (J11-73) | (N73) |
| (J11-30) | (N30) | (J11-74) | (N74) |
| (J11-31) | (N31) | (J11-75) | (N75) |
| (J11-32) | (N32) | (J11-76) | (N76) |
| (J11-33) | (N33) | (J11-77) | (N77) |
| (J11-34) | (N34) | (J11-78) | (N78) |
| (J11-35) | (N35) | (J11-95) | —H |
| (J11-36) | (N36) | (J11-96) | —Me |
| (J11-37) | (N37) | (J11-97) | —Et |
| (J11-38) | (N38) | (J11-98) | —Pr$^n$ |
| (J11-39) | (N39) | (J11-99) | —Pr$^i$ |
| (J11-40) | (N40) | (J11-100) | —Bu$^n$ |
| (J11-41) | (N41) | (J11-101) | —Bu$^i$ |
| (J11-42) | (N42) | (J11-102) | —Bu$^s$ |
| (J11-43) | (N43) | (J11-103) | —Bu$^t$ |
| (J11-44) | (N44) | | |

TABLE 12

(J12)

| Compound | R¹⁵⁵ | Compound | R¹⁵⁵ |
|---|---|---|---|
| (J12-1) | (N1) | (J12-45) | (N45) |
| (J12-2) | (N2) | (J12-46) | (N46) |
| (J12-3) | (N3) | (J12-47) | (N47) |
| (J12-4) | (N4) | (J12-48) | (N48) |
| (J12-5) | (N5) | (J12-49) | (N49) |
| (J12-6) | (N6) | (J12-50) | (N50) |
| (J12-7) | (N7) | (J12-51) | (N51) |
| (J12-8) | (N8) | (J12-52) | (N52) |
| (J12-9) | (N9) | (J12-53) | (N53) |
| (J12-10) | (N10) | (J12-54) | (N54) |
| (J12-11) | (N11) | (J12-55) | (N55) |
| (J12-12) | (N12) | (J12-56) | (N56) |

TABLE 12-continued (J12)

| Compound | R¹⁵⁵ | Compound | R¹⁵⁵ |
|---|---|---|---|
| (J12-13) | (N13) | (J12-57) | (N57) |
| (J12-14) | (N14) | (J12-58) | (N58) |
| (J12-15) | (N15) | (J12-59) | (N59) |
| (J12-16) | (N16) | (J12-60) | (N60) |
| (J12-17) | (N17) | (J12-61) | (N61) |
| (J12-18) | (N18) | (J12-62) | (N62) |
| (J12-19) | (N19) | (J12-63) | (N63) |
| (J12-20) | (N20) | (J12-64) | (N64) |
| (J12-21) | (N21) | (J12-65) | (N65) |
| (J12-22) | (N22) | (J12-66) | (N66) |
| (J12-23) | (N23) | (J12-67) | (N67) |
| (J12-24) | (N24) | (J12-68) | (N68) |
| (J12-25) | (N25) | (J12-69) | (N69) |
| (J12-26) | (N26) | (J12-70) | (N70) |
| (J12-27) | (N27) | (J12-71) | (N71) |
| (J12-28) | (N28) | (J12-72) | (N72) |
| (J12-29) | (N29) | (J12-73) | (N73) |
| (J12-30) | (N30) | (J12-74) | (N74) |
| (J12-31) | (N31) | (J12-75) | (N75) |
| (J12-32) | (N32) | (J12-76) | (N76) |
| (J12-33) | (N33) | (J12-77) | (N77) |
| (J12-34) | (N34) | (J12-78) | (N78) |
| (J12-35) | (N35) | (J12-95) | —H |
| (J12-36) | (N36) | (J12-96) | —Me |
| (J12-37) | (N37) | (J12-97) | —Et |
| (J12-38) | (N38) | (J12-98) | —Pr$^n$ |
| (J12-39) | (N39) | (J12-99) | —Pr$^i$ |
| (J12-40) | (N40) | (J12-100) | —Bu$^n$ |
| (J12-41) | (N41) | (J12-101) | —Bu$^i$ |
| (J12-42) | (N42) | (J12-102) | —Bu$^s$ |
| (J12-43) | (N43) | (J12-103) | —Bu$^t$ |
| (J12-44) | (N44) | | |

TABLE 13

(J13)

| Compound | R¹⁵⁵ | Compound | R¹⁵⁵ |
|---|---|---|---|
| (J13-1) | (N1) | (J13-45) | (N45) |
| (J13-2) | (N2) | (J13-46) | (N46) |
| (J13-3) | (N3) | (J13-47) | (N47) |
| (J13-4) | (N4) | (J13-48) | (N48) |
| (J13-5) | (N5) | (J13-49) | (N49) |
| (J13-6) | (N6) | (J13-50) | (N50) |
| (J13-7) | (N7) | (J13-51) | (N51) |
| (J13-8) | (N8) | (J13-52) | (N52) |
| (J13-9) | (N9) | (J13-53) | (N53) |
| (J13-10) | (N10) | (J13-54) | (N54) |
| (J13-11) | (N11) | (J13-55) | (N55) |
| (J13-12) | (N12) | (J13-56) | (N56) |
| (J13-13) | (N13) | (J13-57) | (N57) |
| (J13-14) | (N14) | (J13-58) | (N58) |
| (J13-15) | (N15) | (J13-59) | (N59) |

TABLE 13-continued (J13)

| Compound | R¹⁵⁵ | Compound | R¹⁵⁵ |
|---|---|---|---|
| (J13-16) | (N16) | (J13-60) | (N60) |
| (J13-17) | (N17) | (J13-61) | (N61) |
| (J13-18) | (N18) | (J13-62) | (N62) |
| (J13-19) | (N19) | (J13-63) | (N63) |
| (J13-20) | (N20) | (J13-64) | (N64) |
| (J13-21) | (N21) | (J13-65) | (N65) |
| (J13-22) | (N22) | (J13-66) | (N66) |
| (J13-23) | (N23) | (J13-67) | (N67) |
| (J13-24) | (N24) | (J13-68) | (N68) |
| (J13-25) | (N25) | (J13-69) | (N69) |
| (J13-26) | (N26) | (J13-70) | (N70) |
| (J13-27) | (N27) | (J13-71) | (N71) |
| (J13-28) | (N28) | (J13-72) | (N72) |
| (J13-29) | (N29) | (J13-73) | (N73) |
| (J13-30) | (N30) | (J13-74) | (N74) |
| (J13-31) | (N31) | (J13-75) | (N75) |
| (J13-32) | (N32) | (J13-76) | (N76) |
| (J13-33) | (N33) | (J13-77) | (N77) |
| (J13-34) | (N34) | (J13-78) | (N78) |
| (J13-35) | (N35) | (J13-95) | —H |
| (J13-36) | (N36) | (J13-96) | —Me |
| (J13-37) | (N37) | (J13-97) | —Et |
| (J13-38) | (N38) | (J13-98) | —Prⁿ |
| (J13-39) | (N39) | (J13-99) | —Prⁱ |
| (J13-40) | (N40) | (J13-100) | —Buⁿ |
| (J13-41) | (N41) | (J13-101) | —Buⁱ |
| (J13-42) | (N42) | (J13-102) | —Buˢ |
| (J13-43) | (N43) | (J13-103) | —Buᵗ |
| (J13-44) | (N44) | | |

TABLE 14

(J14)

| Compound | R¹⁵⁵ | Compound | R¹⁵⁵ |
|---|---|---|---|
| (J14-1) | (N1) | (J14-45) | (N45) |
| (J14-2) | (N2) | (J14-46) | (N46) |
| (J14-3) | (N3) | (J14-47) | (N47) |
| (J14-4) | (N4) | (J14-48) | (N48) |
| (J14-5) | (N5) | (J14-49) | (N49) |
| (J14-6) | (N6) | (J14-50) | (N50) |
| (J14-7) | (N7) | (J14-51) | (N51) |
| (J14-8) | (N8) | (J14-52) | (N52) |
| (J14-9) | (N9) | (J14-53) | (N53) |
| (J14-10) | (N10) | (J14-54) | (N54) |
| (J14-11) | (N11) | (J14-55) | (N55) |
| (J14-12) | (N12) | (J14-56) | (N56) |
| (J14-13) | (N13) | (J14-57) | (N57) |
| (J14-14) | (N14) | (J14-58) | (N58) |
| (J14-15) | (N15) | (J14-59) | (N59) |
| (J14-16) | (N16) | (J14-60) | (N60) |
| (J14-17) | (N17) | (J14-61) | (N61) |

TABLE 14-continued (J14)

| Compound | R¹⁵⁵ | Compound | R¹⁵⁵ |
|---|---|---|---|
| (J14-18) | (N18) | (J14-62) | (N62) |
| (J14-19) | (N19) | (J14-63) | (N63) |
| (J14-20) | (N20) | (J14-64) | (N64) |
| (J14-21) | (N21) | (J14-65) | (N65) |
| (J14-22) | (N22) | (J14-66) | (N66) |
| (J14-23) | (N23) | (J14-67) | (N67) |
| (J14-24) | (N24) | (J14-68) | (N68) |
| (J14-25) | (N25) | (J14-69) | (N69) |
| (J14-26) | (N26) | (J14-70) | (N70) |
| (J14-27) | (N27) | (J14-71) | (N71) |
| (J14-28) | (N28) | (J14-72) | (N72) |
| (J14-29) | (N29) | (J14-73) | (N73) |
| (J14-30) | (N30) | (J14-74) | (N74) |
| (J14-31) | (N31) | (J14-75) | (N75) |
| (J14-32) | (N32) | (J14-76) | (N76) |
| (J14-33) | (N33) | (J14-77) | (N77) |
| (J14-34) | (N34) | (J14-78) | (N78) |
| (J14-35) | (N35) | (J14-95) | —H |
| (J14-36) | (N36) | (J14-96) | —Me |
| (J14-37) | (N37) | (J14-97) | —Et |
| (J14-38) | (N38) | (J14-98) | —Prⁿ |
| (J14-39) | (N39) | (J14-99) | —Prⁱ |
| (J14-40) | (N40) | (J14-100) | —Buⁿ |
| (J14-41) | (N41) | (J14-101) | —Buⁱ |
| (J14-42) | (N42) | (J14-102) | —Buˢ |
| (J14-43) | (N43) | (J14-103) | —Buᵗ |
| (J14-44) | (N44) | | |

TABLE 15

(J15)

| Compound | Ar² | Compound | Ar² |
|---|---|---|---|
| (J15-1) | (A1-1) | (J15-53) | (A12-7) |
| (J15-2) | (A1-2) | (J15-54) | (A12-8) |
| (J15-3) | (A2-1) | (J15-55) | (A12-9) |
| (J15-4) | (A2-2) | (J15-56) | (A12-10) |
| (J15-5) | (A2-3) | (J15-57) | (A12-11) |
| (J15-6) | (A2-4) | (J15-58) | (A13-1) |
| (J15-7) | (A2-5) | (J15-59) | (A13-2) |
| (J15-8) | (A3-1) | (J15-60) | (A13-3) |
| (J15-9) | (A3-2) | (J15-61) | (A13-4) |
| (J15-10) | (A3-3) | (J15-62) | (A13-5) |
| (J15-11) | (A4-1) | (J15-63) | (A13-6) |
| (J15-12) | (A4-2) | (J15-64) | (A13-7) |
| (J15-13) | (A4-3) | (J15-65) | (A13-8) |
| (J15-14) | (A5-1) | (J15-66) | (A13-9) |
| (J15-15) | (A5-2) | (J15-67) | (A13-10) |
| (J15-16) | (A5-3) | (J15-68) | (A13-11) |
| (J15-17) | (A6-1) | (J15-69) | (A13-12) |
| (J15-18) | (A6-2) | (J15-70) | (A13-13) |
| (J15-19) | (A6-3) | (J15-71) | (A13-14) |
| (J15-20) | (A6-4) | (J15-72) | (A13-15) |
| (J15-21) | (A6-5) | (J15-73) | (A13-16) |
| (J15-22) | (A6-6) | (J15-74) | (A13-17) |
| (J15-23) | (A6-7) | (J15-75) | (A13-18) |
| (J15-24) | (A6-8) | (J15-76) | (A13-19) |

TABLE 15-continued

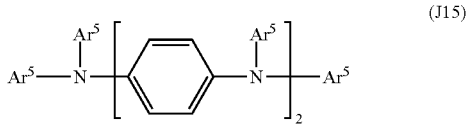
(J15)

| Compound | Ar² | Compound | Ar² |
|---|---|---|---|
| (J15-25) | (A6-9) | (J15-77) | (A13-20) |
| (J15-26) | (A6-10) | (J15-78) | (A13-21) |
| (J15-27) | (A6-11) | (J15-79) | (A13-22) |
| (J15-28) | (A6-12) | (J15-80) | (A13-23) |
| (J15-29) | (A6-13) | (J15-81) | (A13-24) |
| (J15-30) | (A6-14) | (J15-82) | (A14-1) |
| (J15-31) | (A6-15) | (J15-83) | (A14-2) |
| (J15-32) | (A7-1) | (J15-84) | (A14-3) |
| (J15-33) | (A7-2) | (J15-85) | (A14-4) |
| (J15-34) | (A7-3) | (J15-86) | (A15-1) |
| (J15-35) | (A8-1) | (J15-87) | (A15-2) |
| (J15-36) | (A8-2) | (J15-88) | (A15-3) |
| (J15-37) | (A8-3) | (J15-89) | (A15-4) |
| (J15-38) | (A9-1) | (J15-90) | (A17-1) |
| (J15-39) | (A9-2) | (J15-91) | (A17-2) |
| (J15-40) | (A9-3) | (J15-92) | (A17-3) |
| (J15-41) | (A10-1) | (J15-93) | (A17-4) |
| (J15-42) | (A10-2) | (J15-94) | (A17-5) |
| (J15-43) | (A10-3) | (J15-95) | (A17-6) |
| (J15-44) | (A11-1) | (J15-96) | (A17-7) |
| (J15-45) | (A11-2) | (J15-97) | (A17-8) |
| (J15-46) | (A11-3) | (J15-98) | (A17-9) |
| (J15-47) | (A12-1) | (J15-99) | (A17-10) |
| (J15-48) | (A12-2) | (J15-100) | (A17-11) |
| (J15-49) | (A12-3) | (J15-101) | (A17-12) |
| (J15-50) | (A12-4) | (J15-102) | (A18-1) |
| (J15-51) | (A12-5) | (J15-103) | (A18-2) |
| (J15-52) | (A12-6) | | |

TABLE 16

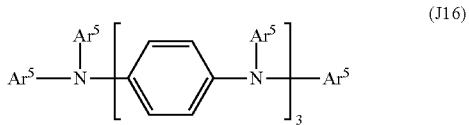
(J16)

| Compound | Ar² | Compound | Ar² |
|---|---|---|---|
| (J16-1) | (A1-1) | (J16-53) | (A12-7) |
| (J16-2) | (A1-2) | (J16-54) | (A12-8) |
| (J16-3) | (A2-1) | (J16-55) | (A12-9) |
| (J16-4) | (A2-2) | (J16-56) | (A12-10) |
| (J16-5) | (A2-3) | (J16-57) | (A12-11) |
| (J16-6) | (A2-4) | (J16-58) | (A13-1) |
| (J16-7) | (A2-5) | (J16-59) | (A13-2) |
| (J16-8) | (A3-1) | (J16-60) | (A13-3) |
| (J16-9) | (A3-2) | (J16-61) | (A13-4) |
| (J16-10) | (A3-3) | (J16-62) | (A13-5) |
| (J16-11) | (A4-1) | (J16-63) | (A13-6) |
| (J16-12) | (A4-2) | (J16-64) | (A13-7) |
| (J16-13) | (A4-3) | (J16-65) | (A13-8) |
| (J16-14) | (A5-1) | (J16-66) | (A13-9) |
| (J16-15) | (A5-2) | (J16-67) | (A13-10) |
| (J16-16) | (A5-3) | (J16-68) | (A13-11) |
| (J16-17) | (A6-1) | (J16-69) | (A13-12) |
| (J16-18) | (A6-2) | (J16-70) | (A13-13) |
| (J16-19) | (A6-3) | (J16-71) | (A13-14) |
| (J16-20) | (A6-4) | (J16-72) | (A13-15) |
| (J16-21) | (A6-5) | (J16-73) | (A13-16) |
| (J16-22) | (A6-6) | (J16-74) | (A13-17) |
| (J16-23) | (A6-7) | (J16-75) | (A13-18) |
| (J16-24) | (A6-8) | (J16-76) | (A13-19) |
| (J16-25) | (A6-9) | (J16-77) | (A13-20) |
| (J16-26) | (A6-10) | (J16-78) | (A13-21) |
| (J16-27) | (A6-11) | (J16-79) | (A13-22) |
| (J16-28) | (A6-12) | (J16-80) | (A13-23) |

TABLE 16-continued

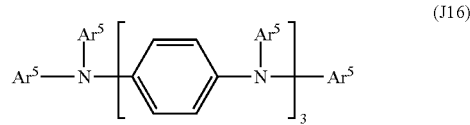
(J16)

| Compound | Ar² | Compound | Ar² |
|---|---|---|---|
| (J16-29) | (A6-13) | (J16-81) | (A13-24) |
| (J16-30) | (A6-14) | (J16-82) | (A14-1) |
| (J16-31) | (A6-15) | (J16-83) | (A14-2) |
| (J16-32) | (A7-1) | (J16-84) | (A14-3) |
| (J16-33) | (A7-2) | (J16-85) | (A14-4) |
| (J16-34) | (A7-3) | (J16-86) | (A15-1) |
| (J16-35) | (A8-1) | (J16-87) | (A15-2) |
| (J16-36) | (A8-2) | (J16-88) | (A15-3) |
| (J16-37) | (A8-3) | (J16-89) | (A15-4) |
| (J16-38) | (A9-1) | (J16-90) | (A17-1) |
| (J16-39) | (A9-2) | (J16-91) | (A17-2) |
| (J16-40) | (A9-3) | (J16-92) | (A17-3) |
| (J16-41) | (A10-1) | (J16-93) | (A17-4) |
| (J16-42) | (A10-2) | (J16-94) | (A17-5) |
| (J16-43) | (A10-3) | (J16-95) | (A17-6) |
| (J16-44) | (A11-1) | (J16-96) | (A17-7) |
| (J16-45) | (A11-2) | (J16-97) | (A17-8) |
| (J16-46) | (A11-3) | (J16-98) | (A17-9) |
| (J16-47) | (A12-1) | (J16-99) | (A17-10) |
| (J16-48) | (A12-2) | (J16-100) | (A17-11) |
| (J16-49) | (A12-3) | (J16-101) | (A17-12) |
| (J16-50) | (A12-4) | (J16-102) | (A18-1) |
| (J16-51) | (A12-5) | (J16-103) | (A18-2) |
| (J16-52) | (A12-6) | | |

TABLE 17

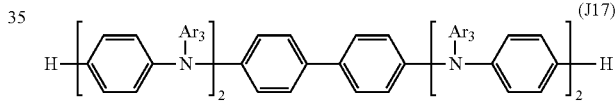
(J17)

| Compound | Ar³ |
|---|---|
| (J17-1) | (C1') |
| (J17-2) | (C2') |
| (J17-3) | (C3') |
| (J17-4) | (C4') |
| (J17-5) | (C5') |
| (J17-6) | (C6') |
| (J17-7) | (C7') |
| (J17-8) | (C8') |

TABLE 18

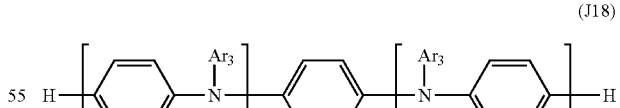
(J18)

| Compound | Ar³ |
|---|---|
| (J18-1) | (C1') |
| (J18-2) | (C2') |
| (J18-3) | (C3') |
| (J18-4) | (C4') |
| (J18-5) | (C5') |
| (J18-6) | (C6') |
| (J18-7) | (C7') |
| (J18-8) | (C8') |

The charge transporting varnish of the present invention contains the charge transporting substance including the aniline derivative represented by the formula (1) or (2), and the organic solvent, and, according to the use of the thin film obtained, may contain a dopant substance for the purpose of enhancing the charge transporting performance thereof.

The dopant substance is not specifically restricted so long as the dopant substance is soluble in at least one solvent used for the varnish. Both inorganic dopant substances and organic dopant substances can be used.

Besides, the inorganic and organic dopant substances may be used either singly or in combination of at least two of them.

Particularly, in the present invention, the inorganic dopant substance is preferably a heteropoly-acid.

The heteropoly-acid is a poly-acid which has a structure having a hetero atom located in the center of the molecule, typically represented by a Keggin type chemical structure represented by the formula (H1) or a Dawson type chemical structure represented by the formula (H2), and in which an isopoly-acid as an oxoacid of vanadium (V), molybdenum (Mo), and tungsten (W) and an oxoacid of a different element are condensed with each other. Examples of such an oxoacid of a different element mainly include oxoacids of silicon (Si), phosphorus (P), and arsenic (As).

[Chemical Formula 118]

(H1)

(H2)

Specific examples of the heteropoly-acid include phosphomolybdic acid, silicomolybdic acid, phosphotungstic acid, silicotungstic acid, and phosphotungstomolybdic acid, and these may be used either singly or in combination of at least two of them. Note that the heteropoly-acids for use in the present invention are commercially available and can be synthesized by known methods.

Particularly, in the case of using one kind of heteropoly-acid, the one kind of heteropoly-acid is preferably phosphotungstic acid or phosphomolybdic acid, and most preferably phosphotungstic acid. In addition, in the case of using at least two kinds of heteropoly-acids, one of the at least two kinds of heteropoly-acids is preferably phosphotungstic acid or phosphomolybdic acid, and more preferably phosphotungstic acid.

Note that even where a heteropoly-acid found by quantitative analysis such as elementary analysis to contain an element in a number greater than or smaller than the number in the structure represented by a general formula, the heteropoly-acid can be used in the present invention so long as the heteropoly-acid is obtained as a commercialized product or is properly synthesized according to a known method of synthesis.

For example, in general, phosphotungstic acid is represented by the chemical formula $H_3(PW_{12}O_{40}) \cdot nH_2O$, and phosphomolybdic acid is represented by the chemical formula $H_3(PMo_{12}O_{40}) \cdot nH_2O$. Where phosphotungstic acid or phosphomolybdic acid is found by quantitative analysis to contain P (phosphorus), O (oxygen) and one of W (tungsten) and Mo (molybdenum) in a number greater or smaller than the number in the chemical formula, the phosphotungstic acid or phosphomolybdic acid can be used in the present invention so long as it is obtained as a commercialized product or is properly synthesized according to a known method of synthesis. In this case, the weight of the heteropoly-acid prescribed in the present invention is not the weight of pure phosphotungstic acid (phosphotungstic acid content) in the synthesized product or commercialized product but means the total weight in the state of containing water of hydration and other impurities, in a commercially available form or in the form of being isolatable by a known method of synthesis.

The heteropoly-acid contained in the charge transporting varnish of the present invention can be approximately 0.001 to 50.0, preferably approximately 0.01 to 20.0, and more preferably approximately 0.1 to 10.0, in weight ratio relative to 1 of the charge transporting substance including the aniline derivative represented by the formula (1) or formula (2).

Besides, the organic dopant substance is preferably a tetracyanoquinodimethane derivative or a benzoquinone derivative, particularly.

Specific examples of the tetracyanoquinodimethane include 7,7,8,8-tetracyanoquinodimethane (TCNQ) or halo-tetracyanoquinodimethanes represented by the formula (H3).

In addition, specific examples of the benzoquinone derivative include tetrafluoro-1,4-benzoquinone (F4BQ), tetrachloro-1,4-benzoquinone (chloranil), tetrabromo-1,4-benzoquinone, and 2,3-dichloro-5,6-dicyano-1,4-benzoquinone (DDQ).

[Chemical Formula 119]

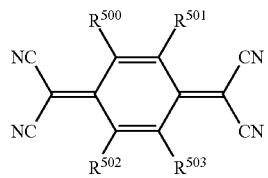

(H3)

In the formula, $R^{500}$ to $R^{503}$ independently represent a hydrogen atom or a halogen atom, at least one of them is a halogen atom, preferably at least two of them are halogen atoms, more preferably at least three of them are halogen atoms, and most preferably all of them are halogen atoms.

Examples of the halogen atom include the same atoms as above-mentioned, and the halogen atom is preferably a fluorine atom or a chlorine atom, more preferably a fluorine atom.

Specific examples of such a halotetracyanoquinodimethane include 2-fluoro-7,7,8,8-tetracyanoquinodimethane, 2-chloro-7,7,8,8-tetracyanoquinodimethane, 2,5-difluoro-7,7,8,8-tetracyanoquinodimethane, 2,5-dichloro-7,7,8,8-tetracyanoquinodimethane, 2,3,5,6-tetrachloro-7,7,8,8-tetracyanoquinodimethane, and 2,3,5,6-tetrafluoro-7,7,8,8-tetracyanoquinodimethane (F4TCNQ).

The content of the tetracyanoquinodimethane derivative and the benzoquinone derivative in the charge transporting varnish of the present invention is preferably 0.0001 to 100 equivalents, more preferably 0.01 to 50 equivalents, and further preferably 1 to 20 equivalents, relative to the aniline derivative represented by the formula (1) or formula (2).

Besides, in the case where the varnish contains the aniline derivative represented by the formula (1) wherein $Ar^1$ or $Ar^2$ is a group represented by any of the formulas (F2-1) to (F5-1), an arylsulfonic acid compound can also be preferably used as the dopant substance.

[Chemical Formula 120]

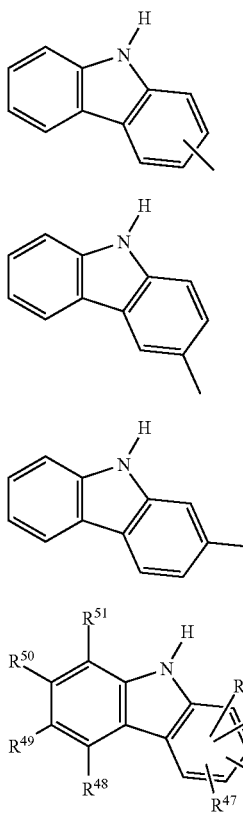

(F2-1)

(F3-1)

(F4-1)

(F5-1)

(In the formulas, $R^{45}$ to $R^{51}$ have the same meanings as above.)

Specific examples of the arylsulfonic acid compound include benzenesulfonic acid, tosyl acid, p-styrenesulfonic acid, 2-naphthalenesulfonic acid, 4-hydroxybenzenesulfonic acid, 5-sulfosalicylic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenesulfonic acid, 2,7-dinonyl-4,5-naphthalenesulfonic acid, the 1,4-benzodioxanedisulfonic acid compounds described in PCT Patent Publication No. WO 2005/000832, the arylsulfonic acid compounds described in PCT Patent Publication No. WO 2006/025342, and the arylsulfonic acid compounds described in PCT Patent Publication No. WO 2009/096352.

Examples of the arylsulfonic acid compound preferable as the dopant substance in the present invention include arylsulfonic acid compounds represented by the formula (H4) or (H5).

[Chemical Formula 121]

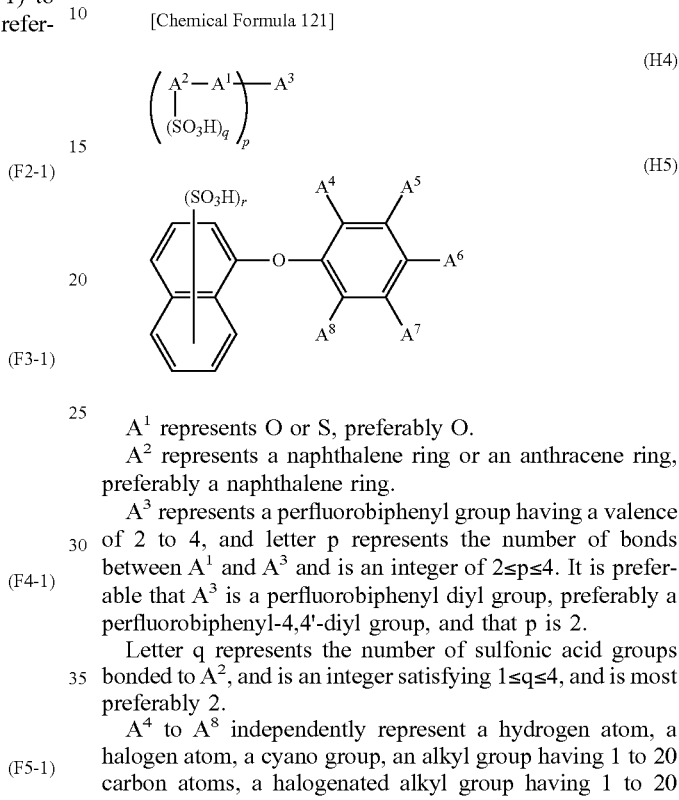

(H4)

(H5)

$A^1$ represents O or S, preferably O.

$A^2$ represents a naphthalene ring or an anthracene ring, preferably a naphthalene ring.

$A^3$ represents a perfluorobiphenyl group having a valence of 2 to 4, and letter p represents the number of bonds between $A^1$ and $A^3$ and is an integer of $2 \leq p \leq 4$. It is preferable that $A^3$ is a perfluorobiphenyl diyl group, preferably a perfluorobiphenyl-4,4'-diyl group, and that p is 2.

Letter q represents the number of sulfonic acid groups bonded to $A^2$, and is an integer satisfying $1 \leq q \leq 4$, and is most preferably 2.

$A^4$ to $A^8$ independently represent a hydrogen atom, a halogen atom, a cyano group, an alkyl group having 1 to 20 carbon atoms, a halogenated alkyl group having 1 to 20 carbon atoms, or a halogenated alkenyl group having 2 to 20 carbon atoms, with at least three of $A^4$ to $A^8$ being halogen atoms.

Examples of the halogenated alkyl group having 1 to 20 carbon atoms include trifluoromethyl group, 2,2,2-trifluoroethyl group, 1,1,2,2,2-pentafluoroethyl group, 3,3,3-trifluoropropyl group, 2,2,3,3,3-pentafluoropropyl group, 1,1,2,2,3,3,3-heptafluoropropyl group, 4,4,4-trifluorobutyl group, 3,3,4,4,4-pentafluorobutyl group, 2,2,3,3,4,4,4-heptafluorobutyl group, and 1,1,2,2,3,3,4,4,4-nonafluorobutyl group.

Examples of the halogenated alkenyl group having 2 to 20 carbon atoms include perfluorovinyl groups, perfluoropropenyl groups (allyl groups), and perfluorobutenyl groups.

In addition, examples of the halogen atom and the alkyl group having 1 to 20 carbon atoms include the same atoms and groups as above-mentioned, and the halogen atom is preferably a fluorine atom.

Among these, $A^4$ to $A^8$ are preferably a hydrogen atom, a halogen atom, a cyano group, an alkyl group having 1 to 10 carbon atoms, a halogenated alkyl group having 1 to 10 carbon atoms or a halogenated alkenyl group having 2 to 10 carbon atoms and at least three of $A^4$ to $A^8$ are a fluorine atom. More preferably, $A^4$ to $A^8$ are a hydrogen atom, a fluorine atom, a cyano group, an alkyl group having 1 to 5 carbon atoms, a fluorinated alkyl group having 1 to 5 carbon atoms, or a fluorinated alkenyl group having 2 to 5 carbon atoms and at least three of $A^4$ to $A^8$ are a fluorine atom. Further preferably, $A^4$ to $A^8$ are a hydrogen atom, a fluorine atom, a cyano group, a perfluoroalkyl group having 1 to 5 carbon atoms, or a perfluoroalkenyl group having 1 to 5 carbon atoms and $A^4$, $A^5$ and $A^8$ are a fluorine atom.

Note that the perfluoroalkyl group is a group in which all the hydrogen atoms of an alkyl group are substituted with a fluorine atom, and the perfluoroalkenyl group is a group in which all the hydrogen atoms of an alkenyl group are substituted with a fluorine atom.

Letter r represents the number of sulfonic acid groups bonded to the naphthalene ring, and is an integer satisfying 1≤r≤4, and is preferably 2 to 4, most preferably 2.

The molecular weight of the arylsulfonic acid compound used as the dopant substance is not particularly limited. In consideration of the solubility of the arylsulfonic acid compound in organic solvents in the case of being used with the aniline derivative of the present invention, however, the molecular weight is preferably up to 2,000, more preferably up to 1,500.

Specific examples of the preferable arylsulfonic acid compound will be given below, but these are not restrictive.

While as the arylsulfonic acid compound a commercialized product may be used, the arylsulfonic acid compound can also be synthesized by a known method such as the methods described in PCT Patent Publication Nos. WO 2006/025342 and WO 2009/096352.

In the present invention, in consideration of obtaining a highly charge transporting thin film with good reproducibility and of availability of the dopant substance, it is preferable that at least one of the halotetracyanoquinodimethane and benzoquinone derivatives is contained, and it is more preferable that at least one of F4TCNQ and DDQ is contained, as the dopant substance.

Besides, in the case of using the thin film obtained as a hole injection layer of an organic EL element, in consideration of obtaining a long-life element with good reproducibility and of availability of the dopant substance, it is preferable that at least one of halotetracyanoquinodimethane and benzoquinone derivatives and heteropoly-acid are contained, it is more preferable that at least one of halotetracyanoquinodimethane and benzoquinone derivatives and at

[Chemical Formula 122]

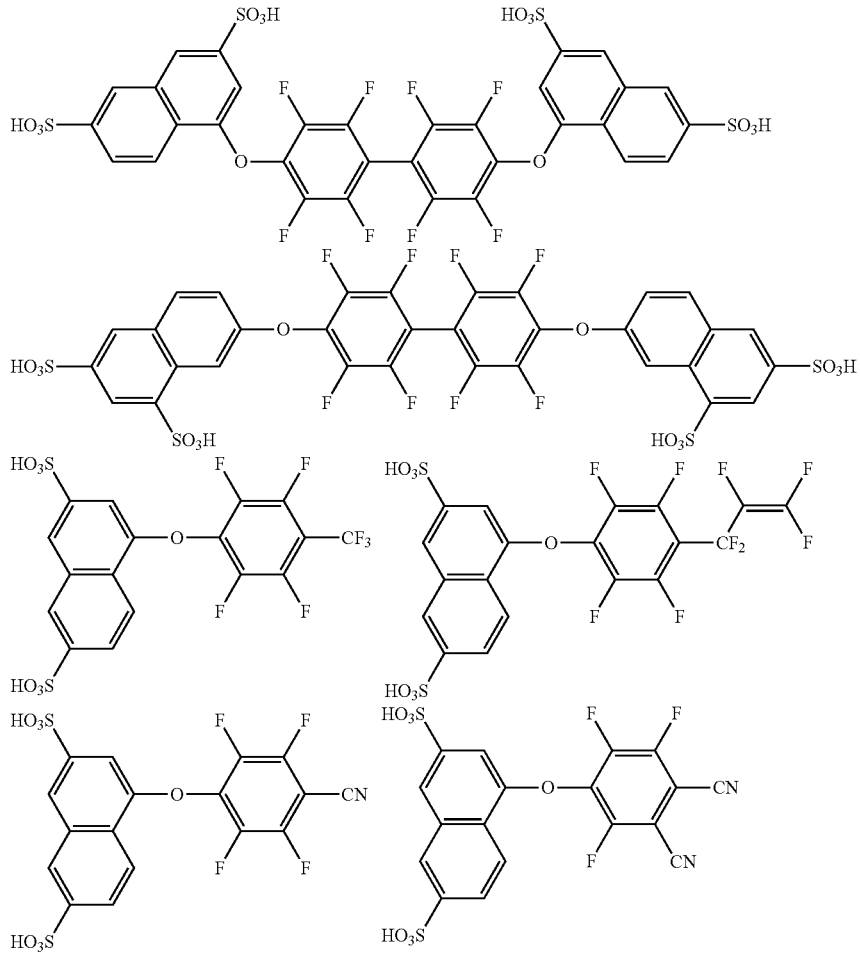

The content of the arylsulfonic acid compound in the charge transporting varnish of the present invention is preferably 0.1 to 10 equivalents, more preferably 0.5 to 5 equivalents, and further preferably 0.8 to 3 equivalents, relative to the aniline derivative represented by the formula (1).

least one of phosphotungstic acid and phosphomolybdic acid are contained, and it is further preferable that at least one of F4TCNQ and DDQ and phosphotungstic acid are contained, as the dopant substance.

Further, in the case of using the thin film obtained as a hole injection layer of an organic EL element, in consideration of obtaining a long-life element with good reproducibility, it is preferable that the charge transporting varnish of the present invention contains an organosilane compound.

Examples of the organosilane compound include dialkoxysilane compounds, trialkoxysilane compounds or tetraalkoxysilane compounds, and these may be used either singly or in combination of at least two of them.

Among others, the organosilane compound is preferably a dialkoxysilane compound or a trialkoxysilane compound, more preferably a trialkoxysilane compound.

Examples of these alkoxysilane compounds include those represented by the formulas (S1) to (S3).

$$Si(OR)_4 \tag{S1}$$

$$SiR'(OR)_3 \tag{S2}$$

$$Si(R')_2(OR)_2 \tag{S3}$$

In the formulas, R independently represents an alkyl group having 1 to 20 carbon atoms which may be substituted with $Z^6$, an alkenyl group having 2 to 20 carbon atoms which may be substituted with $Z^6$, an alkynyl group having 2 to 20 carbon atoms which may be substituted with $Z^6$, an aryl group having 6 to 20 carbon atoms which may be substituted with $Z^7$, or a heteroaryl group having 2 to 20 carbon atoms which may be substituted with $Z^7$; and R' independently represents an alkyl group having 1 to 20 carbon atoms which may be substituted with $Z^8$, an alkenyl group having 2 to 20 carbon atoms which may be substituted with $Z^8$, an alkynyl group having 2 to 20 carbon atoms which may be substituted with $Z^8$, an aryl group having 6 to 20 carbon atoms which may be substituted with $Z^9$, or a heteroaryl group having 2 to 20 carbon atoms which may be substituted with $Z^9$.

$Z^6$ represents a halogen atom, an aryl group having 6 to 20 carbon atoms which may be substituted with $Z^{10}$, or a heteroaryl group having 2 to 20 carbon atoms which may be substituted with $Z^{10}$; and $Z^7$ represents a halogen atom, an alkyl group having 1 to 20 carbon atoms which may be substituted with $Z^{10}$, an alkenyl group having 2 to 20 carbon atoms which may be substituted with $Z^{10}$, or an alkynyl group having 2 to 20 carbon atoms which may be substituted with $Z^{10}$.

$Z^8$ represents a halogen atom, an aryl group having 6 to 20 carbon atoms which may be substituted with $Z^{10}$, a heteroaryl group having 2 to 20 carbon atoms which may be substituted with $Z^{10}$, an epoxycyclohexyl group, a glycidoxy group, a methacryloxy group, an acryloxy group, a ureido group (—NHCONH$_2$), a thiol group, an isocyanate group (—NCO), an amino group, a —NHY$^1$ group, or a —NY$^2$Y$^3$ group; $Z^9$ represents a halogen atom, an alkyl group having 1 to 20 carbon atoms which may be substituted with $Z^{10}$, an alkenyl group having 2 to 20 carbon atoms which may be substituted with $Z^{10}$, an alkynyl group having 2 to 20 carbon atoms which may be substituted with $Z^{10}$, an epoxycyclohexyl group, a glycidoxy group, a methacryloxy group, an acryloxy group, a ureido group (—NHCONH$_2$), a thiol group, an isocyanate group (—NCO), an amino group, a —NHY$^1$ group, or a —NY$^2$Y$^3$ group; and Y$^1$ to Y$^3$ independently represent an alkyl group having 1 to 20 carbon atoms which may be substituted with $Z^{10}$, an alkenyl group having 2 to 20 carbon atoms which may be substituted with $Z^{10}$, an alkynyl group having 2 to 20 carbon atoms which may be substituted with $Z^{10}$, an aryl group having 6 to 20 carbon atoms which may be substituted with $Z^{10}$, or a heteroaryl group having 2 to 20 carbon atoms which may be substituted with $Z^{10}$.

$Z^{10}$ represents a halogen atom, an amino group, a nitro group, a cyano group or a thiol group.

Examples of the halogen atom, alkyl group having 1 to 20 carbon atoms, alkenyl group having 2 to 20 carbon atoms, alkynyl group having 2 to 20 carbon atoms, aryl group having 6 to 20 carbon atoms, and heteroaryl group having 2 to 20 carbon atoms in the formulas (S1) to (S3) include the same atoms and groups as above-mentioned.

In R and R', the numbers of carbon atoms in the alkyl group, alkenyl group and alkynyl group are preferably up to 10, more preferably up to 6, and further preferably up to 4.

Besides, the numbers of carbon atoms in the aryl group and heteroaryl group are preferably up to 14, more preferably up to 10, and further preferably up to 6.

R is preferably an alkyl group having 1 to 20 carbon atoms or alkenyl group having 2 to 20 carbon atoms which may be substituted with $Z^6$, or an aryl group having 6 to 20 carbon atoms which may be substituted with $Z^7$, more preferably an alkyl group having 1 to 6 carbon atoms or alkenyl group having 2 to 6 carbon atoms which may be substituted with $Z^6$, or a phenyl group which may be substituted with $Z^7$, further preferably an alkyl group having 1 to 4 carbon atoms which may be substituted with $Z^6$ or a phenyl group which may be substituted with $Z^7$, and still further preferably a methyl group or ethyl group which may be substituted with $Z^6$.

Besides, R' is preferably an alkyl group having 1 to 20 carbon atoms which may be substituted with $Z^8$ or an aryl group having 6 to 20 carbon atoms which may be substituted with $Z^9$, more preferably an alkyl group having 1 to 10 carbon atoms which may be substituted with $Z^8$ or an aryl group having 6 to 14 carbon atoms which may be substituted with $Z^9$, further preferably an alkyl group having 1 to 6 carbon atoms which may be substituted with $Z^8$ or an aryl group having 6 to 10 carbon atoms which may be substituted with $Z^9$, and still further preferably an alkyl group having 1 to 4 carbon atoms which may be substituted with $Z^8$ or a phenyl group which may be substituted with $Z^9$.

Note that the plurality of R may be all the same or different, and the plurality of R may also be all the same or different.

$Z^6$ is preferably a halogen atom or an aryl group having 6 to 20 carbon atoms which may be substituted with $Z^{10}$, more preferably a fluorine atom or a phenyl group which may be substituted with $Z^{10}$, and most preferably absent (in other words, non-substitution).

Besides, $Z^7$ is preferably a halogen atom or an alkyl group having 6 to 20 carbon atoms which may be substituted with $Z^{10}$, more preferably a fluorine atom or an alkyl group having 1 to 10 carbon atoms which may be substituted with $Z^{10}$, and most preferably absent (in other words, non-substitution).

Besides, $Z^8$ is preferably a halogen atom, a phenyl group which may be substituted with $Z^{10}$, a furanyl group, epoxycyclohexyl group, glycidoxy group, methacryloxy group, acryloxy group, ureido group, thiol group, isocyanate group or amino group which may be substituted with $Z^{10}$, a phenylamino group which may be substituted with $Z^{10}$, or a diphenylamino group which may be substituted with $Z^{10}$, more preferably a halogen atom, and further preferably a fluorine atom or absent (in other words, non-substitution).

Besides, $Z^9$ is preferably a halogen atom, an alkyl group having 1 to 20 carbon atoms which may be substituted with $Z^{10}$, a furanyl group, epoxycyclohexyl group, glycidoxy group, methacryloxy group, acryloxy group, ureido group, thiol group, isocyanate group or amino group which may be substituted with $Z^{10}$, a phenylamino group which may be substituted with $Z^{10}$ or a diphenylamino group which may be substituted with $Z^{10}$, more preferably a halogen atom, and further preferably a fluorine atom or absent (in other words, non-substitution).

In addition, $Z^{10}$ is preferably a halogen atom, and more preferably a fluorine atom or absent (in other words, non-substitution).

Specific examples of the organosilane compound which can be used in the present invention will be given below, but these are not restrictive.

Specific examples of the dialkoxysilane compound include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 4-mercaptopropylmethyldimethoxysilane, γ-aminopropylmethyldiethoxysilane, N-(2-aminoethyl)aminopropylmethyl dimethoxysilane, and 3,3,3-trifluoropropylmethyldimethoxysilane.

Specific examples of the trialkoxysilane compound include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, 3-aminopropyltriethoxysilane, γ-glycidoxypropyltrimethoxysilane, 3-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2-tetrahydrooctyltriethoxysilane, pentafluorophenyltrimethoxysilane, pentafluorophenyltriethoxysilane, 3-(heptafluoroisopropoxy)propyltriethoxysilane, heptadecafluoro-1,1,2,2-tetrahydrodecyltriethoxysilane, triethoxy-2-thienylsilane, and 3-(triethoxysilyl)furan.

Specific examples of the tetraalkoxysilane compound include tetraethoxysilane, tetramethoxysilane, and tetrapropoxysilane.

Among these, preferred are 3,3,3-trifluoropropylmethyldimethoxysilane, triethoxy(4-(trifluoromethyl)phenyl)silane, 3,3,3-trifluroropropyltrimethoxysilane, perfluorooctylethyltriethoxysilane or pentafluorophenyltrimethoxysilane, and pentafluorophenyltriethoxysilane.

In the case where the charge transporting varnish of the present invention contains the organosilane compound, the amount of the organosilane compound contained is normally approximately 0.1 to 50% by weight, relative to the total weight of the charge transporting substance and the dopant substance. In consideration of restraining a lowering in charge transporting properties of the thin film obtained and enhancing the hole injection capability of a layer formed on the aforementioned cathode side in such a manner as to contact the hole injection layer including the thin film obtained from the varnish, the amount of the organosilane compound contained is preferably approximately 0.5 to 40% by weight, more preferably approximately 0.8 to 30% by weight, and further preferably approximately 1 to 20% by weight.

Note that in the charge transporting varnish of the present invention, in addition to the aforementioned charge transporting substance including the aniline derivative, other known charge transporting substances can also be used.

As the organic solvent for use in preparing the charge transporting varnish, there can be used a high-solvency solvent capable of favorably dissolving the charge transporting substance and the dopant substance.

Examples of such a high-solvency solvent include, but are not limited to, organic solvents such as cyclohexanone, N,N-dimethylformamide, N,N-dimethylacetamide, N,N-dimethylisobutylamide, N-methylpyrrolidone, 1,3-dimethyl-2-imidazolidinone, and diethylene glycol monomethyl ether. These solvents may be used either singly or as a mixture of at least two of them, and the amount of the solvent or solvents to be used can be 5 to 100% by weight relative to the whole solvent to be used in the varnish.

Note that both the charge transporting substance and the dopant substance are preferably dissolved entirely in the solvent.

Besides, in the present invention, the varnish may contain at least one kind of high-viscosity organic solvent which has a viscosity of 10 to 200 mPa·s, particularly, 35 to 150 mPa·s at 25° C. and a boiling point of 50 to 300° C., particularly 150 to 250° C. at normal pressure (atmospheric pressure), whereby it becomes easy to adjust the viscosity of the varnish, and, as a result, it becomes possible to control the varnish according to the coating method used, such as to give a highly flatness thin film with good reproducibility.

Examples of the high-viscosity organic solvent include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, and propylene glycol, hexylene glycol. These solvents may be used either singly or as a mixture of at least two of them.

The proportion of the high-viscosity organic solvent added relative to the whole solvent used in the varnish of the present invention is preferably within such a range that precipitation of solids does not occur, and the addition proportion is preferably 5 to 80% by weight so long as precipitation of solids does not occur.

Furthermore, for the purpose of enhancing wettability with respect to a substrate, adjusting the surface tension of the solvent, and adjusting polarity, adjusting the boiling point, other solvents may be mixed in a proportion of 1 to 90% by weight, preferably 1 to 50% by weight, relative to the whole solvent used in the varnish.

Examples of such other solvents include, but are not limited to, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyllactate, and n-hexyl acetate. These solvents may be used either singly or as a mixture of at least two of them.

The viscosity of the varnish of the present invention is appropriately set according to the thickness of the thin film to be formed and the solid concentration, and is normally 1 to 50 mPa·s at 25° C.

In addition, the solid concentration of the charge transporting varnish of the present invention is appropriately set according to the viscosity and surface tension of the varnish, the thickness of the thin film to be formed, and is normally approximately 0.1 to 10.0% by weight. In consideration of enhancing the coating properties of the varnish, the solid concentration is preferably approximately 0.5 to 5.0% by weight, more preferably approximately 1.0 to 3.0% by weight.

The method for preparing the charge transporting varnish is not specifically restricted. Examples of the preparation method include a technique in which the aniline derivative of the present invention is dissolved in the high-solvency solvent, and the high-viscosity organic solvent is added thereto, and a technique in which the high-solvency solvent and the high-viscosity organic solvent are mixed, and the aniline derivative of the present invention is dissolved in the mixed solvent.

In the present invention, from the viewpoint of obtaining a thin film of higher flatness with good reproducibility, the charge transporting varnish is desirably filtered by use of a submicro-order filter after the dissolution of the charge transporting substance and the dopant substance in the organic solvent.

The charge transporting substance and the charge transporting varnish of the present invention as described above make it possible to easily produce a charge transporting thin film by use thereof, and, accordingly, can be preferably used in producing an electronic device, particularly, organic EL organic electroluminescence element.

The charge transporting thin film of the present invention can be formed on a substrate by coating the substrate with the above-described charge transporting varnish, followed by baking.

The method for coating with the varnish is not specifically restricted, and examples of the coating method include dipping method, spin coating method, transfer printing method, roll coating method, brushing method, ink jet method, spraying method, and slit coating method, and it is preferable to control the viscosity and surface tension of the varnish according to the coating method.

Besides, in the case of using the varnish of the present invention, the baking atmosphere is not particularly restricted. Not only in the atmospheric air but also in an inert gas such as nitrogen and in vacuum, a thin film having a uniform formed film surface and a high charge transporting properties can be obtained. Depending on the kind of the dopant substance used in the aniline derivative of the present invention, however, there are cases where a thin film having charge transporting properties can be obtained with good reproducibility by baking the varnish in the atmospheric air.

The baking temperature is appropriately set within the range of approximately 100 to 260° C., taking into account the use of the thin film to be obtained, the degree of charge transporting properties to be imparted to the thin film to be obtained, and the kind and boiling point of the solvent. In the case of using the thin film obtained as a hole injection layer of an organic EL element, the baking temperature is preferably approximately 140 to 250° C., more preferably approximately 145 to 240° C.

Note that at the time of baking, at least two stages of temperature variations may be used for the purpose of developing higher uniform film forming properties or causing a reaction to proceed on a substrate. The heating may be conducted by use of a suitable apparatus such as, for example, a hot plate or an oven.

The film thickness of the charge transporting thin film is not particularly limited. In the case where the charge transporting thin film is used as a hole injection layer, a hole transport layer or a hole injection transport layer of an organic EL element, the film thickness is preferably 5 to 200 nm. Examples of a method for varying the film thickness include a method of varying the solids concentration of the varnish, and a method of varying the amount of the solution on the substrate at the time of coating.

Note that the aniline derivative of the present invention is sublimable, and by using this, an evaporate film can be easily formed. Therefore, depending on the use, a charge transporting thin film obtained by a vapor deposition method using the aniline derivative of the present invention may be used, instead of the charge transporting thin film obtained from the charge transporting varnish described above.

The organic EL element of the present invention has a pair of electrodes, and has the aforementioned charge transporting thin film of the present invention between these electrodes.

Examples of a typical configuration of the organic EL element include, but are not limited to, the following (a) to (f). Note that in the following configurations, if necessary, an electron block layer may be provided between a light emitting layer and an anode, and a hole block layer may be provided between the light emitting layer and a cathode. In addition, a hole injection layer, a hole transport layer or a hole injection transport layer may also have the function as an electron block layer. Besides, the hole injection layer, the hole transport layer or the hole injection transport layer may also have the function as a hole block layer.

(a) Anode/hole injection layer/hole transport layer/light emitting layer/electron injection layer/electron transport layer/cathode (b) Anode/hole injection layer/hole transport layer/light emitting layer/electron injection transport layer/cathode (c) Anode/hole injection transport layer/light emitting layer/electron injection layer/electron transport layer/cathode (d) Anode/hole injection transport layer/light emitting layer/electron injection transport layer/cathode (e) Anode/hole injection layer/hole transport layer/light emitting layer/cathode (f) Anode/hole injection transport layer/light emitting layer/cathode The "hole injection layer," the "hole transport layer" and the "hole injection transport layer" are layers which are formed between the light emitting layer and the anode and which have the function of transporting holes from the anode to the light emitting layer. In the case where only one layer of a hole transporting material is provided between the light emitting layer and the anode, the layer is the "hole injection transport layer." In the case where at least two layers of a hole transporting material are provided between the light emitting layer and the anode, the layer nearer to the anode is the "hole injection layer," and the other layer or layers are the "hole transport layers." Particularly, as the hole injection (transport) layer, there is used a thin film excellent in not only a property for accepting holes from the anode but also a property for injecting holes into the hole transport (light emitting) layer.

The "electron injection layer," the "electron transport layer" and the "electron injection transport layer" are layers which are formed between the light emitting layer and the cathode and which have the function of transporting electrons from the cathode to the light emitting layer. In the case where only one layer of an electron transporting material is provided between the light emitting layer and the cathode, the layer is the "electron injection transport layer." In the case where at least two layers of an electron transporting material are provided between the light emitting layer and the cathode, the layer nearer to the cathode is the "electron injection layer," and the other layer or layers are the "electron transport layers."

The "light emitting layer" is an organic layer which has a light emitting function, and which contains a host material and a dopant material in the case where a doping system is adopted. In this instance, the host material has the function of mainly promoting recombination between electrons and holes and confining excitons within the light emitting layer, whereas the dopant material has the function of causing the excitons obtained by the recombination to emit light efficiently. In the case of a phosphorescence element, the host material has the function of mainly confining the excitons generated from the dopant within the light emitting layer.

The charge transporting thin film of the present invention can be preferably used as a hole injection layer, a hole transport layer or a hole injection transport layer, and can be more preferably used as a hole injection layer, in an organic EL element.

In the case of producing an organic EL element by use of the charge transporting varnish of the present invention, examples of the materials to be used and the producing method include, but are not limited to, the followings.

An electrode substrate to be used is preferably cleaned preliminarily by performing washing with liquid such as a detergent, alcohol, and pure water. For example, an anode substrate is preferably subjected immediately before use to a surface treatment such as a UV ozone treatment, and an oxygen-plasma treatment. It is to be noted, however, that a surface treatment may not necessarily be conducted in the case where the anode material contains an organic matter as a main constituent.

An example of the method for producing an organic EL element having a hole injection layer including a thin film obtained from the charge transporting varnish of the present invention is as follows.

By the aforementioned method, an anode substrate is coated with the charge transporting varnish of the present invention, followed by baking, to produce a hole injection layer on the electrode.

Over this hole injection layer, there are provided a hole transport layer, a light emitting layer, an electron transport layer, an electron injection layer, and a cathode in this order. The hole transport layer, the light emitting layer, the electron transport layer and the electron injection layer may be formed by either a vapor deposition method or a coating method (wet process) according to the characteristic properties of the used materials.

Examples of the anode material include transparent electrodes represented by indium tin oxide (ITO) and indium zinc oxide (IZO), metallic anodes including metals represented by aluminum or their alloys, and are preferably those which have been subjected to a flattening treatment. Polythiophene derivatives and polyaniline derivatives which have high charge transporting properties may also be used.

Note that examples of other metals for constituting the metallic anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and their alloys.

Examples of the material for forming the hole transport layer include hole transporting low-molecular materials such as (triphenylamine)dimer derivatives, [(triphenylamine)diamer]spirodimer, N,N'-bis(naphthalen-1-yl)-N,N'-bis(phenyl)-benzidine (α-NPD), N,N'-bis(naphthalen-2-yl)-N,N'-bis(phenyl)-benzidine, N,N'-bis(3-methylphenyl)-N,N'-bis(phenyl)-benzidine, N,N'-bis(3-methylphenyl)-N,N'-bis(phenyl)-9,9-spirobifluorene, N,N'-bis(naphthalen-1-yl)-N,N'-bis(phenyl)-9,9-spirobifluorene, N,N'-bis(3-methylphenyl)-N,N'-bis(phenyl)-9,9-dimethylfluorene, N,N'-bis(naphthalen-1-yl)-N,N'-bis(phenyl)-9,9-dimethylfluorene, N,N'-bis(3-methylphenyl)-N,N'-bis(phenyl)-9,9-diphenyl-fluorene, N,N'-bis(naphthalen-1-yl)-N,N'-bis(phenyl)-9,9-diphenyl-fluorene, N,N'-bis(naphthalen-1-yl)-N,N'-bis(phenyl)-2,2'-dimethylbenzidine, 2,2',7, 7'-tetrakis(N,N-diphenylamino)-9,9-spirobifluorene, 9,9-bis[4-(N,N-bis-biphenyl-4-yl-amino)phenyl]-9H-fluorene, 9,9-bis[4-(N,N-bis-naphthalen-2-yl-amino)phenyl]-9H-fluorene, 9,9-bis[4-(N-naphthalen-1-yl-N-phenylamino)-phenyl]-9H-fluorene, 2,2',7,7'-tetrakis[N-naphthalenyl(phenyl)-amino]-9,9-spirobifluorene, N,N'-bis(phenanthren-9-yl)-N,N'-bis(phenyl)-benzidine, 2,2'-bis[N,N-bis(biphenyl-4-yl)amino]-9,9-spirobifluorene, 2,2'-bis(N,N-diphenylamino)-9,9-spirobifluorene, di-[4-(N,N-di(p-tolyl)amino)-phenyl]cyclohexane, 2,2',7,7'-tetra(N,N-di(p-tolyl)amino-9,9-spirobifluorene, N,N,N',N'-tetra-naphthalen-2-yl-benzidine, N,N,N',N'-tetra-(3-methylphenyl)-3,3'-dimethylbenzidine, N,N'-di(naphthalenyl)-N,N'-di(naphthalene-2-yl)-benzidine, N,N,N',N'-tetra(naphthalenyl)-benzidine, N,N'-di(naphthalene-2-yl)-N,N'-diphenylbenzidine-1,4-diamine, $N^1,N^4$-diphenyl-$N^1,N^4$-di(m-tolyl)benzene-1, 4-diamine, $N^2,N^2,N^6,N^6$-tetraphenylnaphthalene-2,6-diamine, tris(4-(quinolin-8-yl)phenyl)amine, 2,2'-bis(3-(N,N-di(p-tolyl)amino)phenyl)biphenyl, 4,4',4''-tris[3-methylphenyl(phenyl)amino]triphenylamine (m-MTDATA), 4,4',4''-tris[1-naphthyl(phenyl)amino]triphenylamine (1-TNATA) and the like triarylamines and 5,5''-bis-{4-[bis(4-methylphenyl)amino]phenyl}-2,2':5',2''-terthiophene (BMA-3T) and the like oligothiophenes.

Examples of the material for forming the light emitting layer include tris(8-quinolinolato)aluminum(III) ($Alq_3$), bis (8-quinolinolato)zinc(II) ($Znq_2$), bis(2-methyl-8-quinolinolato)-4-(p-phenylphenolato)-aluminum(III) (BAlq), 4,4'-bis (2,2-diphenylvinyl)biphenyl, 9,10-di(naphthalen-2-yl) anthracene, 2-t-butyl-9,10-di(naphthalen-2-yl)anthracene, 2,7-bis[9,9-di(4-methylphenyl)-fluoren-2-yl]-9,9-di(4-methylphenyl) fluorine, 2-methyl-9,10-bis(naphthalen-2-yl) anthracene, 2-(9,9-spirobifluoren-2-yl)-9,9-spirobifluorene, 2,7-bis(9,9-spirobifluoren-2-yl)-9,9-spirobifluorene, 2-[9,9-di(4-methylphenyl)-fluoren-2-yl]-9,9-di(4-methylphenyl) fluorene, 2,2'-dipyrenyl-9,9-spirobifluorene, 1,3,5-tris (pyren-1-yl)benzene, 9,9-bis[4-(pyrenyl)phenyl]-9H-fluoren, 2,2'-bi(9,10-diphenylanthracene), 2,7-dipyrenyl-9, 9-spirobifluoren, 1,4-di(pyren-1-yl)benzene, 1,3-di(pyren-1-yl)benzene, 6,13-di(biphenyl-4-yl)pentacene, 3,9-di (naphthalen-2-yl)perillene, 3,10-di(naphthalen-2-yl) perillene, tris[4-(pyrenyl)-phenyl]amine, 10,10'-di (biphenyl-4-yl)-9,9'-bianthracene, N,N'-di(naphthalen-1-yl)-N,N'-diphenyl-[1,1':4',1'':4''',1'''-quaterphenyl]4,4'''-diamine, 4,4'-di[10-(naphthalen-1-yl)anthracen-9-yl] biphenyl, dibenzo{[f,f']-4,4',7,7'-tetraphenyl}diindeno[1,2, 3-cd:1',2',3'-lm]perillene, 1-(7-(9,9'-bianthracen-10-yl)-9,9-dimethyl-9H-fluoren-2-yl)pyrene, 1-(7-(9,9'-bianthracen-10-yl)-9,9-dihexyl-9H-fluoren-2-yl)pyrene, 1,3-bis (carbazol-9-yl)benzene, 1,3,5-tris(carbazol-9-yl)benzene, 4,4',4"-tris(carbazol-9-yl)triphenylamine, 4,4'-bis(carbozol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorine, 9,9-bis[4-(carbazol-9-yl)-phenyl]fluorine, 2,7-bis(carbazol-9-yl)-9,9-spirobifluorene, 1,4-bis(triphenylsilyl)benzene, 1,3-bis(triphenylsilyl)benzene, bis(4-N,N-diethylamino-2-methylphenyl)-4-methylphenylmethane, 2,7-bis(carbazol-9-yl)-9,9-dioctylfluorene, 4,4"-di(triphenylsilyl)-p-terphenyl, 4,4'-di(triphenylsilyl)biphenyl, 9-(4-t-butylphenyl)-3,6-bis(triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benzo[d]imidazol-2-yl)phenyl)-9H-fluorene-2-amine, 3,5-bis(3-(9H-carbazol-9-yl)phenyl)pyridine, 9,9-spirobifluoren-2-yl-diphenyl-phosphine oxide, 9,9'-(5-(triphenylsilyl)-1,3-phenylene)bis(9H-carbazole), 3-(2,7-bis(diphenylphosphoryl)-9-phenyl-9H-fluoren-9-yl)-9-phenyl-9H-carbazole, 4,4,8,8,12,12-hexa(p-tolyl)-4H-8H-12H-12C-azadibenzo[cd,mn]pyrene, 4,7-di(9H-carbazol-9-yl)-1,10-phenanthroline, 2,2'-bis(4-(carbazol-9-yl)phenyl)biphenyl, 2,8-bis(diphenylphosphoryl)dibenzo[b,d]thiophene, bis(2-methylphenyl)diphenylsilane, bis[3,5-di(9H-carbazol-9-yl)phenyl]diphenylsilane, 3,6-bis(carbazol-9-yl)-9-(2-ethyl-hexyl)-9H-carbazole, 3-(diphenylphosphoryl)-9-(4-(diphenylphosphoryl)phenyl)-9H-carbazole, and 3,6-bis[(3,5-diphenyl)phenyl]-9-phenyl-carbazole, and these materials may be used to form the light emitting layer by co-evaporation with a light emitting dopant.

Examples of the light emitting dopant include 3-(2-benzothiazolyl)-7-(diethylamino)coumarin, 2,3,6,7-tetrahydro-1,1,7,7-tetramethyl-1H,5H,11H-10-(2-benzothiazolyl)quinolizino[9,9a,1gh]coumarin, quinacridone, N,N'-dimethyl-quinacridone, tris(2-phenylpyridine)iridium(III) (Ir(ppy)$_3$), bis(2-phenylpyridine)(acetylacetonate)iridum (III) (Ir(ppy)$_2$(acac)), tris[2-(p-tolyl)pyridine]iridium(III) (Ir(mppy)$_3$), 9,10-bis[N,N-di(p-tolyl)amino]anthracene, 9,10-bis[phenyl(m-tolyl)amino]anthracene, bis[2-(2-hydroxyphenyl)benzothiazolato]zinc(II), $N^{10},N^{10},N^{10'},N^{10'}$-tetra(p-tolyl)-9,9'-bianthracene-10,10'-diamine, $N^{10},N^{10},N^{10'},N^{10'}$-tetraphenyl-9,9'-bianthracene-10,10'-diamine, diphenyl-$N^{10},N^{10'}$-dinaphthalenyl-9,9'-bianthracene-10,10'-diamine, 4,4'-bis(9-ethyl-3-carbazovinylene)-1,1'-biphenyl, perillene, 2,5,8,11-tetra-t-butylperillene, 1,4-bis[2-(3-N-ethylcarbazolyl)vinyl]benzene, 4,4'-bis[4-(di-p-tolylamino)styryl]biphenyl, 4-(di-p-tolylamino)-4'-[(di-p-tolylamino)styryl]stilbene, bis[3,5-difluoro-2-(2-pyridyl)phenyl-(2-carboxypyridyl)]-iridium(III), 4,4'-bis[4-(diphenylamino)styryl]biphenyl, bis(2,4-difluorophenylpyridinato)tetrakis(1-pyrazolyl)borate-iridium(III), N,N'-bis(naphthalen-2-yl)-N,N'-bis(phenyl)-tris(9,9-dimethyl-fluorenylene), 2,7-bis{2-[phenyl(m-tolyl)amino]-9,9-dimethyl-fluoren-7-yl}-9,9-dimethylfluorene, N-(4-((E)-2-(6((E)-4-(diphenylamino)styryl)naphthalen-2-yl)vinyl)phenyl)-N-phenylbenzeneamine, fac-idirium(III) tris(1-phenyl-3-methylbenzimidazolin-2-ylidene-C,C$^{2'}$), mer-iridum(III) tris(1-phenyl-3-methylbenzimidazolin-2-ylidene-C,C$^{2'}$), 2,7-bis[4-(diphenylamino)styryl]-9,9-spirobifluorene, 6-methyl-2-(4-(9-(4-(6-methylbenzo[d]thiazol-2-yl)phenyl)-anthracen-10-yl)phenyl)benzo[d]thiazole, 1,4-di[4-(N,N-diphenyl)amino]styrylbenzene, 1,4-bis(4-(9H-carbazol-9-yl)styryl)benzene, (E)-6-(4-(diphenylamino)styryl)-N,N-diphenylnaphthalene-2-amine, bis(2,4-difluorophenylpyridinato)(5-(pyridin-2-yl)-1H-tetrazolate)iridium(III), bis(3-trifluoromethyl-5-(2-pyridyl)pyrazole)((2,4-difluoro-benzyl)diphenylphosphinate)iridium(III), bis(3-trifluoromethyl-5-(2-pyridyl)pyrazolate)(benzyl-diphenylphosphinate)iridium(III), bis(1-(2,4-difluorobenzyl)-3-methylbenzimidazolium)(3-(trifluoromethyl)-5-(2-pyridyl)-1,2,4-triazolate)iridium(III), bis(3-trifluoromethyl-5-(2-pyridyl)pyrazolate)(4',6'-difluorophenylpyridinate)iridium(III), bis(4',6'-difluorophenylpyridinato)(3,5-bis(trifluoromethyl)-2-(2'-pyridyl)pyrrolate)iridium(III), bis(4',6'-difluorophenylpyridinato)(3-(trifluoromethyl)-5-(2-pyridyl)-1,2,4-triazolate)iridum(III), (Z)-6-mesityl-N-(6-mesitylquinolin-2(1H)-ylidene)quinoline-2-amine-BF$_2$, (E)-2-(2-(4-(dimethylamino)styryl)-6-methyl-4H-pyran-4-ylidene)malononitrile, 4-(dicyanomethylene)-2-methyl-6-julolidyl-9-enyl-4H-pyran, 4-(dicyanomethylene)-2-methyl-6-(1,1,7,7-tetramethyl-julolidyl-9-enyl)-4H-pyran, 4-(dicyanomethylene)-2-t-butyl-6-(1,1,7,7-tetramethyl-julolidin-4-yl-vinyl)-4H-pyran, tris(dibenzoylmethane)phenanthrolineeuropium(III), 5,6,11,12-tetraphenylnaphthacene, bis(2-benzo[b]thiophen-2-yl-pyridine)(acetylacetonate)-iridium(III), tris(1-phenylisoquinoline)iridium(III), bis(1-phenylisoquinoline)(acetylacetonate)iridum(III), bis[1-(9,9-dimethyl-9H-fluoren-2-yl)-isoquinoline](acetyl-acetonate)iridium(III), bis[2-(9,9-dimethyl-9H-fluoren-2-yl)quinoline](acetyl-acetonate)iridium(III), tris[4,4'-di-t-butyl-(2,2')-bipyridine]ruthenium(III)•bis(hexafluorophosphate), tris(2-phenylquinoline)iridium(III), bis(2-phenylquinoline)(acetylacetonate)iridium(III), 2,8-di-t-butyl-5,11-bis(4-t-butylphenyl)-6,12-diphenyl-tetracene, bis(2-phenylbenzothiazolato)(acetylacetonate)iridium(III), 5,10,15,20-tetraphenyltetrabenzoporphyrinplatinum, osmium(II) bis(3-trifluoromethyl-5-(2-pyridine)-pyrazolate)-dimethylphenylphosphine, osmium(II) bis(3-(trifluoromethyl)-5-(4-t-butylpyridyl)-1,2,4-triazolate)diphenylmethylphosphine, osmium(II) bis(3-(trifluoromethyl)-5-(2-pyridyl)-1,2,4-triazole)dimethylphenylphosphine, osmium(II) bis(3-(trifluoromethyl)-5-(4-t-butylpyridyl)-1,2,4-triazolate)dimethylphenylphosphine, bis[2-(4-n-hexylphenyl)quinoline](acetylacetonate)iridium(III), tris[2-(4-n-hexylphenyl)quinoline]iridium(III), tris[2-phenyl-4-methylquinoline]iridium(III), bis(2-phenylquinoline)(2-(3-methylphenyl)pyridinate)-iridium(III), bis(2-(9,9-diethylfluoren-2-yl)-1-phenyl-1H-benzo[d]-imidazolato)(acetylacetonate)iridium(III), bis(2-phenylpyridine)(3-(pyridin-2-yl)-2H-chromen-2-onate)-iridium(III), bis(2-phenylquinoline)(2,2,6,6-tetramethylheptane-3,5-dionate)iridium(III), bis(phenylisoquinoline)(2,2,6,6-tetramethylheptane-3,5-dionate)iridium(III), iridium(III) bis(4-phenylthieno[3,2-c]pyridinato-N,C$^{2'}$)-acetylacetonate, (E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)-malononitrile, bis(3-trifluoromethyl-5-(1-isoquinolyl)pyrazolate)(methyl-diphenylphosphine) ruthenium, bis[(4-n-hexylphenyl) isoquinoline](acetylacetonate)-iridium(III), platinum(II) octaethylporphine, bis(2-methyl-dibenzo[f,h]quinoxaline)(acetylacetonate)-iridium(III), and tris[(4-n-hexylphenyl)xoquinoline]iridium(III).

Examples of the material for forming the electron transport layer include 8-hydroxyquinolinolate-lithium, 2,2',2"-(1,3,5-benzynetolyl)-tris(1-phenyl-1-H-benzimidazole), 2-(4-biphenyl)5-(4-t-butylphenyl)-1,3,4-oxadiazole, 2,9-dimethyl-4,7-diphenyl-1,10-phenanthroline, 4,7-diphenyl-1,10-phenanthroline, bis(2-methyl-8-quinolinolate)-4-(phenylphenolato)aluminum, 1,3-bis[2-(2,2'-bipyridin-6-yl)-1,3,4-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo-[4,5f][1,10]phenanthroline, 2-(naphthalen-2-yl)-4,7-diphenyl-1,10-phenanthroline, phenyl-dipyrenylphosphine oxide, 3,3',5,5'-tetra[(m-pyridyl)-phen-3-yl]biphenyl, 1,3,5-tris[(3-pyridyl)-phen-3-yl]benzene, 4,4'-bis(4,6-diphenyl-1,3,5-triazin-2-yl)biphenyl, 1,3-bis[3,5-di(pyridin-3-yl)phenyl]benzene, bis(10-hydroxybenzo[h]quinolinato)beryllium, diphenylbis(4-(pyridin-3-yl)phenyl)silane, and 3,5-di(pyren-1-yl)pyridine.

Examples of the material for forming the electron injection layer include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), and lithium acetate, lithium benzoate.

Examples of the cathode material include aluminum, magnesium-silver alloy, aluminum-lithium alloy, lithium, sodium, potassium, and cesium.

Besides, another example of the method of producing an organic EL element having the hole injection layer including the thin film obtained from the charge transporting varnish of the present invention is as follows.

An organic EL element having the charge transporting thin film formed by using the charge transporting varnish of the present invention can be produced by sequentially forming a hole transport layer (hereinafter, hole transporting polymer layer) and a light emitting layer (hereinafter, light emitting polymer layer), in place of performing the vapor deposition operations for the hole transport layer, the light emitting layer, the electron transport layer, and the electron injection layer in the production of the EL element described above.

Specifically, an anode substrate is coated with the charge transporting varnish of the present invention to produce the hole injection layer by the aforementioned method, then the hole transporting polymer layer and the light emitting polymer layer are sequentially formed thereover, and further, a cathode electrode is vapor deposited to obtain an organic EL element.

As the cathode and anode materials to be used, the same materials as aforementioned can be used, and a cleaning treatment and a surface treatment which are the same as above can be performed.

Examples of the method for forming the hole transporting polymer layer and the light emitting polymer layer include a method in which the hole transporting polymer material or the light emitting polymer material, or a material obtained by adding a dopant substance to these materials is added to a solvent to dissolve or uniformly disperse the material in the solvent, the resulting liquid is applied to the hole injection layer or the hole transporting polymer layer, followed by baking to form a film.

Examples of the hole transporting polymer material include poly[(9,9-dihexylfluorenyl-2,7-diyl)-co-(N,N'-bis{p-butylphenyl}-1,4-diaminophenylene)], poly[(9,9-dioctylfluorenyl-2,7-diyl)-co-(N,N'-bis{p-butylphenyl}-1,1'-biphenylene-4,4-diamine)], poly[(9,9-bis{1'-penten-5'-yl}fluorenyl-2,7-diyl)-co-(N,N'-bis{p-butylphenyl}-1,4-diaminophenylene)], poly[N,N'-bis(4-butylphenyl)-N,N'-bis(phenyl)-benzidine]-endcapped with polysilsesquioxane, and poly[(9,9-didioctylfluorenyl-2,7-diyl)-co-(4,4'-(N-(p-butylphenyl))diphenylamine)].

Examples of the light emitting polymer material include polyfluorene derivatives such as poly(9,9-dialkylfluorenes) (PDAF), polyphenylenevinylene derivatives such as poly(2-methoxy-5-(2'-ethylhexoxy)-1,4-phenylenevinylene) (MEH-PPV), polythiophene derivatives such as poly(3-alkylthiophenes) (PAT), and polyvinylcarbazole (PVCz).

Examples of the solvent include toluene, xylene, and chloroform. Examples of the method of dissolving or uniformly dispersing include such method as agitation, agitation with heating, and ultrasonic dispersing.

The coating method is not specifically restricted, and examples of the coating method include ink jet method, spraying method, dipping method, spin coating method, transfer printing method, roll coating method, and brushing method.

Examples of the baking method include methods of heating by an oven or a hot plate in an inert gas atmosphere or in vacuum.

An example of the method of producing an organic EL element having a hole transport layer including the thin film obtained from the charge transporting varnish of the present invention is as follows.

A hole injection layer is formed on an anode substrate. The layer is coated with the charge transporting varnish of the present invention, followed by baking, by the aforementioned method, to produce a hole transport layer.

A light emitting layer, an electron transport layer, an electron injection layer, and a cathode are provided in this order over the hole transport layer. Specific examples of the methods of forming the light emitting layer, the electron transport layer and the electron injection layer and of these layers include the same ones as aforementioned. Besides, the hole injection layer may be formed either by a vapor deposition method or by a coating method (wet process), according to the characteristic properties of the material to be used.

Examples of the material for forming the hole injection layer include copper phthalocyanine, titanium oxide phthalocyanine, platinum phthalocyanine, pyradino[2,3-f][1,10]phenanthroline-2,3-dicarbonitrile, N,N,N',N'-tetrakis(4-methoxyphenyl)benzidine, 2,7-bis[N,N-bis(4-methoxyphenyl)amino]-9,9-spirobifluorene, 2,2'-bis[N,N-bis(4-methoxy-phenyl)amino]-9,9-spirobifluorene, N,N'-diphenyl-N,N'-di[4-(N,N-ditolylamino)phenyl]benzidine, N,N'-diphenyl-N,N'-di[4-(N,N-diphenylamino)phenyl]benzidine, $N^4,N^{4'}$-(biphenyl-4,4'-diyl)bis($N^4,N^{4'},N^{4'}$-triphenyl-biphenyl-4,4-diamine)$N^1,N^{1'}$-(biphenyl-4,4'-diyl)bis($N^1$-phenyl-$N^4,N^{4'}$-di-m-tolylbenzene-1,4-diamine), and the charge transport materials described in PCT Patent Publication Nos. WO 2004/043117, WO 2004/105446, WO 2005/000832, WO 2005/043962, WO 2005/042621, WO 2005/107335, WO 2006-006459, WO 2006/025342, WO 2006/137473, WO 2007/049631, WO 2007/099808, WO 2008/010474, WO 2008/032617, WO 2008/032616, WO 2008/129947, WO 2009/096352, WO 2010/041701, WO 2010/058777, WO 2010/058776, WO 2013/042623, WO 2013/129249, WO 2014/115865, WO 2014/132917, WO 2014/141998, and WO 2014/132834.

Examples of the anode material, the light emitting layer, the light emitting dopant, the materials for forming the electron transport layer and the electron block layer, and the cathode material include the same ones as aforementioned.

An example of the method of producing an organic EL element having the hole injection transport layer including the thin film obtained from the charge transporting varnish of the present invention is as follows.

A hole injection transport layer is formed on an anode substrate, and a light emitting layer, an electron transport layer, an electron injection layer, and a cathode are provided in this order over the hole injection transport layer. Specific examples of the methods for forming the light emitting layer, the electron transport layer and the electron injection layer and of these layers include the same ones as aforementioned.

Examples of the anode material, the light emitting layer, the light emitting dopant, the materials for forming the electron transport layer and the electron block layer and the cathode material include the same ones as aforementioned.

Note that if necessary, a hole block layer and an electron block layer may be provided between any ones of the electrodes and the layers. For example, as the material for forming an electron block layer, there may be mentioned tris(phenylpyrazole)iridium.

The materials for constituting the anode and the cathode and the layers formed between them differ depending on whether the element to be produced has a bottom mission structure or a top emission structure, and, therefore, the materials are appropriately selected taking this point into account.

Normally, in an element of the bottom emission structure, a transparent anode is used on the substrate side, and light is taken out from the substrate side. On the other hand, in an element of the top emission structure, a reflective anode including metal is used, and light is taken out from the side of a transparent electrode (cathode) disposed on the opposite side from the substrate. Therefore, as for the anode material, for example, a transparent anode of ITO is used in the case of producing an element of the bottom emission structure, whereas a reflective anode of Al/Nd is used in the case of producing an element of the top emission structure.

The organic EL element of the present invention may be sealed, if necessary, together with a water capturing agent according to an ordinary method, for preventing characteristic properties from being degraded.

EXAMPLES

The present invention will be described more specifically below by showing Preparation Examples and Examples, but the present invention is not to be limited to the following Examples. Note that the apparatuses used are as follows.
(1) MALDI-TOF-MS: autoflex III smartbeam, manufactured by Bruker Corporation.
(2) $^1$H-NMR: JNM-ECP300 FT NMR SYSTEM, manufactured by JEOL Ltd.
(3) Substrate cleaning: Substrate cleaning equipment (reduced pressure plasma system), manufactured by Choshu Industry Co., Ltd.
(4) Coating with varnish: Spin coater MS-A100, manufactured by Mikasa Co., Ltd.
(5) Film thickness measurement: Microfigure measuring instrument SURFCORDER ET-4000, manufactured by Kosaka Laboratory Ltd.
(6) Production of EL element: Multi-functional deposition apparatus system C-E2L1G1-N, manufactured by Choshu Industry Co., Ltd.
(7) Measurement of luminance of EL element: I-V-L measuring system, manufactured by limited liability company Tech-world.
(8) Measurement of life (measurement of half-life) of EL element: Organic El luminance life evaluation system PEL-105S, manufactured by EHC Co., Ltd.

[1] Synthesis of Compound

Preparation Example 1

[Chemical Formula 123]

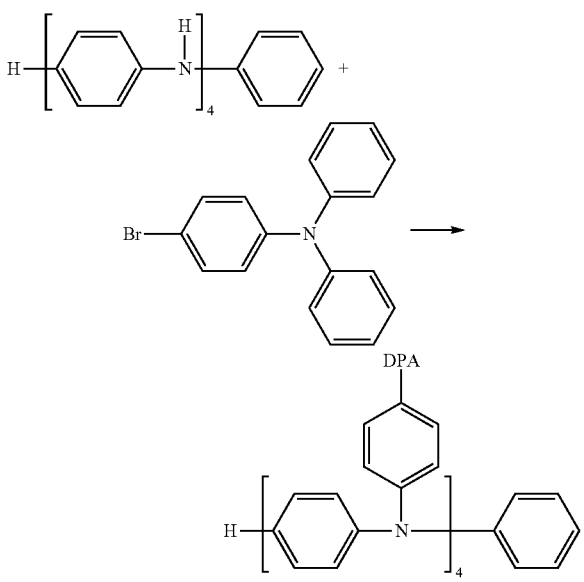

(In the formula, DPA represents a diphenylamino group, here and hereafter.)

A flask was charged with 1.94 g of N1,N1'-(1,4-phenylene)bis(N4-phenylbenzene-1,4-diamine), 4.68 g of 4-bromo-N,N-diphenylaniline, 75.3 mg of Pd(dba)$_2$, and 1.69 g of t-butoxysodium, and the atmosphere in the flask was replaced with nitrogen. Into the flask were put 30 mL of toluene and 1.3 mL of a preliminarily prepared toluene solution of tri-t-butylphosphine (concentration 40.5 g/L), followed by stirring at 50° C. for 4.5 hours.

After the stirring was over, the reaction mixture was cooled to room temperature, toluene was added thereto, filtration was conducted, the resulting filtrate was mixed with saturated saline, and liquid separation treatment was conducted. To the organic layer thus obtained was added 0.2 g of activated carbon, followed by stirring at room temperature for 30 minutes.

Thereafter, the activated carbon was removed by filtration, and the filtrate was condensed. Then, the thus condensed liquid was mixed with the filter cake obtained upon the filtration of the reaction mixture, the resulting mixture was mixed with toluene/tetrahydrofuran mixed solvent and ion-exchanged water, and a liquid separation treatment was performed. The organic layer thus obtained was dried with sodium sulfate and then condensed, the condensed liquid was added dropwise to methanol/ethyl acetate mixed solvent (300 mL/200 mL), and the slurry thus obtained was stirred at room temperature.

Finally, the slurry was filtered, and the resulting filter cake was dried, to obtain a desired aniline derivative 1 (amount 4.72 g, yield 76%).

MALDI-TOF-MS m/Z found: 1414.17 ([M]⁺calcd: 1414.63).

Preparation Example 2

[Chemical Formula 124]

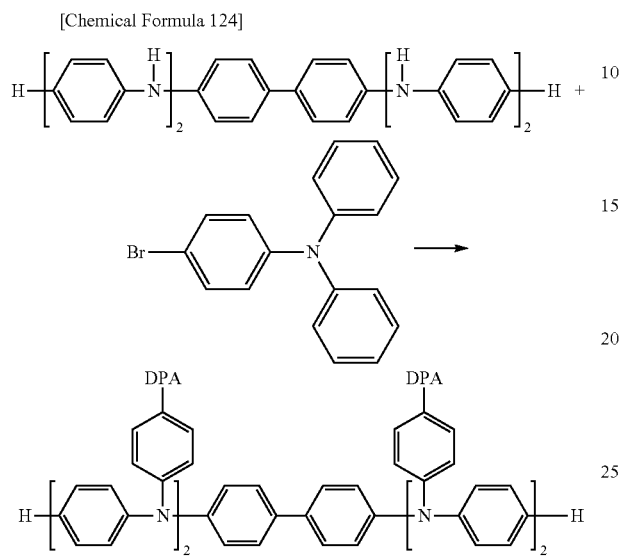

A flask was charged with 1.00 g of N1,N1'-([1,1'-biphenyl]-4,4'-diyl)bis(N4-phenylbenzene-1,4-diamine), 3.13 g of 4-bromo-N,N-diphenylaniline, 44.8 mg of Pd(dba)₂ and 1.13 g of t-butoxysodium, and then the atmosphere in the flask was replaced by nitrogen. Into the flask were put 20 mL of toluene and 0.73 mL of a preliminarily prepared toluene solution of tri-t-butylphosphine (concentration 43 g/L), followed by stirring at 50° C. for one hour and at 40° C. for 12 hours.

After the stirring was over, the reaction mixture was cooled to room temperature, the thus cooled reaction mixture was mixed with chloroform and ion-exchanged water, and a liquid separation treatment was conducted. The organic layer thus obtained was dried with sodium sulfate, and 0.5 g of activated carbon was added to the dried organic layer, followed by stirring overnight at room temperature.

Thereafter, the activated carbon was removed by filtration, the filtrate was condensed, the condensed liquid obtained was added dropwise to methanol/ethyl acetate mixed solvent (400 mL/200 mL), and the resulting slurry was stirred at room temperature for three hours.

Finally, the slurry was filtered, and the filter cake obtained was dried, to obtain a desired aniline derivative 2 (amount 2.69 g, yield 94%).

¹H-NMR (300 MHz, THF-d6) δ [ppm]: 7.46 (d, J=8.6 Hz, 4H), 7.18 to 7.24 (m, 19H), and 6.92 to 7.12 (m, 55H).

Preparation Example 3

[Chemical Formula 125]

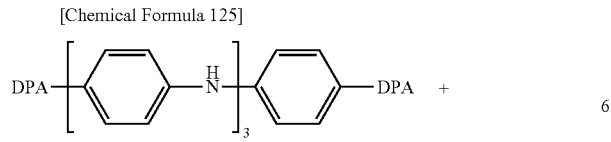

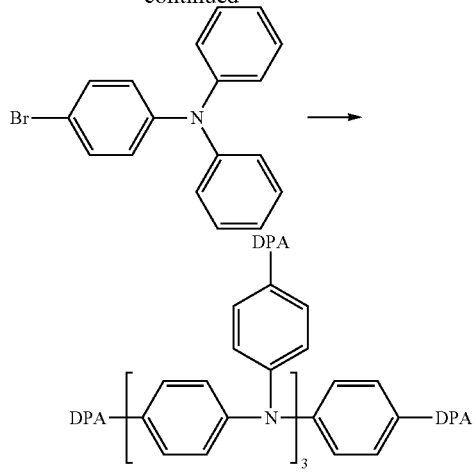

A flask was charged with 3.00 g of N1-(4-((4-((4-diphenylamino)phenyl)amino)phenyl)amino)phenyl)-N4,N4-diphenylbenzene-1,4-diamine, 7.09 g of 4-bromo-N,N-diphenylaniline, 75.1 mg of Pd(dba)₂, and 2.54 g of t-butoxysodium, and the atmosphere in the flask was replaced by nitrogen. Into the flask were put 50 mL of toluene and 1.3 mL of a preliminarily prepared toluene solution of tri-t-butylphosphine (concentration 40.5 g/L), followed by stirring at 50° C. for 15 hours.

After the stirring was over, the reaction mixture was cooled to room temperature, followed by filtration, then the filtrate was mixed with toluene and saturated saline, and a liquid separation treatment was conducted (twice). The organic layer thus obtained was dried with sodium sulfate, and 0.5 g of activated carbon was added to the dried organic layer, followed by stirring at room temperature for 30 minutes.

Thereafter, the activated carbon was removed by filtration, the filtrate was condensed, then the condensed liquid was added dropwise to methanol/ethyl acetate mixed solvent (300 mL/200 mL), and the resulting slurry was stirred at room temperature for 30 minutes.

Finally, the slurry was filtered, the filter cake obtained was dried, to obtain a desired aniline derivative 3 (amount 5.95 g, yield 96%).

¹H-NMR (300 MHz, THF-d6) δ [ppm]: 7.17 to 7.27 (m, 22H), and 6.91 to 7.05 (m, 56H).

MALDI-TOF-MS m/Z found: 1414.04 ([M]⁺calcd: 1414.63).

Preparation Example 4

[Chemical Formula 126]

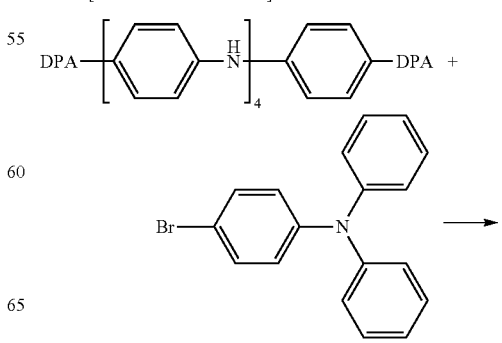

-continued

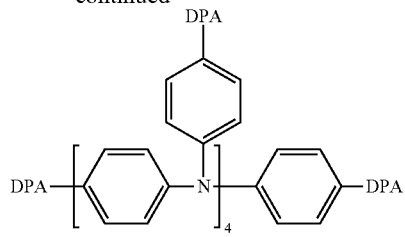

A flask was charged with 2.00 g of N1,N1'-((1,4-phenylenebis(azanediyl))bis(4,1-phenylene))-bis(N4,N4-diphenylbenzene-1,4-diamine), 4.17 g of 4-bromo-N,N-diphenylaniline, 59.3 mg of Pd(dba)$_2$ and 1.50 g of t-butoxysodium, and the atmosphere in the flask was replaced by nitrogen. Into the flask were put 20 mL of toluene and 1.0 mL of a preliminarily prepared toluene solution of tri-t-butylphosphine (concentration 43 g/L), followed by stirring at 50° C. for one hour and at 40° C. for 12 hours.

After the stirring was over, the reaction mixture was cooled to room temperature, followed by filtration, the filtrate was mixed with saturated saline, and a liquid separation treatment was conducted. The organic layer thus obtained was dried with sodium sulfate, and 0.5 g of activated carbon was added to the dried organic layer, followed by stirring at room temperature for 30 minutes.

Thereafter, the activated carbon was removed by filtration, the filtrate was condensed, the thus condensed liquid was added dropwise to methanol/ethyl acetate mixed solvent (300 mL/200 mL), and the resulting slurry was stirred at room temperature.

Finally, the slurry was filtered, and the filter cake obtained was dried, to obtain a desired aniline derivative 4 (amount 4.37 g, yield 97%).

$^1$H-NMR (300 MHz, THF-d6) δ [ppm]: 7.16 to 7.21 (m, 24H), and 6.90 to 7.04 (m, 72H).

Preparation Example 5

[Chemical Formula 127]

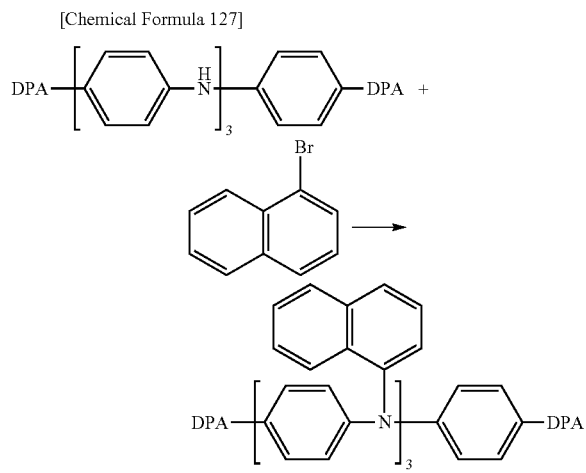

A flask was charged with 3.00 g of N1-(4-((4-((4-(diphenylamino)phenyl)amino)phenyl)amino)phenyl)-N4,N4-diphenylbenzene-1,4-diamine, 3.1 mL of 1-bromonaphthalene, 75.5 mg of Pd(dba)$_2$ and 2.53 g of t-butoxysodium, and the atmosphere in the flask was replaced by nitrogen. Into the flask were put 40 mL of toluene and 1.3 mL of a preliminarily prepared toluene solution of tri-t-butylphosphine (concentration 42.6 g/L), followed by stirring at 50° C. for four hours.

After the stirring was over, the reaction mixture was cooled to room temperature, followed by filtration, and the filtrate was mixed with toluene and saturated saline, followed by a liquid separation treatment (twice). The organic layer thus obtained was dried with sodium sulfate, and 0.5 g of activated carbon was added to the dried organic layer, followed by stirring at room temperature for 30 minutes.

Thereafter, the activated carbon was removed by filtration, the filtrate was condensed, the condensed liquid was added dropwise to methanol/ethyl acetate mixed solvent (300 mL/200 mL), and the resulting slurry was stirred at room temperature for one hour.

Finally, the slurry was filtered, and the filter cake obtained was dried, to obtain a desired aniline derivative 5 (amount 4.21 g, yield 90%).

$^1$H-NMR (300 MHz, THF-d6) δ [ppm]: 7.95 to 8.00 (m, 4H), 7.82 to 7.86 (m, 4H), 7.69 to 7.73 (m, 4H), 7.28 to 7.46 (m, 15H), and 6.80 to 7.00 (m, 30H).

MALDI-TOF-MS m/Z found: 1063.39 ([M]$^+$calcd: 1063.46).

Preparation Example 6

[Chemical Formula 128]

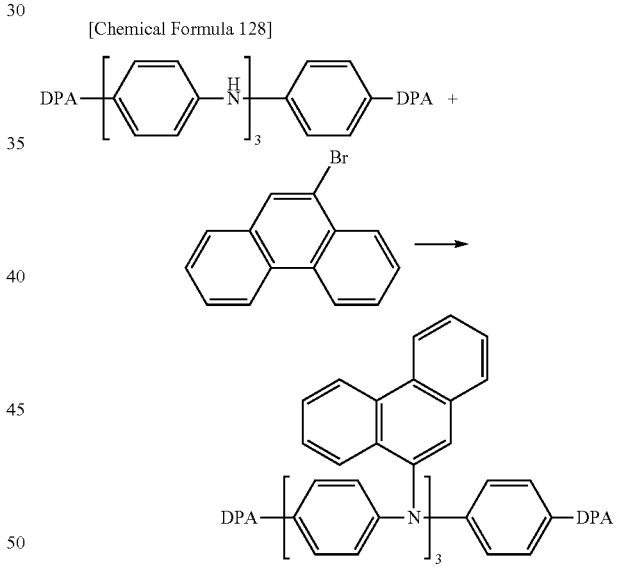

A flask was charged with 3.01 g of N1-(4-((4-((4-(diphenylamino)phenyl)amino)phenyl)amino)phenyl)-N4,N4-diphenylbenzene-1,4-diamine, 5.63 g of 9-bromophenanthrene, 76.0 mg of Pd(dba)$_2$ and 2.54 g of t-butoxysodium, and the atmosphere in the flask was replaced by nitrogen. Into the flask were put 40 mL of toluene and 1.3 mL of a preliminarily prepared toluene solution of tri-t-butylphosphine (concentration 42.6 g/L), followed by stirring at 50° C. for six hours.

After the stirring was over, the reaction mixture was cooled to room temperature, the cooled reaction mixture was mixed with tetrahydrofuran and toluene and with ion-exchanged water, and a liquid separation treatment was conducted. From the organic layer thus obtained, the solvent was distilled off at reduced pressure, the solid matter thus obtained was mixed with tetrahydrofuran/toluene/ethyl acetate mixed solvent (40 g/5 g/5 g) and 0.5 g of activated carbon, and the resulting mixture was stirred at 60° C. for 30 minutes.

Thereafter, the activated carbon was removed by hot filtration, the filtrate was cooled to 0° C. with stirring, to which 25 mL of methanol and 2 mL of ethyl acetate were added sequentially, and the resulting slurry was stirred further at 0° C. for two hours.

Finally, the slurry was filtered, and the filter cake obtained was dried, to obtain a desired aniline derivative 6 (amount 4.75 g, yield 89%).

$^1$H-NMR (300 MHz, THF-d6) δ [ppm]: 8.70 to 8.78 (m, 6H), 8.09 to 8.12 (m, 3H), 7.75 to 7.79 (m, 3H), 7.44 to 7.65 (m, 14H), 7.06 to 7.21 (m, 12H), and 6.84 to 6.99 (m, 25H).

MALDI-TOF-MS m/Z found: 1213.52 ([M]$^+$calcd: 1213.51).

Preparation Example 7

[Chemical Formula 129]

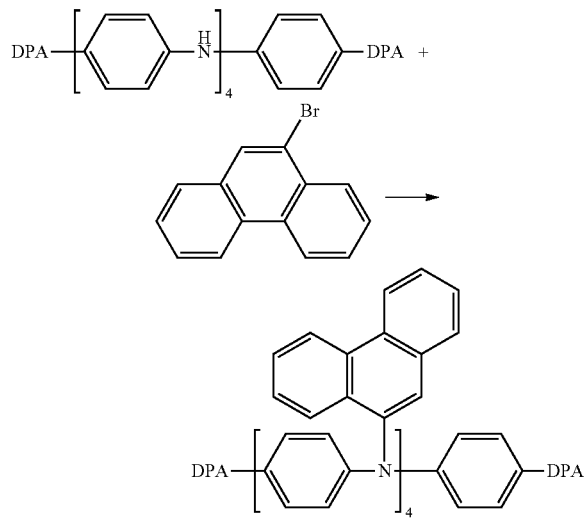

A flask was charged with 2.00 g of N1,N1'-((1,4-phenyle-nebis(azanediyl)bis(4,1-phenylene)bis-(N4,N4-diphenyl-benzene-1,4-diamine), 3.17 g of 9-bromophenanthrene, 59.2 mg of Pd(dba)$_2$ and 1.44 g of tertiary-butoxysodium, and the atmosphere in the flask was replaced by nitrogen. Into the flask were put 20 mL of toluene and 0.880 mL of a preliminarily prepared toluene solution of tri-t-butylphosphine (concentration 47.2 g/L), followed by stirring at 50° C. for 6.5 hours.

After the stirring was over, the reaction mixture was cooled to room temperature, followed by filtration, the filter cake was washed sequentially with ion-exchanged water and methanol.

Finally, the washed filter cake was dried, to obtain a desired aniline derivative 7 (amount 3.24 g, yield 85%).

$^1$H-NMR (300 MHz, DMSO-d6) δ [ppm]: 8.75 to 8.86 (m, 7H), 7.81 to 8.00 (m, 7H), 7.47 to 7.70 (m, 18H), 7.12 to 7.28 (m, 16H), and 6.78 to 6.94 (m, 28H).

Preparation Example 8

[Chemical Formula 130]

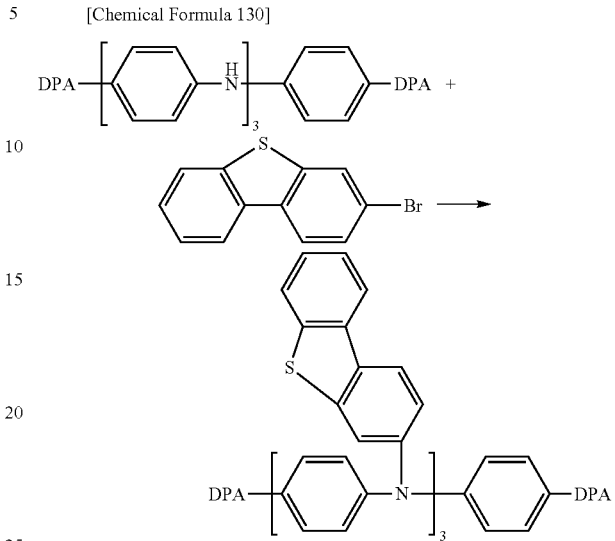

A flask was charged with 2.00 g of N1-(4-((4-((4-(diphenylamino)phenyl)amino)phenyl)amino)phenyl)-N4,N4-diphenylbenzene-1,4-diamine, 2.79 g of 2-bromodibenzo[b,d]thiophene, 50.3 mg of Pd(dba)$_2$, and 1.21 g of t-butoxysodium, and the atmosphere in the flask was replaced by nitrogen. Into the flask were put 20 mL of toluene and 0.750 mL of a preliminarily prepared toluene solution of tri-t-butylphosphine (concentration 47.2 g/L), followed by stirring at 50° C. for seven hours.

After the stirring was over, the reaction mixture was cooled to room temperature, the cooled reaction mixture was mixed with toluene and saturated saline, and a liquid separation treatment was conducted. The organic layer thus obtained was dried with sodium sulfate, and then 0.2 g of activated carbon was added to the dried organic layer, followed by stirring at room temperature for 30 minutes.

Thereafter, the activated carbon was removed by filtration, the solvent was distilled off from the filtrate at reduced pressure, and the thus obtained residue was dissolved in 20 mL of toluene. The solution obtained was added dropwise to methanol/ethyl acetate mixed solvent (300 mL/200 mL), the resulting slurry was stirred at room temperature, and then the slurry was filtered to recover the filter cake. By use of a solution obtained by dissolving the resulting filter cake in 20 mL of toluene, the operation from dropwise addition to the mixed solvent to the recovery of the filter cakes was performed in the same manner as above.

Finally, the recovered filter cake was dried, to obtain a desired aniline derivative 8 (amount 3.23 g, yield 90%).

$^1$H-NMR (300 MHz, DMSO-d6) δ [ppm]: 8.19 (d, J=7.8 Hz, 3H), 8.05 (s, 3H), 7.91 to 8.00 (m, 6H), 7.42 to 7.51 (m, 6H), 7.24 to 7.29 (m, 11H), and 6.94 to 7.04 (m, 28H).

Preparation Example 9

9-1

A flask was charged with 10.0 g of 3-bromocarbazole, 1.75 g of sodium hydroxide, and 100 mL of N,N-dimethylformamide, and the atmosphere in the flask was replaced by nitrogen. To the flask, 7.42 g of benzyl bromide was added dropwise, followed by stirring at room temperature for 19 hours, then the reaction mixture was added dropwise to ion-exchanged water being stirred, and stirring was further conducted at room temperature.

Finally, the slurry obtained was filtered, and the filter cake was dried, to obtain the desired 9-benzyl-3-bromocarbazole (amount 13.1 g, yield 96%).

$^1$H-NMR (300 MHz, CDCl$_3$) δ [ppm]: 8.23 (d, J=2.1 Hz, 1H), 8.07 (d, J=8.0 Hz, 1H), 7.49 (dd, J=8.6, 2.1 Hz, 1H), 7.42 to 7.45 (m, 1H), 7.36 (d, J=8.0 Hz, 1H), 7.21 to 7.31 (m, 5H), 7.08 to 7.11 (m, 2H), and 5.49 (s, 2H).

[9-2]

[Chemical Formula 131]

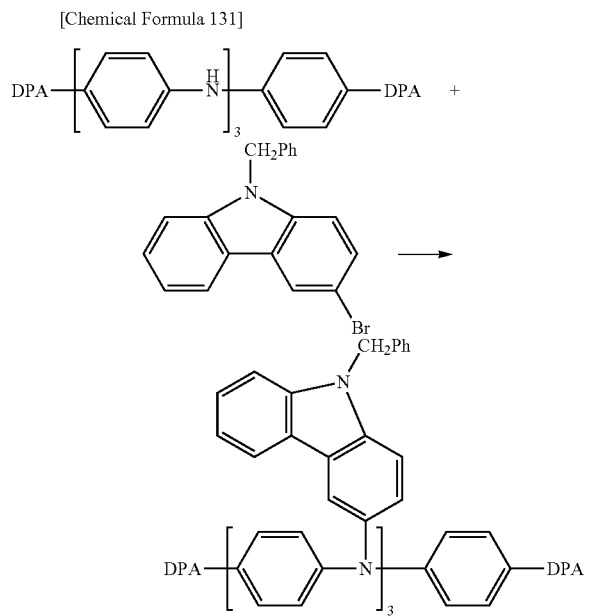

A flask was charged with 2.00 g of N1-(4-((4-((4-(diphenylamino)phenyl)amino)phenyl)amino)phenyl)-N4,N4-diphenylbenzene-1,4-diamine, 3.24 g of the above-obtained 9-benzyl-3-bromocarbazole, 50.5 mg of Pd(dba)$_2$, and 1.21 g of t-butoxysodium, and the atmosphere in the flask was replaced by nitrogen. Into the flask were put 20 mL of toluene and 0.56 mL of a preliminarily prepared toluene solution of tri-t-butylphosphine (concentration 63.4 g/L), followed by stirring at 50° C. for 24 hours.

After the stirring was over, the reaction mixture was cooled to room temperature, the cooled reaction mixture was mixed with toluene and saturated saline, and a liquid separation treatment was conducted. To the organic layer obtained, activated carbon was added, followed by stirring at room temperature for 30 minutes, then the activated carbon was removed by filtration, and the filtrate was condensed. The condensed liquid thus obtained was added dropwise to methanol/ethyl acetate mixed solvent, and the resulting slurry was stirred at room temperature.

Finally, the slurry was filtered, and the filter cake was dried, to obtain the N1,N4-bis(9-benzyl-9H-carbazol-3-yl)-N1-(4-((9-benzyl-9H-carbazol-3-yl)(4-(diphenylamino)phenyl)amino)phenyl)-N4-(4-(diphenylamino)phenyl)benzene-1,4-diamine (amount 3.92 g, yield 93%).

MALDI-TOF-MS m/Z found: 1451.52 ([M]$^+$calcd: 1450.63).

[9-3]

[Chemical Formula 132]

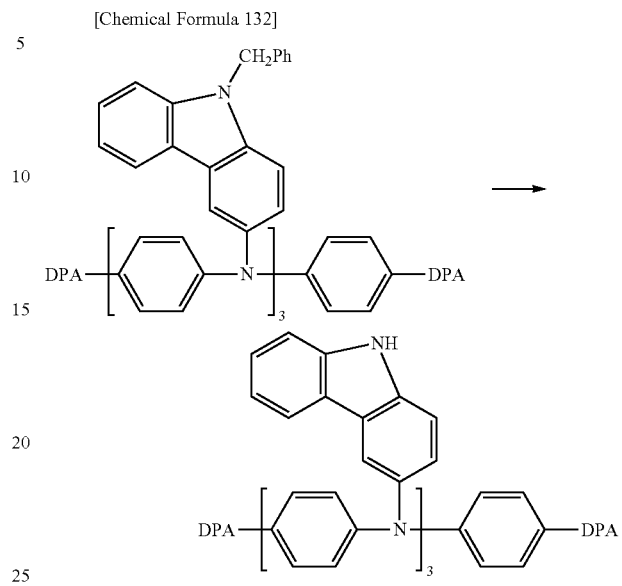

A flask was charged with 2.00 g of the N1,N4-bis(9-benzyl-9H-carbazol-3-yl)-N1-(4-((9-benzyl-9H-carbazol-3-yl)(4-(diphenylamino)phenyl)amino)phenyl)-N4-(4-(diphenylamino)phenyl)benzene-1,4-diamine obtained above and 40 mL of dimethyl sulfoxide, and then the atmosphere in the flask was replaced by oxygen. To the flask, 25 mL of a preliminarily prepared tetrahydrofuran solution of t-butoxypotassium (concentration 1M) was added dropwise, followed by stirring at room temperature for 23 hours.

After the stirring was over, the reaction mixture was added dropwise to ion-exchanged water/methanol mixed solvent, the resulting mixture was stirred, then 5 mL of 5 M hydrochloric acid was added dropwise thereto, and stirring was further conducted.

Finally, the slurry was filtered, and the filter cake was dried, to obtain a desired aniline derivative 9 (amount 1.62 g, yield 99%).

MALDI-TOF-MS m/Z found: 1180.10 ([M]$^+$calcd: 1180.49).

Preparation Example 10

[Chemical Formula 133]

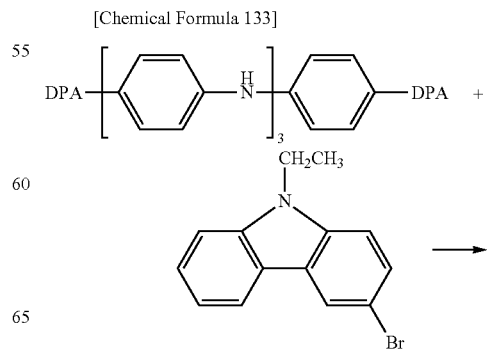

-continued

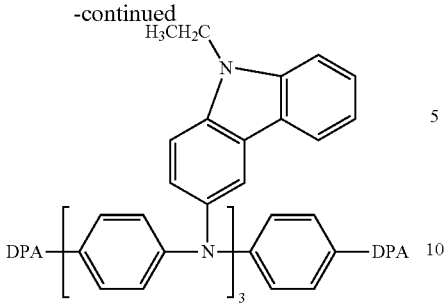

-continued

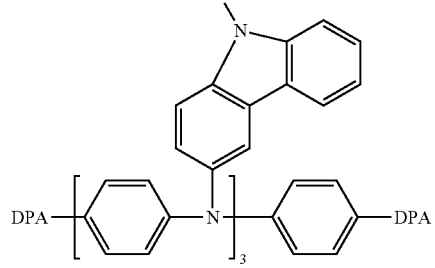

A flask was charged with 1.50 g of N1-(4-((4-((4-(diphenylamino)phenyl)amino)phenyl)amino)phenyl)-N4,N4-diphenylbenzene-1,4-diamine, 3.00 g of 3-bromo-9-ethyl-9H-carbazole, 37.9 mg of Pd(dba)$_2$, and 1.28 g of t-butoxysodium, and the atmosphere in the flask was replaced by nitrogen. Into the flask were put 15 mL of toluene and 0.64 mL of a preliminarily prepared toluene solution of tri-t-butylphosphine (concentration 41.7 g/L), followed by stirring at 50° C. for six hours.

After the stirring was over, the reaction mixture was cooled to room temperature, the cooled reaction mixture was mixed with chloroform and saturated saline, and a liquid separation treatment was performed (twice). The organic layer thus obtained was dried with sodium sulfate, and then 0.5 g of activated carbon was added to the dried organic layer, followed by stirring at room temperature for 30 minutes.

Thereafter, the activated carbon was removed by filtration, the filtrate was condensed, the condensed liquid was added dropwise to methanol, and the resulting slurry was stirred overnight at room temperature.

Finally, the slurry was filtered, then column chromatography (eluent: toluene/hexane=70/30→90/10) was conducted using the thus obtained filter cake, and by checking the presence/absence of the target product by a thin layer chromatography (TLC) method, a fraction containing the target product was isolated. Finally, the solvent was removed from the isolated fraction at reduced pressure, to obtain a desired aniline derivative 10 (amount 1.41 g, yield 51%).

MALDI-TOF-MS m/Z found: 1264.03 ([M]$^+$calcd: 1264.59).

Preparation Example 11

[Chemical Formula 134]

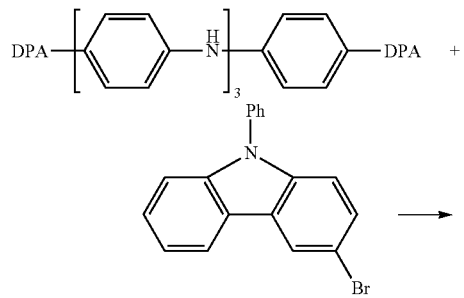

A flask was charged with 2.00 g of N1-(4-((4-((4-(diphenylamino)phenyl)amino)phenyl)amino)phenyl)-N4,N4-diphenylbenzene-1,4-diamine, 3.38 g of 3-bromo-9-phenyl-9H-carbazole, 51.1 mg of Pd(dba)$_2$, and 1.21 g of t-butoxysodium, and the atmosphere in the flask was replaced by nitrogen. Into the flask were put 30 mL of toluene and 0.720 mL of a preliminarily prepared toluene solution of tri-t-butylphosphine (concentration 49.1 g/L), followed by stirring at 50° C. for six hours.

After the stirring was over, the reaction mixture was cooled to room temperature, the cooled reaction mixture was mixed with toluene and saturated saline, and a liquid separation treatment was performed. The organic layer thus obtained was dried with sodium sulfate.

Next, the solvent was distilled off from the dried organic layer at reduced pressure, and the residue was dissolved in toluene. Then, the solution obtained was added dropwise to methanol/ethyl acetate mixed solvent (200 mL/200 mL), and the resulting slurry was stirred at room temperature.

Finally, the slurry was filtered, and the filter cake obtained was dried, to obtain a desired aniline derivative 11 (amount 3.35 g, yield 81%).

$^1$H-NMR (300 MHz, THF-d6) δ [ppm]: 7.96 to 8.07 (m, 6H), 7.57 to 7.64 (m, 11H), 7.46 to 7.48 (m, 3H), 7.14 to 7.34 (m, 24H), and 6.87 to 7.04 (m, 28H).

MALDI-TOF-MS m/Z found: 1409.48 ([M]$^+$calcd: 1408.59).

Preparation Example 12

[12-1]

A flask was charged with 3.00 g of 3-bromocarbazole, 0.52 g of sodium hydroxide and 30 mL of N,N-dimethylformamide, and the atmosphere in the flask was replaced by nitrogen. To the flask, 1.9 mL of 4-(chloromethyl)styrene was added dropwise, followed by stirring at room temperature for 20 hours.

Thereafter, the reaction mixture thus obtained was added dropwise to ion-exchanged water being stirred, and stirring was conducted further at room temperature.

Finally, the resulting slurry was filtered, and the filter cake was dried, to obtain the desired N-(4-vinylbenzyl)-3-bromocarbazole (amount 3.97 g, yield 90%).

$^1$H-NMR (300 MHz, CDCl$_3$) δ [ppm]: 8.23 (d, J=2.1 Hz, 1H), 8.07 (d, J=7.7 Hz, 1H), 7.20 to 7.51 (m, 7H), 7.05 (d, J=8.1 Hz, 2H), 6.64 (dd, J=17.7, 10.8 Hz, 1H), 5.67 (d, J=17.7 Hz, 1H), 5.47 (s, 2H), and 5.20 (d, J=10.8 Hz, 1H).

[12-2]

[Chemical Formula 135]

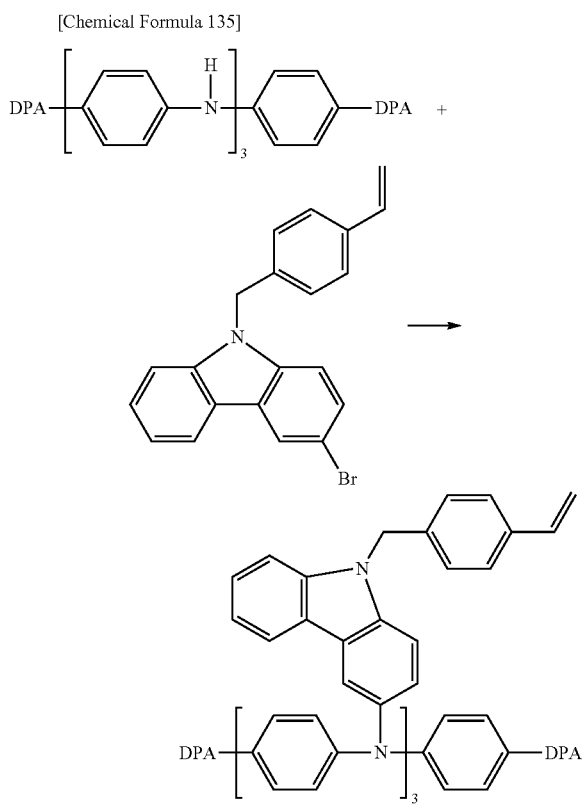

A flask was charged with 2.18 g of N1-(4-((4-((4-(diphenylamino)phenyl)amino)phenyl)amino)phenyl)-N4,N4-diphenylbenzene-1,4-diamine, 3.80 g of 3-bromo-9-(4-vinylbenzyl)carbazole, 1110 mg of Pd(dba)$_2$, and 1.32 g of t-butoxysodium, and the atmosphere in the flask was replaced by nitrogen. Into the flask were put 20 mL of toluene and 1.1 mL of a preliminarily prepared toluene solution of tri-t-butylphosphine (concentration 70.9 g/L), followed by stirring at 50° C. for five hours.

After the stirring was over, the reaction mixture was cooled to room temperature, the cooled reaction mixture was mixed with toluene and saturated saline, and a liquid separation treatment was conducted. Activated carbon was added to the thus obtained organic layer, followed by stirring at room temperature for 30 minutes, then the activated carbon was removed by filtration, and the filtrate was condensed. The condensed liquid thus obtained was added dropwise to methanol/ethyl acetate mixed solvent, and the resulting slurry was stirred at room temperature.

Finally, the slurry was filtered, and the filter cake was dried, to obtain a desired aniline derivative 12 (amount 4.51 g, yield 93%).

MALDI-TOF-MS m/Z found: 1527.85 ([M]$^+$calcd: 1528.68).

Preparation Example 13

[13-1]

A flask was charged with 2.00 g of 3-bromocarbazole, 0.349 g of sodium hydroxide, and 20 mL of N,N-dimethylformamide, and then the atmosphere in the flask was replaced by nitrogen. To the flask, 1.10 mL of 4-(bromomethyl)-1,2-difluorobenzene was added dropwise, followed by stirring at room temperature for three days.

Thereafter, the reaction mixture obtained was added dropwise to ion-exchanged water being stirred, and the resulting slurry was stirred further at room temperature.

Finally, the slurry was filtered, and the filter cake was dried, to obtain 3-bromo-9-(3,4-difluorobenzyl)carbazole (amount 2.91 g, yield 96%).

$^1$H-NMR (300 MHz, CDCl$_3$) δ [ppm]: 8.23 (d, J=2.1 Hz, 1H), 8.07 (d, J=7.7 Hz, 1H), 7.43 to 7.52 (m, 2H), 7.28 to 7.32 (m, 2H), 7.17 (d, J=8.6 Hz, 1H), 7.00 to 7.09 (m, 1H), 6.80 to 6.91 (m, 2H), and 5.41 (s, 2H).

[13-2]

[Chemical Formula 136]

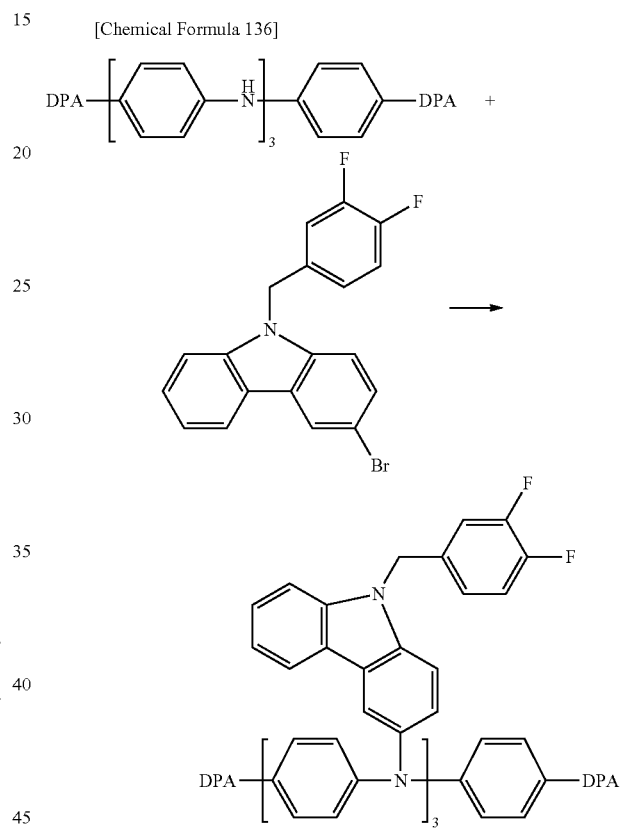

A flask was charged with 1.03 g of N1-(4-((4-((4-(diphenylamino)phenyl)amino)phenyl)amino)phenyl)-N4,N4-diphenylbenzene-1,4-diamine, 1.84 g of 3-bromo-9-(3,4-difluorobenzyl)carbazole, 26.3 mg of Pd(dba)$_2$, and 0.635 g of t-butoxysodium, and then the atmosphere in the flask was replaced by nitrogen. Into the flask were put 10 mL of toluene and 0.20 mL of a preliminarily prepared toluene solution of tri-t-butylphosphine (concentration 93.2 g/L), followed by stirring at 50° C. for nine hours.

After the stirring was over, the resulting reaction mixture was cooled to room temperature, the cooled reaction mixture was mixed with toluene and saturated saline, and a liquid separation treatment was conducted. The organic layer obtained was dried with sodium sulfate, and then activated carbon was added to the dried organic layer, followed by stirring at room temperature for three hours.

Thereafter, the activated carbon was removed by filtration, the filtrate was condensed, and the condensed liquid thus obtained was added dropwise to methanol/ethyl acetate mixed solvent, and the resulting slurry was stirred at room temperature.

Finally, the slurry was filtered, and the filter cake obtained was dried, to obtain a desired aniline derivative 13 (amount 2.18 g, yield 93%).

MALDI-TOF-MS m/Z found: 1559.48 ([M]⁺calcd: 1558.58).

Preparation Example 14

[14-1]

A flask was charged with 2.00 g of 3-bromocarbazole, 0.352 g of sodium hydroxide, and 20 mL of N,N-dimethylformamide, and the atmosphere in the flask was replaced by nitrogen. To the flask, 2.05 g of 1-(bromomethyl)-4-(trifluoromethyl)benzene was added dropwise, followed by stirring at room temperature for 15 hours.

Thereafter, the reaction mixture was added dropwise to ion-exchanged water being stirred, and the resulting slurry was stirred further at room temperature.

Finally, the slurry was filtered, and the filter cake was dried, to obtain the desired 3-bromo-9-(4-(trifluoro-methyl) benzyl)carbazole (amount 3.20 g, yield 97%).

$^1$H-NMR (300 MHz, CDCl$_3$) δ [ppm]: 8.24 (d, J=1.5 Hz, 1H), 8.08 (d, J=8.0 Hz, 1H), 7.43 to 7.53 (m, 4H), 7.16 to 7.32 (m, 5H), and 5.53 (s, 2H).

[14-2]

[Chemical Formula 137]

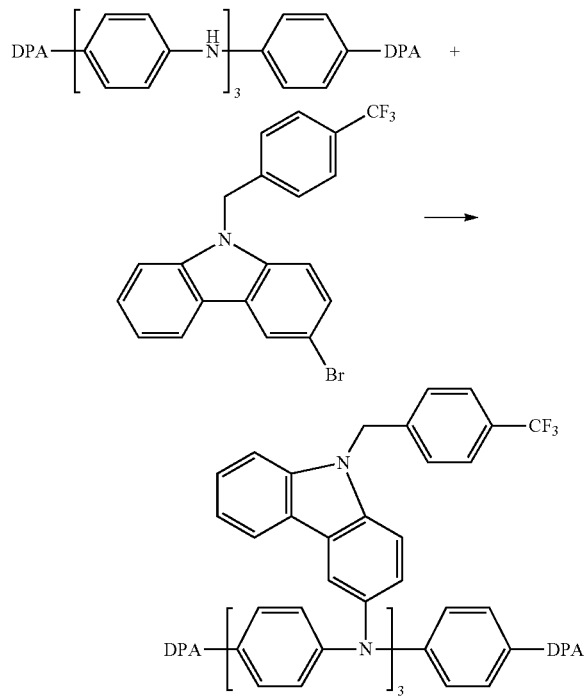

A flask was charged with 1.03 g of N1-(4-((4-((4-(diphenylamino)phenyl)amino)phenyl)amino)phenyl)-N4,N4-diphenylbenzene-1,4-diamine, 2.00 g of 3-bromo-9-(4-(trifluoromethyl)benzyl)carbazole, 26.0 mg of Pd(dba)$_2$, and 0.637 g of t-butoxysodium, and then the atmosphere in the flask was replaced by nitrogen. Into the flask were put 10 mL of toluene and 0.20 mL of a preliminarily prepared toluene solution of tri-t-butylphosphine (concentration 93.2 g/L), followed by stirring at 50° C. for 2.5 hours.

After the stirring was over, the reaction mixture was cooled to room temperature, the cooled reaction mixture was mixed with toluene and saturated saline, and a liquid separation treatment was performed. The organic layer obtained was dried with sodium sulfate, and then activated carbon was put into the dried organic layer, followed by stirring at room temperature for 30 minutes.

Thereafter, the activated carbon was removed by filtration, the filtrate was condensed, the condensed liquid was added dropwise to methanol/ethyl acetate mixed solvent, and the resulting slurry was stirred at room temperature.

Finally, the slurry was filtered, and the resulting filter cake was dried, to obtain a desired aniline derivative 14 (amount 2.25 g, yield 91%).

MALDI-TOF-MS m/Z found: 1655.44 ([M]⁺calcd: 1654.60).

Preparation Example 15

[Chemical Formula 138]

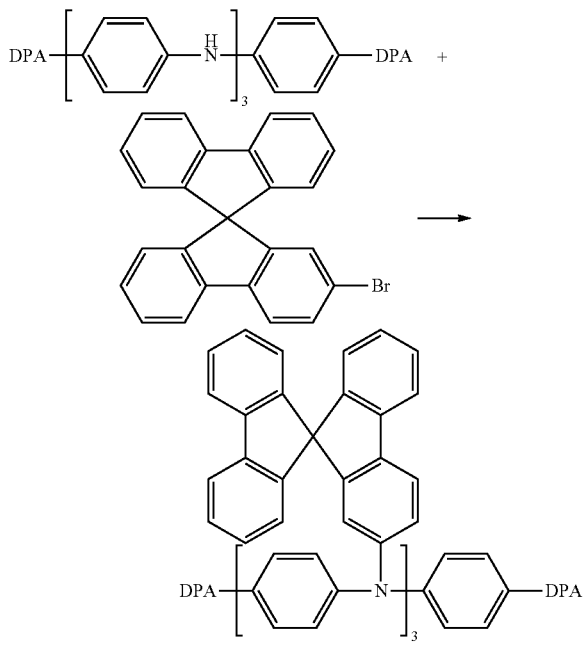

A flask was charged with 1.00 g of N1-(4-((4-((4-(diphenylamino)phenyl)amino)phenyl)amino)phenyl)-N4,N4-diphenylbenzene-1,4-diamine, 2.08 g of 2-bromo-9,9'-spirobi [fluorene], 25 mg of Pd(dba)$_2$, and 0.607 g of t-butoxysodium, and then the atmosphere in the flask was replaced by nitrogen. Into the flask were put 10 mL of toluene and 0.35 mL of a preliminarily prepared toluene solution of tri-t-butylphosphine (concentration 0.050 g/L), followed by stirring at 50° C. for four hours.

After the stirring was over, the reaction mixture was cooled to room temperature, the cooled reaction mixture was mixed with toluene and ion-exchanged water, and a liquid separation treatment was conducted. The organic layer obtained was dried with sodium sulfate, and 0.2 g of activated carbon was added to the organic layer, followed by stirring at room temperature for 30 minutes.

Thereafter, the activated carbon was removed by filtration, the solvent was distilled off from the filtrate at reduced pressure, and the residue was dissolved in 15 mL of toluene. The solution obtained was added dropwise to methanol/ethyl acetate mixed solvent (200 mL/50 mL), the resulting slurry was stirred at room temperature, and then the slurry was filtered, to recover the filter cake.

Then, the filter cake obtained was again dissolved in 10 mL of toluene, the resulting solution was added dropwise to methanol/ethyl acetate mixed solvent (200 mL/200 mL), and the slurry thus obtained was stirred at room temperature.

Finally, the slurry was filtered, and the resulting filter cake was dried, to obtain a desired aniline derivative 15 (amount 1.86 g, yield 78%).

MALDI-TOF-MS m/Z found: 1628.01 ([M]⁺calcd: 1627.65).

Preparation Example 16

[16-1]

[Chemical Formula 139]

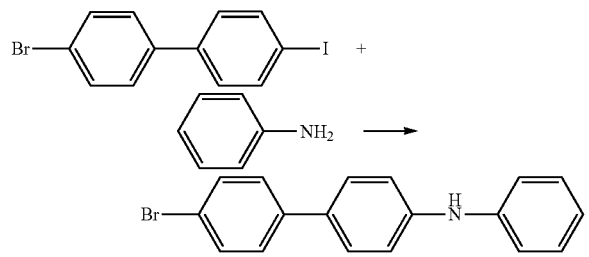

A flask was charged with 20 g of 4-bromo-4'-iodo-1,1'-biphenyl, 3.2 g of Pd(PPh₃)₄, and 6.4 g of t-butoxysodium, and then the atmosphere in the flask was replaced by nitrogen. Into the flask were put 200 mL of toluene and 6.1 g of aniline, followed by stirring for 6.5 hours under reflux conditions.

After the stirring was over, the reaction mixture was cooled to room temperature, the cooled reaction mixture was mixed with chloroform and ion-exchanged water, and a liquid separation treatment was performed. The solvent was distilled off from the separated organic layer at reduced pressure, column chromatography was conducted using a solution obtained by dissolving the residue in chloroform, and, by checking the presence/absence of the target product by a thin layer chromatography (TLC) method, a fraction containing the target product was isolated.

The isolated fraction was condensed, and the condensed liquid was mixed with 100 g of methanol/toluene mixed solvent (3/1 (w/w)). The mixture thus obtained was stirred under reflux conditions to dissolve the solid matter, followed by stirring for 30 minutes under the reflux conditions, then by cooling to room temperature, and by stirring further at room temperature for one hour.

Finally, the precipitated solid matter was filtered, and the filter cake was dried, to obtain 4'-bromo-N-phenyl-[1,1'-biphenyl]-4-amine (amount 11.20 g, yield 62%).

¹H-NMR (300 MHz, CDCl₃) δ [ppm]: 7.53 to 7.40 (m, 6H), 7.32 to 7.26 (m, 2H), 7.11 (d, J=8.6 Hz, 4H), 6.99 to 6.94 (t, J=7.4 Hz, 1H), and 5.78 (s, 1H).

[16-2]

[Chemical Formula 140]

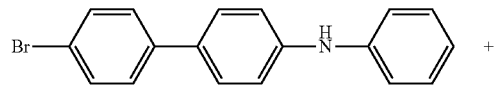

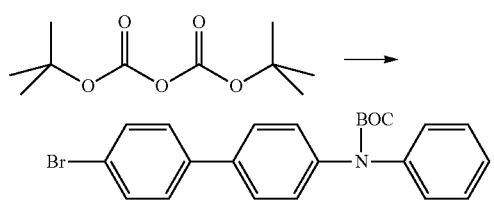

(In the formula, BOC means a t-butoxycarbonyl group, here and hereafter.)

A flask was charged with 5.0 g of 4'-bromo-N-phenyl-[1,1'-biphenyl]-4-amine, 0.09 g of N,N-dimethyl-4-aminopyridine, and 50 mL of tetrahydrofuran, then the mixture was refluxed by heating, 10 g of di-t-butyl dicarbonate was added dropwise thereto, and the resulting mixture was stirred under reflux conditions for 1.5 hours.

Thereafter, the reaction mixture was let cool to room temperature, the solvent was distilled off from the reaction mixture thus let cool at reduced pressure, and the residue was dissolved in chloroform. Column chromatography was conducted using the resulting solution, and, by checking the presence/absence of the target product by a thin layer chromatography (TLC) method, a fraction containing the target product was isolated, and the solvent was distilled off from the isolated fraction at reduced pressure.

Finally, the residue obtained was mixed with 20 mL of n-hexane, the precipitated solid matter was recovered by filtration and dried, to obtain the desired t-butyl(4'-bromo-[1,1'-biphenyl]-4-yl)(phenyl)carbamate (amount 5.4 g, yield 83%).

¹H-NMR (300 MHz, CDCl₃) δ [ppm]: 7.54 (d, J=6.3 Hz, 2H), 7.41 to 7.49 (m, 4H), 7.18 to 7.36 (m, 7H), and 1.47 (s, 9H).

[16-3]

[Chemical Formula 141]

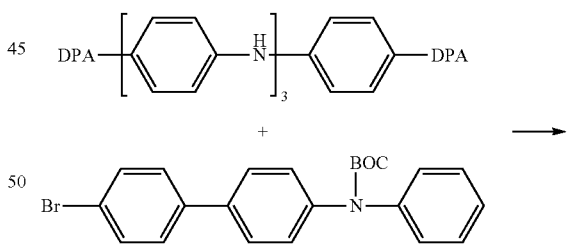

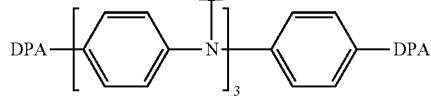

-continued

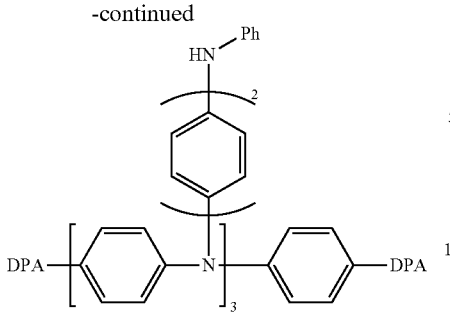

A flask was charged with 2.00 g of N1-(4-((4-((4-(diphenylamino)phenyl)amino)phenyl)amino)phenyl)-N4,N4-diphenylbenzene-1,4-diamine, 4.09 g of t-butyl(4'-bromo-[1,1'-biphenyl]-4-yl)(phenyl)carbamate, 50 mg of Pd(dba)$_2$, and 1.40 g of t-butoxysodium, and then the atmosphere in the flask was replaced by nitrogen. Into the flask were put 20 mL of toluene and 0.88 mL of a toluene solution of tri-t-butylphosphine (concentration 0.040 g/L), followed by stirring at 50° C. for seven hours.

After the stirring was over, the reaction mixture was let cool to room temperature, the reaction mixture thus let cool was mixed with chloroform and ion-exchanged water, and a liquid separation treatment was performed. The organic layer thus obtained was dried with sodium sulfate, and then 0.2 g of activated carbon was added to the dried organic layer, followed by stirring at room temperature for 30 minutes.

Thereafter, the activated carbon was removed by filtration, the filtrate was condensed, the condensed liquid was mixed with 30 mL of toluene, the resulting mixture was added dropwise to methanol/ethyl acetate mixed solvent (300 mL/200 mL), the resulting slurry was stirred at room temperature, and then the slurry was filtered to recover the filter cake (filter cake A). Then, the filtrate obtained was again condensed, the condensed liquid was mixed with 15 mL of toluene, the resulting mixture was added dropwise to methanol/ethyl acetate mixed solvent (180 mL/60 mL), the resulting slurry was stirred at room temperature, and the slurry was filtered to recover the filter cake (filter cake B).

The filter cake A and the filter cake B recovered were washed with methanol, then dissolved in toluene, the solvent was distilled off from the resulting solution at reduced pressure, and the residue was dried to obtain a solid matter.

The solid matter thus obtained, 21 mL of toluene and 6.29 g of trifluoroacetic acid were mixed, the resulting mixture was stirred at room temperature for four hours, and then 100 mL of saturated aqueous solution of sodium hydrogen carbonate and 300 mL of toluene were added thereto, followed by stirring further at room temperature.

After the stirring was over, the reaction mixture was filtered, the filter cake was washed with methanol, then dissolved in 200 mL of tetrahydrofuran, and the resulting solution was put to celite filtration. The solvent was distilled off from the resulting filtrate at reduced pressure, the residue obtained was dissolved in 20 mL of tetrahydrofuran, the resulting solution was added dropwise to methanol/ethyl acetate mixed solvent (300 mL/200 mL), and the slurry obtained was stirred at room temperature.

Finally, the slurry was filtered, and the filter cake was dried, to obtain the desired N4-(4-(diphenylamino)phenyl)-N4(4-((4-((4-(diphenylamino)phenyl)(4'-(phenylamino)-[1,1'-biphenyl]-4-yl)amino)phenyl)(4'-(phenylamino)-[1,1'-biphenyl]-4-yl)amino)phenyl)-N4'-phenyl-[1,1'-biphenyl]-4,4'-diamine (amount 2.18 g, yield 63%).

MALDI-TOF-MS m/Z found: 1414.23 ([M]$^+$calcd: 1414.63).

[16-4]

[Chemical Formula 142]

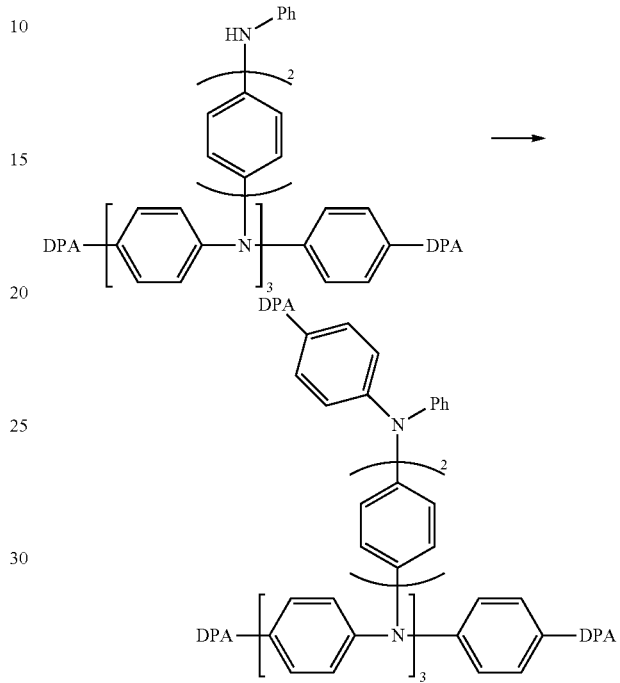

A flask was charged with 2.00 g of N4-(4-(diphenylamino)phenyl)-N4(4-((4-((4-(diphenylamino)-phenyl)(4'-(phenylamino)-[1,1'-biphenyl]-4-yl)amino)phenyl)-(4'-(phenylamino)-[1,1'-biphenyl]-4-yl)amino)phenyl)-N4'-phenyl-[1,1'-biphenyl]-4,4'-diamine, 1.65 g of 4-bromo-N,N'-diphenylaniline, 24.9 mg of Pd(dba)$_2$, and 0.584 g of t-butoxysodium, and then the atmosphere in the flask was replaced by nitrogen. Into the flask were put 20 mL of toluene and 0.43 mL of a preliminarily prepared toluene solution of tri-t-butylphosphine (concentration 40.1 g/L), followed by stirring at 50° C. for four hours, then the temperature was raised to 80° C., and after the temperature rise, stirring was conducted for 12 hours.

After the stirring was over, the reaction mixture was let cool to room temperature, the reaction mixture thus let cool was mixed with chloroform and saturated saline, and a liquid separation treatment was conducted. The organic layer obtained was dried with sodium sulfate, and then 0.2 g of activated carbon was added to the dried organic layer, followed by stirring at room temperature for 30 minutes.

Thereafter, the activated carbon was removed by filtration, the filtrate was condensed, the condensed liquid was mixed with 30 mL of toluene, the resulting mixture was added dropwise to methanol/ethyl acetate mixed solvent (300 mL/200 mL), and the resulting slurry was stirred at room temperature.

Finally, the slurry was filtered, and the filter cake was dried, to obtain a desired aniline derivative 16 (amount 2.34 g, yield 77%).

MALDI-TOF-MS m/Z found: 2144.64 ([M]$^+$calcd: 2143.95).

Preparation Example 17

[17-1]

[Chemical Formula 143]

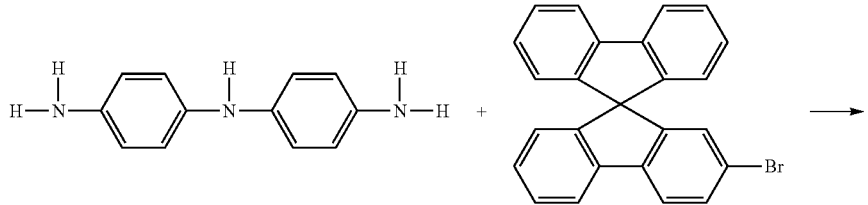

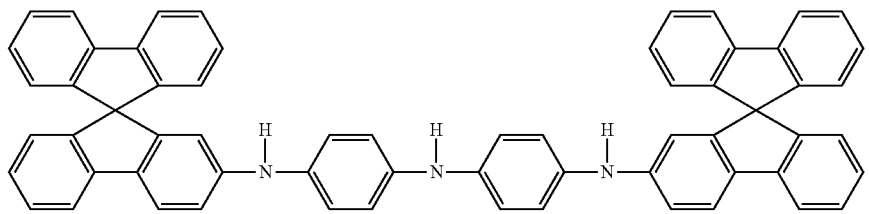

A flask was charged with 0.500 g of bis(4-aminophenyl)amine, 2.18 g of 2-bromo-9,9'-spirobi[fluorene], 0.117 g of Pd(PPh$_3$)$_4$, and 0.579 g of t-butoxysodium, and then the atmosphere in the flask was replaced by nitrogen. Into the flask was put 20 mL of xylene, followed by stirring for five hours under heating and reflux conditions.

Thereafter, the reaction mixture was cooled to room temperature, the cooled reaction mixture was mixed with toluene and ion-exchanged water, a liquid separation treatment was conducted, and the organic layer obtained was washed with ion-exchanged water and further washed with saturated saline.

Next, the organic layer after washed was dried with sodium sulfate and then condensed, silica gel column chromatography (eluent: toluene) was conducted using the condensed liquid, and, by checking the presence/absence of the target product by a thin layer chromatography (TLC) method, a fraction containing the target product was isolated.

Finally, the solvent was removed from the isolated fraction at reduced pressure, to obtain the desired N1-(9,9'-spirobi[fluorene]-2-yl)-N4-(4-(9,9'-spirobi-[fluorene]-2-ylamino)phenyl)benzene-1,4diamine (amount 0.926 g, yield 46%).

MALDI-TOF-MS m/Z found: 826.45 ([M]$^+$calcd: 827.33).

[17-2]

[Chemical Formula 144]

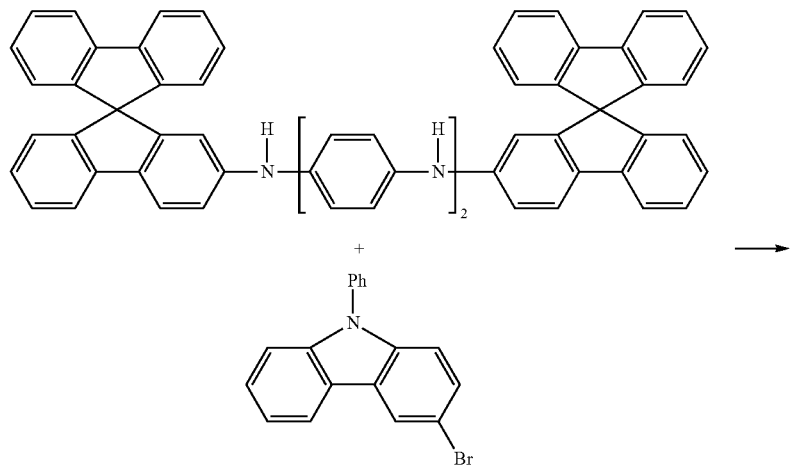

-continued

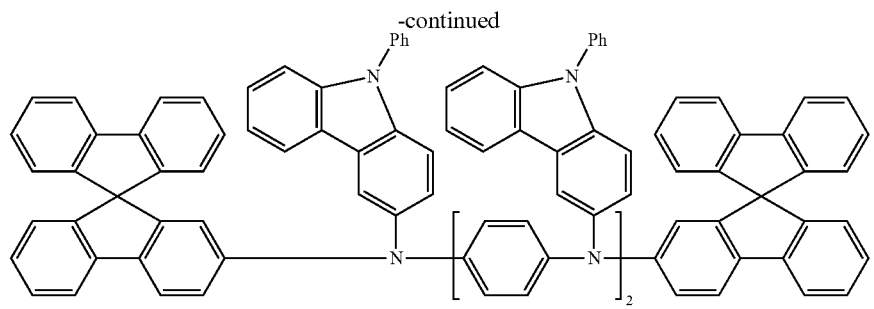

A flask was charged with 0.500 g of N1-(9,9'-spirobi[fluorene]-2-yl)-N4-(4-(9,9'-spirobi-[fluorene]-2-ylamino)phenyl)benzene-1,4diamine, 0.700 g of 3-bromo-9-phenyl-carbazole, 10.7 mg of Pd(dba)$_2$, and 0.259 g of t-butoxysodium, and then the atmosphere in the flask was replaced by nitrogen. Into the flask were put 10 mL of toluene and 0.11 mL of a preliminarily prepared toluene solution of tri-t-butylphosphine (concentration 65.6 g/L), followed by stirring at 50° C. for five hours.

After the stirring was over, the reaction mixture was cooled to room temperature, the cooled reaction mixture was mixed with toluene and saturated saline, and a liquid separation treatment was conducted. The organic layer obtained was dried with sodium sulfate, and activated carbon was added to the dried organic layer, followed by stirring at room temperature for 30 minutes.

Next, the activated carbon was removed by filtration, the filtrate was condensed, the condensed liquid was added dropwise to methanol/ethyl acetate mixed solvent being stirred, and the resulting slurry was stirred further at room temperature.

Finally, the slurry was filtered, and the filter cake was dried, to obtain an aniline derivative 17 (amount 0.772 g, yield 83%).

MALDI-TOF-MS m/Z found: 1551.41 ([M]$^+$calcd: 1550.60).

Preparation Example 18

[Chemical Formula 145]

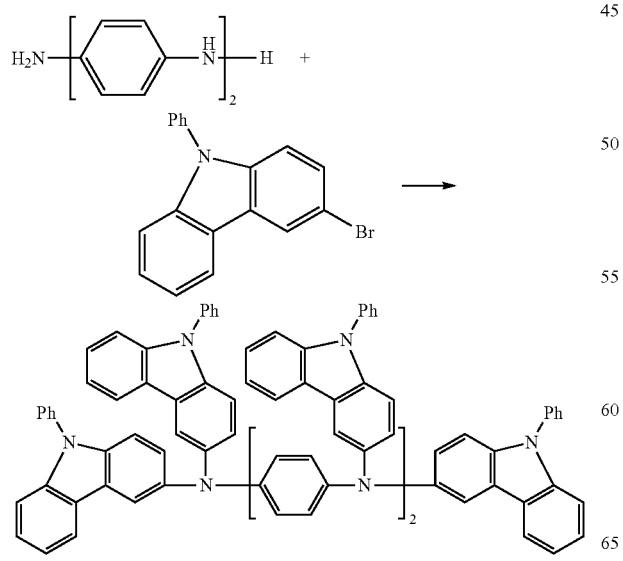

A flask was charged with 1.00 g of N1-(4-aminophenyl)benzene-1,4-diamine, 8.89 g of 3-bromo-9-phenyl-9H-carbazole, 112 mg of palladium acetate, and 3.47 g of t-butoxysodium, and then the atmosphere in the flask was replaced by nitrogen. Into the flask were put 30 mL of toluene and 2.75 mL of a preliminarily prepared toluene solution of di-t-butyl(phenyl)phosphine (concentration 81.0 g/L), followed by stirring at 90° C. for six hours.

After the stirring was over, the reaction mixture was cooled to room temperature, the cooled reaction mixture was mixed with toluene and ion-exchanged water, and a liquid separation treatment was conducted. The organic layer obtained was dried with sodium sulfate, and condensed. The condensed liquid was filtered using silica gel, and 0.2 g of activated carbon was added to the thus obtained filtrate, followed by stirring at room temperature for 30 minutes.

Thereafter, the activated carbon was removed by filtration, and the filtrate was condensed. The condensed liquid was added dropwise to methanol/ethyl acetate mixed solvent (500 mL/500 mL), the resulting slurry was stirred overnight at room temperature, and then the slurry was filtered to recover the filter cake. The filter cake obtained was dried, to obtain a desired aniline derivative 18 (amount 5.88 g, yield 83%).

$^1$H-NMR (300 MHz, THF-d8) δ [ppm]: 8.08 (d, J=7.7 Hz, 2H), 7.99 (d, J=7.7 Hz, 8H), 7.60 to 7.64 (m, 19H), 7.42 to 7.47 (m, 6H), 7.28 to 7.36 (m, 19H), 7.09 to 7.21 (m, 6H), and 7.00 (m, 8H).

MALDI-TOF-MS m/Z found: 1404.68 ([M]$^+$calcd: 1404.56).

Preparation Example 19

[19-1]

[Chemical Formula 146]

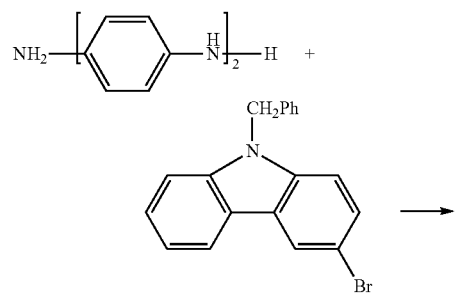

-continued

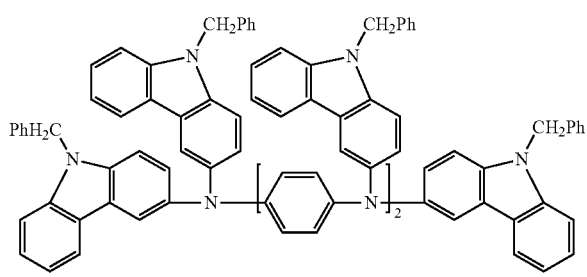

A flask was charged with 5.00 g of N1-(4-aminophenyl)benzene-1,4-diamine, 8.09 g of 9-benzyl-3-bromo-9H-carbazole, 252 mg of Pd(dba)$_2$, and 3.03 g of tertiary-butoxysodium, and then the atmosphere in the flask was replaced by nitrogen. Into the flask were put 50 mL of toluene and 2.02 mL of a preliminarily prepared toluene solution of di-t-butyl(phenyl)phosphine (concentration 96.4 g/L), followed by stirring at 90° C. for three hours.

After the stirring was over, the reaction mixture was cooled to room temperature, the cooled reaction mixture was mixed with 200 mL of toluene and 150 mL of saturated saline, and a liquid separation treatment was performed. To the thus obtained organic layer was added 0.5 g of activated carbon, followed by stirring at room temperature for one hour.

Thereafter, the activated carbon was removed by filtration, and the filtrate was condensed. The condensed liquid was added dropwise to methanol/ethyl acetate mixed solvent (200 mL/200 mL), the resulting slurry was stirred at room temperature for one hour, and then the slurry was filtered to recover a filter cake. The filter cake obtained was dried, to obtain the desired N1,N1,N4-tris(9-benzyl-9H-carbazol-3-yl)-N4-(4-(bis(9-benzyl-9H-carbazol-3-yl)amino)-phenyl)benzene-1,4-diamine (amount 8.46 g, yield 80%).

$^1$H-NMR (300 MHz, THF-d8) δ [ppm]: 7.91 to 8.00 (m, 10H), 7.52 to 7.58 (m, 10H), 7.34 to 7.39 (m, 6H), 7.17 to 7.26 (m, 29H), 7.03 to 7.11 (m, 5H), 6.83 (d, J=9.0 Hz, 4H), 6.76 (d, J=9.0 Hz, 4H), and 5.58 (s, 10H).

[19-2]

[Chemical Formula 147]

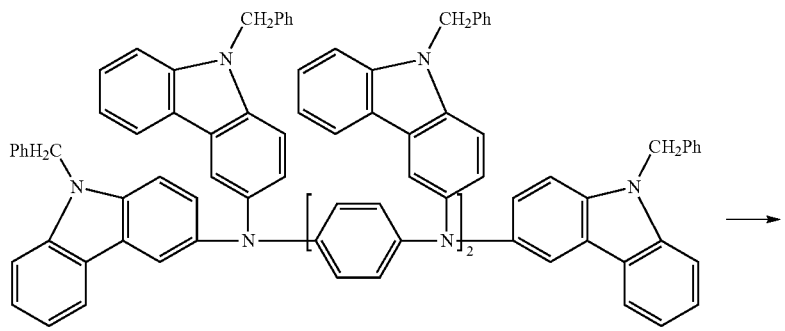

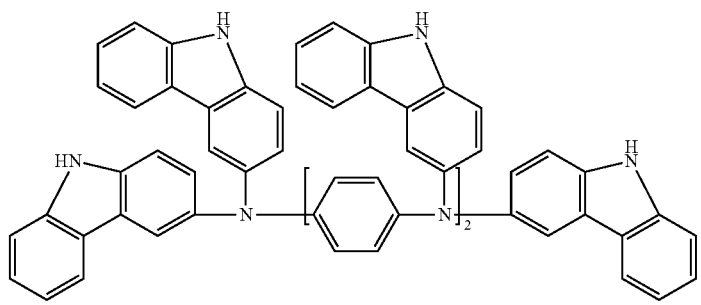

A flask was charged with 5.05 g of t-butoxypotassium, 18 mL of dimethyl sulfoxide, and 6 mL of tetrahydrofuran, and the atmosphere in the flask was replaced by oxygen. A solution prepared by mixing 3.00 g of the N1,N1,N4-tris(9-benzyl-9H-carbazol-3-yl)-N4-(4-(bis(9-benzyl-9H-carbazol-3-yl)amino)phenyl)benzene-1,4-diamine obtained above and 9 mL of tetrahydrofuran was added dropwise to the flask at 10° C., and the resulting mixture was heated up to room temperature and then stirred for four hours.

After the stirring was over, the reaction mixture was added dropwise to 120 mL of ion-exchanged water, then 9 mL of hydrochloric acid (5 M) was added dropwise thereto, and the resulting slurry was stirred at room temperature for one hour. Then, the slurry was filtered, to recover a filter cake. The filter cake obtained was mixed well with 90 mL of tetrahydrofuran, the resulting mixture was filtered using silica gel, and the filtrate obtained was condensed. The condensed liquid was added dropwise to 150 mL of methanol, and the resulting slurry was stirred at room temperature for one hour.

Finally, the slurry was filtered to recover a filter cake, and the filter cake obtained was dried, to obtain a desired aniline derivative 19 (amount 2.20 g, yield 90%).

MALDI-TOF-MS m/Z found: 1024.13 ([M]$^+$calcd: 1024.40).

Preparation Example 20

[20-1]

A flask was charged with 0.30 g of bis(aminophenyl)amine, 3.51 g of t-butyl(4'-bromo-[1,1'-biphenyl]-4-yl(phenyl)-carbamate, 44 mg of Pd(dba)$_2$, and 1.05 g of t-butoxysodium, and then the atmosphere in the flask was replaced by nitrogen. Into the flask were put 30 mL of toluene and 510 μL of a preliminarily prepared toluene solution of tri-t-butylphosphine (concentration 60 g/L), followed by stirring at 50° C. for 26 hours.

After the stirring was over, the reaction mixture was let cool to room temperature, the reaction mixture thus let cool was mixed with toluene and saturated saline, and a liquid separation treatment was conducted. The organic layer obtained was dried with sodium sulfate, and activated carbon was added to the dried organic layer, followed by stirring at room temperature for one hour.

Next, the activated carbon was removed by filtration, and the filtrate was condensed. The condensed liquid was added dropwise to methanol being stirred, and the resulting slurry was stirred further at room temperature.

Finally, the slurry was filtered, and the resulting filter cake was dried, to obtain a desired intermediate (amount 2.40 g, yield 83%).

$^1$H-NMR (300 MHz, DMSO-d6) δ [ppm]: 7.56 to 7.58 (m, 20H), 7.33 to 7.38 (m, 11H), 7.19 to 7.24 (m, 24H), 7.06 to 7.11 (m, 18H), and 1.38 (s, 45H).

[Chemical Formula 148]

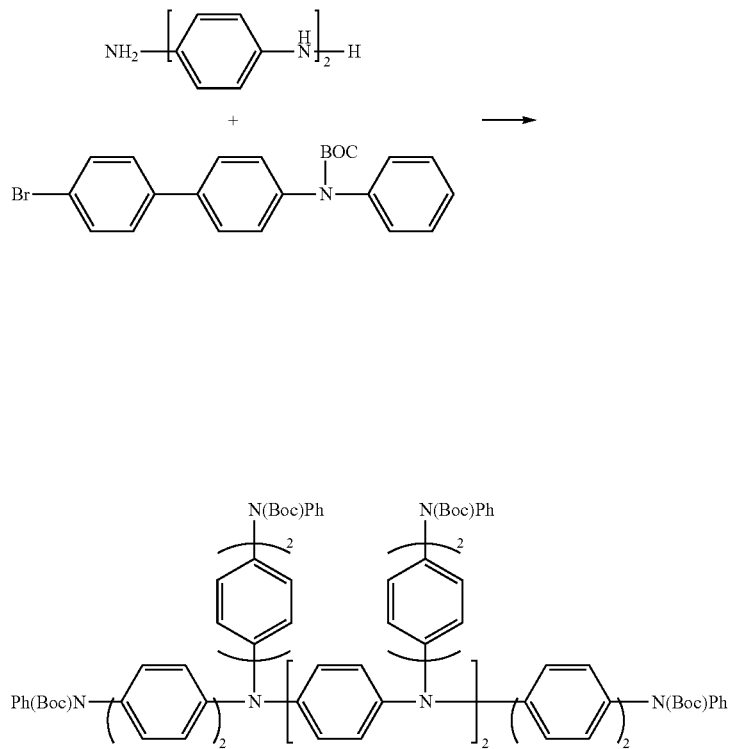

[20-2]

[Chemical Formula 149]

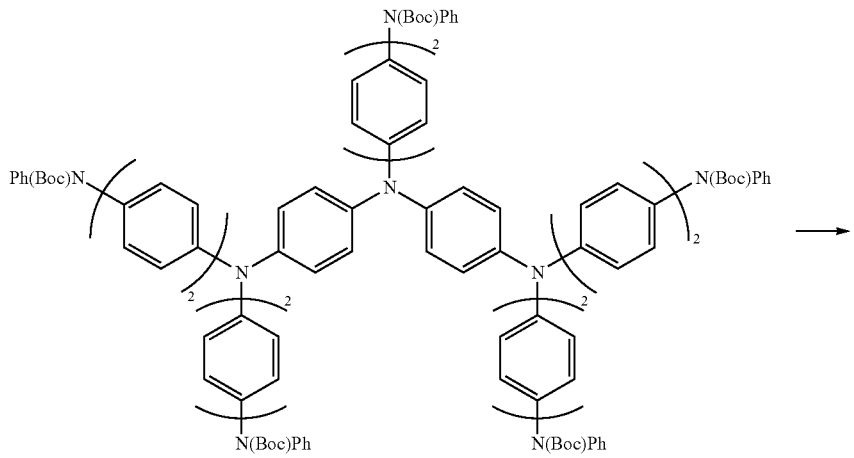

A flask was charged with 2.20 g of the intermediate obtained above, 15 mL of toluene, and 2.5 mL of trifluoroacetic acid, followed by stirring at room temperature for six hours. After the stirring was over, toluene and saturated aqueous solution of sodium hydrogen carbonate were added to the reaction mixture, and the resulting slurry was stirred.

Next, the slurry was filtered, the filter cake obtained was dissolved in tetrahydrofuran, the resulting solution was added dropwise to methanol/ethyl acetate mixed solvent being stirred, and the resulting slurry was stirred further at room temperature.

Finally, the slurry was filtered, and the filter cake obtained was dried, to obtain an aniline derivative 20 (amount 1.24 g, yield 74%).

$^1$H-NMR (300 MHz, THF-d8) δ [ppm]: 7.46 to 7.51 (m, 23H), 7.39 (s, 5H), 7.07 to 7.22 (m, 44H), and 6.78 to 6.83 (m, 6H).

MALDI-TOF-MS m/Z found: 1414.17 ([M]$^+$calcd: 1414.63).

Preparation Example 21

[Chemical Formula 150]

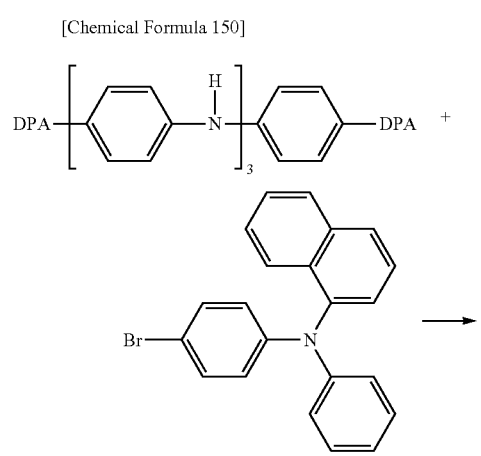

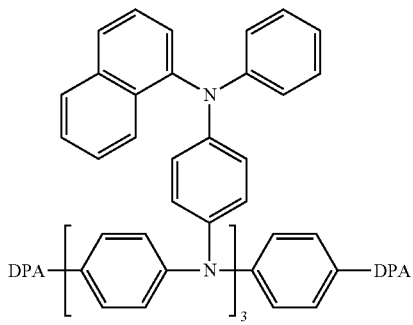

A flask was charged with 1.00 g of N1-(4-((4-((4-(diphenylamino)phenyl)amino)phenyl)amino)phenyl) N4,N4-diphenylbenzene-1,4-diamine, 1.96 g of N-(4-bromophenyl)-N-phenylnaphthalene-1-amine, 51.0 mg of Pd(dba)$_2$, and 0.61 g of t-butoxysodium, and then the atmosphere in the flask was replaced by nitrogen. Into the flask were put 10 mL of toluene and 410 μL of a preliminarily prepared toluene solution of di-t-butyl(phenyl)phosphine (concentration 96 g/L), followed by stirring at 100° C. for 2.5 hours.

After the stirring was over, the reaction mixture was let cool to room temperature, the reaction mixture thus let cool was mixed with toluene and saturated saline, and a liquid separation treatment was performed. Activated carbon was added to the organic layer obtained, followed by stirring at room temperature for 30 minutes.

Next, the activated carbon was removed by filtration, and the filtrate was condensed. The condensed liquid was added dropwise to methanol/ethyl acetate mixed solvent being stirred, and the resulting slurry was stirred further at room temperature.

Finally, the slurry was filtered, and the filter cake obtained was dried, to obtain an aniline derivative 21 (amount 1.58 g, yield 69%).

MALDI-TOF-MS m/Z found: 1565.38 ([M]$^+$calcd: 1564.68).

Preparation Example 22

[Chemical Formula 151]

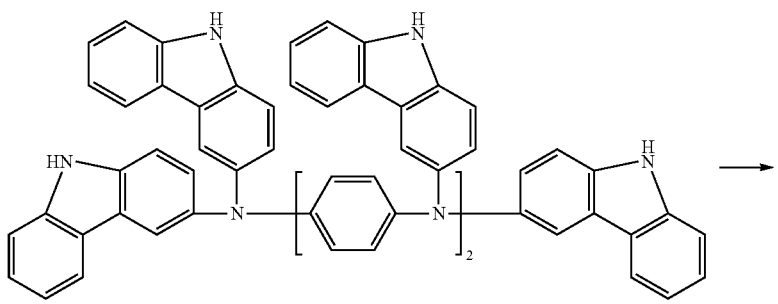

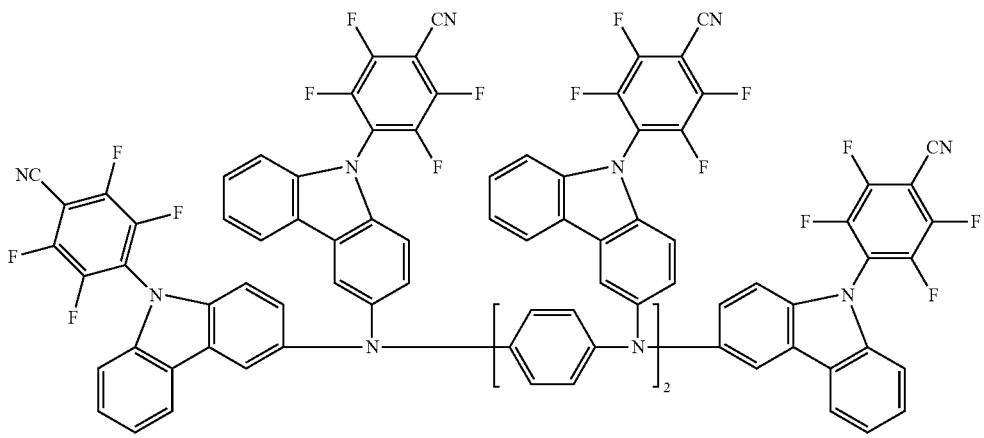

A flask was charged with 0.50 g of the aniline derivative 19, 0.67 g of potassium carbonate, and 5 mL of N,N-dimethylformamide, and then the atmosphere in the flask was replaced by nitrogen. To the flask, 330 μL of pentafluorobenzonitrile was added dropwise, followed by stirring at room temperature for 15 hours.

After the stirring was over, the reaction mixture was added dropwise to ion-exchanged water, and the resulting slurry was stirred at room temperature for 30 minutes. Next, the slurry was filtered, the filter cake was dried, silica gel column chromatography (eluent: toluene) was conducted using a solution obtained by dissolving the thus obtained powder in toluene, and, by checking the presence/absence of the target product by a thin layer chromatography (TLC) method, a fraction containing the target product was isolated. The solvent was distilled off from the isolated fraction at reduced pressure, and the resulting solid matter was dried, to obtain an aniline derivative 22 (amount 0.37 g, yield 40%).

MALDI-TOF-MS m/Z found: 1890.54 ([M]$^+$calcd: 1889.34).

Preparation Example 23

[23-1]

A flask was charged with 1.59 g of sodium hydride (60%/fluid paraffin), and then the atmosphere in the flask was replaced by nitrogen. Into the flask were put 20 mL of N,N-dimethylformamide and 7.46 g of 1,2,3,4,5-pentafluoro-6-methylbenzene, and then 40 mL of a preliminarily prepared N,N-dimethylformamide solution of 3-bromo-9H-carbazole (concentration 123 g/L) was added dropwise thereto, followed by stirring at room temperature for one hour.

After the stirring was over, the reaction mixture, ion-exchanged water, and chloroform were mixed, a liquid separation treatment was conducted, and the solvent was distilled off from the resulting organic layer at reduced pressure. Next, the residue obtained, n-hexane, and ion-exchanged water were mixed, a liquid separation treatment was performed, and the solvent was distilled off from the resulting organic layer at reduced pressure. Further, the residue thus obtained, hexane/ethyl acetate mixed solvent (1/1 (v/v)), and ion-exchanged water were mixed, a liquid separation treatment was conducted, the resulting organic layer was mixed with saturated saline, and a liquid separation treatment was again conducted.

The organic layer thus obtained was dried with sodium sulfate, the solvent was distilled off from the dried organic layer at reduced pressure, and the resulting residue was dissolved in hexane/ethyl acetate mixed solvent (1/1 (v/v)). Silica gel column chromatography (eluent: hexane/ethyl acetate) was conducted using the thus obtained solution, and, by checking the presence/absence of the target product by a thin layer chromatography (TLC) method, a fraction containing the target product was isolated.

The solvent was distilled off from the isolated fraction at reduced pressure, and the solid matter obtained was dried, to obtain 3-bromo-9-(2,3,5,6-tetrafluoro-4-methylphenyl)-9H-carbazole (amount 6.21 g, yield 76%).

$^1$H-NMR (300 MHz, CDCl$_2$) δ [ppm]: 8.24 (d, J=2.0 Hz, 1H), 8.08 (d, J=7.8 Hz, 1H), 7.52 (dd, J=8.9, 2.0 Hz, 1H), 7.47 (td, J=7.8, 1.4 Hz, 1H), 7.34 (t, J=7.8 Hz, 1H), 7.13 (d, J=7.8 Hz, 1H), 7.02 (d, J=8.9 Hz, 1H), and 1.55 (s, 3H).

[23-2]

[Chemical Formula 152]

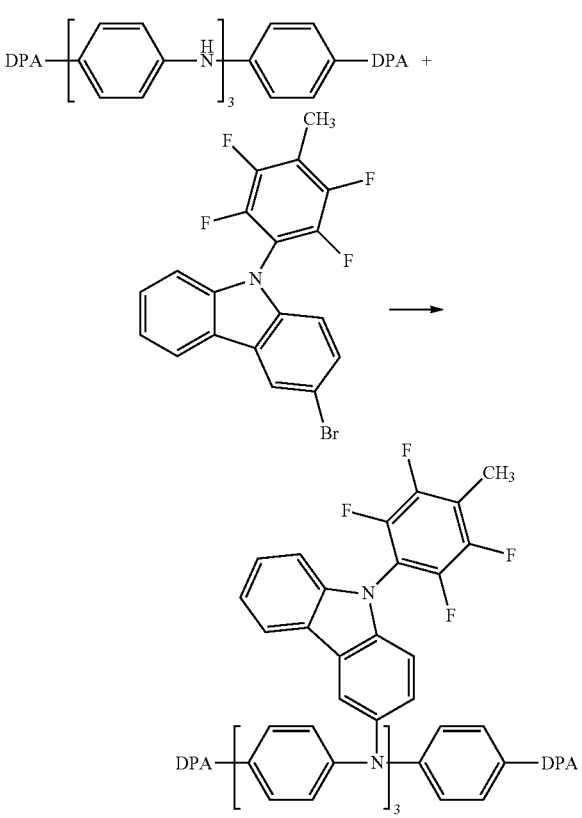

A flask was charged with 1.37 g of N1-(4-((4-((4-(diphenylamino)phenyl)amino)phenyl)amino)phenyl) N4,N4-diphenylbenzene-1,4-diamine, 3.32 g of 3-bromo-9-(2,3,5,6-tetrafluoro-4-methylphenyl)-9H-carbazole, 211 mg of Pd(dba)$_2$, and 2.48 g of t-butoxysodium, and then the atmosphere in the flask was replaced by nitrogen. Into the flask were put 15 mL of toluene and 2.1 mL of a preliminarily prepared toluene solution of tri-t-butylphosphine (concentration 70 g/L), followed by stirring at 50° C. for 51 hours.

After the stirring was over, the reaction mixture was let cool to room temperature, the reaction mixture thus let cool, ethyl acetate, and ion-exchanged water were mixed, and a liquid separation treatment was conducted. The organic layer thus obtained was dried with magnesium sulfate, and activated carbon was added to the dried organic layer, followed by stirring at room temperature for 30 minutes.

Next, the activated carbon was removed by filtration, the filtrate was condensed, a solution obtained by dissolving the thus obtained residue in tetrahydrofuran was added dropwise to acetonitrile being stirred, and the resulting slurry was stirred further at room temperature.

Finally, the slurry was filtered, and the filter cake obtained was dried to obtain an aniline derivative 23 (amount 1.18 g, yield 35%).

$^1$H-NMR (300 MHz, THF-d8) δ [ppm]: 8.08 (d, J=7.7 Hz, 3H), 8.02 (d, J=1.5 Hz, 3H), 6.88 to 7.42 (m, 51H), and 2.50 (s, 9H).

MALDI-TOF-MS m/Z found: 1667.79 ([M]$^+$calcd: 1667.53).

Preparation Example 24

[24-1]

A flask was charged with 1.43 g of sodium hydride (60%/fluid paraffin), and then the atmosphere in the flask was replaced by nitrogen. Into the flask were put 9 mL of N,N-dimethylformamide and 20.2 g of 1,2,3,4,5-pentafluoro-6-(trifluoromethyl)benzene, and 18 mL of a preliminarily prepared N,N-dimethylformamide solution of 3-bromo-9H-carbazole (concentration 123 g/L) was added dropwise thereto, followed by stirring at room temperature for one hour.

After the stirring was over, the reaction mixture, ion-exchanged water, and ethyl acetate were mixed, a liquid separation treatment was conducted, the organic layer obtained was washed sequentially with ion-exchanged water and saturated saline, and the washed organic layer was dried with sodium sulfate. The solvent was distilled off from the dried organic layer at reduced pressure, silica gel column chromatography (eluent: hexane/ethyl acetate) was conducted using a solution obtained by dissolving the thus obtained residue in hexane/ethyl acetate mixed solvent (1/1 (v/v)), and, by checking the presence/absence of the target product by a thin layer chromatography (TLC) method, a fraction containing the target product was isolated.

The solvent was distilled off from the isolated fraction at reduced pressure, and the solid matter thus obtained was dried, to obtain 3-bromo-9-(2,3,5,6-tetrafluoro-4-(trifluoromethyl)phenyl)-9H-carbazole (amount 4.10 g, yield 98%).

$^1$H-NMR (300 MHz, CDCl$_3$) δ [ppm]: 8.10 (d, J=1.7 Hz, 1H), 7.91 (d, J=7.5 Hz, 1H), 7.41 (dd, J=8.9, 1.7 Hz, 1H), 7.37 (t, J=7.5 Hz, 1H), 7.24 (t, J=7.5 Hz, 1H), 7.08 (d, J=7.5 Hz, 1H), and 6.92 (d, J=8.9 Hz, 1H).

[24-2]

[Chemical Formula 153]

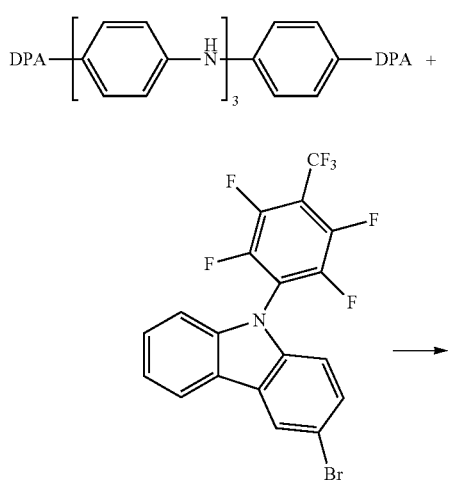

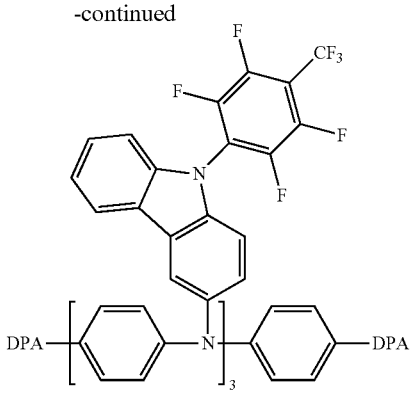

A flask was charged with 1.37 g of N1-(4-((4-((4-(diphenylamino)phenyl)amino)phenyl)amino)phenyl) N4,N4-diphenylbenzene-1,4-diamine, 3.16 g of 3-bromo-9-(2,3,5,6-tetrafluoro-4-(trifluoromethyl)phenyl)-9H-carbazole, 70.4 mg of Pd(dba)$_2$, and 0.83 g of t-butoxysodium, and then the atmosphere in the flask was replaced by nitrogen. Into the flask were put 15 mL of toluene and 750 μL of a preliminarily prepared toluene solution of tri-t-butylphosphine (concentration 65 g/L), followed by stirring at 50° C. for five hours.

After the stirring was over, the reaction mixture was let cool to room temperature, the reaction mixture thus let cool, ethyl acetate, and ion-exchanged water were mixed, and a liquid separation treatment was conducted. The organic layer obtained was washed sequentially with ion-exchanged water and saturated saline, and the washed organic layer was dried with magnesium sulfate. The solvent was distilled off from the dried organic layer at reduced pressure, the resulting condensed liquid was added dropwise to methanol being stirred, and the resulting slurry was stirred at room temperature.

Finally, the slurry was filtered, and the filter cake obtained was dried, to obtain an aniline derivative 24 (amount 3.24 g, yield 89%).

$^1$H-NMR (300 MHz, THF-d8) δ [ppm]: 8.09 (d, J=8.0 Hz, 3H), 8.03 (d, J=1.8 Hz, 3H), and 6.90 to 7.46 (m, 51H).

MALDI-TOF-MS m/Z found: 1829.52 ([M]$^+$calcd: 1829.44).

Preparation Example 25

[25-1]

A flask was charged with 3.97 g of sodium hydride (60%/fluid paraffin), and then the atmosphere in the flask was replaced by nitrogen. Into the flask were put 25 mL of N,N-dimethylformamide and 10.7 g of 2,3,4,5,6-pentafluorostyrene, and then 50 mL of a preliminarily prepared N,N-dimethylformamide solution of 3-bromo-9H-carbazole (concentration 246 g/L) was added dropwise thereto, followed by stirring at room temperature for two hours.

After the stirring was over, the reaction mixture, ion-exchanged water, and chloroform were mixed, and a liquid separation treatment was conducted. The organic layer obtained was washed sequentially with ion-exchanged water and saturated saline, and the washed organic layer was dried with magnesium sulfate. Then, the solvent was distilled off from the dried organic layer at reduced pressure, silica gel column chromatography (eluent: hexane/ethyl acetate) was conducted using a solution obtained by dissolving the thus obtained residue in hexane/ethyl acetate mixed solvent (1/1

(v/v)), and, by checking the presence/absence of the target product by a thin layer chromatography (TLC) method, a fraction containing the target product was isolated.

The solvent was distilled off from the isolated fraction at reduced pressure, and the solid matter obtained was dried, to obtain 3-bromo-9-(2,3,5,6-tetrafluoro-4-vinylphenyl)-9H-carbazole (amount 12.7 g, yield 59%).

$^1$H-NMR (300 MHz, CDCl$_3$) δ [ppm]: 8.40 (d, J=2.0 Hz, 1H), 8.17 (d, J=7.8 Hz, 1H), 7.66 (dd, J=8.9, 2.0 Hz, 1H), 7.59 (t, J=7.8 Hz, 1H), 7.45 (t, J=7.8 Hz, 1H), 7.36 (d, J=7.8 Hz, 1H), 7.21 (d, J=8.9 Hz, 1H), 6.91 (dd, J=18.1, 11.9 Hz, 1H), 6.37 (d, J=18.1 Hz, 1H), and 5.90 (d, J=11.9 Hz, 1H).
[25-2]

[Chemical Formula 154]

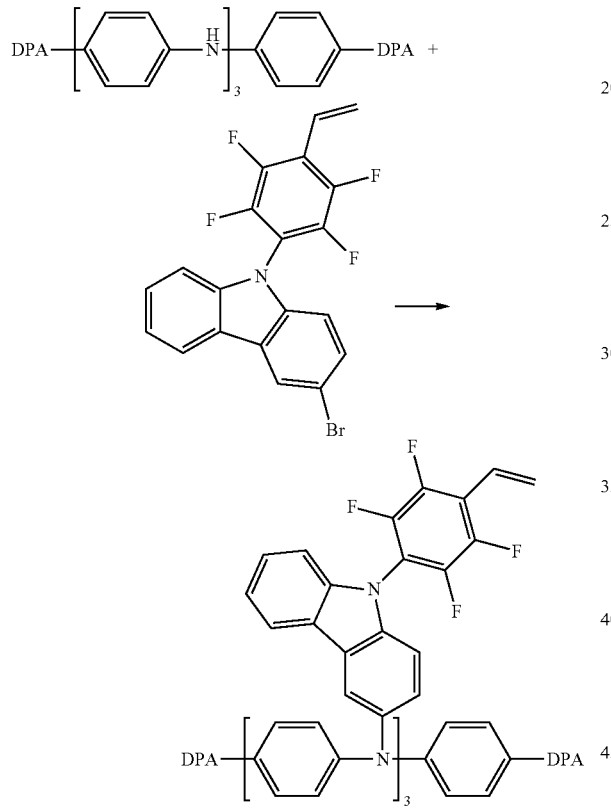

A flask was charged with 1.37 g of N1-(4-((4-((4-(diphenylamino)phenyl)amino)phenyl)amino)phenyl) N4,N4-diphenylbenzene-1,4-diamine, 69.7 mg of Pd(dba)$_2$, and 0.83 g of t-butoxysodium, and then the atmosphere in the flask was replaced by nitrogen. Into the flask were put 8.4 mL of a preliminarily prepared toluene solution of 3-bromo-9-(2,3,5,6-tetrafluoro-4-vinylphenyl)-9H-carbazole (concentration 31 g/L), 0.70 mL of a preliminarily prepared toluene solution of tri-t-butylphosphine (concentration 12 g/L), and 6.5 mL of toluene, followed by stirring at 50° C. for three hours.

After the stirring was over, the reaction mixture was let cool to room temperature, the reaction mixture thus let cool, ethyl acetate, and ion-exchanged water were mixed, and a liquid separation treatment was conducted. The organic layer thus obtained was washed sequentially with ion-exchanged water and saturated saline, and the washed organic layer was dried with magnesium sulfate. Then, the solvent was distilled off from the dried organic layer at reduced pressure, a solution obtained by dissolving the resulting residue in tetrahydrofuran was added dropwise to acetonitrile being stirred, and the resulting slurry was stirred at room temperature.

Finally, the slurry was filtered, and the filter cake obtained was dried, to obtain an aniline derivative 25 (amount 2.88 g, yield 85%).

$^1$H-NMR (300 MHz, THF-d8) δ [ppm]: 8.07 (d, J=7.8 Hz, 3H), 8.03 (d, J=1.7 Hz, 3H), 6.83 to 7.43 (m, 54H), 6.24 (d, J=17.7 Hz, 3H), and 5.87 (d, J=11.9 Hz, 3H).

MALDI-TOF-MS m/Z found: 1703.84 ([M]$^+$calcd: 1703.53).

Preparation Example 26

[Chemical Formula 155]

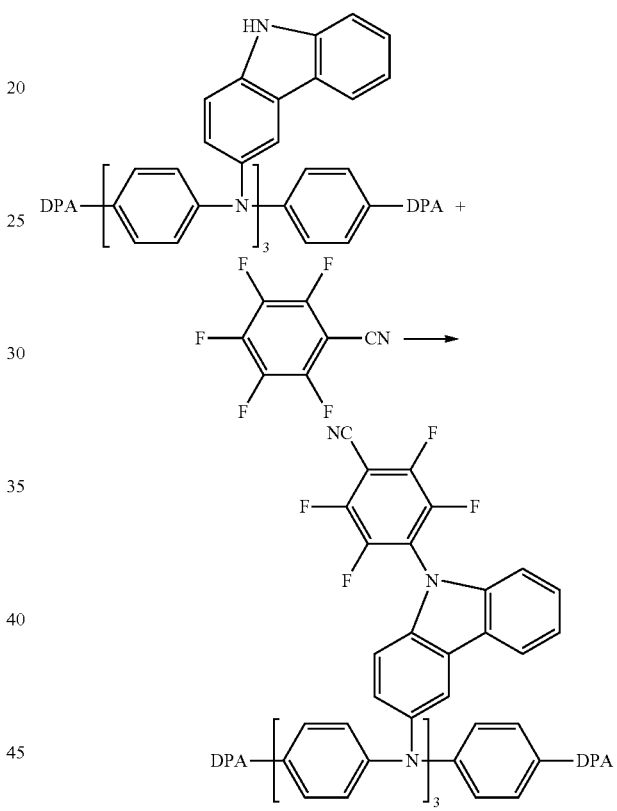

A flask was charged with 2.36 g of the aniline derivative 9, 20 mL of N,N-dimethylformamide, and 1.66 g of potassium carbonate, and then the atmosphere in the flask was replaced by nitrogen. Next, while cooling the flask on ice bath, 1.29 g of pentafluorobenzonitrile was added dropwise thereto, the temperature was gradually raised to room temperature with stirring, and the stirring was continued at room temperature for 24 hours.

After the stirring was over, the reaction mixture was filtered, and the solvent was distilled off from the resulting filtrate at reduced pressure. Silica gel column chromatography (eluent: toluene/hexane) was conducted using a solution obtained by dissolving the thus obtained residue in toluene/n-hexane mixed solvent (3/2 (v/v)), and, by checking the presence/absence of the target product by a thin layer chromatography (TLC) method, a fraction containing the target product was isolated.

The solvent was distilled off from the isolated fraction at reduced pressure, and the solid matter obtained was dried, to obtain an aniline derivative 26 (amount 1.34 g, yield 40%).

$^1$H-NMR (300 MHz, THF-d8) δ [ppm]: 8.02 to 8.10 (m, 6H), and 6.90 to 7.46 (m, 51H).

MALDI-TOF-MS m/Z found: 1699.75 ([M]$^+$calcd: 1700.46).

Preparation Example 27

[Chemical Formula 156]

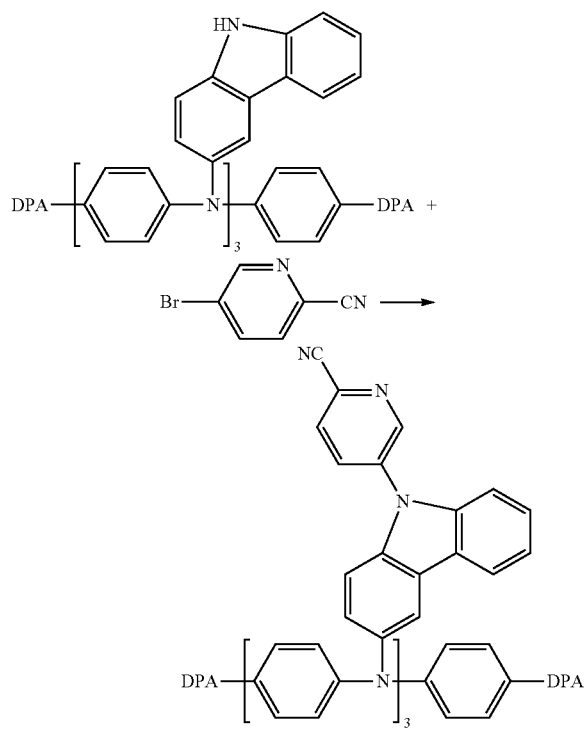

A flask was charged with 2.84 g of the aniline derivative 9, 420 mg of Pd(dba)$_2$, 1.45 g of 5-bromopicolinonitrile, and 1.40 g of t-butoxysodium, and then the atmosphere in the flask was replaced by nitrogen. Into the flask were put 120 mL of toluene and 2.5 mL of a preliminarily prepared toluene solution of tri-t-butylphosphine (concentration 175 g/L), followed by stirring at 120° C. for two hours.

After the stirring was over, the reaction mixture was let cool to room temperature, and the reaction mixture thus let cool was filtered. Then, the filtrate was condensed, a solution obtained by dissolving the resulting residue in tetrahydrofuran was added dropwise to methanol being stirred, and the resulting slurry was stirred further at room temperature.

Next, the slurry was filtered, silica gel column chromatography (eluent: toluene/ethyl acetate) was conducted using a solution obtained by dissolving the resulting filter cake in toluene, and, by checking the presence/absence of the target product by a thin layer chromatography (TLC) method, a fraction containing the target product was isolated.

The solvent was distilled off from the isolated fraction at reduced pressure, and the solid matter obtained was dried, to obtain an aniline derivative 27 (amount 1.59 g, yield 45%).

$^1$H-NMR (300 MHz, THF-d8) δ [ppm]: 9.06 (d, J=2.7 Hz, 3H), 8.28 (dd, J=8.5, 2.7 Hz, 3H), 8.11 (d, J=8.5 Hz, 3H), 8.08 (d, J=7.8 Hz, 3H), 8.01 (d, J=2.1 Hz, 3H), 7.38 to 7.51 (m, 9H), 7.16 to 7.31 (m, 14H), and 6.89 to 7.04 (m, 28H).

MALDI-TOF-MS m/Z found: 1487.02 ([M]$^+$calcd: 1487.56).

Preparation Example 28

[Chemical Formula 157]

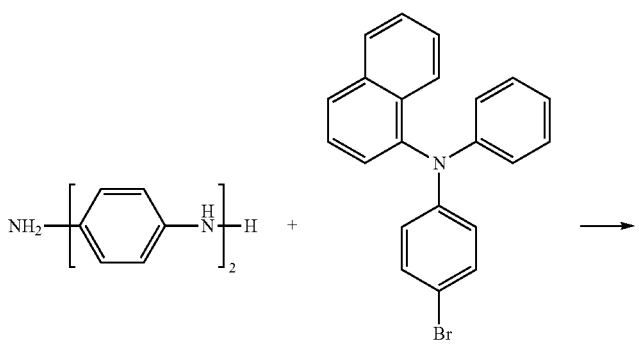

-continued

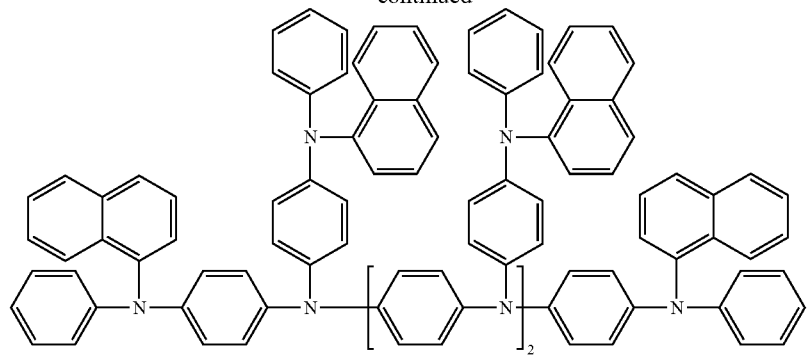

A flask was charged with 0.25 g of bis(aminophenyl) amine, 2.58 g of N-(4-bromophenyl)-N-phenylnaphthalene-1-amine, 72.2 mg of Pd(dba)$_2$ and 0.87 g of tertiary-butoxysodium, and then the atmosphere in the flask was replaced by nitrogen. Into the flask were put 15 mL of toluene and 530 μL of a preliminarily prepared toluene solution of di-t-butyl (phenyl)phosphine (concentration 96 g/L), followed by stirring at 100° C. for 3.5 hours.

After the stirring was over, the reaction mixture was cooled to room temperature, the cooled reaction mixture, toluene, and saturated saline were mixed, and a liquid separation treatment was conducted. Activated carbon was added to the resulting organic layer, followed by stirring at room temperature for one hour.

Next, the activated carbon was removed by filtration, the filtrate was condensed, the condensed liquid was added dropwise to methanol/ethyl acetate mixed solvent being stirred, and the resulting slurry was stirred further at room temperature.

Finally, the slurry was filtered, and the filter cake obtained was dried, to obtain an aniline derivative 28 (amount 1.70 g, yield 81%).

MALDI-TOF-MS m/Z found: 1665.40 ([M]$^+$calcd: 1664.71).

Preparation Example 29

[29-1]

A flask was charged with 790 mg of sodium hydroxide, 50 mL of N,N-dimethylformamide, and 4.43 g of 3-bromo-9H-carbazole, and 5.04 g of pentafluorobenzyl bromide was added dropwise thereto with stirring under ice bath conditions. After the dropwise addition was over, the resulting mixture was returned to room temperature, and was stirred further for four days.

After the stirring was over, the reaction mixture was poured into ion-exchanged water, the resulting mixture was mixed with ethyl acetate, and a liquid separation treatment was conducted. The organic layer thus obtained was washed with ion-exchanged water, the solvent was distilled off from the washed organic layer at reduced pressure, and recrystallization was conducted by use of the resulting residue and hexane/ethyl acetate.

Finally, the solid matter obtained was dried, to obtain 3-bromo-9-pentafluorobenzylcarbazole (amount 3.31 g, yield 43%).

$^1$H-NMR (300 MHz, CDCl$_3$) δ [ppm]: 8.15 (d, J=1.4 Hz, 1H), 7.99 (d, J=7.8 Hz, 1H), 7.44 to 7.55 (m, 3H), 7.23 to 7.35 (m, 2H), and 5.46 (s, 2H).

[29-2]

[Chemical Formula 158]

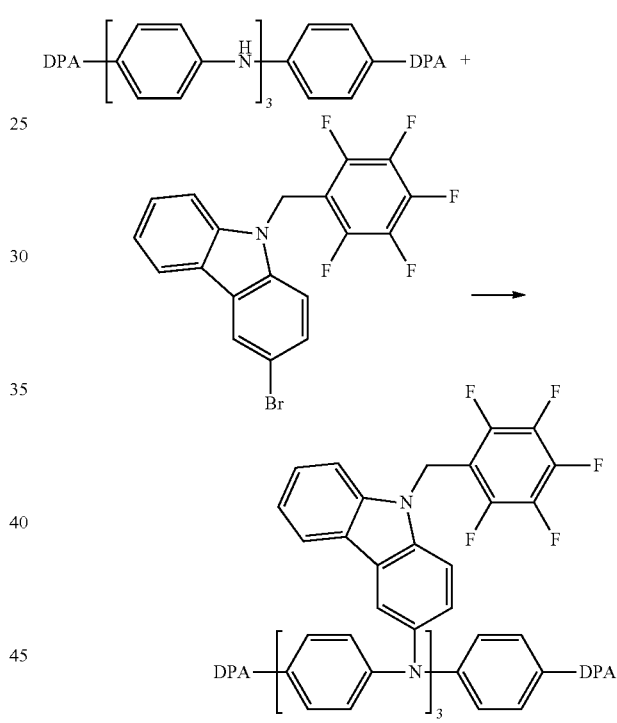

A flask was charged with 1.37 g of N1-(4-((4-((4-(diphenylamino)phenyl)amino)phenyl)amino)phenyl) N4,N4-diphenylbenzene-1,4-diamine, 2.81 g of 3-bromo-9-pentafluorobenzylcarbazole, 69.6 mg of Pd(dba)$_2$, and 861 mg of t-butoxysodium, and then the atmosphere in the flask was replaced by nitrogen. Into the flask were put 1.0 mL of a preliminarily prepared toluene solution of tri-t-butylphosphine (concentration 47 g/L) and 15 mL of toluene, followed by stirring at 50° C. for seven hours.

After the stirring was over, the reaction mixture was let cool to room temperature, the reaction mixture thus let cool, ethyl acetate, ion-exchanged water, and saturated saline were mixed, and a liquid separation treatment was conducted. The organic layer thus obtained was dried with magnesium sulfate, and then activated carbon was added to the dried organic layer, followed by stirring at room temperature for 0.5 hour.

Thereafter, the activated carbon was removed by filtration, the filtrate was condensed, the condensed liquid was dissolved in ethyl acetate, the resulting solution was added dropwise to methanol/ethyl acetate mixed solvent being stirred, and the resulting slurry was stirred at room temperature.

Finally, the slurry was filtered, and the filter cake obtained was dried, to obtain an aniline derivative 29 (amount 2.14 g, yield 62%).

$^1$H-NMR (300 MHz, THF-d8) δ [ppm]: 7.94 to 7.99 (m, 6H), 6.87 to 7.55 (m, 51H), and 5.67 (s, 6H).

MALDI-TOF-MS m/Z found: 1719.19 ([M]$^+$calcd: 1721.50).

[2] Preparation of Charge Transporting Varnish

Example 1-1

0.105 g of the aniline derivative 1 as a charge transporting substance, 0.202 g of phosphotungstic acid (PTA) as a dopant substance, and 0.097 g of tetrafluorotetracyanoquinodimethane (F4TCNQ) were dissolved in 20 g of cyclohexanone. To the resulting solution were added 0.007 g of 3,3,3-trifluoropropyltrimethoxysilane (Shin-Etsu Chemical Co., Ltd.) and 0.013 g of phenyltrimethoxysilane (Shin-Etsu Chemical Co., Ltd.), followed by stirring, and the resulting solution was filtered using a PTFE-made filter having a pore diameter of 0.2 μm, to prepare a charge transporting varnish.

Examples 1-2 to 1-64

Charge transporting varnishes were prepared in the same manner as in Example 1-1, except for changing the kind of aniline derivative and the amounts of constituents blended together according to Tables 19 to 21.

Note that in the tables, "F4BQ" means tetrafluoro-1,4-benzoquinone, "PMA" means phosphomolybdic acid, "DDQ" means 2,3-dichloro-5,6-dicyano-1,4-benzoquinone, "SAC" means an arylsulfonic acid compound represented by the formula (H4-1), "silane A" means 3,3,3-trifluoropropyltrimethoxysilane, "silane B" means phenyltrimethoxysilane, "CHN" means cyclohexanone, "DMI" means 1,3-dimethyl-2-imidazolidinone, "2,3-B,D" means 2,3-butanediol, "PGME" means propylene glycol monomethyl ether, "PG" means propylene glycol, "ECA" means diethylene glycol monoethyl ether acetate, "CHA" means cyclohexanol, "DPM" means dipropylene glycol monomethyl ether, "DMIB" means N,N-dimethylisobutylamide, and the parenthesized numerals means the amounts used (unit: g).

Note that the arylsulfonic acid compound represented by the formula (H4-1) was synthesized according to the method described in PCT Patent Publication No. WO 2006/025342, here and hereinafter.

[Chemical Formula 159]

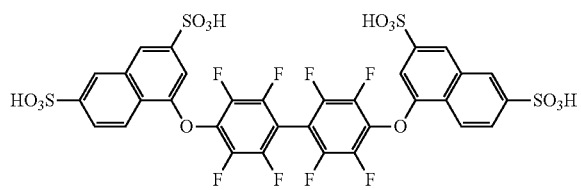

(H4-1)

TABLE 19

| Example | Charge transporting substance | Dopant substance | Organosilane | Organic solvent |
|---|---|---|---|---|
| 1-1 | Aniline derivative 1 (0.105) | PTA (0.202) F4TCNQ (0.097) | Silane A (0.007) Silane B (0.013) | CHN (20) |
| 1-2 | Aniline derivative 2 (0.102) | PTA (0.202) F4TCNQ (0.100) | Silane A (0.007) Silane B (0.013) | CHN (20) |
| 1-3 | Aniline derivative 3 (0.102) | PTA (0.202) F4TCNQ (0.100) | Silane A (0.007) Silane B (0.013) | CHN (20) |
| 1-4 | Aniline derivative 4 (0.113) | PTA (0.202) F4TCNQ (0.089) | Silane A (0.007) Silane B (0.013) | CHN (20) |
| 1-5 | Aniline derivative 5 (0.088) | PTA (0.202) F4TCNQ (0.114) | Silane A (0.007) Silane B (0.013) | CHN (20) |
| 1-6 | Aniline derivative 6 (0.095) | PTA (0.202) F4TCNQ (0.107) | Silane A (0.007) Silane B (0.013) | CHN (20) |
| 1-7 | Aniline derivative 7 (0.105) | PTA (0.202) F4TCNQ (0.097) | Silane A (0.007) Silane B (0.013) | CHN (20) |
| 1-8 | Aniline derivative 7 (0.071) | PTA (0.202) F4TCNQ (0.131) | Silane A (0.007) Silane B (0.013) | CHN (20) |
| 1-9 | Aniline derivative 8 (0.062) | PTA (0.202) F4TCNQ (0.140) | Silane A (0.007) Silane B (0.013) | CHN (20) |
| 1-10 | Aniline derivative 9 (0.061) | PTA (0.202) F4TCNQ (0.140) | Silane A (0.007) Silane B (0.013) | CHN (20) |
| 1-11 | Aniline derivative 10 (0.063) | PTA (0.202) F4TCNQ (0.139) | Silane A (0.007) Silane B (0.013) | CHN (20) |
| 1-12 | Aniline derivative 11 (0.052) | PTA (0.102) F4TCNQ (0.050) | Silane A (0.003) Silane B (0.007) | CHN (5) |
| 1-13 | Aniline derivative 11 (0.133) | PTA (0.263) F4TCNQ (0.130) | Silane A (0.009) Silane B (0.018) | CHN (5) |
| 1-14 | Aniline derivative 12 (0.053) | PTA (0.101) F4TCNQ (0.048) | Silane A (0.003) Silane B (0.007) | CHN (10) |
| 1-15 | Aniline derivative 12 (0.113) | PTA (0.309) F4TCNQ (0.147) | Silane A (0.010) Silane B (0.021) | CHN (10) |
| 1-16 | Aniline derivative 13 (0.063) | PTA (0.202) F4TCNQ (0.139) | Silane A (0.007) Silane B (0.013) | CHN (20) |
| 1-17 | Aniline derivative 13 (0.223) | PTA (0.619) F4TCNQ (0.395) | Silane A (0.021) Silane B (0.041) | CHN (20) |
| 1-18 | Aniline derivative 14 (0.076) | PTA (0.202) F4TCNQ (0.126) | Silane A (0.007) Silane B (0.013) | CHN (20) |

TABLE 19-continued

| Example | Charge transporting substance | Dopant substance | Organosilane | Organic solvent |
|---|---|---|---|---|
| 1-19 | Aniline derivative 14 (0.232) | PTA (0.619) F4TCNQ (0.387) | Silane A (0.021) Silane B (0.041) | CHN (20) |
| 1-20 | Aniline derivative 15 (0.075) | PTA (0.202) F4TCNQ (0.127) | Silane A (0.007) Silane B (0.013) | CHN (20) |
| 1-21 | Aniline derivative 16 (0.088) | PTA (0.202) F4TCNQ (0.114) | Silane A (0.007) Silane B (0.013) | CHN (20) |
| 1-22 | Aniline derivative 17 (0.073) | PTA (0.202) F4TCNQ (0.129) | Silane A (0.007) Silane B (0.13) | CHN (20) |
| 1-23 | Aniline derivative 18 (0.321) | PTA (0.619) F4TCNQ (0.306) | Silane A (0.021) Silane B (0.041) | DMI (14) 2,3-B,D (4) PGME (2) |
| 1-24 | Aniline derivative 18 (0.171) | PTA (0.309) F4TCNQ (0.138) | Silane A (0.010) Silane B (0.021) | DMI (7) 2,3-B,D (2) PGME (1) |

TABLE 20

| Example | Charge transporting substance | Dopant substance | Organosilane | Organic solvent |
|---|---|---|---|---|
| 1-25 | Aniline derivative 9 (0.093) | SAC (0.107) | — | DMI (3.3) CHA (4.9) PG (1.6) |
| 1-26 | Aniline derivative 9 (0.093) | SAC (0.107) | Silane A (0.007) Silane B (0.013) | DMI (3.3) CHA (4.9) PG (1.6) |
| 1-27 | Aniline derivative 9 (0.047) | PTA (0.101) F4TCNQ (0.054) | Silane A (0.003) Silane B (0.007) | DMI (4.0) 2,3-BD (4.5) ECA (1.5) |
| 1-28 | Aniline derivative 11 (0.056) | PTA (0.101) DDQ (0.045) | Silane A (0.003) Silane B (0.007) | CHN (10) |
| 1-29 | Aniline derivative 11 (0.062) | PTA (0.101) F4BQ (0.039) | Silane A (0.003) Silane B (0.007) | CHN (10) |
| 1-30 | Aniline derivative 11 (0.051) | PMA (0.101) F4TCNQ (0.039) | Silane A (0.003) Silane B (0.007) | CHN (10) |
| 1-31 | Aniline derivative 11 (0.102) | PTA (0.202) F4TCNQ (0.100) | Silane A (0.007) Silane B (0.013) | DMI (8.0) 2,3-BD (9.0) ECA (3.0) |
| 1-32 | Aniline derivative 13 (0.054) | PTA (0.101) F4TCNQ (0.047) | Silane A (0.003) Silane B (0.007) | DMI (4.0) 2,3-BD (4.5) ECA (1.5) |
| 1-33 | Aniline derivative 14 (0.055) | PTA (0.101) F4TCNQ (0.046) | Silane A (0.003) Silane B (0.007) | DMI (4.0) 2,3-BD (4.5) ECA (1.5) |
| 1-34 | Aniline derivative 18 (0.102) | PMA (0.202) F4TCNQ (0.100) | Silane A (0.003) Silane B (0.007) | CHN (20) |
| 1-35 | Aniline derivative 18 (0.102) | PTA (0.202) F4TCNQ (0.100) | Silane A (0.007) Silane B (0.013) | DMI (8.0) 2,3-BD (9.0) ECA (3.0) |
| 1-36 | Aniline derivative 18 (0.051) | PTA (0.093) DDQ (0.041) | Silane A (0.003) Silane B (0.006) | DMI (2.1) 2,3-BD (0.6) PGME (0.3) |
| 1-37 | Aniline derivative 18 (0.157) | PTA (0.309) DDQ (0.152) | Silane A (0.010) Silane B (0.021) | DMI (7.0) 2,3-BD (2.0) PGME (1.0) |
| 1-38 | Aniline derivative 18 (0.145) | PTA (0.309) DDQ (0.164) | Silane A (0.010) Silane B (0.021) | DMI (7.0) 2,3-BD (2.0) PGME (1.0) |
| 1-39 | Aniline derivative 18 (0.135) | PTA (0.309) DDQ (0.174) | Silane A (0.010) Silane B (0.021) | DMI (7.0) 2,3-BD (2.0) PGME (1.0) |
| 1-40 | Aniline derivative 18 (0.113) | DDQ (0.091) | Silane A (0.007) Silane B (0.014) | DMI (7.0) 2,3-BD (2.0) PGME (1.0) |
| 1-41 | Aniline derivative 18 (0.113) | PTA (0.102) DDQ (0.091) | Silane A (0.007) Silane B (0.014) | DMI (7.0) 2,3-BD (2.0) PGME (1.0) |
| 1-42 | Aniline derivative 18 (0.113) | PTA (0.306) DDQ (0.091) | Silane A (0.007) Silane B (0.014) | DMI (7.0) 2,3-BD (2.0) PGME (1.0) |
| 1-43 | Aniline derivative 18 (0.113) | PTA (0.408) DDQ (0.091) | Silane A (0.007) Silane B (0.014) | DMI (7.0) 2,3-BD (2.0) PGME (1.0) |

TABLE 20-continued

| Example | Charge transporting substance | Dopant substance | Organosilane | Organic solvent |
|---|---|---|---|---|
| 1-44 | Aniline derivative 18 (0.113) | PTA (0.204) DDQ (0.091) | Silane A (0.007) Silane B (0.014) | DMI (7.0) 2,3-BD (2.0) PGME (1.0) |
| 1-45 | Aniline derivative 19 (0.062) | SAC (0.138) | — | DMI (3.3) CHA (4.9) PG (1.6) |
| 1-46 | Aniline derivative 19 (0.062) | SAC (0.138) | Silane A (0.007) Silane B (0.013) | DMI (3.3) CHA (4.9) PG (1.6) |
| 1-47 | Aniline derivative 19 (0.043) | PTA (0.101) F4TCNQ (0.058) | Silane A (0.003) Silane B (0.007) | DMI (4.0) 2,3-BD (4.5) ECA (1.5) |
| 1-48 | Aniline derivative 19 (0.117) | SAC (0.128) | — | DMI (4.0) CHA (6.0) PG (2.0) |

TABLE 21

| Example | Charge transporting substance | Dopant substance | Organosilane | Organic solvent |
|---|---|---|---|---|
| 1-49 | Aniline derivative 21 (0.082) | PTA (0.155) F4TCNQ (0.072) | Silane A (0.005) Silane B (0.010) | DMI (3.5) 2,3-BD (1.0) PGME (0.5) |
| 1-50 | Aniline derivative 21 (0.090) | PTA (0.0155) DDQ (0.065) | Silane A (0.005) Silane B (0.010) | DMI (3.5) 2,3-BD (1.0) PGME (0.5) |
| 1-51 | Aniline derivative 23 (0.055) | PTA (0.101) F4TCNQ (0.046) | Silane A (0.003) Silane B (0.007) | DMI (4.0) 2,3-BD (4.5) ECA (1.5) |
| 1-52 | Aniline derivative 24 (0.058) | PTA (0.101) F4TCNQ (0.043) | Silane A (0.003) Silane B (0.007) | DMI (4.0) 2,3-BD (4.5) ECA (1.5) |
| 1-53 | Aniline derivative 25 (0.056) | PTA (0.101) F4TCNQ (0.045) | Silane A (0.003) Silane B (0.007) | DMI (4.0) 2,3-BD (4.5) ECA (1.5) |
| 1-54 | Aniline derivative 25 (0.230) | PTA (0.416) F4TCNQ (0.187) | Silane A (0.014) Silane B (0.028) | DMI (14.0) 2,3-BD (4.0) DPM (2.0) |
| 1-55 | Aniline derivative 25 (0.250) | PTA (0.416) DDQ (0.167) | Silane A (0.014) Silane B (0.028) | DMI (14.0) 2,3-BD (4.0) DPM (2.0) |
| 1-56 | Aniline derivative 28 (0.085) | PTA (0.155) F4TCNQ (0.070) | Silane A (0.005) Silane B (0.010) | DMI (3.5) 2,3-BD (1.0) PGME (0.5) |
| 1-57 | Aniline derivative 28 (0.085) | PTA (0.155) DDQ (0.063) | Silane A (0.005) Silane B (0.010) | DMI (3.5) 2,3-BD (1.0) PGME (0.5) |
| 1-58 | Aniline derivative 29 (0.056) | PTA (0.101) F4TCNQ (0.045) | Silane A (0.003) Silane B (0.007) | DMI (4.0) 2,3-BD (4.5) ECA (1.5) |
| 1-59 | Aniline derivative 18 (0.421) | PTA (0.833) F4TCNQ (0.412) | Silane A (0.028) Silane B (0.056) | DMI (28.0) 2,3-BD (8.0) DPM (4.0) |
| 1-60 | Aniline derivative 18 (0.842) | PTA (1.666) F4TCNQ (0.824) | Silane A (0.056) Silane B (0.111) | DMI (56.0) 2,3-BD (16.0) PGME (8.0) |
| 1-61 | Aniline derivative 18 (0.076) | PTA (0.151) F4TCNQ (0.075) | Silane A (0.005) Silane B (0.010) | DMI (8.0) 2,3-BD (9.0) ECA (3.0) |
| 1-62 | Aniline derivative 24 (0.204) | — | — | CHN (10) |
| 1-63 | Aniline derivative 22 (0.208) | — | — | DMIB (10) |
| 1-64 | Aniline derivative 26 (0.208) | — | — | DMIB (10) |

[3] Production of Organic EL Elements and Evaluation of their Characteristics

[3-1] Use as Hole Injection Layer

Example 2-1

The varnish obtained in Example 1-1 was applied to an ITO substrate by use of a spin coater, and then dried at 80° C. for one minute. Further, the varnish was baked in the atmospheric air at 150° C. for five minutes, to form a 30 nm-thick uniform thin film on the ITO substrate. As the ITO substrate, a glass substrate measuring 25 mm by 25 mm and 0.7 thick provided thereon with a pattern of 150 nm-thick film of indium tin oxide (ITO) was used, by removing impurities on its surface by an $O_2$ plasma cleaning apparatus (150 W, 30 minutes) before use.

Next, on the ITO substrate thus formed with the thin film, a 30 nm-thick film of a-NPD (N,N'-di(1-naphthyl)-N,N'-diphenylbenzidine) was formed at 0.2 nm/second by use of a vapor deposition system (vacuum degree $1.0 \times 10^{-5}$ Pa). Subsequently, CBP and Ir(PPy)$_3$ were co-evaporated. The co-evaporation was conducted while controlling the vapor deposition rates in such a manner as to obtain an Ir(PPy)$_3$ concentration of 6%, the film thickness being 40 nm. Next, thin films of BAlq, lithium fluoride, and aluminum were sequentially formed, to obtain an organic EL element. In this case, the vapor deposition rate was 0.2 nm/second for BAlq and aluminum, and 0.02 nm/second for lithium fluoride, and the thicknesses of the thin films were each set to be 20 nm, 0.5 nm, and 120 nm.

Note that in order to prevent characteristics from being degraded under influences of oxygen and water in air, the organic EL element was sealed with sealing substrates, before evaluation of the characteristics thereof. The sealing was conducted by the following procedure. The organic EL element was placed between the sealing substrates in a nitrogen atmosphere with an oxygen concentration of up to 2 ppm and a dew point of up to −85° C., and the sealing substrates were adhered to each other using an adhesive (XNR5516Z-B1, manufactured by Nagase ChemteX Corporation). In this instance, a water capturing agent (HD-071010W-40, manufactured by Dynic Corporation) was placed inside the sealing substrates together with the organic EL element. After the thus adhered sealing substrates were irradiated with UV light (wavelength: 365 nm, irradiation amount: 6,000 mJ/cm$^2$), an annealing treatment was conducted at 80° C. for one hour, to cure the adhesive.

[Chemical Formula 160]

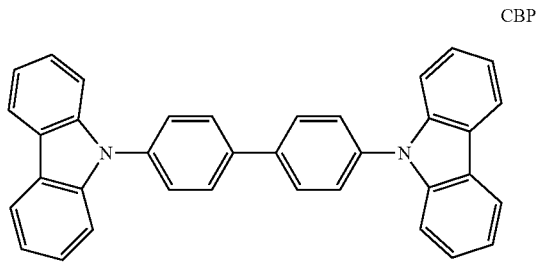

CBP

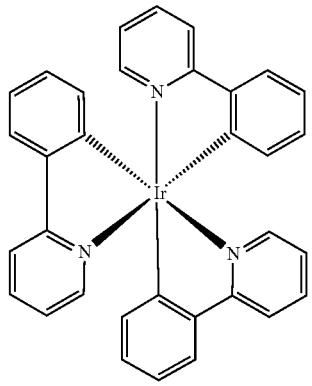

Ir(PPy)$_3$

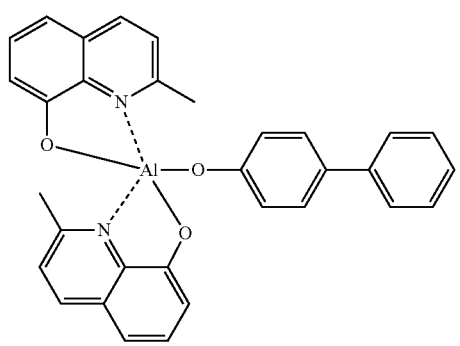

BAlq

Examples 2-2 to 2-12, 2-14, 2-16, 2-18, and 2-20 to 2-24

Organic EL elements were produced by the same method as in Example 2-1, except for each using the varnishes obtained in Examples 1-2 to 1-12, 1-14, 1-16, 1-18, and 1-20 to 1-24 in place of the varnish obtained in Example 1-1.

Examples 2-13, 2-15, 2-17 and 2-19

Organic EL elements were produced by the same method as in Example 2-1, except for each using the varnishes obtained in Examples 1-13, 1-15, 1-17, and 1-19 in place of the varnish obtained in Example 1-1 and setting the thickness of the thin film formed on the ITO substrate to 100 nm.

Examples 2-25 to 2-38

Organic EL elements were produced by the same method as in Example 2-1, except for setting the aluminum film thickness to 100 nm, each using the varnishes obtained in Examples 1-27 to 1-35, 1-47, 1-51 to 1-53, and 1-58 in place of the varnish obtained in Example 1-1.

Examples 2-39 to 2-53

Organic EL elements were produced by the same method as in Example 2-1, except for setting the aluminum film thickness to 100 nm, each using the varnishes obtained in Examples 1-23, 1-36 to 1-43, 1-49, 1-50, and 1-54 to 1-57 in place of the varnish obtained in Example 1-1, and setting the baking time at 150° C. to 10 minutes.

Example 2-54

An organic EL element was produced by the same method as in Example 2-1, except for setting the aluminum film thickness to 100 nm, using the varnish obtained in Example 1-44 in place of the varnish obtained in Example 1-1, setting the baking time at 150° C. to 10 minutes, and setting the thickness of the thin film formed on the ITO substrate to 90 nm.

Example 2-55

An organic EL element was produced by the same method as in Example 2-1, except for setting the aluminum film thickness to 100 nm, using the varnish obtained in Example 1-23 in place of the varnish obtained in Example 1-1, setting the baking time at 150° C. to 10 minutes, and setting the thickness of the thin film formed on the ITO substrate to 100 nm.

Example 2-56

An organic EL element was produced by the same method as in Example 2-1, except for setting the aluminum film thickness to 100 nm, using the varnish obtained in Example 1-52 in place of the varnish obtained in Example 1-1, and baking in vacuum instead of baking in the atmospheric air.

Example 2-57

An organic EL element was produced by the same method as in Example 2-1, except for setting the aluminum film thickness to 100 nm, using the varnish obtained in Example 1-23 in place of the varnish obtained in Example 1-1, setting the baking time at 150° C. to 10 minutes, and baking in vacuum instead of baking in the atmospheric air.

Example 2-58

An organic EL element was produced by the same method as in Example 2-1, except for setting the aluminum film thickness to 100 nm, using the varnish obtained in Example 1-23 in place of the varnish obtained in Example 1-1, setting the baking time at 150° C. to 10 minutes, baking in vacuum instead of baking in the atmospheric air, and setting the thickness of the thin film formed on the ITO substrate to 100 nm.

Examples 2-59 to 2-67

Organic EL elements were produced by the same method as in Example 2-1, except for setting the aluminum film thickness to 100 nm, each using the varnishes obtained in Examples 1-23, 1-25, 1-26, 1-44 to 1-46, 1-48, 1-54, and 1-55 in place of the varnish obtained in Example 1-1, and baking at 230° C. for 15 minutes instead of baking at 150° C. for five minutes.

Example 2-68

An organic EL element was produced by the same method as in Example 2-1, except for setting the aluminum film thickness to 100 nm, using the varnish obtained in Example 1-44 in place of the varnish obtained in Example 1-1, baking at 230° C. for 15 minutes instead of baking at 150° C. for five minutes, and setting the thickness of the thin film formed on the ITO substrate to 90 nm.

Examples 2-69 and 2-70

Organic EL elements were produced by the same method as in Example 2-1, except for setting the aluminum film thickness to 100 nm, each using the varnishes obtained in Examples 1-63 and 1-64 in place of the varnish obtained in Example 1-1, and setting the baking time at 150° C. to 10 minutes.

Driving voltage, luminance, and luminous efficiency at a driving current of 0.7 mA as well as luminance half-life (the time required for the luminance to reach one half the initial value in the case where the element is continuously driven with a driving current kept at 0.7 mA) were measured, for the elements obtained in Examples 2-1 to 2-22, 2-25 to 2-39, 2-55 to 2-61, and 2-63 to 2-65.

In addition, driving voltage, current density, and luminous efficiency in the case of driving at a luminance of 5,000 cd/m$^2$ as well as luminance half-life (the time required for luminance to reach one half the initial luminance of 5,000 cd/m$^2$) were measured, for the elements obtained in Examples 2-23, 2-24, 2-40 to 2-54, 2-62, and 2-66 to 2-68. The results are set forth in Tables 22 to 25.

TABLE 22

| Example | Thickness of charge transporting thin film (nm) | Driving voltage (V) | Luminance (cd/m$^2$) | Luminous efficiency (cd/A) | Half-life (hours) |
|---|---|---|---|---|---|
| 2-1 | 30 | 8.9 | 4820 | 27.5 | 301 |
| 2-2 | 30 | 9.6 | 5040 | 28.8 | 173 |
| 2-3 | 30 | 9.1 | 5070 | 29.0 | 280 |
| 2-4 | 30 | 8.9 | 4970 | 28.4 | 307 |
| 2-5 | 30 | 9.3 | 4920 | 28.1 | 276 |
| 2-6 | 30 | 8.8 | 4550 | 26.0 | 263 |
| 2-7 | 30 | 8.3 | 3660 | 20.9 | 351 |
| 2-8 | 30 | 9.0 | 4810 | 27.5 | 295 |
| 2-9 | 30 | 8.8 | 4290 | 24.6 | 419 |
| 2-10 | 30 | 8.9 | 4724 | 27.0 | 239 |
| 2-11 | 30 | 9.0 | 4880 | 27.9 | 351 |
| 2-12 | 30 | 9.2 | 5100 | 29.2 | 380 |
| 2-13 | 100 | 9.5 | 5350 | 30.6 | 227 |
| 2-14 | 30 | 9.3 | 5180 | 29.6 | 307 |
| 2-15 | 100 | 9.2 | 5460 | 31.2 | 278 |
| 2-16 | 30 | 9.2 | 5095 | 29.1 | 404 |
| 2-17 | 100 | 9.0 | 5328 | 30.5 | 323 |
| 2-18 | 30 | 9.2 | 5146 | 29.4 | 412 |
| 2-19 | 100 | 9.2 | 5336 | 30.5 | 291 |
| 2-20 | 30 | 9.2 | 4470 | 25.6 | 358 |
| 2-21 | 30 | 9.2 | 4970 | 28.4 | 195 |
| 2-22 | 30 | 9.4 | 4708 | 26.9 | 258 |

TABLE 23

| Example | Thickness of charge transporting thin film (nm) | Driving voltage (V) | Current density (mA/cm$^2$) | Luminous efficiency (cd/A) | Half-life (hours) |
|---|---|---|---|---|---|
| 2-23 | 30 | 9.39 | 17.6 | 28.4 | 242 |
| 2-24 | 30 | 9.43 | 17.9 | 27.9 | 388 |

TABLE 24

| Example | Thickness of charge transporting thin film (nm) | Driving voltage (V) | Luminance (cd/m$^2$) | Luminous efficiency (cd/A) | Half-life (hours) |
|---|---|---|---|---|---|
| 2-25 | 30 | 9.10 | 5060 | 24.4 | 129 |
| 2-26 | 30 | 9.38 | 4643 | 26.5 | 362 |
| 2-27 | 30 | 10.30 | 4530 | 25.9 | 283 |
| 2-28 | 30 | 9.43 | 4770 | 27.3 | 365 |
| 2-29 | 30 | 9.41 | 5020 | 28.9 | 145 |
| 2-30 | 30 | 9.38 | 5000 | 28.8 | 182 |
| 2-31 | 30 | 9.38 | 5100 | 29.2 | 183 |

TABLE 24-continued

| Example | Thickness of charge transporting thin film (nm) | Driving voltage (V) | Luminance (cd/m$^2$) | Luminous efficiency (cd/A) | Half-life (hours) |
|---|---|---|---|---|---|
| 2-32 | 30 | 9.87 | 4994 | 28.5 | 230 |
| 2-33 | 30 | 9.40 | 4920 | 28.4 | 226 |
| 2-34 | 30 | 9.31 | 5020 | 27.3 | 165 |
| 2-35 | 30 | 9.61 | 5169 | 29.5 | 204 |
| 2-36 | 30 | 9.45 | 5149 | 29.4 | 189 |
| 2-37 | 30 | 9.61 | 4842 | 27.7 | 261 |
| 2-38 | 30 | 9.31 | 5080 | 27.8 | 170 |
| 2-39 | 30 | 9.26 | 4925 | 28.1 | 369 |
| 2-55 | 100 | 9.26 | 5042 | 28.8 | 310 |
| 2-56 | 30 | 9.58 | 5132 | 29.3 | 231 |
| 2-57 | 30 | 9.50 | 5063 | 28.9 | 347 |
| 2-58 | 100 | 9.29 | 5014 | 28.7 | 270 |
| 2-59 | 30 | 9.8 | 4987 | 28.5 | 376 |
| 2-60 | 30 | 9.6 | 4906 | 28.0 | 466 |
| 2-61 | 30 | 9.3 | 4865 | 27.8 | 504 |
| 2-63 | 30 | 9.5 | 4647 | 26.6 | 220 |
| 2-64 | 30 | 9.6 | 4807 | 27.5 | 209 |
| 2-65 | 30 | 9.8 | 4739 | 27.1 | 300 |
| 2-69 | 30 | 11.1 | 18.9 | 26.5 | 375 |
| 2-70 | 30 | 11.2 | 20.6 | 24.2 | 398 |

TABLE 25

| Example | Thickness of charge transporting thin film (nm) | Driving voltage (V) | Current density (mA/cm$^2$) | Luminous efficiency (cd/A) | Half-life (hours) |
|---|---|---|---|---|---|
| 2-40 | 30 | 9.52 | 18.0 | 27.8 | 271 |
| 2-41 | 30 | 9.49 | 18.0 | 27.8 | 289 |
| 2-42 | 30 | 9.39 | 18.2 | 27.6 | 313 |
| 2-43 | 30 | 9.42 | 18.6 | 26.9 | 300 |
| 2-44 | 30 | 9.76 | 17.4 | 28.8 | |
| 2-45 | 30 | 9.70 | 17.9 | 27.9 | 206 |
| 2-46 | 30 | 9.49 | 18.4 | 27.1 | 270 |
| 2-47 | 30 | 9.40 | 18.3 | 27.4 | 194 |
| 2-48 | 30 | 9.43 | 17.9 | 27.9 | 388 |
| 2-49 | 30 | 9.39 | 17.6 | 28.4 | 242 |
| 2-50 | 30 | 9.40 | 18.3 | 27.3 | 294 |
| 2-51 | 30 | 9.31 | 18.4 | 27.1 | 388 |
| 2-52 | 30 | 9.41 | 17.8 | 28.1 | 382 |
| 2-53 | 30 | 9.44 | 17.9 | 28.0 | 220 |
| 2-54 | 90 | 9.48 | 17.4 | 28.8 | 188 |
| 2-62 | 30 | 9.50 | 18.9 | 26.5 | 413 |
| 2-66 | 30 | 9.40 | 18.6 | 26.9 | 378 |
| 2-67 | 30 | 9.34 | 19.1 | 26.1 | 596 |
| 2-68 | 90 | 9.50 | 17.8 | 28.0 | 443 |

As shown in Tables 22 to 25, it is seen that the organic EL elements having a charge transporting thin film obtained from the charge transporting varnish of the present invention as a hole injection layer show high luminance and are excellent in durability not only when the film thickness is comparatively small (30 nm) but also when the film thickness is comparatively large (90 nm, 100 nm).

Example 3-1

The varnish obtained in Example 1-59 was applied to an Al/Nd substrate by use of a spin coater, dried at 80° C. for one minute, and further baked in the atmospheric air at 150° C. for five minutes, to form a 30 nm-thick uniform thin film on the Al/Nd substrate. Note that the Al/Nd substrate was produced by sputtering Al and Nd by 150 nm onto a glass substrate, and impurities on the surface of the Al/Nd substrate were removed by use of an O$_2$ plasma cleaning apparatus (150 W, 30 minutes) before use.

Next, on the Al/Nd substrate formed thereon with the thin film, a 30 nm-thick film of a-NPD was formed at 0.2 nm/second by use of a vapor deposition system (vacuum degree $1.0 \times 10^{-5}$ Pa). Subsequently, CBP and Ir(PPy)$_3$ were co-evaporated. Note that the co-evaporation was conducted by controlling the vapor deposition rates in such a manner as to obtain an Ir(PPy)$_3$ concentration of 6%, the film thickness being 40 nm.

Next, thin films of BAlq and lithium fluoride were sequentially formed. In this case, the vapor deposition rate was 0.2 nm/second for BAlq and 0.02 nm/second for lithium fluoride, and the thicknesses of the thin films were each 20 nm and 0.5 nm.

Finally, magnesium and silver were co-evaporated, to obtain an organic EL element. Note that the co-evaporation was conducted by controlling the vapor deposition rates in such a manner as to obtain a magnesium concentration of 90%, the film thickness being 20 nm.

Note that the element was sealed by the same method as in Example 2-1, before put to evaluation of characteristics thereof.

Examples 3-2 and 3-3

Organic EL elements were produced by the same method as in Example 3-1, except for each using the varnishes obtained in Examples 1-60 and 1-61 in place of the varnish obtained in Example 1-59.

Driving voltage, current density, and luminous efficiency in the case of driving at a luminance of 3,000 cd/m$^2$ as well as luminance half-life (the time required for luminance to reach one half the initial luminance of 3,000 cd/m$^2$) were measured, for the elements obtained in Examples 3-1 to 3-3. The results are set forth in Table 26.

TABLE 26

| Example | Thickness of charge transporting thin film (nm) | Driving voltage (V) | Current density (mA/cm$^2$) | Luminous efficiency (cd/A) | Half-life (hours) |
|---|---|---|---|---|---|
| 3-1 | 30 | 11.5 | 13.5 | 22.2 | 1287 |
| 3-2 | 30 | 11.5 | 13.1 | 23.0 | 1291 |
| 3-3 | 30 | 11.5 | 12.3 | 24.4 | 1063 |

As shown in Table 26, it is seen that the charge transporting thin films obtained from the charge transporting varnishes of the present invention can be used also as a hole injection layer in an organic EL element of a top emission structure.

Example 4-1

0.165 g of a triphenylamine derivative represented by the formula (H6-1) and 0.325 g of an arylsulfonic acid compound represented by the formula (H4-1) were dissolved in 8 g of 1,3-dimethyl-2-imidazolidinone in a nitrogen atmosphere. To the resulting solution were added 12 g of cyclohexanol and 4 g of propylene glycol, followed by stirring, and 0.016 g of 3,3,3-trifluoropropyltrimethoxysilane (manufactured by Shin-Etsu Chemical Co., Ltd.) and 0.033 g of phenyltrimethoxysilane (manufactured by Shin-Etsu Chemical Co., Ltd.) were further added thereto, followed by stirring, to obtain a hole injection layer forming composition. Note that the triphenylamine derivative represented by the formula (H6-1) was synthesized according to the method described in PCT Patent Publication No. WO 2013/084664, here and hereafter.

[Chemical Formula 161]

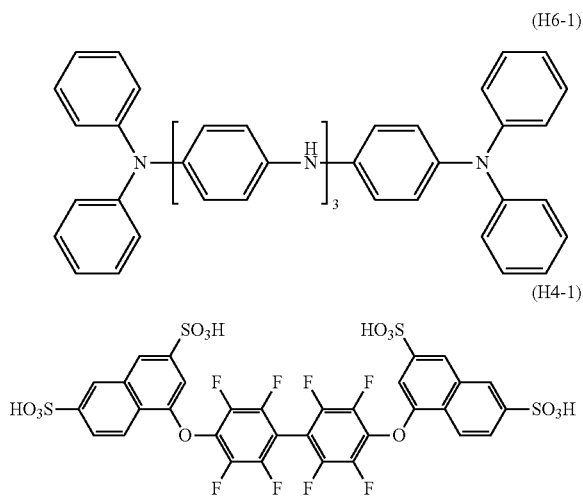

Next, the hole injection layer forming composition was applied to an ITO substrate by use of a spin coater, then dried at 80° C. for one minute, and further baked at 230° C. for 15 minutes in the atmospheric air, to form a 30 nm-thick uniform thin film on the ITO substrate as a hole injection layer. As the ITO substrate, a glass substrate measuring 25 mm by 25 mm and 0.7 thick formed thereon with a pattern of a 150 nm-thick film of indium tin oxide (ITO) was used, and impurities on the surface thereof were removed by an $O_2$ plasma cleaning apparatus (150 W, 30 minutes) before use.

Subsequently, on the ITO substrate thus formed with the thin film, vapor deposition method (vapor deposition rate 0.2 nm/second) using the aniline derivative 6 as a vapor source was conducted, to form a 30 nm-thick uniform thin film composed only of the aniline derivative 6 on the hole injection layer.

Then, CBP and Ir(PPy)$_3$ were co-evaporated by use of a vapor deposition system (vacuum degree $1.0\times10^{-5}$ Pa). The co-evaporation was conducted by controlling the vapor deposition rates in such a manner as to obtain an Ir(PPy)$_3$ concentration of 6%, the film thickness being 40 nm.

Finally, thin films of BAlq, lithium fluoride and aluminum were sequentially formed, to obtain an organic EL element. In this case, the vapor deposition rate was 0.2 nm/second for BAlq and aluminum and 0.02 nm/second for lithium fluoride, and the thicknesses of the thin films were each 20 nm, 0.5 nm and 100 nm.

Note that the element was sealed by the same method as in Example 2-1, before put to evaluation of characteristics thereof.

Driving voltage, luminance and luminous efficiency at a driving current of 0.7 mA were measured, for the element obtained in Example 4-1. The results are set forth in Table 27.

TABLE 27

| Example | Thickness of charge transporting thin film (nm) | Driving voltage (V) | Current density (mA/cm$^2$) | Luminous efficiency (cd/A) | Half-life (hours) |
|---|---|---|---|---|---|
| 4-1 | 30 | 11.1 | 54.2 | 9.2 | |

As shown in FIG. 27, it was found that the charge transporting thin film composed of the vapor-deposited film of the aniline derivative of the present invention is also excellent in charge transporting properties and is preferable as a hole injection layer in an organic EL element.

[3-2] Use of Thin Film as Hole Transport Layer or Hole Injection Transport Layer Example 5-1

An organic EL element was produced by the same method as in Example 4-1, except that instead of forming a vapor-deposited film of the aniline derivative 6 on the hole injection layer, the varnish obtained in Example 1-62 was applied by use of a spin coater, dried at 80° C. for one minute, and further baked in the atmospheric air at 150° C. for five minutes, to form a 30 nm-thick uniform thin film on the hole injection layer.

Example 5-2

An organic EL element was produced by the same method as in Example 5-1, except that the baking time was 10 minutes.

Example 5-3

An organic EL element was produced by the same method as in Example 5-1, except that the baking temperature was 230° C.

Example 6-1

The varnish obtained in Example 1-62 was applied to an ITO substrate by use of a spin coater, dried at 80° C. for one minute, and further baked in the atmospheric air at 150° C. for five minutes, to form a 30 nm-thick uniform thin film on the ITO substrate. As the ITO substrate, a glass substrate measuring 25 mm by 25 mm and 0.7 thick formed thereon with a pattern of a 150 nm-thick film of indium tin oxide (ITO) was used, and impurities on the surface thereof were removed by an $O_2$ plasma cleaning apparatus (150 W, 30 minutes) before use.

Next, on the ITO substrate thus formed with the thin film, CBP and Ir(PPy)$_3$ were co-evaporated by use of a vapor deposition system (vacuum degree $1.0\times10^{-5}$ Pa). The co-evaporation was conducted by controlling the vapor deposition rates in such a manner as to obtain an Ir(PPy)$_3$ concentration of 6%, the film thickness being 40 nm. Subsequently, thin films of BAlq, lithium fluoride, and aluminum were sequentially formed, to obtain an organic EL element. In this case, the vapor deposition rate was 0.2 nm/second for BAlq and aluminum and 0.02 nm/second for lithium fluoride, and the thicknesses of the thin films were each 20 nm, 0.5 nm, and 100 nm.

Note that the element was sealed by the same method as in Example 2-1, before put to evaluation of characteristics thereof.

Driving voltage, current density, and luminous efficiency in the case of driving at a luminance of 1,000 cd/m$^2$ as well as luminance half-life at a driving current of 0.7 mA (the time required for luminance to reach one half the initial value in the case where the element is continuously driven with the driving current kept at 0.7 mA) were measured, for the elements obtained in Examples 5-1 to 5-3, and 6-1. The results are set forth in Table 28.

TABLE 28

| Example | Thickness of charge transporting thin film (nm) | Driving voltage (V) | Current density (mA/cm²) | Luminous efficiency (cd/A) | Half-life (hours) |
| --- | --- | --- | --- | --- | --- |
| 5-1 | 30 | 8.8 | 6.3 | 15.9 | 314 |
| 5-2 | 30 | 8.8 | 6.4 | 15.6 | 320 |
| 5-3 | 30 | 8.5 | 5.1 | 19.5 | 266 |
| 6-1 | 30 | 9.0 | 5.6 | 17.8 | 255 |

As shown in Table 28, it is seen that the charge transporting thin films obtained from the charge transporting varnishes of the present invention can be preferably used also as a hole transport layer and a hole injection transport layer, and by use of the thin films, organic EL elements excellent in luminance characteristics and durability can be obtained.

The invention claimed is:

1. An aniline derivative represented by the formula (1) or (2):

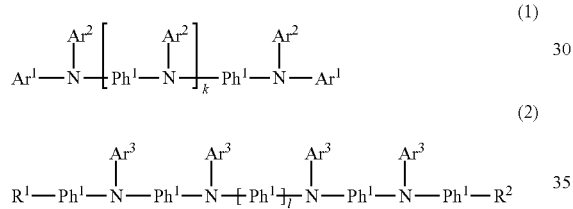

(1)

(2)

wherein $R^1$ and $R^2$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $Ph^1$ represents a group represented by the formula (P1):

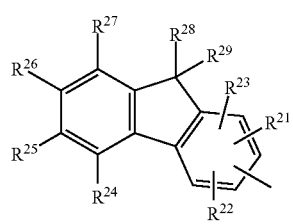

(P1)

wherein $R^3$ to $R^6$ independently represent a hydrogen atom, a halogen atom, a nitro group, a cyano group, or an alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $Ar^1$ independently represents a group represented by any of the formulas (B1) to (B11):

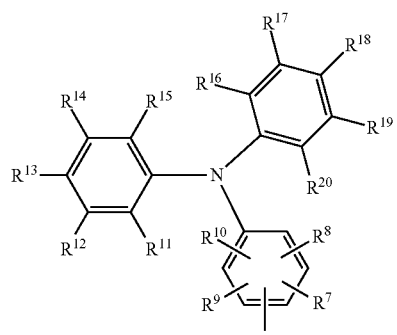

(B1)

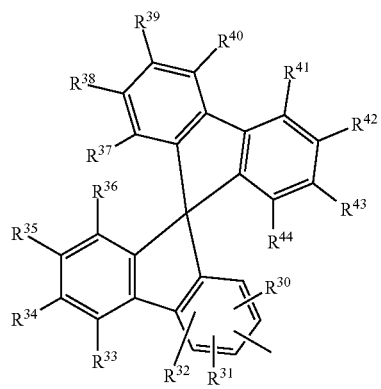

(B2)

(B3)

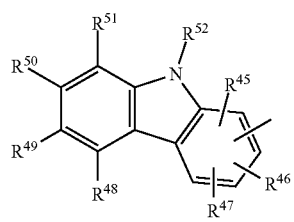

(B4)

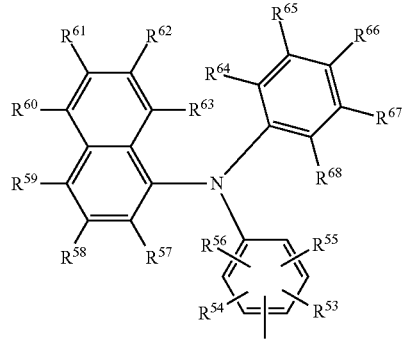

(B5)

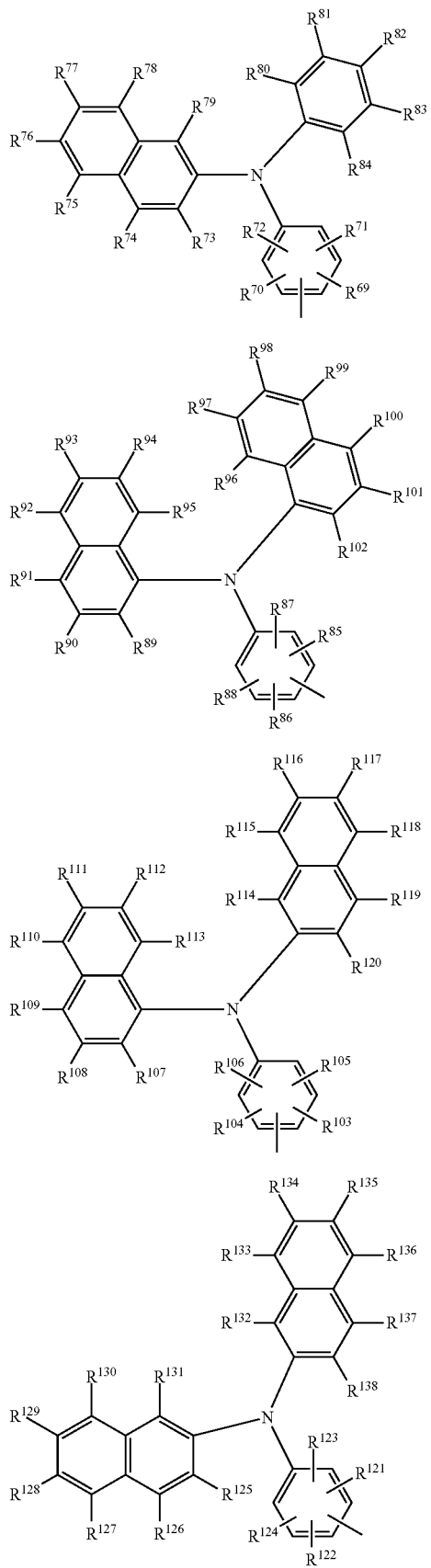

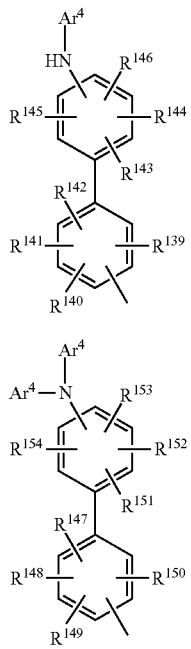

wherein $R^7$ to $R^{27}$, $R^{30}$ to $R^{51}$ and $R^{53}$ to $R^{154}$ independently represent a hydrogen atom, a halogen atom, a nitro group, a cyano group, or a diphenylamino group, alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with a halogen atom, $R^{28}$ and $R^{29}$ independently represent an aryl group having 6 to 20 carbon atoms or heteroaryl group having 2 to 20 carbon atoms which may be substituted with $Z^1$, $R^{52}$ represents a hydrogen atom, an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $Ar^4$ independently represents an aryl group having 6 to 20 carbon atoms which may be substituted with a di(aryl groups having 6 to 20 carbon atoms)amino group, $Z^1$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^2$, $Z^2$ represents a halogen atom, a nitro group, a cyano group, or an aryl group having 6 to 20 carbon atoms or heteroaryl group having 2 to 20 carbon atoms which may be substituted with $Z^3$, $Z^3$ represents a halogen atom, a nitro group or a cyano group, $Z^4$ represents a halogen atom, a nitro group, a cyano group, or an aryl group having 6 to 20 carbon atoms or heteroaryl group having 2 to 20 carbon atoms which may be substituted with $Z^5$, and $Z^5$ represents a halogen atom, a nitro group, a cyano group, or an alkyl group having 1 to 20 carbon atoms, alkenyl group having 2 to 20 carbon atoms or alkynyl group having 2 to 20 carbon atoms which may be substituted with $Z^3$,
$Ar^2$ independently represents a group represented by any of the formulas (A1) to (A5) or (A7) to (A12) or (A14) to (A18):
(A1)
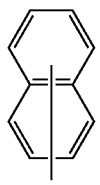
(A2)
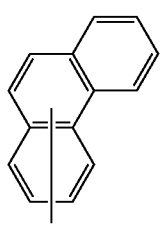
(A3)
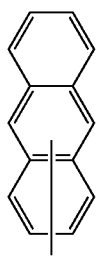
(A4)
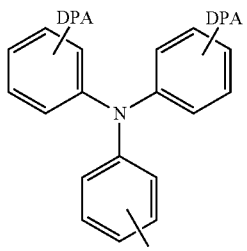
(A5)
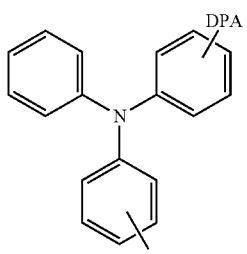
(A7)
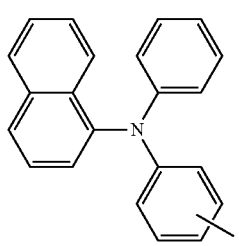
(A8)
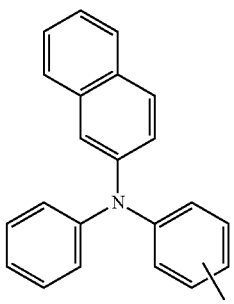
(A9)
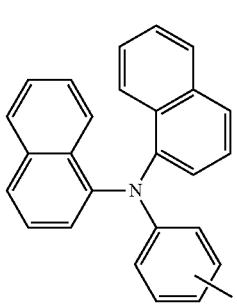
(A10)
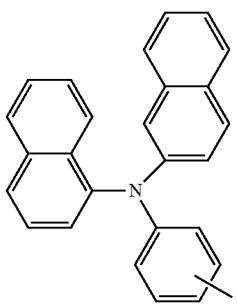
(A11)
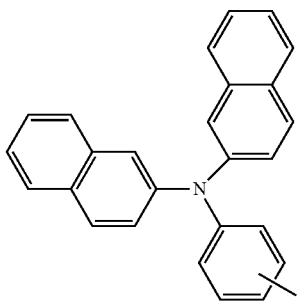
(A12)
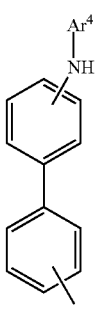

-continued

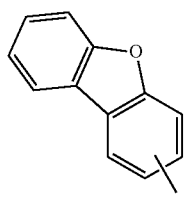 (A14)

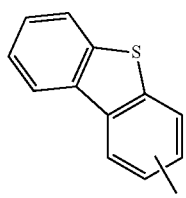 (A15)

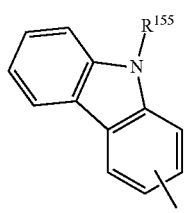 (A16)

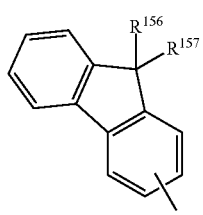 (A17)

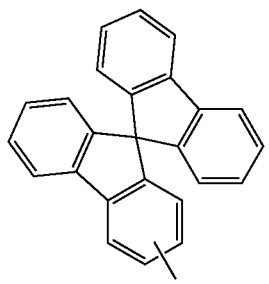 (A18)

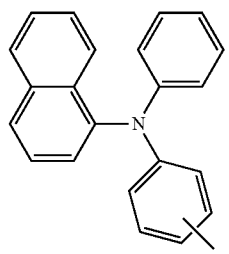 (C2)

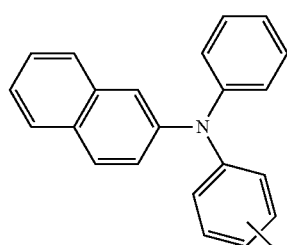 (C3)

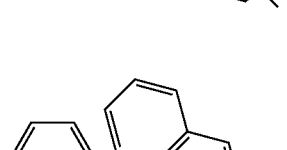 (C4)

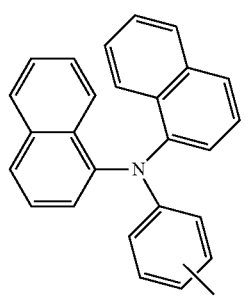 (C4)

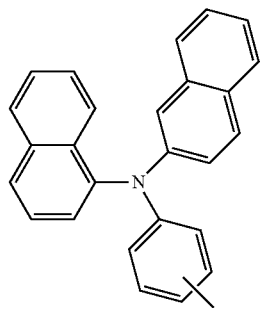 (C5)

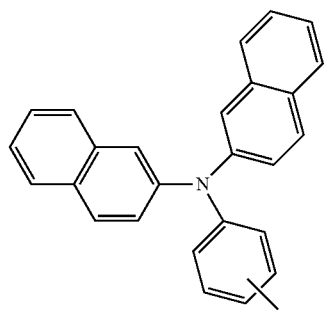 (C6)

wherein $R^{155}$ represents an hydrogen atom or an alkyl group having 1 to 20 carbon atoms, alkenyl group having 2 to 20 carbon atoms or alkynyl group having 2 to 20 carbon atoms which may be substituted with $Z^4$, or an aryl group having 6 to 20 carbon atoms or heteroaryl group having 2 to 20 carbon atoms which may be substituted with $Z^1$, $R^{156}$ and $R^{157}$ independently represent an aryl group having 6 to 20 carbon atoms or heteroaryl group having 2 to 20 carbon atoms which may be substituted with $Z^1$, DPA represents a diphenylamino group, and $Ar^4$, $Z^1$ and $Z^3$ to $Z^5$ have the same meanings as above, $Ar^3$ represents a group represented by any of the formulas (C2) to (C8):

(C7) 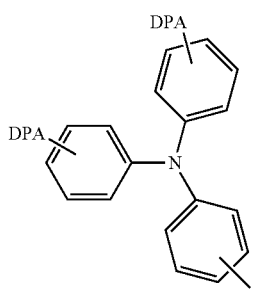
(C8) 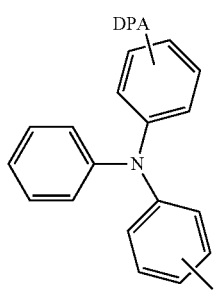
letter k represents an integer of 1 to 10, and
letter l represents 1 or 2.
2. The aniline derivative of claim 1,
wherein Ar¹ is a group represented by any of the formulas (B1') to (B11'):
(B1') 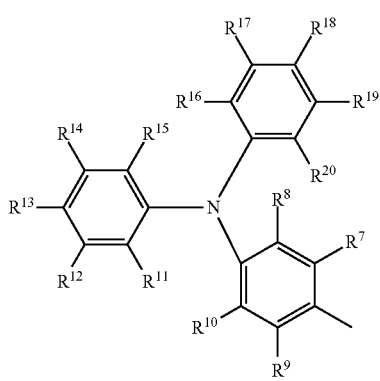
(B2') 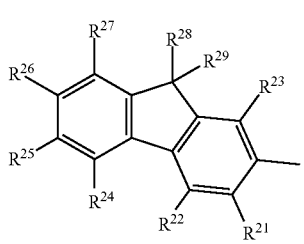
(B3') 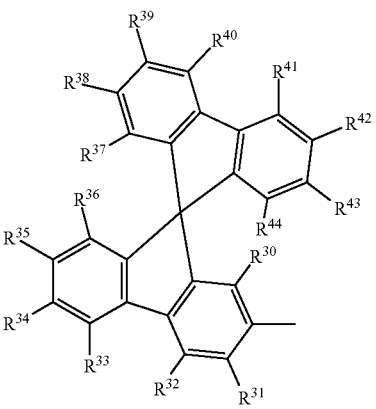
(B4') 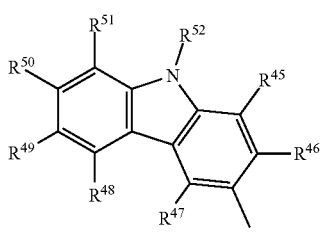
(B5') 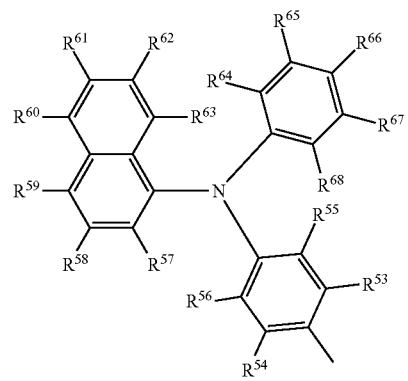
(B6') 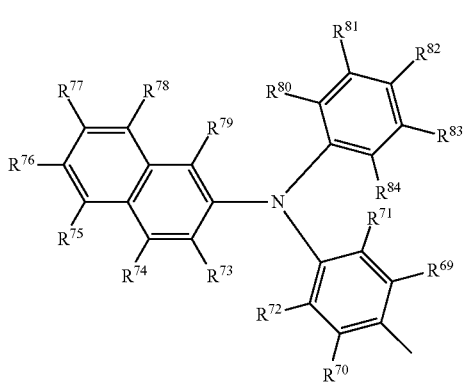

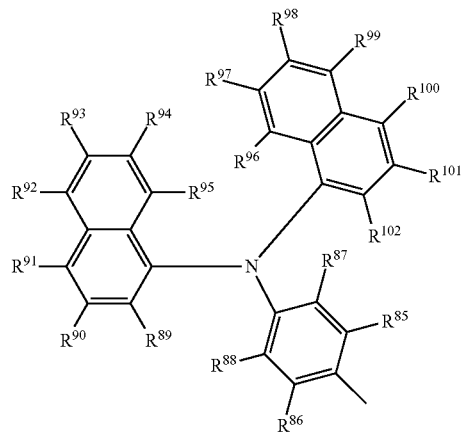
(B7')
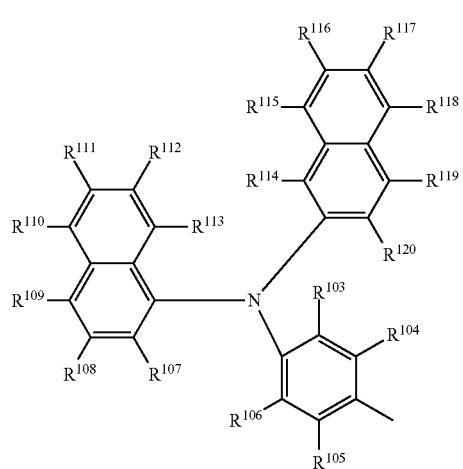
(B8')
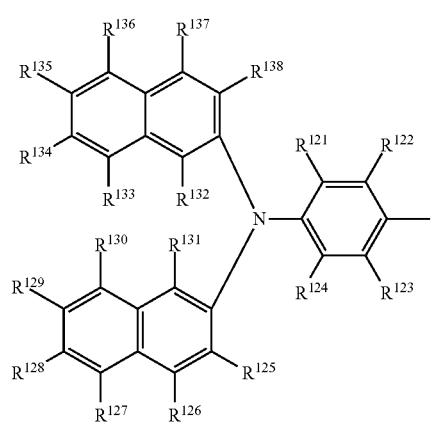
(B9')
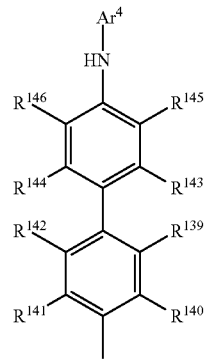
(B10')
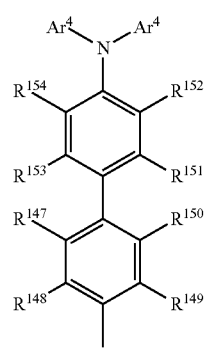
(B11')
wherein $R^7$ to $R^{154}$ and $Ar^4$ have the same meanings as above, and
$Ar^3$ is a group represented by any of the formulas (C2') to (C8'):
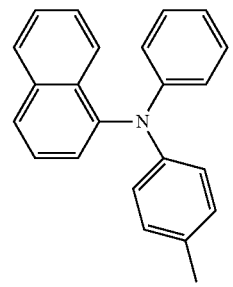
(C2')
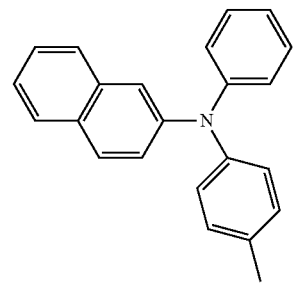
(C3')

(C4')
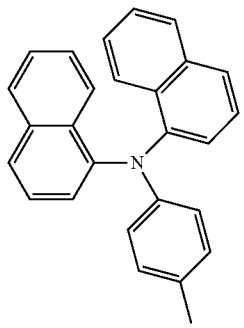

(C5')
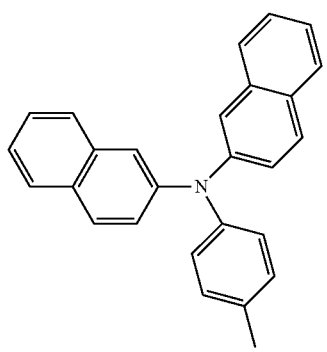

(C6')
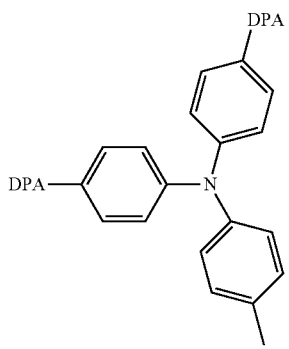

(C7')
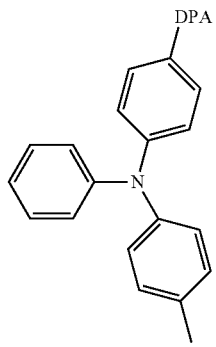

(C8')
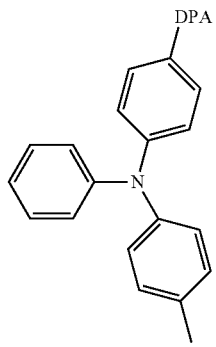

wherein DPA has the same meaning as above.

3. The aniline derivative of claim 1 or 2, wherein the $R^3$ to $R^6$, $R^7$ to $R^{27}$, $R^{30}$ to $R^{51}$ and $R^{53}$ to $R^{154}$ are each a hydrogen atom.

4. The aniline derivative of claim 1, represented by the formula (1-1):

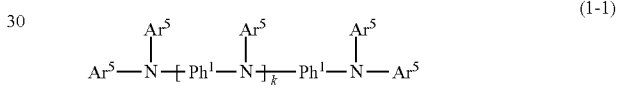

(1-1)

wherein $Ar^5$ simultaneously represent a group represented by any of the formulas (D1), (D2), (D4) to (D9), or (D11) to (D13), and $Ph^1$ and letter k have the same meanings as above:

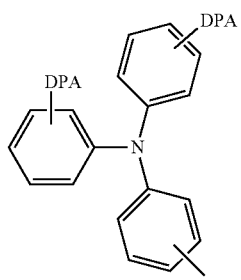

(D1)

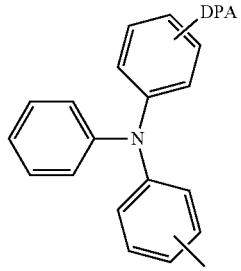

(D2)

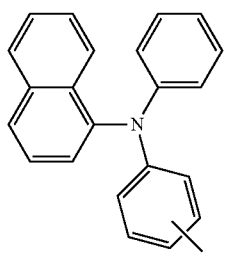
(D4)
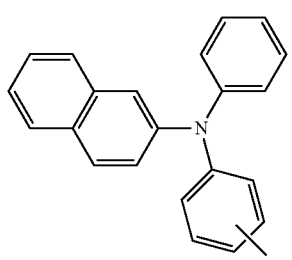
(D5)
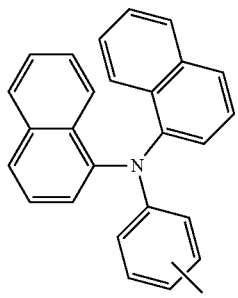
(D6)
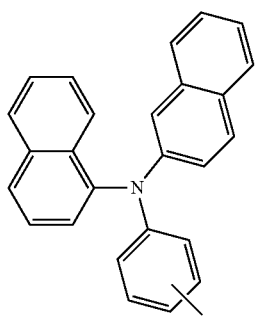
(D7)
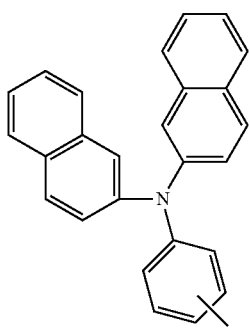
(D8)
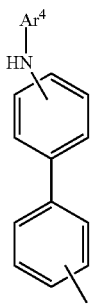
(D9)
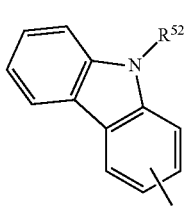
(D11)
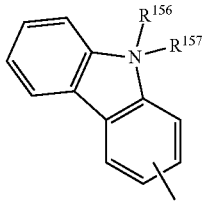
(D12)
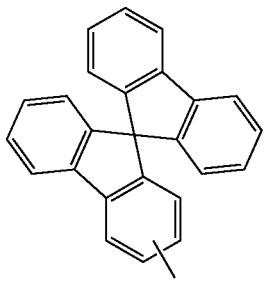
(D13)
wherein $R^{52}$, $R^{156}$, $R^{157}$, $A^4$ and DPA have the same meanings as above.
5. The aniline derivative of claim 1, represented by the formula (1-3), (1-4), (1-9) or (1-10):
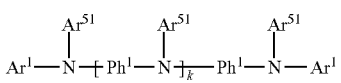
(1-3)
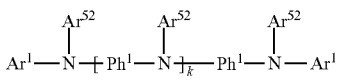
(1-4)
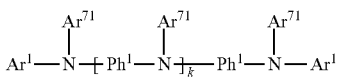
(1-9)
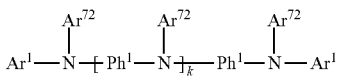
(1-10)
wherein $Ar^{51}$ represents a group represented by the formula (F1-1), $Ar^{52}$ represents a group represented by the formula (F2-1), Ar$^{71}$ represents a group represented by the formula (F2-2), Ar$^{72}$ represents a group represented by the formula (F1-2), and Ph$^1$, Ar$^1$ and letter k have the same meanings as above:

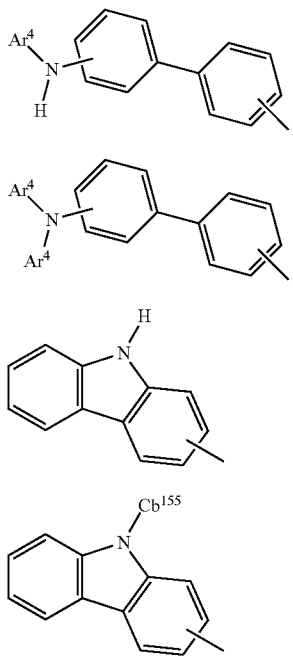

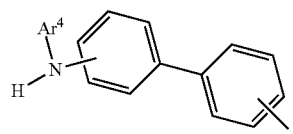   (F1-1)

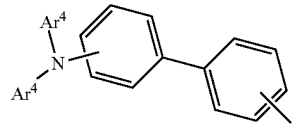   (F1-2)

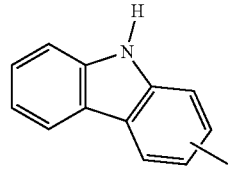   (F2-1)

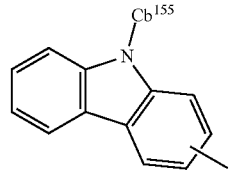   (F2-2)

wherein Cb$^{155}$ represents an alkyl group having 1 to 20 carbon atoms, alkenyl group having 2 to 20 carbon atoms or alkynyl group having 2 to 20 carbon atoms which may be substituted with Z$^4$, or an aryl group having 6 to 20 carbon atoms or heteroaryl group having 2 to 20 carbon atoms which may be substituted with Z$^1$, and Z$^1$, Z$^4$ and Ar$^4$ have the same meanings as above.

7. A charge transporting substance comprising the aniline derivative of claim 1.

8. A charge transporting material comprising the charge transporting substance of claim 7.

9. A charge transporting varnish comprising the charge transporting substance of claim 7 and an organic solvent.

10. The charge transporting varnish of claim 9, further comprising a dopant substance.

11. The charge transporting varnish of claim 10, wherein the dopant substance includes at least one selected from halotetracyanoquinodimethanes and benzoquinone derivatives.

12. The charge transporting varnish of claim 11, wherein the dopant substance further includes a heteropoly-acid compound.

13. The charge transporting varnish of claim 9, further comprising an organic silane compound.

14. A charge transporting thin film produced by use of the charge transporting varnish of claim 9.

15. A charge transporting thin film produced by a vapor deposition method using the aniline derivative of claim 1.

16. An organic electroluminescence element comprising the charge transporting thin film of claim 14 or 15.

17. An organic electroluminescence element of claim 16, wherein the charge transporting thin film is a hole injection layer, a hole transport layer or a hole injection transport layer.

wherein Cb$^{155}$ represents an alkyl group having 1 to 20 carbon atoms, alkenyl group having 2 to 20 carbon atoms or alkynyl group having 2 to 20 carbon atoms which may be substituted with Z$^4$, or an aryl group having 6 to 20 carbon atoms or heteroaryl group having 2 to 20 carbon atoms which may be substituted with Z$^1$, and Z$^1$, Z$^4$ and Ar$^4$ have the same meanings as above.

6. The aniline derivative of claim 1, represented by the formula (1-5), (1-6), (1-11) or (1-12):

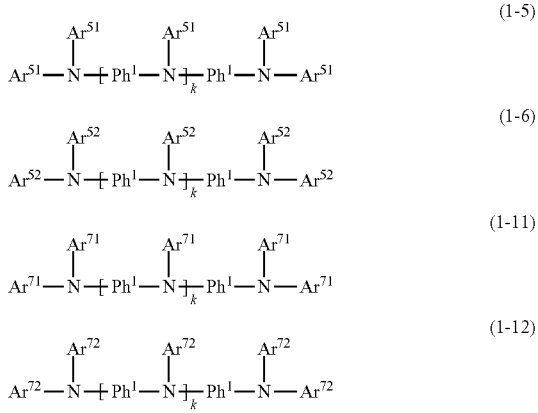

wherein Ar$^{51}$ represents a group represented by the formula (F1-1), Ar$^{52}$ represents a group represented by the formula (F2-1), Ar$^{71}$ represents a group represented by the formula (F2-2), Ar$^{72}$ represents a group represented by the formula (F1-2), and Ph$^1$ and letter k have the same meanings as above:

* * * * *